US012589488B2

(12) United States Patent
Song et al.

(10) Patent No.: US 12,589,488 B2
(45) Date of Patent: Mar. 31, 2026

(54) SURGICAL ROBOT ARM

(71) Applicant: LIVSMED INC., Seongnam-si (KR)

(72) Inventors: Youngjae Song, Seongnam-si (KR);
Jung Joo Lee, Seongnam-si (KR);
Heejin Kim, Seongnam-si (KR);
Dongkyu Jang, Seongnam-si (KR)

(73) Assignee: LIVSMED INC., Seongnam-si (KR)

( * ) Notice: Subject to any disclaimer, the term of this
patent is extended or adjusted under 35
U.S.C. 154(b) by 0 days.

(21) Appl. No.: 18/661,707

(22) Filed: May 12, 2024

(65) Prior Publication Data

US 2024/0300090 A1     Sep. 12, 2024

Related U.S. Application Data

(63) Continuation of application No.
PCT/KR2022/017859, filed on Nov. 14, 2022.

(30) Foreign Application Priority Data

Nov. 12, 2021     (KR) ........................ 10-2021-0156114

(51) Int. Cl.
B25J 9/10     (2006.01)
A61B 34/37     (2016.01)
B25J 3/00     (2006.01)
B25J 9/12     (2006.01)
A61B 34/30     (2016.01)

(52) U.S. Cl.
CPC ............... B25J 9/106 (2013.01); A61B 34/37
(2016.02); B25J 3/00 (2013.01); B25J 9/123
(2013.01); A61B 2034/302 (2016.02)

(58) Field of Classification Search
CPC .... B25J 9/106; A61B 34/37; A61B 2034/305;
A61B 2034/302; A61B 2034/306; A61B
34/70
See application file for complete search history.

(56) References Cited

U.S. PATENT DOCUMENTS

| 2011/0282359 A1* | 11/2011 | Duval .................... H04N 23/60 |
| | | 606/130 |
| 2012/0132018 A1 | 5/2012 | Tang et al. |
| 2017/0020615 A1 | 1/2017 | Koenig et al. |
| 2018/0065254 A1 | 3/2018 | Okahisa et al. |
| 2019/0000576 A1 | 1/2019 | Mintz et al. |
| 2019/0365489 A1* | 12/2019 | Kasai ..................... A61B 1/055 |
| 2021/0030496 A1 | 2/2021 | Devengenzo et al. |

(Continued)

FOREIGN PATENT DOCUMENTS

| JP | 2018-198750 A | 12/2018 |
| JP | 2019-013445 A | 1/2019 |

(Continued)

*Primary Examiner* — Darwin P Erezo
*Assistant Examiner* — Christina C Lauer
(74) *Attorney, Agent, or Firm* — Bridgeway IP Law
Group, PLLC; Sang Ho Lee; Hyun Woo Shin

(57)     ABSTRACT

The present disclosure provides a robot arm for minimally
invasive surgery and a method of controlling the same and
is directed to providing a surgical robot arm in which a
remote center of motion (RCM) control is implemented
through an electronic control so that an overall size of an
instrument is reduced and a configuration is simplified,
thereby increasing space efficiency and preventing collisions
between robot arms.

9 Claims, 80 Drawing Sheets

(56)                References Cited

U.S. PATENT DOCUMENTS

2021/0045817 A1 *   2/2021   Koenig ................. A61B 34/37
2021/0244489 A1     8/2021   Lim et al.
2021/0330405 A1    10/2021   Gonenc et al.

FOREIGN PATENT DOCUMENTS

JP              6791859 B2    11/2020
KR     10-2012-0014758 A      2/2012
WO         2018/067696 A1     4/2018
WO         2019/240453 A1    12/2019
WO         2021/021200 A1     2/2021

* cited by examiner

Figure 2:
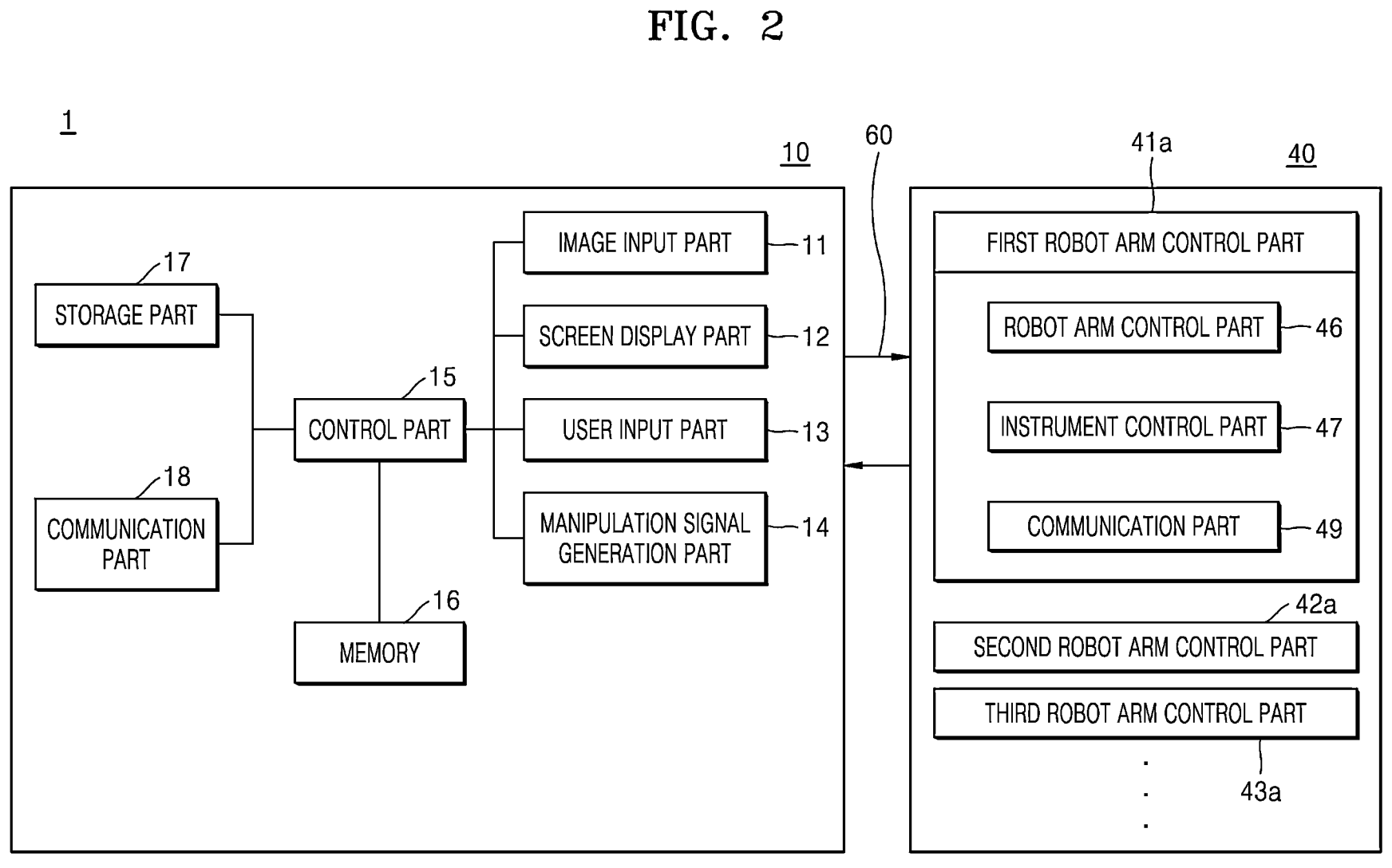

IMAGE INPUT PART — 11

SCREEN DISPLAY PART — 12

USER INPUT PART — 13

MANIPULATION SIGNAL GENERATION PART — 14

CONTROL PART — 15

MEMORY — 16

STORAGE PART — 17

COMMUNICATION PART — 18

60

40

41a

FIRST ROBOT ARM CONTROL PART

ROBOT ARM CONTROL PART — 46

INSTRUMENT CONTROL PART — 47

COMMUNICATION PART — 49

42a

SECOND ROBOT ARM CONTROL PART

43a

THIRD ROBOT ARM CONTROL PART

. . .

RCM

SURGICAL ROBOT ARM

CROSS-REFERENCE TO RELATED APPLICATION(S)

This application is a continuation application of international application No. PCT/KR2022/017859, filed on Nov. 14, 2022, and claims priority to Korean Patent Application No. 10-2021-0156114, filed on Nov. 12, 2021, with the Korean Intellectual Property Office, the entire disclosures of which are incorporated herein by reference.

TECHNICAL FIELD

The present disclosure relates to a robot arm for minimally invasive surgery and a method of controlling the same.

BACKGROUND ART

In medical terms, surgery refers to curing an illness by cutting, incising, or manipulating the skin, mucous membranes, or other tissues by using medical devices. In particular, open surgery, which involves cutting open the skin at the surgical site and treating, shaping, or removing the organs inside, causes problems such as bleeding, side effects, patient pain, and scarring. Therefore, surgery using a robot or surgery performed by forming a certain hole in the skin and inserting only a medical device, such as a laparoscope, a surgical instrument, or a microsurgical microscope, has recently attracted attention as an alternative.

Here, surgical robots refer to robots that have the function to replace surgical operations performed by surgeons. Such surgical robots have advantages of being able to perform more accurate and precise operations than humans and enabling remote surgery.

Surgical robots that are currently being developed around the world include bone surgery robots, laparoscopic surgery robots, and stereotactic surgery robots. Here, laparoscopic surgery robots perform minimally invasive surgery by using a laparoscope and small surgical tools.

Laparoscopic surgery is a cutting-edge surgical technique that involves drilling a small hole in a navel area and inserting a laparoscope, which is an endoscope to observe the inside of the abdomen, and then performing the surgery. The laparoscopic surgery is a field where much progress is expected in the future. Recent laparoscopes are provided with computer chips so as to obtain clearer and enlarged images than those seen with the naked eye. In addition, advances have been made to make it possible to perform any surgery by using a specially designed laparoscopic surgical instrument while viewing a screen on a monitor.

Furthermore, the extent of laparoscopic surgery is almost the same as the extent of open surgery, and laparoscopic surgery has advantages in that fewer complications are caused than open surgery, treatment may begin much earlier after the procedure, and the ability to maintain the physical strength and immune function of surgical patients is excellent. Due to this, laparoscopic surgery is gradually being recognized as a standard surgery in the treatment of colon cancer in the United States and Europe.

On the other hand, a surgical robot generally includes a master robot and a slave robot. When an operator operates a control lever (e.g., a handle) provided on a master robot, a surgical tool coupled to a robot arm of a slave robot or held by the robot arm is manipulated to perform surgery.

The aforementioned background technology is technical information possessed by the inventor for derivation of the present disclosure or acquired by the inventor during the derivation of the present disclosure, and is not necessarily prior art disclosed to the public before the application of the present disclosure.

DETAILED DESCRIPTION OF THE DISCLOSURE

Technical Problem

In order to solve the problems described above, the present disclosure is directed to providing a surgical robot arm in which a remote center of motion (RCM) control is implemented through an electronic control so that an overall size of an instrument is reduced and a configuration is simplified, thereby increasing space efficiency and preventing collisions between robot arms.

Technical Solution to Problem

According to an aspect of the present disclosure, there is provided a surgical robot arm, on which a surgical instrument is mounted, includes a base link including an extension portion extending in one direction and a roll rotation base portion formed at one end of the extension portion and formed to have a certain angle with the extension portion, a first link coupled to the roll rotation base portion of the base link and formed to be roll-rotatable around a first axis, a second link coupled to the first link and formed to be linearly movable along a second axis with respect to the first link, and an instrument mounting link axially coupled to the second link by a link rotation shaft formed in a third axis direction and formed to be rotatable around the link rotation shaft.

In the present disclosure, a remote center of motion (RCM) may be formed on a trocar into which the surgical instrument is inserted, and the trocar and the surgical instrument inserted thereinto may be controlled to rotate around the RCM.

In the present disclosure, the first link may include a first region coupled to the base link and a second region coupled to the second link, and a central axis of the first region and a central axis of the second region may form a certain angle with each other.

In the present disclosure, the RCM may be located on an extension line of the central axis of the first region.

In the present disclosure, the RCM may be disposed on an extension line of the first axis.

In the present disclosure, the first link may include a first region coupled to the roll rotation base portion of the base link and formed to be roll-rotatable around the first axis, and a second region axially coupled to the first region by a pitch rotation shaft formed in a fifth axis direction and formed to be rotatable around the pitch rotation shaft.

In the present disclosure, the third axis and the fifth axis may be formed to be substantially parallel to each other.

In the present disclosure, a distance from one end of the trocar to the RCM may be controllable to be maintained constant by rotating the second region around the pitch rotation shaft with respect to the first region.

In the present disclosure, the first region of the first link may include a first-1 region coupled to the base link, and a first-2 region disposed between the first-1 region and the second region and connected to each of the first-1 region and the second region, and the first-1 region and the first-2 region may be axially coupled to each other so that the first-2 region is rotatable around a seventh axis with respect to the first-1 region.

In the present disclosure, an RCM motion may be possible even when the RCM and the first axis are spaced apart from each other on an XY plane.

In the present disclosure, the second link may include a first region coupled to the first link and formed to be linearly movable along the second axis with respect to the first link, and a second region axially coupled to the first region by a pitch rotation shaft and formed to be rotatable around the pitch rotation shaft.

In the present disclosure, a distance from one end of the trocar to the RCM may be controllable to be maintained constant by rotating the second region around the pitch rotation shaft with respect to the first region.

In the present disclosure, the surgical robot arm may further include a base configured to form a base portion of the surgical robot arm and having one surface to which the base link is coupled.

In the present disclosure, the base link may be formed to be linearly movable along a sixth axis with respect to the base.

In the present disclosure, an RCM motion may be possible even when the RCM and the first axis are spaced apart from each other on the sixth axis.

In the present disclosure, the base link may be formed to be roll-rotatable around a sixth axis with respect to the base.

In the present disclosure, an RCM motion may be possible even when the RCM and the first axis are spaced apart from each other on an XY plane.

In the present disclosure, the instrument mounting link may include a guide rail extending in a fourth axis direction, and an instrument mounting portion to which the surgical instrument is coupled and which is formed to be linearly movable along the guide rail.

In the present disclosure, a distance from an end of an end tool of the surgical instrument to the RCM may be controllable to be maintained constant by a linear motion of the instrument mounting portion with respect to the guide rail.

In the present disclosure, the surgical robot arm may further include a trocar holder portion to which the trocar is coupled and which is coupled to the instrument mounting link and formed to be linearly movable along the instrument mounting link.

In the present disclosure, a distance from an end of the trocar to the RCM may be controllable to be maintained constant by a linear motion of the trocar holder portion with respect to the instrument mounting link.

In the present disclosure, a control of an RCM motion around the RCM in a first direction may be performed by a roll rotational motion of the first link around the first axis with respect to the base link, a control of a rotational motion of the instrument mounting link around the third axis with respect to the second link, and a control of a linear motion of the second link with respect to the first link moving along the second axis.

In the present disclosure, for the RCM control in the first direction, a roll motion of the surgical instrument may be controlled together.

In the present disclosure, a direction of an end tool of the surgical instrument may be controlled to be maintained constant by the roll motion of the surgical instrument.

In the present disclosure, the surgical robot arm may further include a base configured to form a base portion of the surgical robot arm and having one surface to which the base link is coupled, and, for the control of the RCM motion around the RCM in the first direction, a control of a rotational motion the base link with respect to the base may be further performed.

In the present disclosure, an RCM control in a second direction may be implemented by a linear motion of the second link with respect to the first link moving along the second axis and a control of a rotational motion of the instrument mounting link around the third axis with respect to the second link.

In the present disclosure, the first link may include a first region coupled to the roll rotation base portion of the base link and formed to be roll-rotatable around the first axis, and a second region axially coupled to the first region by a pitch rotation shaft and formed to be rotatable around the pitch rotation shaft, and, for the RCM control in the second direction, a rotational motion of the second region with respect to the first region may be controlled together.

In the present disclosure, the second link may include a first region coupled to the first link and formed to be linearly movable along the second axis with respect to the first link, and a second region axially coupled to the first region by a pitch rotation shaft and formed to be rotatable around the pitch rotation shaft, and, for the RCM control in the second direction, a rotational motion of the second region with respect to the first region may be controlled together.

In the present disclosure, the second link and the instrument mounting link may be coupled to each other only by the link rotation shaft, and the link rotation shaft may be actively controlled by a motor.

Aspects, features, and advantages other than those described above will become better understood through the accompanying drawings, the claims, and the detailed description.

Advantageous Effects of Disclosure

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm and reducing the driving force required for operation may be obtained.

BRIEF DESCRIPTION OF DRAWINGS

FIG. 2 is a block diagram illustrating the internal configuration of the surgical robot system of FIG. 1.

FIGS. 6A to 8B are side views and plan views illustrating an X-axis remote center of motion (RCM) motion (a pitch motion) of the surgical robot arm of FIG. 4.

FIGS. 19A to 21B are side views and plan views illustrating an X-axis RCM motion (a pitch motion) of the surgical robot arm of FIG. 17.

FIGS. 29A to 31B are side views and plan views illustrating an X-axis RCM motion (a pitch motion) of the surgical robot arm of FIG. 26.

FIGS. 38A to 40B are side views and plan views illustrating an X-axis RCM motion (a pitch motion) of the surgical robot arm of FIG. 36.

FIGS. 47A to 49B are side views and plan views illustrating an X-axis RCM motion (a pitch motion) of the surgical robot arm of FIG. 45.

FIGS. 56A to 58B are side views and plan views illustrating an X-axis RCM motion (a pitch motion) of the surgical robot arm of FIG. 54.

FIGS. 65A to 67B are side views and plan views illustrating an X-axis RCM motion (a pitch motion) of the surgical robot arm of FIG. 63.

FIGS. 74A to 76B are side views and plan views illustrating an X-axis RCM motion (a pitch motion) of the surgical robot arm of FIG. 72.

BEST MODE

Figure 1:
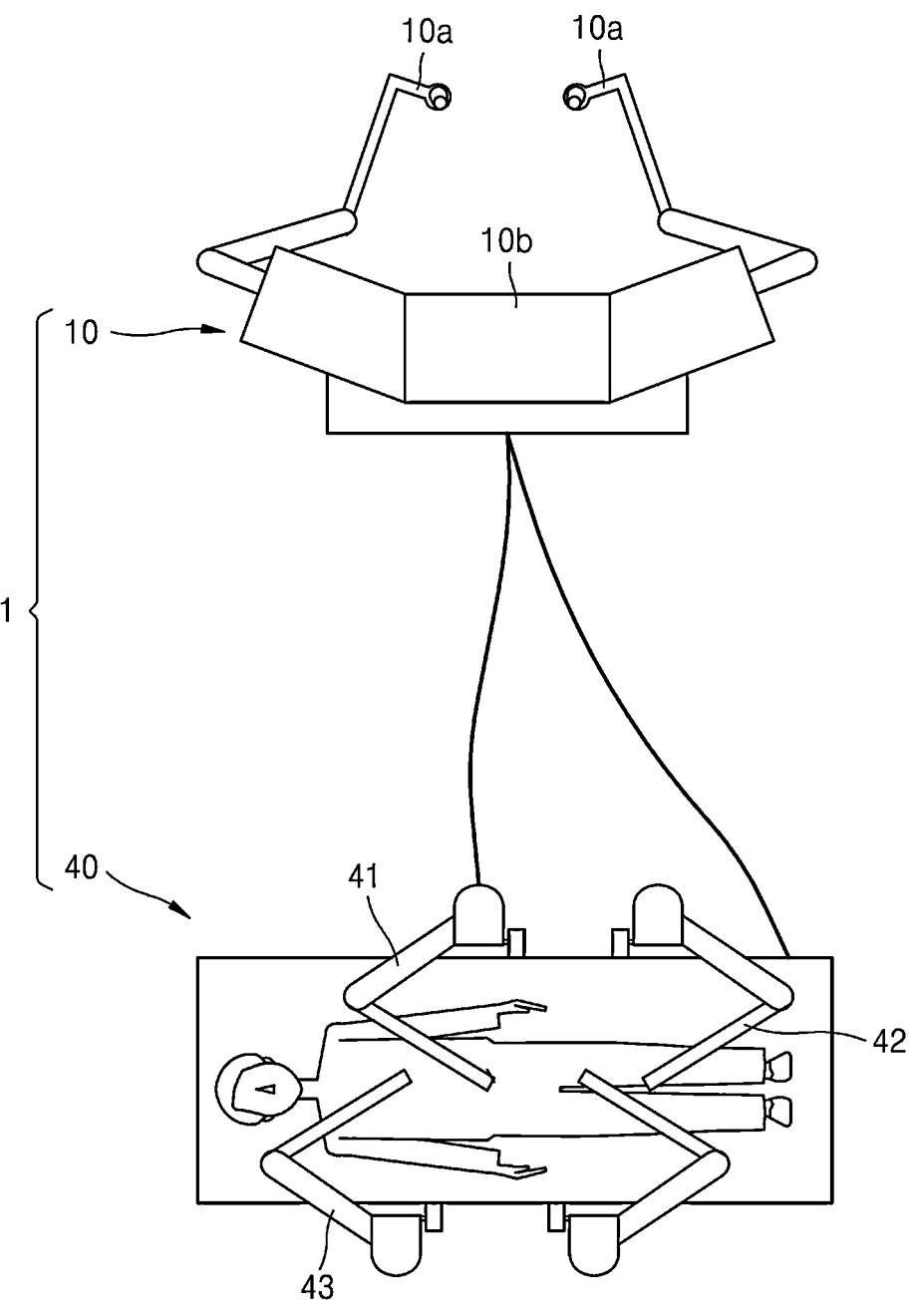
FIG. 1 is a conceptual diagram illustrating a surgical robot system including a surgical robot arm, according to an embodiment of the present disclosure.

The present disclosure may include various modifications and embodiments, and therefore, the present disclosure will be described in detail with reference to specific embodiments. However, this is not intended to limit the present disclosure to particular embodiments, and it should be understood that the present disclosure is intended to include all variations, equivalents, and substitutes falling within the spirit and scope of the present disclosure. In describing the present disclosure, when the detailed description of the relevant known technology is determined to obscure the gist of the present disclosure, the detailed description thereof may be omitted.

While such terms as "first" and "second" may be used to describe various elements, such elements should not be limited by the above terms. These terms are only used to distinguish one element from another.

The terms as used herein are only used to describe particular embodiments, and are not intended to limit the present disclosure. The singular forms as used herein are intended to include the plural forms as well unless the context clearly indicates otherwise. The terms "comprise," "include," or "have" as used in the present application are inclusive and therefore specify the presence of one or more stated features, integers, steps, operations, elements, components, or any combination thereof, but do not preclude the presence or addition of one or more other features, integers, steps, operations, elements, components, or any combination thereof.

Hereinafter, the embodiments of the present disclosure will be described in detail with reference to the accompanying drawings. When describing the embodiments of the present disclosure with reference to the accompanying drawings, the same or corresponding elements are denoted by the same reference numerals and redundant descriptions thereof are omitted.

In addition, in describing various embodiments of the present disclosure, each embodiment does not have to be interpreted or practiced independently. It should be understood that the technical ideas described in each embodiment may be interpreted or implemented in combination with other individually described embodiments.

Figure 3:
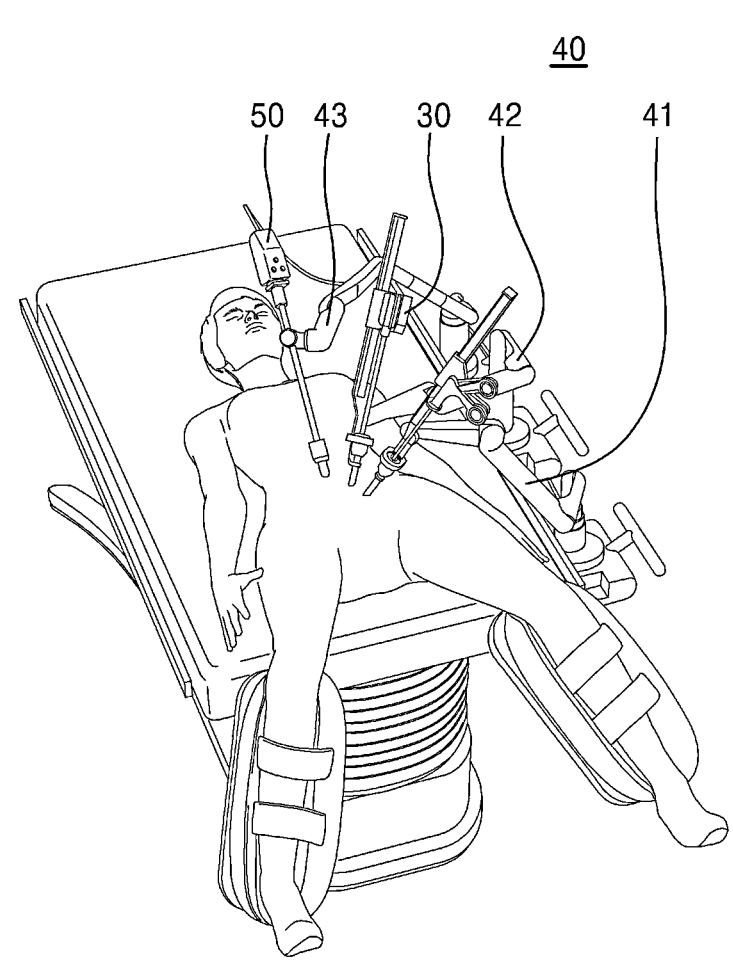
FIG. 3 is a perspective view illustrating a slave robot of the surgical robot system of FIG. 1 and a surgical instrument mounted thereon.

FIG. 1 is a conceptual diagram illustrating a surgical robot system including a surgical robot arm, according to an embodiment of the present disclosure, FIG. 2 is a block diagram illustrating the internal configuration of the surgical robot system of FIG. 1, and FIG. 3 is a perspective view illustrating a slave robot of the surgical robot system of FIG. 1 and a surgical instrument mounted thereon.

Referring to FIGS. 1 to 3, a surgical robot system 1 includes a master robot 10, a slave robot 40, and a surgical instrument 20.

The master robot 10 includes a manipulation member 10a and a display member 10b, and the slave robot 40 includes one or more surgical robot arms 41, 42, and 43.

In detail, the master robot 10 includes the manipulation member 10a manipulated by an operator while the operator holds the manipulation member 10a with both hands. The manipulation member 10a may be implemented with two or more handles, as illustrated in FIG. 1. Manipulation signals according to the handle manipulation of the operator are transmitted to the slave robot 40 via a wired or wireless communication network so as to control the surgical robot arms 41, 42, and 43. That is, surgical operations, such as position movement, rotation, and cutting operations of the surgical robot arms 41, 42, and 43, may be performed by the handle manipulation of the operator.

For example, the operator may manipulate the surgical robot arms 41, 42, and 43 by using a handle-shaped manipulation lever. The manipulation lever may have various mechanical configurations according to a manipulation method thereof. The manipulation lever may be provided in various forms for operating the surgical robot arm 41, 42, and 43 of the slave robot 40 and/or other surgical instruments, for example, a master handle that manipulates the operations of the surgical robot arms 41, 42, and 43, and various input tools, such as joysticks, keypads, trackballs, foot pedals, and touch screens, which are attached to the master robot 10 so as to manipulate the functions of the entire system. Here, the manipulation member 10a is not limited to the shape of the handle and may be applied without any restrictions as long as the manipulation member 10a is capable of controlling the motions of the surgical robot arms 41, 42, and 43 via a network, such as a wired or wireless communication network.

Alternatively, voice input or motion input may also be applied for user input. That is, a laparoscope 50 may be moved according to a direction in which a user gazes while wearing glasses or a head mount display (HMD) with a sensor on a user's head. Alternatively, when the user gives a voice command, such as "left," "right," "arm 1," "arm 2," etc., the command may be recognized and the motion may be performed.

An image captured through the laparoscope 50, which will be described later, is displayed as a video image on the display member 10b of the master robot 10. In addition, a certain virtual manipulation panel may be displayed on the display member 10b together with the image captured through the laparoscope 50, or may be displayed independently. Detailed descriptions of the arrangement and configuration of the virtual manipulation panel are omitted.

Here, the display member 10b may include one or more monitors, and information necessary for surgery may be individually displayed on each monitor. The number of monitors may be determined in various ways according to the type or kind of information required to be displayed.

On the other hand, the slave robot 40 may include one or more surgical robot arms 41, 42, and 43. Here, the surgical robot arms 41, 42, and 43 may be provided in the form of modules that are operable independently of each other, and in this case, an algorithm for preventing collisions between the surgical robot arms 41, 42, and 43 may be applied to the surgical robot system 1.

In general, the robot arm refers to a device that has functions similar to a human arm and/or wrist and may attach a certain tool to a wrist area. In the present specification, the surgical robot arms 41, 42, and 43 may be defined as a concept encompassing all of components, such as an upper arm, a lower arm, a wrist, and an elbow, and multi-joint surgical devices to be coupled to the wrist area. Alternatively, the surgical robot arms 41, 42, and 43 may be defined as a concept encompassing only components for driving the multi-joint surgical devices, excluding the multi-joint surgical devices to be coupled to the wrist area.

As such, the surgical robot arms 41, 42, and 43 of the slave robot 40 may be implemented to be driven with multiple degrees of freedom. The surgical robot arms 41, 42, 43 may be configured to include, for example, a surgical instrument to be inserted into a patient's surgical site, a yaw driving part that rotates the surgical instrument in a yaw direction according to the surgical position, a pitch driving part that rotates the surgical instrument in a pitch direction perpendicular to the rotary driving of the yaw driving part, a transfer driving part that moves the surgical instrument in a longitudinal direction, a rotary driving part that rotates the surgical instrument, and a surgical instrument driving part that incises or cuts a surgical lesion by driving an end effector at the end of the surgical instrument. However, the configuration of the surgical robot arms 41, 42, and 43 is not limited thereto, and it should be understood that such examples do not limit the scope of the present disclosure. Here, a detailed description of an actual control process, in which the surgical robot arms 41, 42, and 43 are rotated and moved in the corresponding direction when the operator manipulates the manipulation member 10a, is omitted.

Here, the surgical instrument 20 may be attached to two of the surgical robot arms 41, 42, and 43, and the laparoscope 50 may be attached to one of the surgical robot arms 41, 42, and 43. A surgeon may select the surgical robot arms 41, 42, and 43 to be controlled through the master robot 10.

A such, since the surgeon directly controls three or more surgical instruments through the master robot 10, the manipulation of various instruments may be performed accurately and freely as intended by the surgeon without the need for a surgical assistant.

On the other hand, one or more slave robots 40 may be provided to perform surgery on a patient. The laparoscope 50 for displaying the surgical site on the display member 10b as a video image may be implemented as the independent slave robot 40. In addition, as described above, embodiments of the present disclosure may be universally used in surgeries using various surgical endoscopes (e.g., a thoracoscope, an arthroscope, a rhinoscope, etc.) other than laparoscopes.

Referring to FIG. 2, in an embodiment of the present disclosure, the master robot 10 may include an image input part 11, a screen display part 12, a user input part 13, a manipulation signal generation part 14, a control part 15, a memory 16, a storage part 17, a communication part 18.

The image input part 11 may receive an image, which is captured by a camera provided on the laparoscope 50 of the slave robot 40, via a wired or wireless communication network.

The screen display part 12 outputs, as visual information, a video image corresponding to the image received through the image input part 11. In addition, when biometric information of a patient is input, the screen display part 12 may further output information corresponding to the biometric information. In addition, the screen display part 12 may further output image data related to the surgical site of the patient (e.g., an X-ray image, a computed tomography (CT) image, a magnetic resonance imaging (MRI) image, etc.). Here, the screen display part 12 may be implemented in the form of the display member (see 10b of FIG. 1), etc. An image processing process for outputting a received image through the screen display part 12 as a video image may be executed by the control part 15.

In the embodiment illustrated in FIG. 2, it is illustrated that the image input part and the screen display part are components included in the master robot 10, but are not limited thereto. That is, the display member may be provided as a separate member spaced apart from the master robot 10. Alternatively, the display member may be provided as one component of the master robot 10. In addition, in another embodiment, a plurality of display members may be provided. One of the display members may be arranged adjacent to the master robot 10, and some of the display members may be arranged slightly apart from the master robot 10.

Here, the screen display part 12 (i.e., the display member 10b of FIG. 1) may be provided as a three-dimensional display device. In detail, the three-dimensional display device refers to an image display device that adds depth information to a two-dimensional image by applying a stereoscopic technology and uses the depth information to allow an observer to feel vividness and reality of three dimensions. The surgical robot system 1 according to an embodiment of the present disclosure may be provided with the three-dimensional display device as the screen display part 12 to provide a more realistic virtual environment to a user.

The user input part 13 is a means for allowing the operator to manipulate the positions and functions of the surgical robot arms 41, 42, and 43 of the slave robot 40. The user input part 13 may be formed in the form of the handle-shaped manipulation member (see 10a of FIG. 1), as illustrated in FIG. 1, but the shape of the user input part 13 is not limited thereto. The user input part 13 may be modified and implemented in various shapes so as to achieve the same purpose. In addition, the user input part 13 may be formed to have different shapes. For example, the user input part 13 may have a portion formed in a handle shape and another portion formed in a clutch button shape. In order to facilitate the manipulation of surgical tools, the user input part 13 may further include a finger insertion tube or a finger insertion ring formed to allow a finger of an operator to be inserted and fixed.

When the operator manipulates the user input part 13 so as to move the positions of the surgical robot arms 41, 42, and 43 or manipulate the surgical operation, the manipulation signal generation part 14 generates a corresponding manipulation signal and transmits the generated manipulation signal to the slave robot 40 through the communication part 18. The manipulation signal may be transmitted and received via the wired or wireless communication network.

The control part 15 is a kind of central processing unit and controls the operations of the respective components to execute the functions described above. As an example, the control part 15 may execute a function to convert an image input through the image input part 11 into a video image to be displayed on the screen display part 12.

The memory 16 may execute a function to temporarily or permanently store data that is processed by the control part 15. Here, the memory 16 may include magnetic storage media or flash storage media, but the scope of the present disclosure is not limited thereto.

The storage part 17 may store data received from the slave robot 40. In addition, the storage part 17 may store various input data (e.g., patient data, device data, surgery data, etc.).

The communication part 18 provides a communication interface necessary to transmit and receive image data transmitted from the slave robot 40 and control data transmitted from the master robot 10 in conjunction with the communication network 60.

The slave robot 40 includes a plurality of surgical robot arm control parts 41a, 42a, and 43a. The surgical robot arm control part 41a includes a robot arm control part 46, an instrument control part 47, and a communication part 49. In addition, the surgical robot arm control part 41a may further include a rail control part 48.

The robot arm control part 46 may receive the manipulation signal generated by the manipulation signal generation part 14 of the master robot 10 and may serve to control the surgical robot arms 41, 42, and 43 to operate according to the manipulation signal.

The instrument control part 47 may receive the manipulation signal generated by the manipulation signal generation part 14 of the master robot 10 and may serve to control the surgical instrument 20 to operate according to the manipulation signal.

The communication part 49 provides a communication interface necessary to transmit and receive image data transmitted from the slave robot 40 and control data transmitted from the master robot 10 in conjunction with the communication network 60.

On the other hand, the communication network 60 serves to connect the master robot 10 to the slave robot 40. That is, the communication network 60 refers to a communication network that provides a connection path through which the master robot 10 and the slave robot 40 are connected to each other, and then, transmit and receive data with each other. The communication network 60 may include, for example, wired networks, such as local area networks (LANs), wide area networks (WANs), metropolitan area networks (MANs), and integrated service digital networks (ISDNs), or wireless networks, such as wireless LANs, code division multiple access (CDMA), Bluetooth, and satellite communications, but the scope of the present disclosure is not limited thereto.

<First Embodiment of Surgical Robot Arm>

Hereinafter, embodiments of the present disclosure will be described with reference to the accompanying drawings.

Figure 4:
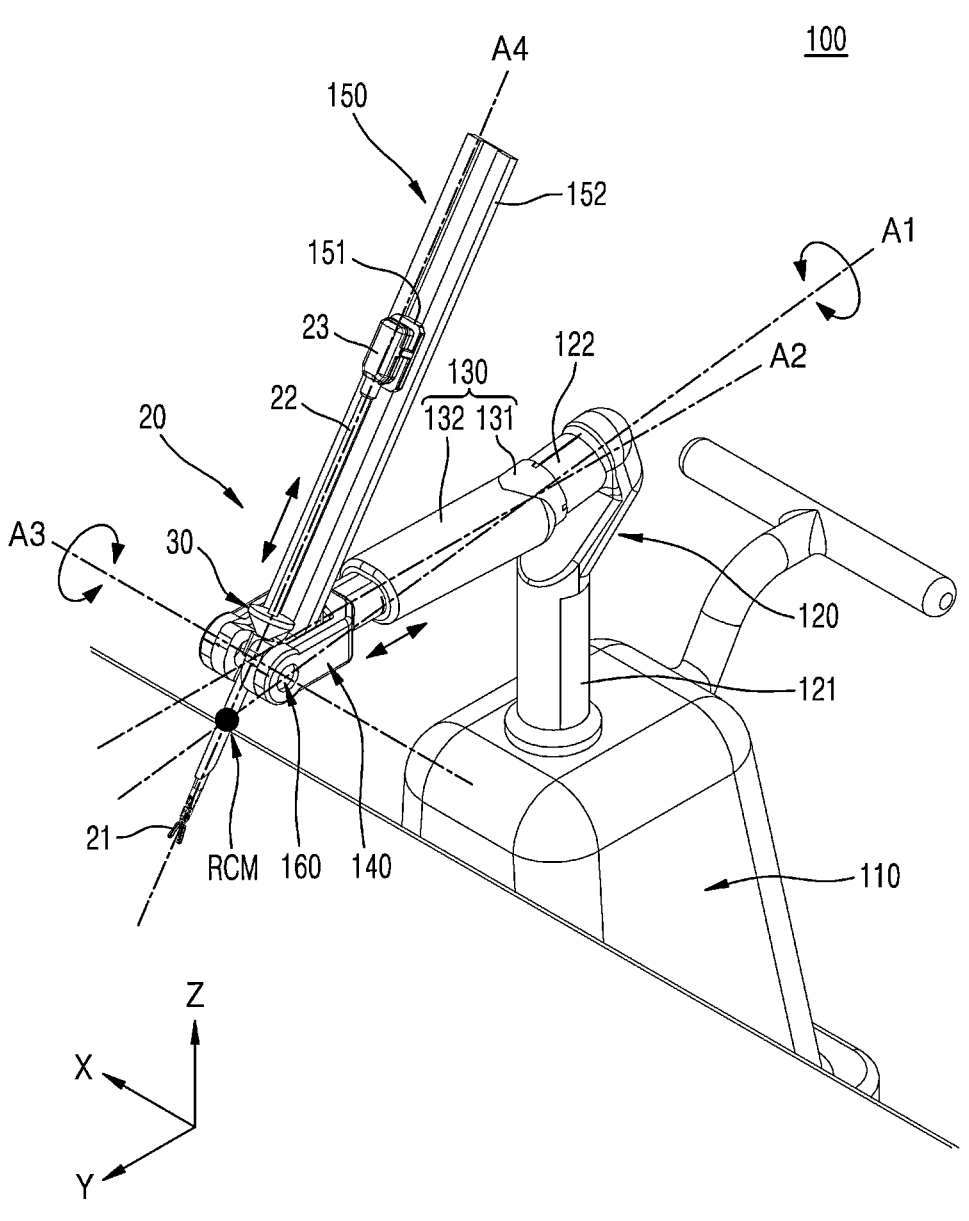
FIG. 4 is a perspective view illustrating an overall structure of a surgical robot arm (100) according to a first embodiment of the present disclosure.
Figure 5:
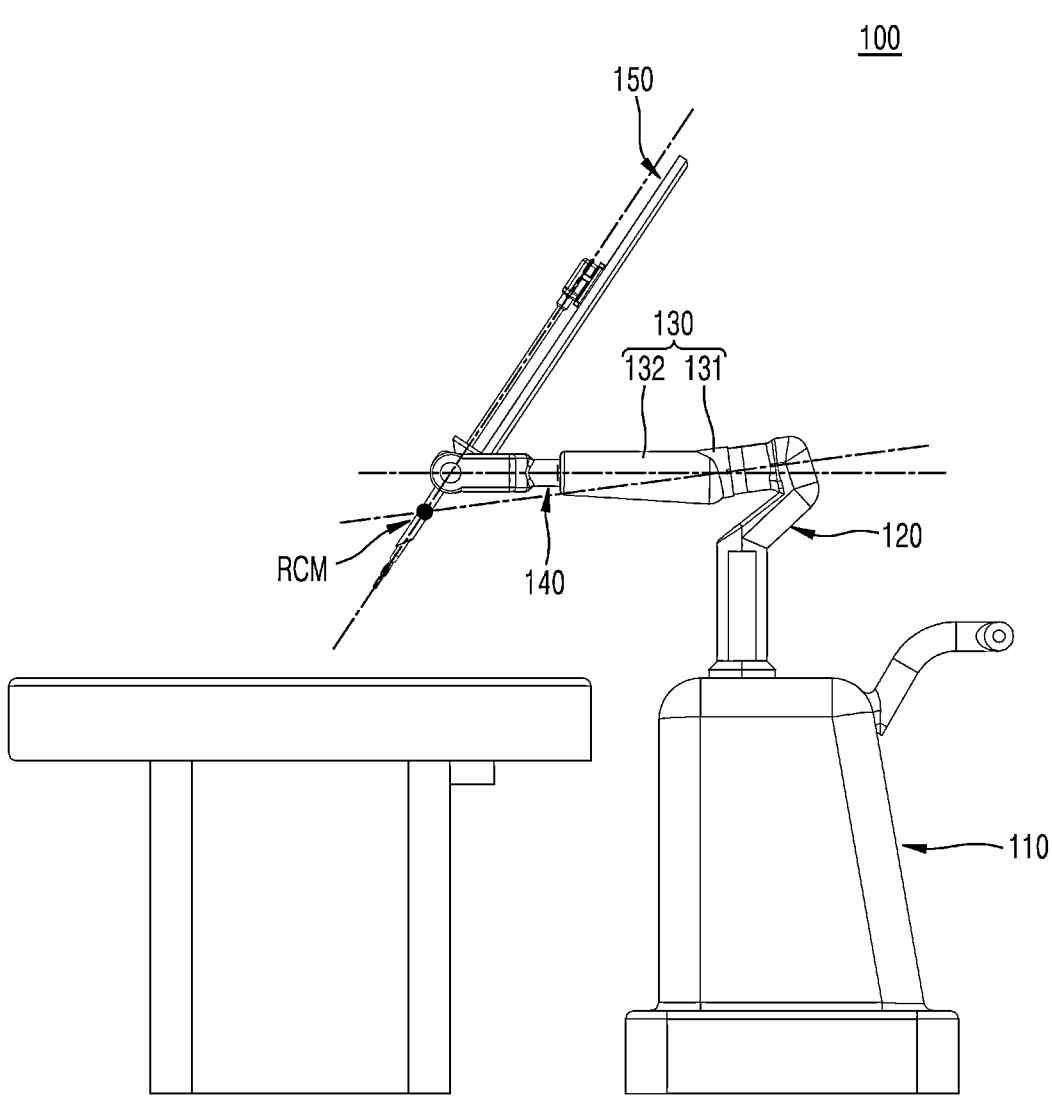
FIG. 5 is a side view of the surgical robot arm of FIG. 4.
Figures 6A, 6B:
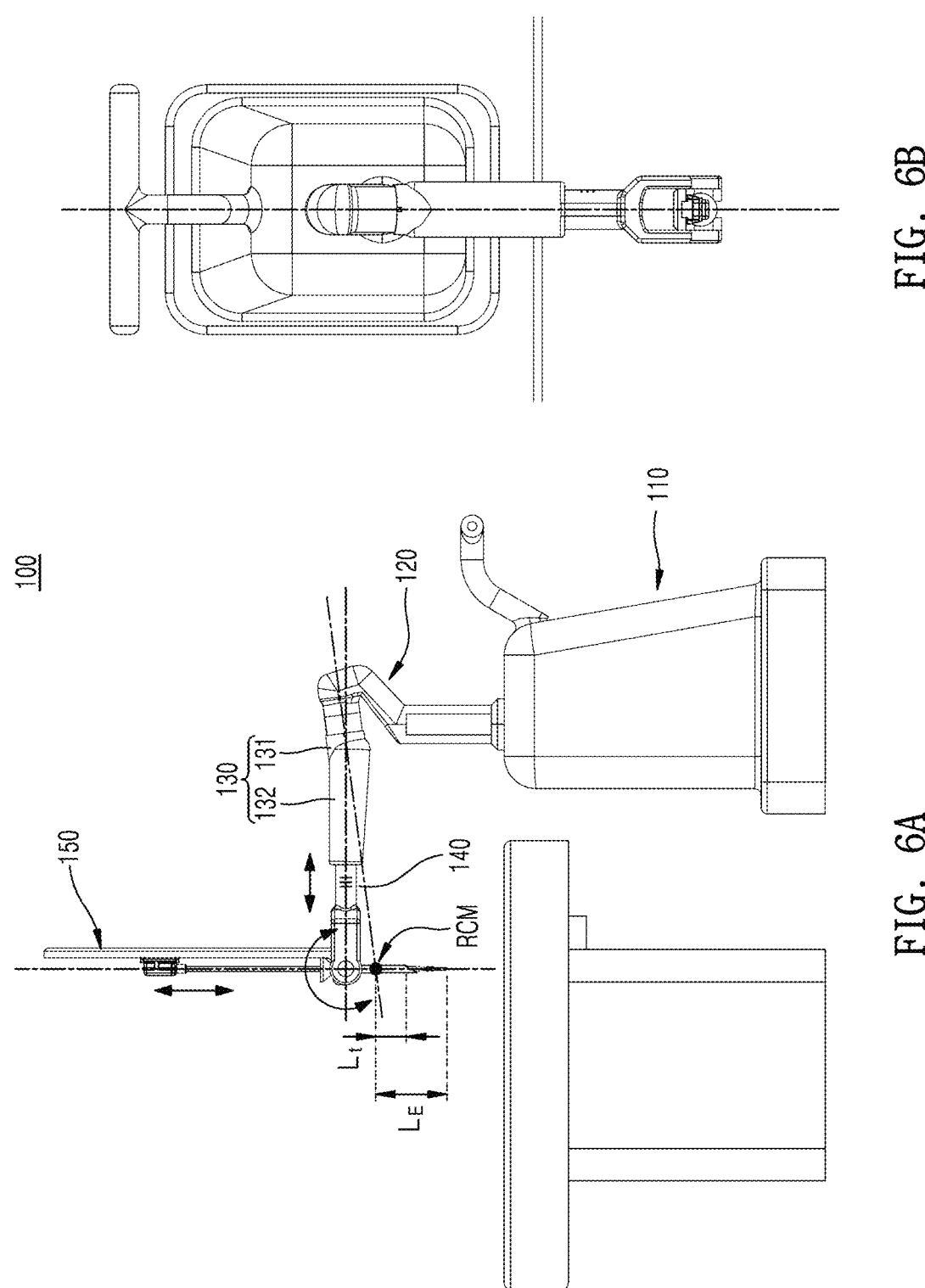
Figures 7A, 7B:
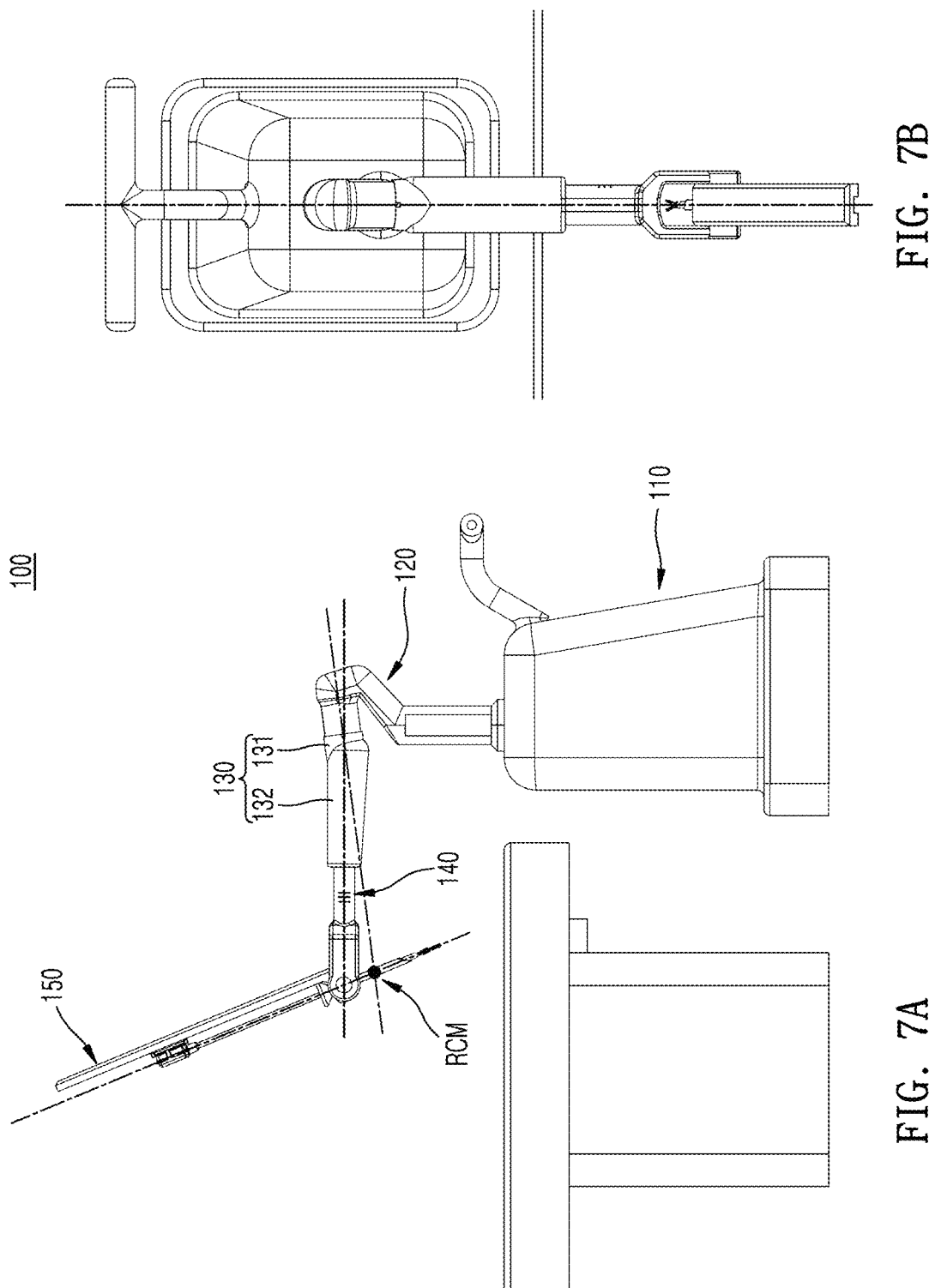
Figures 8A, 8B:
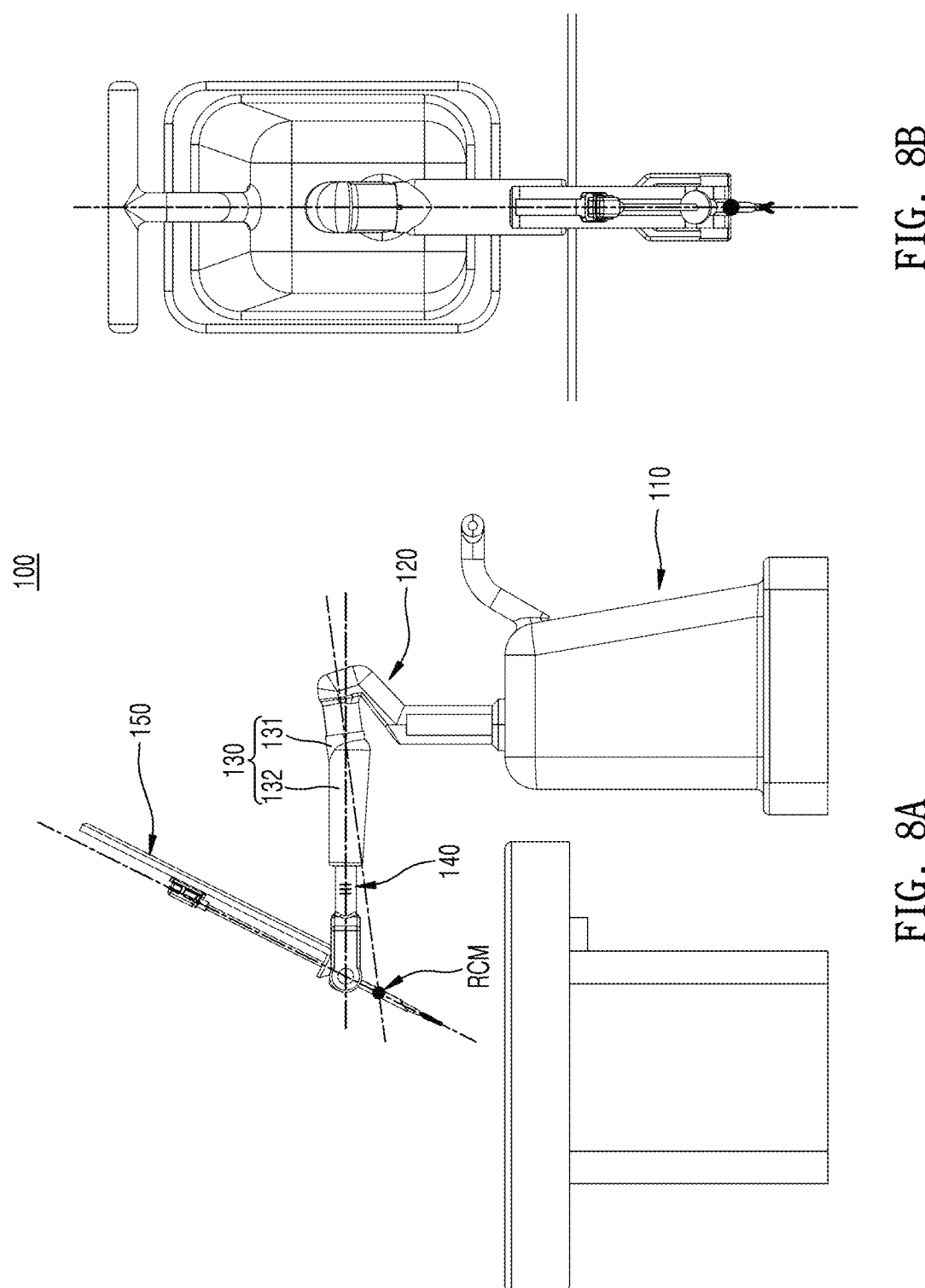
Figure 9:
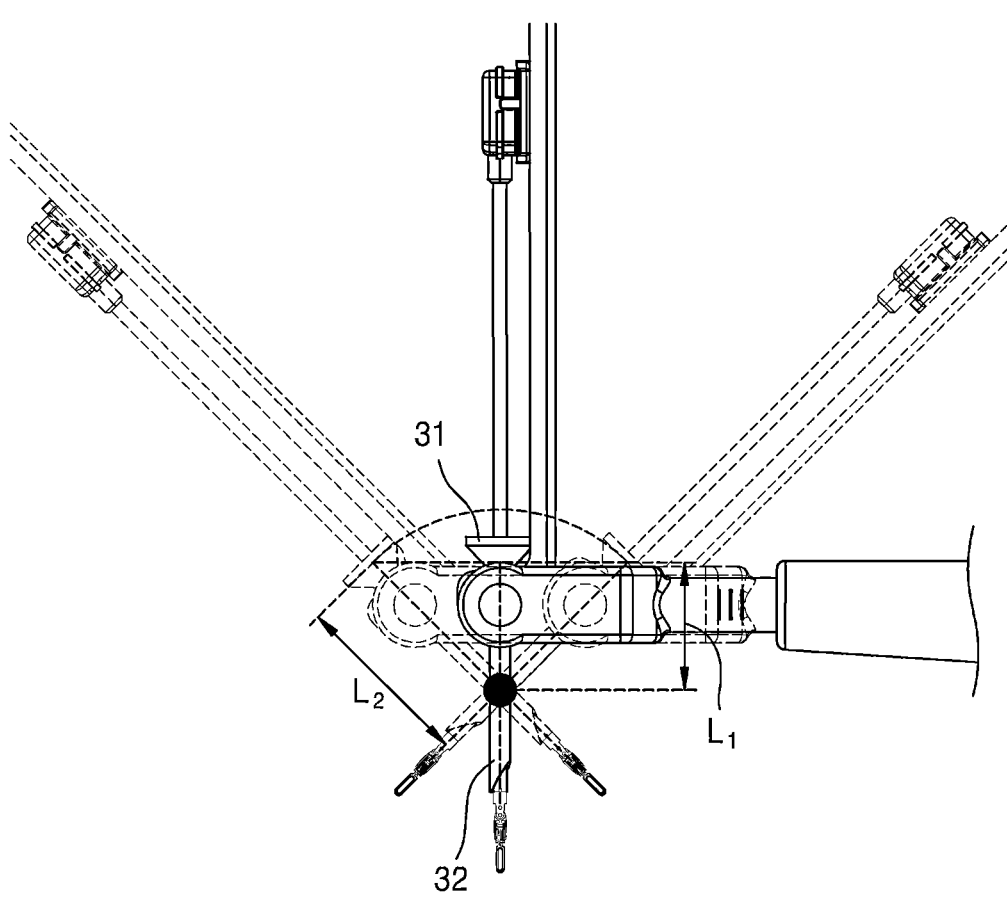
FIG. 9 is a diagram describing the X-axis RCM motion (the pitch motion) of FIGS. 6 to 8 in more detail.
Figure 10:
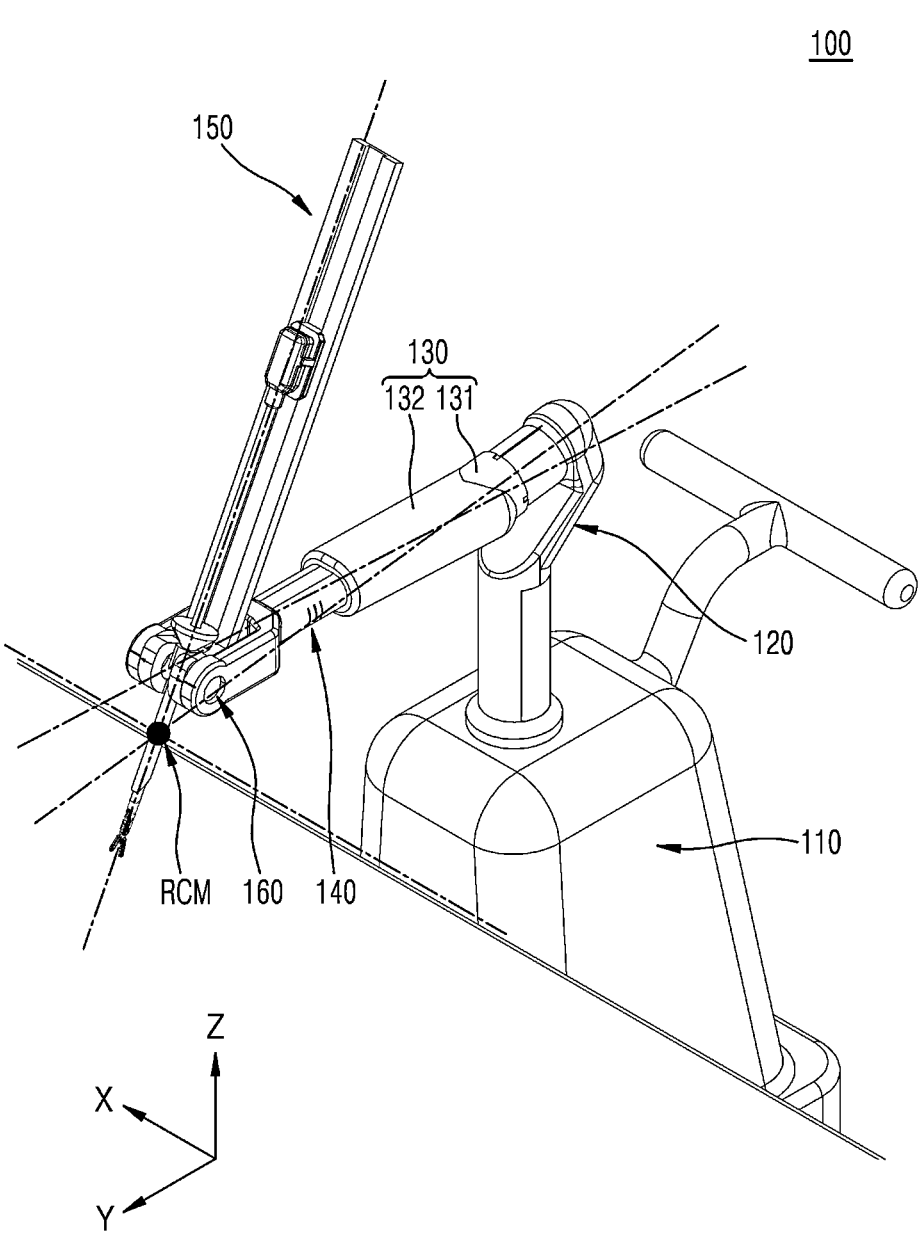
FIGS. 10 to 12 are perspective views illustrating a Y-axis RCM motion (a yaw motion) of the surgical robot arm of FIG. 4.
Figure 11:
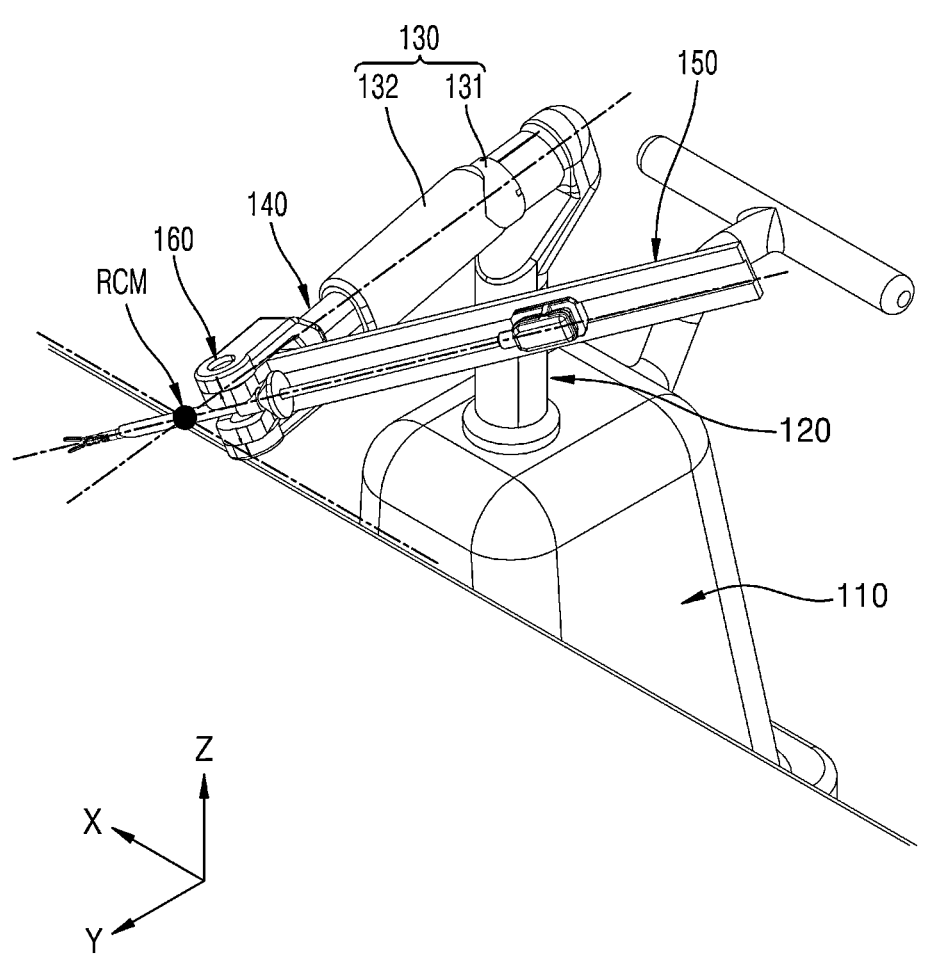
Figure 12:
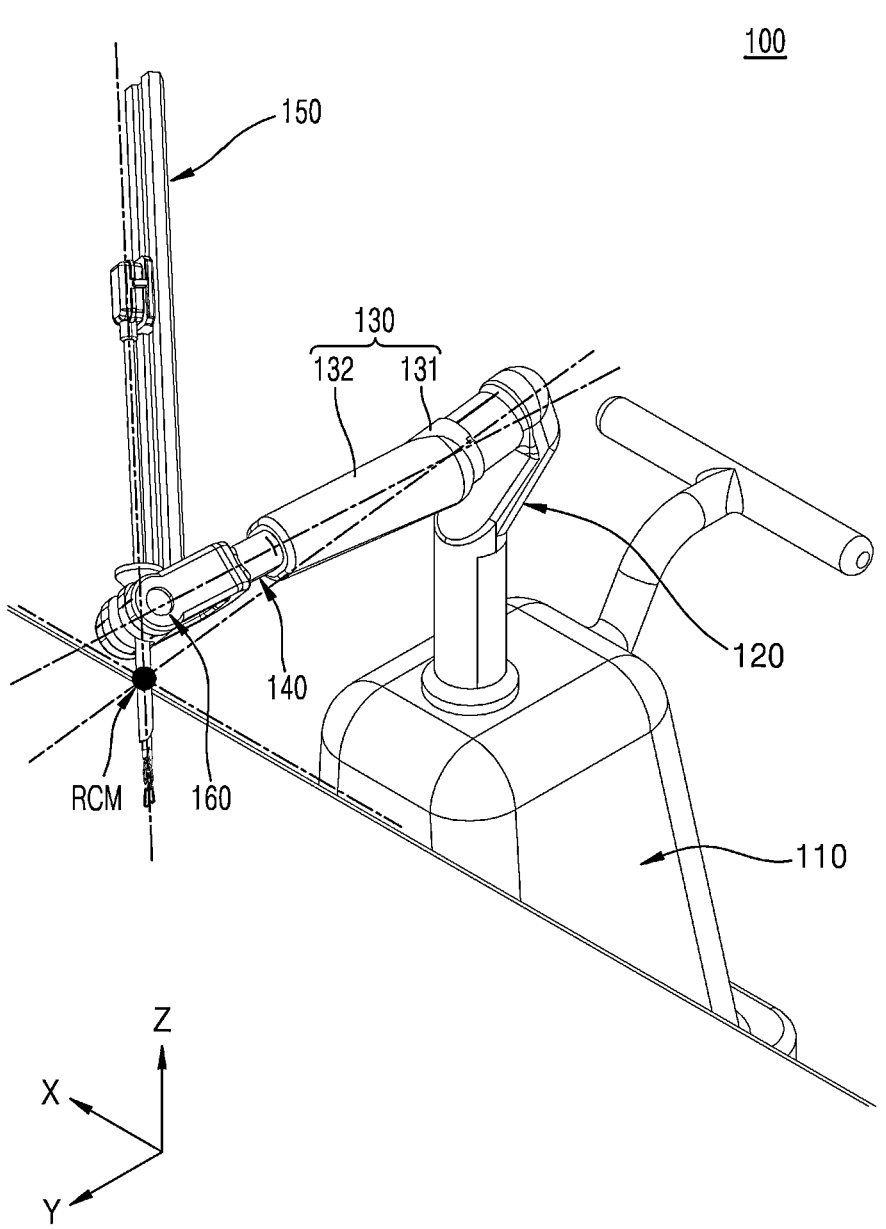
Figures 13A, 13B:
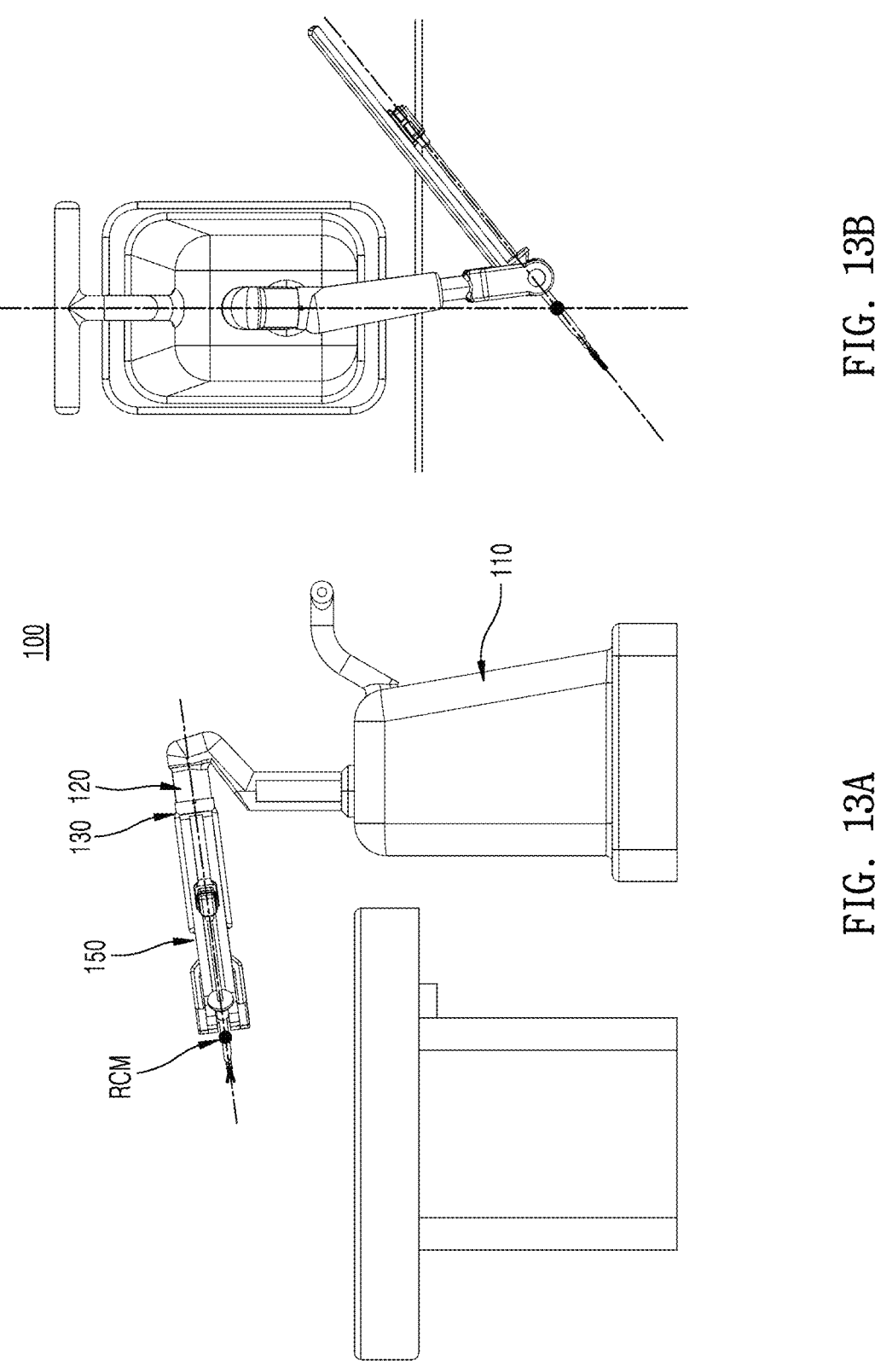
FIGS. 13A and 13B are a side view and a plan view, respectively, illustrating a state in which the surgical robot arm of FIG. 4 lies on its side.

FIG. 4 is a perspective view illustrating an overall structure of a surgical robot arm 100 according to a first embodiment of the present disclosure. FIG. 5 is a side view of the surgical robot arm of FIG. 4. FIGS. 6 to 8 are side views and plan views illustrating an X-axis remote-center-of-motion (RCM) motion (a pitch motion) of the surgical robot arm of FIG. 4. FIG. 9 is a diagram describing the X-axis RCM motion (the pitch motion) of FIGS. 6 to 8 in more detail. FIGS. 10 to 12 are perspective views illustrating a Y-axis RCM motion (a yaw motion) of the surgical robot arm of FIG. 4. FIG. 13 is a side view and a plan view illustrating a state in which the surgical robot arm of FIG. 4 lies on its side.

Referring to FIGS. 4 to 13, the surgical robot arm 100 according to the first embodiment of the present disclosure includes a base 110, a base link 120, a first link 130, a second link 140, and an instrument mounting link 150. A trocar 30 and a surgical instrument 20 are coupled to the instrument mounting link 150 of the surgical robot arm 100. This will be described in more detail as follows.

A surgical robot includes one or more surgical robot arms for surgical manipulation, and a surgical instrument is mounted on a front end of the surgical robot arm.

In general, the robot arm refers to a device that has functions similar to a human arm and/or wrist and may attach a certain tool to a wrist area. In the present specification, the robot arm may be defined as a concept encompassing all of components, such as an upper arm, a lower arm, a wrist, and an elbow, and multi-joint surgical devices to be coupled to the wrist area. As such, the surgical robot arm may be implemented to have multiple degrees of freedom.

As such, when the surgical instrument is mounted on the tip of the surgical robot arm and surgery is performed, the surgical instrument is also moved as the surgical robot arm is moved. This may cause unnecessary damage to human skin in the process of performing surgery by drilling a portion of the patient's skin and inserting the surgical instrument into the drilled portion. In addition, when the surgical site is wide, there is a concern that the advantages of robotic surgery may be halved since the skin has to be incised to correspond to the path along which the surgical instrument is moved or the skin has to be drilled for each surgical site.

Therefore, a virtual rotation center point is set at a certain position of the surgical instrument mounted on the tip of the surgical robot arm (mainly a pivot point at which the trocar penetrates the patient's skin), and the robot arm is controlled so that the instrument rotates around the point. Such a virtual center point is referred to as a "remote center" or an "RCM."

A mechanical RCM structure has been applied to a conventional surgical robot arm. Accordingly, a robot arm is configured with multiple links so that nodes of each link are connected to each other to form a parallelogram, and control is performed so that each link maintains the parallelogram even during the operation of the robot arm. In theory, this "parallelogram RCM structure" is a structure that may perform control so that the virtual line forming one side of the parallelogram rotates around the RCM point. However, the conventional "parallelogram RCM structure" inevitably occupies a lot of space as the size of the structure for implementing the parallelogram RCM structure is inevitably large. In addition, due to this, there were problems of collisions between multiple robot arms.

To solve such problems, the surgical robot arm 100 according to the first embodiment of the present disclosure implements an RCM control through an electronic control rather than a mechanical control through the "parallelogram RCM structure" so that the overall size of the instrument is reduced and the configuration of the instrument is simplified. Therefore, there is provided a surgical robot arm that increases space efficiency and prevents collisions between robot arms.

Hereinafter, this will be described in more detail.

In the present embodiment, for convenience, the longitudinal direction of the bed on which the patient lies is defined as the X-axis, the width direction of the bed is defined as the Y-axis, and the direction perpendicular to the ground is defined as the Z-axis.

Referring again to FIGS. 4 to 13, the base 110 serves as a base part of the entire surgical robot arm 100. Here, a moving means (not shown) such as wheels may be formed on the lower surface of the base 110 so that the base 110 may serve as a kind of cart. In addition, a position fixing means (not shown) may be further formed on the base 110 so that the position of the base 110 may be fixed during surgery. However, the concept of the present disclosure is not limited thereto, and the base 110 may be formed in a shape that is detachably attachable to a bed, or may be formed in a shape that is detachably attachable a wall.

The base link 120 includes an extension portion 121 and a roll rotation base portion 122. The extension portion 121 may extend in one direction from the base 110. In the drawings, it is illustrated that the extension portion 121 of the base link 120 extends from the base 110 in the Z-axis direction. In other words, one end of the base link 120 is connected to the base 110. In the present embodiment, a case where the base link 120 is fixedly coupled to the base 110 is assumed.

On the other hand, the roll rotation base portion 122 is formed at the other end of the base link 120. The roll rotation base portion 122 may be formed to be inclined to a certain extent so as to have a certain angle with the extension portion 121.

Here, the roll rotation base portion 122 of the base link 120 may be formed in a cylindrical shape with respect to a first axis A1 formed in a first direction. The first link 130 connected to the roll rotation base portion 122 (and the second link 140, the instrument mounting link 150, and the surgical instrument 20 sequentially connected to the first link 130) may be formed to roll around the first axis A1.

Here, the first axis A1 may be formed in an oblique direction that is not parallel to the X-axis/Y-axis/Z-axis. An RCM, which will be described later, may be located on an extension line of the first axis A1.

The first link 130 may be coupled to the base link 120, and more specifically, to the roll rotation base portion 122 of the base link 120 and may be formed such that the entire first link 130 is rotatable around the first axis A1 of the roll rotation base portion 122. Alternatively, it may be expressed that the first link 130 rolls around the base link 120. In order to implement the rotational motion of the first link 130 with respect to the base link 120, a motor may be provided on either the base link 120 or the first link 130. The rotational motion of the first link 130 with respect to the base link 120 may be actively controlled by the motor.

On the other hand, the first link 130 may include a first region 131 coupled to the base link 120 and a second region 132 coupled to the second link 140. Here, a central axis of the first region 131 and a central axis of the second region 132 may be defined to form a certain angle with each other.

In this case, the central axis of the first region 131 may coincide with the first axis A1, and therefore, the RCM may be located on an extension line of the central axis of the first region 131.

In the drawings, it is illustrated that the first link 130 includes two parts, that is, the first region 131 and the second region 132, and the first region 131 and the second region 132 each having a straight-line shape form a certain angle with each other. However, the concept of the present disclosure is not limited thereto. The first link 130 may be divided into two or more regions, each of which may be gently curved. In addition, in the present embodiment, it is illustrated that the first region 131 is integrally formed with the second region 132, but the first region 131 and the second region 132 may also be formed as separate members and coupled together.

Here, when the first link 130 is rotated around the first axis A1, the second link 140, the instrument mounting link 150, and the surgical instrument 20 connected to the first link 130 are rotated together. Due to this, the coordinate systems of the second link 140 and the instrument mounting link 150 are not fixed, but relatively continuously change according to the rotation of the first link 130. That is, FIG. 1, etc. illustrates that the second link 140 is parallel to the Y-axis and the instrument mounting link 150 is parallel to the Z-axis. However, when the first link 130 is rotated, the coordinate systems of the second link 140 and the instrument mounting link 150 are also rotated together. However, in the present specification, for convenience of explanation, the following description is given based on the state in which the second link 140 is located parallel to the Y-axis and the instrument mounting link 150 is located parallel to the Z-axis, as illustrated in FIG. 4, unless otherwise stated.

Similarly, when the second link 140 is moved linearly, the instrument mounting link 150 and the surgical instrument 20 is moved linearly together. Due to this, the coordinate systems of the instrument mounting link 150 and the surgical instrument 20 are not fixed and relatively continuously change according to the rotation of the first link 140.

Similarly, when the instrument mounting link 150 is rotated, the surgical instrument 20 is rotated together. Due to this, the coordinate system of the surgical instrument 20 is not fixed and relatively continuously changes according to the rotation of the instrument mounting link 150.

The second link 140 may be coupled to the first link 130 and may perform a linear reciprocating motion in both directions along the second axis A2 with respect to the first link 130. Here, in the drawings, it is illustrated that the second link 140 performs a linear reciprocating motion in the X-axis direction with respect to the first link 130, but the concept of the present disclosure is not limited thereto, and a linear reciprocating axis of the second link 140 may be variously formed according to the shape and configuration of the links.

In order to implement such a linear motion, a linear actuator (not shown) may be provided on either the first link 130 or the second link 140. The linear motion of the second link 140 with respect to the first link 130 may be actively controlled by the linear actuator (not shown).

Here, the first axis A1 and the second axis A2 may generally be different axes. Alternatively, even when the first link 130 or the second link 140 is bent to a certain extent and the first axis A1 and the second axis A2 are formed to be parallel to each other, the second axis A2 may be formed so as not to pass through the RCM.

The instrument mounting link 150 is axially coupled to the second link 140 by a link rotation shaft 160 coupled in the direction of the third axis A3, and thus, the instrument mounting link 150 is formed to be rotatable around the third axis A3 with respect to the second link 140. This is, the instrument mounting link 150 may be rotatable around the X-axis when viewed from the drawing.

In order to implement such a rotational motion, a motor may be provided on either the second link 140 or the instrument mounting link 150. The rotational motion of the instrument mounting link 150 with respect to the second link 140 may be actively controlled by the motor.

Here, the second link 140 is coupled to the instrument mounting link 150 only by the link rotation shaft 160, and the link rotation shaft 160 may be actively controlled by a motor (not shown).

On the other hand, an instrument mounting portion 151 and a guide rail 152 may be formed in the instrument mounting link 150. While the surgical instrument 20 is mounted on the instrument mounting portion 151, the instrument mounting portion 151 may perform a linear motion along the guide rail 152 formed in a direction of a fourth axis A4. In order to implement such a linear motion, a linear actuator (not shown) may be provided in the instrument mounting portion 151.

Here, the fourth axis A4 may be a direction in which the guide rail 152 is formed, and simultaneously, may be an extension direction of a shaft 22 of the surgical instrument 20 coupled to the instrument mounting link 150.

The surgical instrument 20 is mounted on the instrument mounting portion 151 of the instrument mounting link 150 of the surgical robot arm 100.

Here, although not illustrated in the drawings, an interface part (not shown) coupled to the surgical instrument 20 and configured to control the motion of the surgical instrument 20 may be further formed in the instrument mounting portion 151. The interface part (not shown) may include a component configured to couple with a driving part 23 of the surgical instrument 20, a motor configured to transmit a driving force from the surgical robot arm 100 to the surgical instrument 20, and the like. The interface part (not shown) may allow an end tool 21 of the surgical instrument 20 to perform a pitch, yaw, or actuation motion. Furthermore, the interface part (not shown) may allow the shaft 22 and the end tool 21 of the surgical instrument 20 to perform a roll motion around the fourth axis A4.

On the other hand, the trocar 30, which serves as an insertion passage for inserting the surgical instrument 20 into the patient's body, may be coupled to the instrument mounting link 150. While the trocar 30 is inserted into the body, the surgical instrument 20 may be inserted into the patient's body through the trocar 30. An RCM may be formed at a certain position on the trocar 30. As described above, the first axis A1, which is the roll rotation axis of the first link 130, may be formed to pass through the RCM.

In addition, the surgical instrument 20 may further include the driving part 23. A component configured to couple with the interface part (not shown) and a driving wheel operated in engagement with the motor may be formed in the driving part 23. As such, a coupling means and a driving transmission means may be respectively formed in the interface part (not shown) and the driving part 23 to correspond to each other. Accordingly, the surgical instrument 20 is operated by receiving a driving force from the surgical robot arm 100 in a state of being mounted on the instrument mounting link 150.

In the present disclosure, the RCM structure of the surgical robot arm 100 is a structure in which the surgical instrument 20 is mounted on one side of the surgical robot arm 100, and the surgical instrument 20 is operated and controlled to rotate around a certain point RCM on the trocar 30 into which the surgical instrument 20 is inserted. Here, the RCM structure according to the present embodiment is implemented through the electronic control for each link rather than the existing mechanical parallelogram link structure.

Hereinafter, for convenience, the control in the X-axis direction and the control in the Y-axis direction in the drawing are described separately, but it may be stated that the overall control is performed by combining the control in the X-axis direction with the control in the Y-axis direction. In addition, the coordinate system of each component may change relatively due to the rotation and linear motion of each link. However, for convenience, the following description is given based on the X-axis direction and the Y-axis direction of the bed by using the bed as the reference point. This will be described in more detail as follows.

First, referring to FIGS. 6 to 8, the control in the X-axis direction, that is, the control of the pitch motion may be implemented by a combination of:

1) the control of the linear motion of the second link 140 with respect to the first link 130, 2) the control of the rotational motion of the instrument mounting link 150 with respect to the second link 140, and 3) the control of the linear motion of the instrument mounting portion 151 with respect to the guide rail 152 of the instrument mounting link 150.

In detail, in order to control the rotational motion of the surgical instrument 20 around the X-axis, the second link 140 first performs a linear motion along the second axis A2 with respect to the first link 130. At the same time, an RCM motion is performed by controlling the instrument mounting link 150 to perform a rotational motion around the third axis A3 with respect to the second link 140. Accordingly, even when the links are moved, the RCM maintains a position thereof.

In addition, even when the surgical instrument 20 performs a rotational motion around the X-axis, an insertion depth LE of the instrument should not change. Accordingly, the insertion depth LE of the instrument may be maintained constant by linearly moving the instrument mounting portion 151 (and the surgical instrument 20 coupled thereto) along the guide rail 152 formed along the fourth axis A4.

To explain this from another viewpoint, a length L2 from an inlet portion 31 of the trocar 30 to the RCM when the second link 140 performs a linear motion with respect to the first link 130 and is withdrawn from the first link 130 (see FIG. 7) or is inserted into the first link 130 (see FIG. 8) becomes longer than a length L1 from the inlet portion 31 of the trocar 30 to the RCM when the surgical instrument 20 is perpendicular to the Z-axis (see FIG. 6). In contrast, at this time, a distance from an outlet portion 32 of the trocar 30 to the RCM becomes shorter. Therefore, when the surgical instrument 20 is moved together with the trocar 30, the trocar 30 and the surgical instrument 20 therein are moved relatively in an exiting direction from the inside of the human body to the outside.

Therefore, in order to ensure that at least the insertion depth (LE) of the surgical instrument 20 into the patient's body is maintained constant, the distance LE from the end of the end tool 21 to the RCM is maintained constant by linearly moving the instrument mounting portion 151 (and the surgical instrument 20 coupled thereto) along the guide rail 152 in the direction of insertion into the human body.

As such, even when the links are moved, the RCM in the X-axis direction maintains a position thereof by performing a combination of 1) the control of the linear motion of the second link 140 with respect to the first link 130, 2) the control of the rotational motion of the instrument mounting link 150 with respect to the second link 140, and 3) the control of the linear motion of the instrument mounting portion 151 with respect to the guide rail 152 of the instrument mounting link 150.

Of course, strictly speaking, the RCM of the surgical robot arm 100 itself may be implemented only by 1) the control of the linear motion of the second link 140 with respect to the first link 130 and 2) the control of the rotational motion of the instrument mounting link 150 with respect to the second link 140. However, during actual surgery, the RCM of the surgical robot arm 100 itself has to be maintained and the insertion depth of the surgical instrument 20 into the human body has also to be maintained constant. Therefore, 3) the control of the linear motion of the instrument mounting portion 151 with respect to the guide rail 152 is also performed together.

Next, referring to FIGS. 10 to 12, the RCM control in the Y-axis direction, that is, the control of the yaw motion may be implemented by a combination of:

1) the control of the roll rotational motion of the first link 130 around the first link A1, 2) the control of the rotational motion of the instrument mounting link 150 with respect to the second link 140, 3) the control of the linear motion of the second link 140 with respect to the first link 130, and 4) the control of the roll motion of the surgical instrument 20.

In detail, in order to control the rotational motion of the surgical instrument 20 around the Y axis, the first link 130 first performs a roll rotational motion around the first axis A1. The first link 130, and the second link 140, the instrument mounting link 150, and the surgical instrument 20, which are sequentially connected to the first link 130, may perform a roll motion around the first axis A1.

In this case, since the first axis A1, which is the rotation axis of the first link 130, and the Y-axis do not coincide with each other and are formed to be oblique, unintended motions are mixed when only the first link 130 is rotated. That is, as illustrated in the drawings, when the first link 130 is rotated, the second link 140, the instrument mounting link 150, and the surgical instrument 20 perform a kind of rolling.

In order to compensate for this, with the rotation of the first link 130, the instrument mounting link 150 is controlled to perform a rotational motion around the link rotation shaft 160 with respect to the second link 140, and simultaneously, the second link 140 is controlled to perform a linear motion with respect to the first link 130. In this manner, the RCM motion is performed. That is, even when the links are moved, the RCM maintains a position thereof.

In addition, the shaft 22 and the end tool 21 of the surgical instrument 20 are controlled to perform a roll motion around the fourth axis A4, so that the end tool 21 may also be compensated to maintain a posture thereof, regardless of the rotation of the first link 130.

As such, even when the links are moved, the RCM in the Y-axis direction maintains a position thereof by performing a combination of 1) the control of the roll rotational motion of the first link 130 around the first link A1, 2) the control of the rotational motion of the instrument mounting link 150 with respect to the second link 140, 3) the control of the linear motion of the second link 140 with respect to the first link 130, and 4) the control of the roll motion of the surgical instrument 20.

In conclusion, from the viewpoint of the degree of freedom of the surgical robot arm 100 itself (excluding the surgical instrument 20), the surgical robot arm 100 according to the first embodiment of the present disclosure may operate with four degrees of freedom of: 1) the roll rotational motion of the first link 130 around the first axis A1, 2) the linear motion of the second link 140 with respect to the first link 130, 3) the rotational motion of the instrument mounting link 150 with respect to the second link 140, and 4) the linear motion of the instrument mounting portion 151 with respect to the guide rail 152 of the instrument mounting link 150.

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm 100 and reducing the driving force required for operation may be obtained.

Mode of Disclosure

<First-1 Embodiment of Surgical Robot Arm>

Hereinafter, a surgical robot arm 200 according to a first-1 embodiment of the present disclosure will be described. Here, the surgical robot arm 200 according to the first-1 embodiment of the present disclosure characteristically differs from the surgical robot arm (see 100 of FIG. 4) according to the first embodiment of the present disclosure in terms of a configuration of an instrument mounting link 250 of the robot arm 200. In other words, the robot arm 200 according to the first-1 embodiment of the present disclosure is an embodiment in which a trocar holder portion 270 is added, compared to the embodiment of FIG. 4. Compared to the first embodiment, the change in configuration will be described in detail later.

Figure 14:
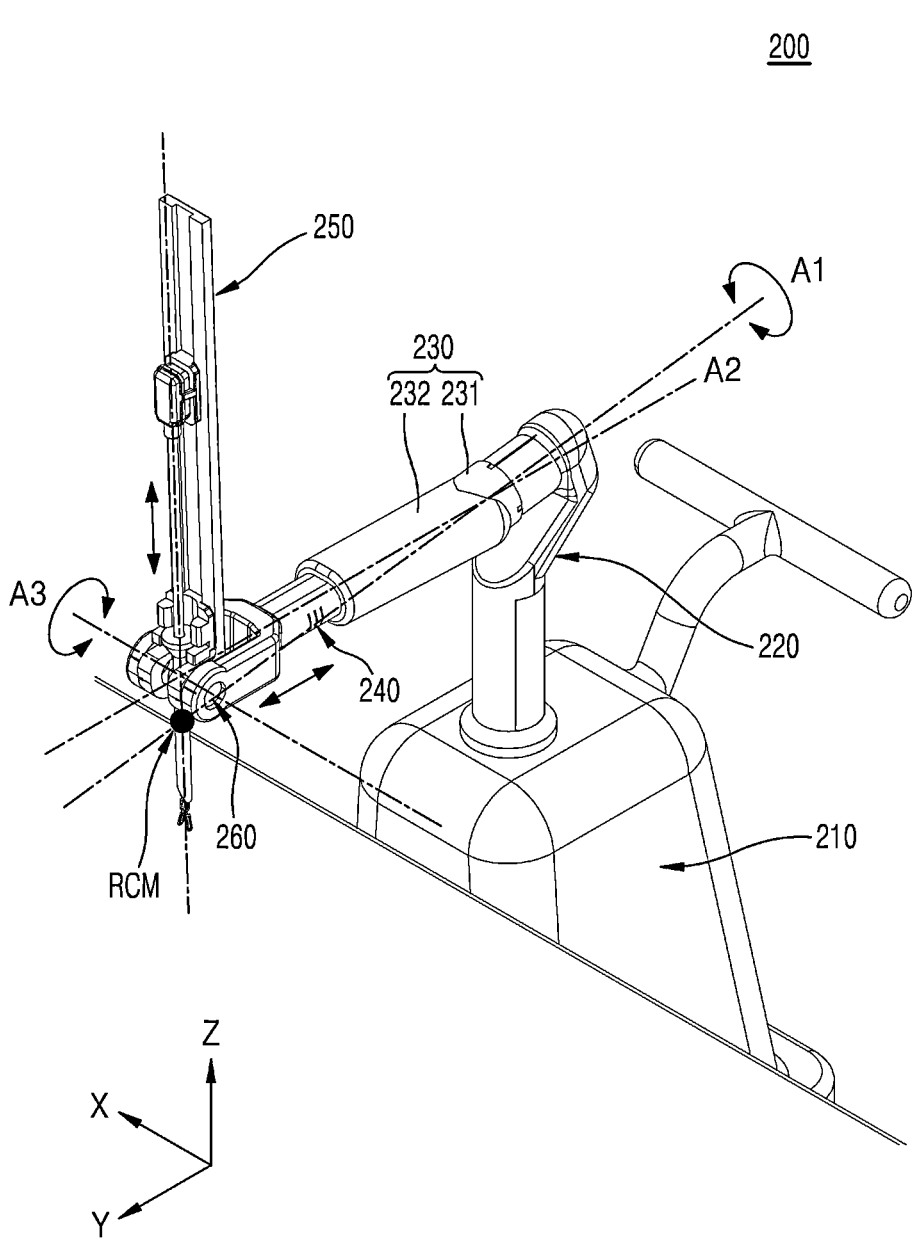
FIG. 14 is a perspective view illustrating an overall structure of a surgical robot arm (200) according to a first-1 embodiment of the present disclosure.
Figure 15:
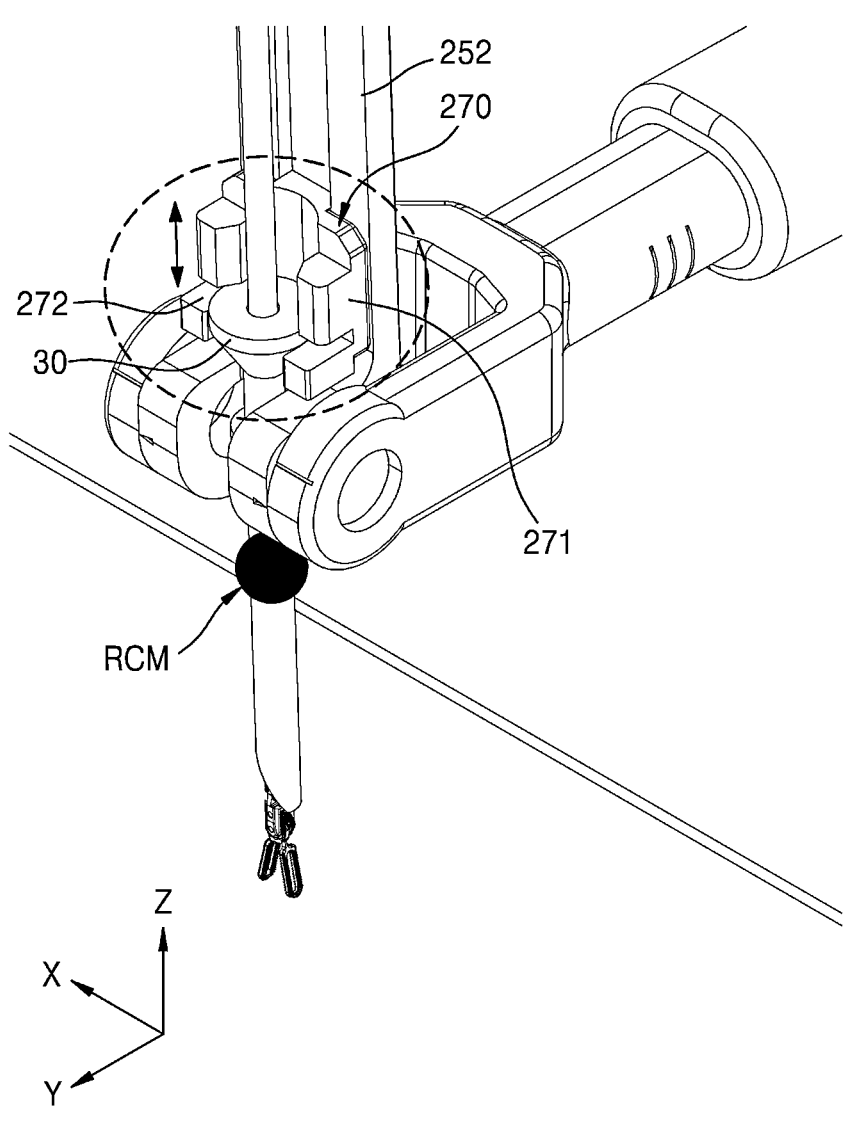
FIG. 15 is an enlarged view of part A of FIG. 14.
Figure 16:
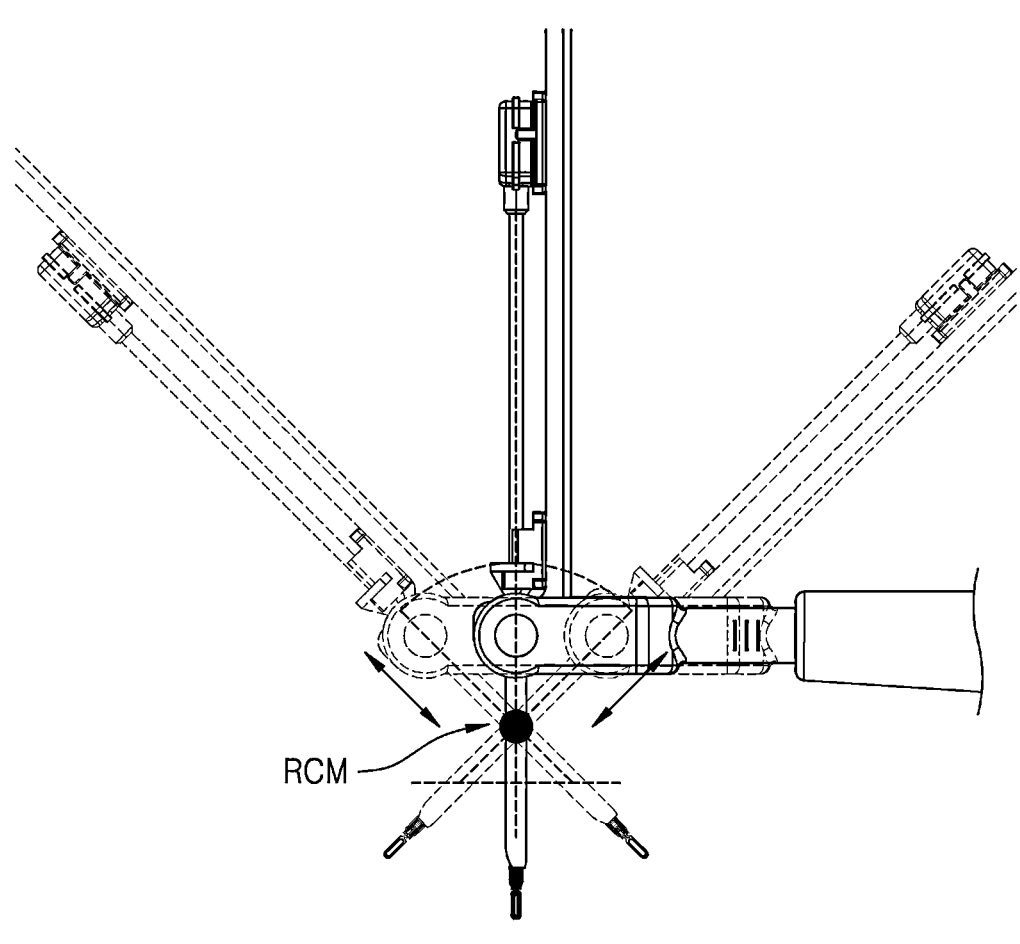
FIG. 16 is a diagram describing an X-axis RCM motion (a pitch motion) of the surgical robot arm of FIG. 14 in more detail.

FIG. 14 is a perspective view illustrating the overall structure of the surgical robot arm 200 according to the first-1 embodiment of the present disclosure. FIG. 15 is an enlarged view of part A of FIG. 14. FIG. 16 is a diagram describing an X-axis RCM motion (a pitch motion) of the surgical robot arm of FIG. 14 in more detail.

Referring to FIGS. 14 to 16, the surgical robot arm 200 according to the first-1 embodiment of the present disclosure includes a base 210, a base link 220, a first link 230, a second link 240, and an instrument mounting link 250. In addition, the surgical robot arm 200 according to the first-1 embodiment of the present disclosure further includes the trocar holder portion 270. This will be described in more detail as follows.

As described above, in order to control the rotational motion of the surgical instrument 20 around an X-axis, the second link 240 first performs a linear motion along a second axis A2 with respect to the first link 230. At the same time, an RCM motion is performed by controlling the instrument mounting link 250 to perform a rotational motion around a third axis A3 with respect to the second link 240. In this case, as the second link 240 performs a linear motion with respect to the first link 230, the distance (see Lt of FIG. 6) from the RCM to the end of the trocar 30 inevitably changes. At this time, when Lt becomes too short, the trocar 30 may come out of the patient's abdomen, which causes danger to the patient.

In order to solve such a problem, the surgical robot arm 200 according to the first-1 embodiment of the present disclosure further includes the trocar holder portion 270. The insertion depth of the trocar 30 is maintained constant by linearly moving the trocar holder portion 270 along a fourth axis A4 in response to the motions of the instrument mounting link 250 and the second link 240.

In detail, the trocar holder portion 270 may include a main body portion 271 and a trocar coupling portion 272. The main body portion 271 may be formed to be coupled to the guide rail 252 of the instrument mounting link 250 and may be formed to perform a linear motion along the guide rail 252 in a direction of the fourth axis A4. The trocar coupling portion 272 may protrude from one side of the main body portion 271 and may be formed to enable the trocar 30 to be coupled to one side.

The control in the X-axis direction in the present embodiment may be implemented in a combination of:

1) the control of the linear motion of the second link 240 with respect to the first link 230, 2) the control of the rotational motion of the instrument mounting link 250 with respect to the second link 240, 3) the control of the linear motion of the instrument mounting portion 251 with respect to the guide rail 252 of the instrument mounting link 250, and 4) the control of the linear motion of the trocar holder portion 270 with respect to the guide rail 252 of the instrument mounting link 250.

In detail, in order to control the rotational motion of the surgical instrument 20 around the X-axis, the second link 240 first performs a linear motion along the second axis A2 with respect to the first link 230. At the same time, an RCM motion is performed by controlling the instrument mounting link 250 to perform a rotational motion around the third axis A3 with respect to the second link 240. That is, even when the links are moved, the RCM maintains a position thereof.

In addition, even when the surgical instrument 20 performs a rotational motion around the X-axis, the insertion depth (see LE of FIG. 6) of the instrument should not change. Accordingly, the insertion depth (see LE of FIG. 6) of the instrument may be maintained constant by linearly moving the instrument mounting portion 251 (and the surgical instrument 20 coupled thereto) along the guide rail 252 formed along the fourth axis A4.

That is, when the surgical instrument 20 is rotated from a state perpendicular to a Z-axis in a direction inclined by a certain extent, the surgical instrument 20 is moved relatively in an exiting direction from the inside of the human body to the outside. In this case, in order to ensure that at least the insertion depth (see LE of FIG. 6) of the surgical instrument 20 into the patient's body is maintained constant, the distance from the end of the end tool 21 to the RCM is maintained constant by linearly moving the instrument mounting portion 251 (and the surgical instrument 20 coupled thereto) along the guide rail 252 in the direction of insertion into the human body.

On the other hand, in this case, as the second link 240 performs a linear motion with respect to the first link 230, the distance (Lt) from the RCM to the end of the trocar 30 inevitably changes. In particular, when Lt becomes too short as in the left and right situations of FIG. 16, the trocar 30 may come out of the patient's abdomen, which causes danger to the patient.

To explain this from another viewpoint, the length (see L2 of FIG. 9) from the inlet portion (see 31 of FIG. 9) of the trocar 30 to the RCM when the second link 240 performs a linear motion with respect to the first link 230 and is withdrawn from the first link 230 or is inserted into the first link 230 becomes longer than the length (see L1 of FIG. 9) from the inlet portion (see 31 of FIG. 9) of the trocar 30 to the RCM when the surgical instrument 20 is perpendicular to the Z-axis. In contrast, at this time, the distance from the outlet portion (see 32 of FIG. 9) of the trocar 30 to the RCM becomes shorter.

Accordingly, the trocar 30 is moved relatively in an exiting direction from the inside of the human body to the outside. In order to compensate for this, the insertion depth of the trocar 30 is maintained constant by linearly moving the trocar holder portion 270 along the guide rail 252 in a direction of insertion into the human body.

As such, even when the links are moved, the RCM in the X-axis direction maintains a position thereof by performing a combination of 1) the control of the linear motion of the second link 240 with respect to the first link 230, 2) the control of the rotational motion of the instrument mounting link 250 with respect to the second link 240, 3) the control of the linear motion of the instrument mounting portion 251 with respect to the guide rail 252 of the instrument mounting link 250, and 4) the control of the linear motion of the trocar holder portion 270 with respect to the guide rail 252 of the instrument mounting link 250.

Of course, strictly speaking, the RCM of the surgical robot arm 200 itself may be implemented only by 1) the control of the linear motion of the second link 240 with respect to the first link 230 and 2) the control of the rotational motion of the instrument mounting link 250 with respect to the second link 240. However, during actual surgery, the RCM of the surgical robot arm 200 itself has to be maintained and the insertion depths of the surgical instrument 20 and the trocar 30 into the human body have also to be maintained constant. Therefore, 3) the control of the linear motion of the instrument mounting portion 251 with respect to the guide rail 252 and 4) the control of the linear motion of the trocar holder portion 270 with respect to the guide rail 252 of the instrument mounting link 250 are also performed together.

In conclusion, from the viewpoint of the degree of freedom of the surgical robot arm 200 itself (excluding the surgical instrument 20), the surgical robot arm 200 according to the first-1 embodiment of the present disclosure may operate with five degrees of freedom of: 1) the roll rotational motion of the first link 230 around the first axis A1, 2) the linear motion of the second link 240 with respect to the first link 230, 3) the rotational motion of the instrument mounting link 250 with respect to the second link 240, 4) the linear motion of the instrument mounting portion 151 with respect to the guide rail 252 of the instrument mounting link 250; and 5) the linear motion of the trocar holder portion 270 with respect to the instrument mounting link 250.

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm 100 and reducing the driving force required for operation may be obtained. Furthermore, the trocar holder portion 270 is provided to control the insertion depth of the trocar 30 to a constant level, and thus, the risk of the trocar 30 coming out of the abdomen during surgery may be eliminated, thereby further improving safety.

<Second Embodiment of Surgical Robot Arm>

Hereinafter, a surgical robot arm 300 according to a second embodiment of the present disclosure will be described. Here, the surgical robot arm 300 according to the second embodiment of the present disclosure characteristically differs from the surgical robot arm (see 100 of FIG. 4) according to the first embodiment of the present disclosure in terms of a configuration of a first link 330 of the robot arm 300. In other words, compared to the embodiment of FIG. 4, the robot arm 300 according to the second embodiment of the present disclosure is an embodiment in which the first region 331 and the second region 332 of the first link 330 are formed to be rotatable around a pitch rotation shaft 335 with respect to each other. Compared to the first embodiment, the change in configuration will be described in detail later.

Figure 17:
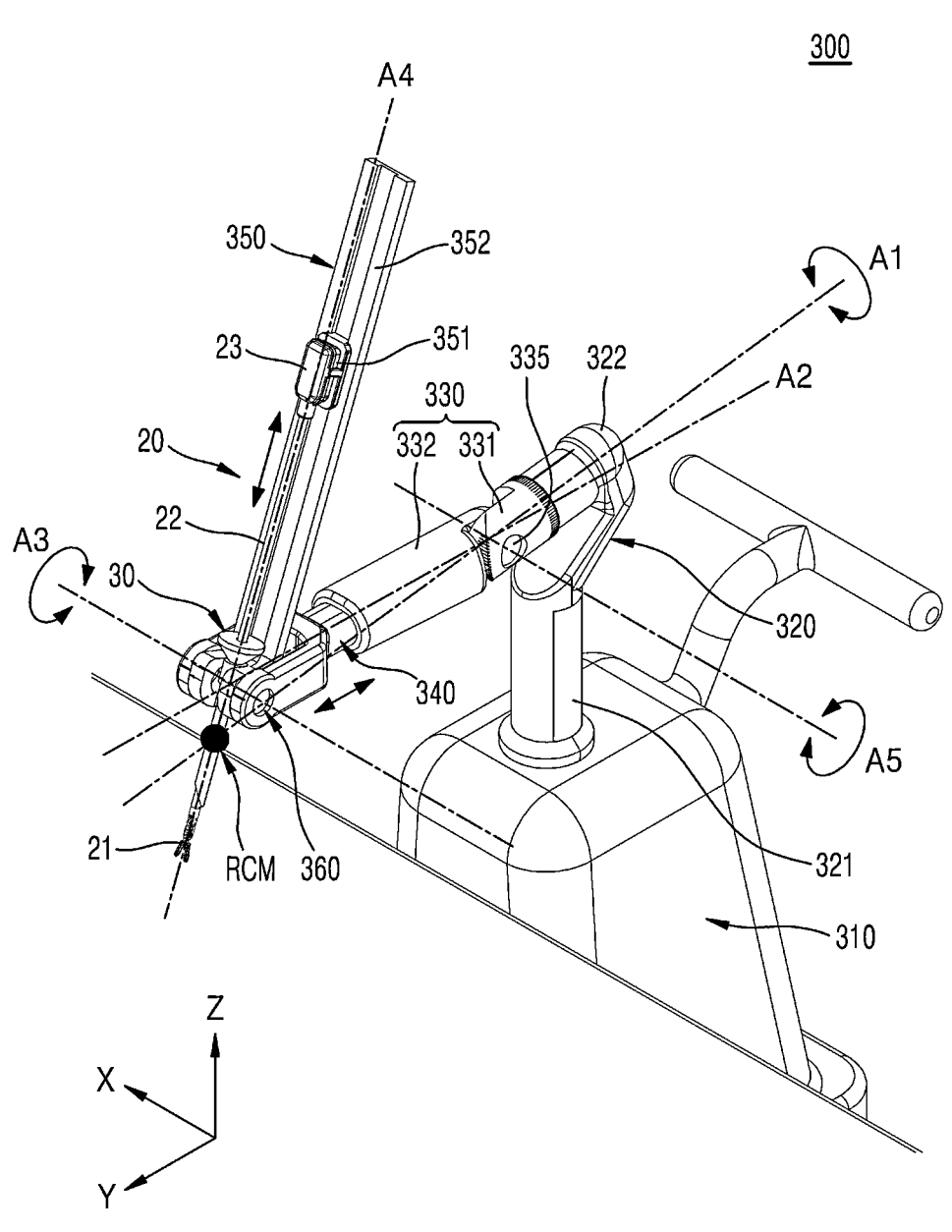
FIG. 17 is a perspective view illustrating an overall structure of a surgical robot arm (300) according to a second embodiment of the present disclosure.
Figure 18:
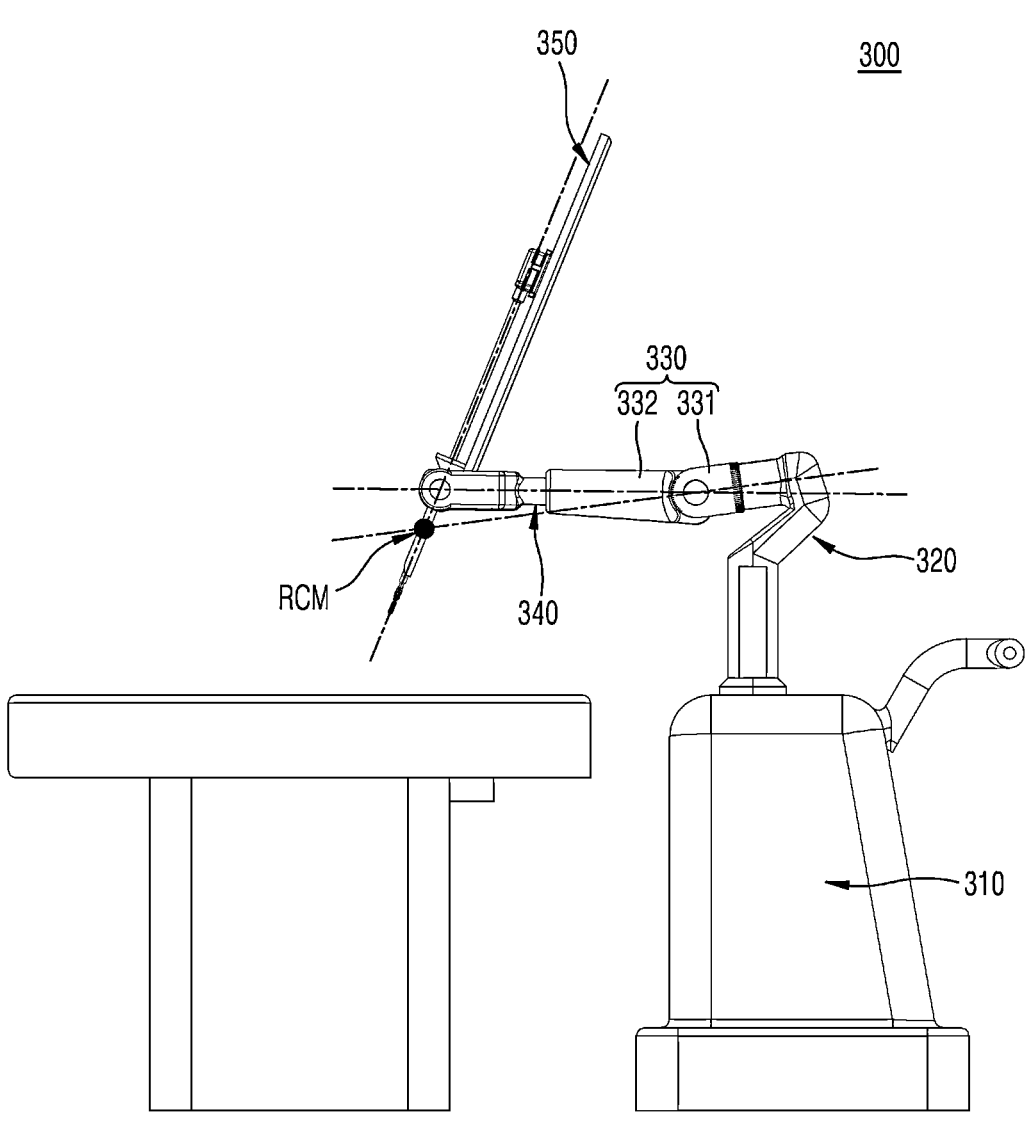
FIG. 18 is a side view of the surgical robot arm of FIG. 4.
Figure 19B:
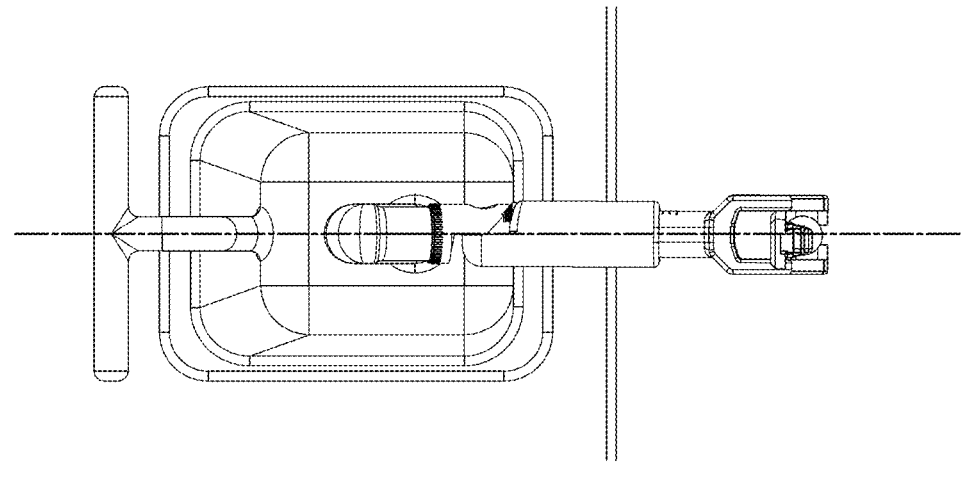
Figure 19A:
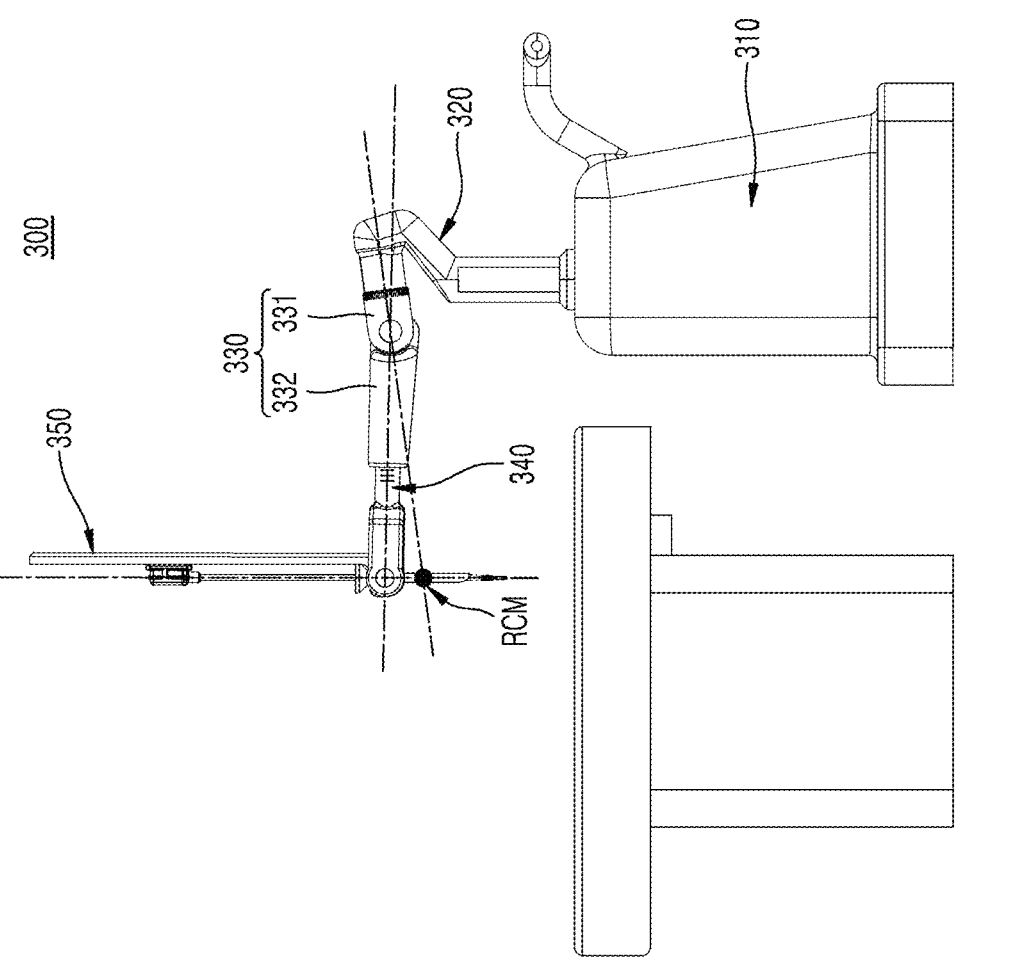
Figures 20A, 20B:
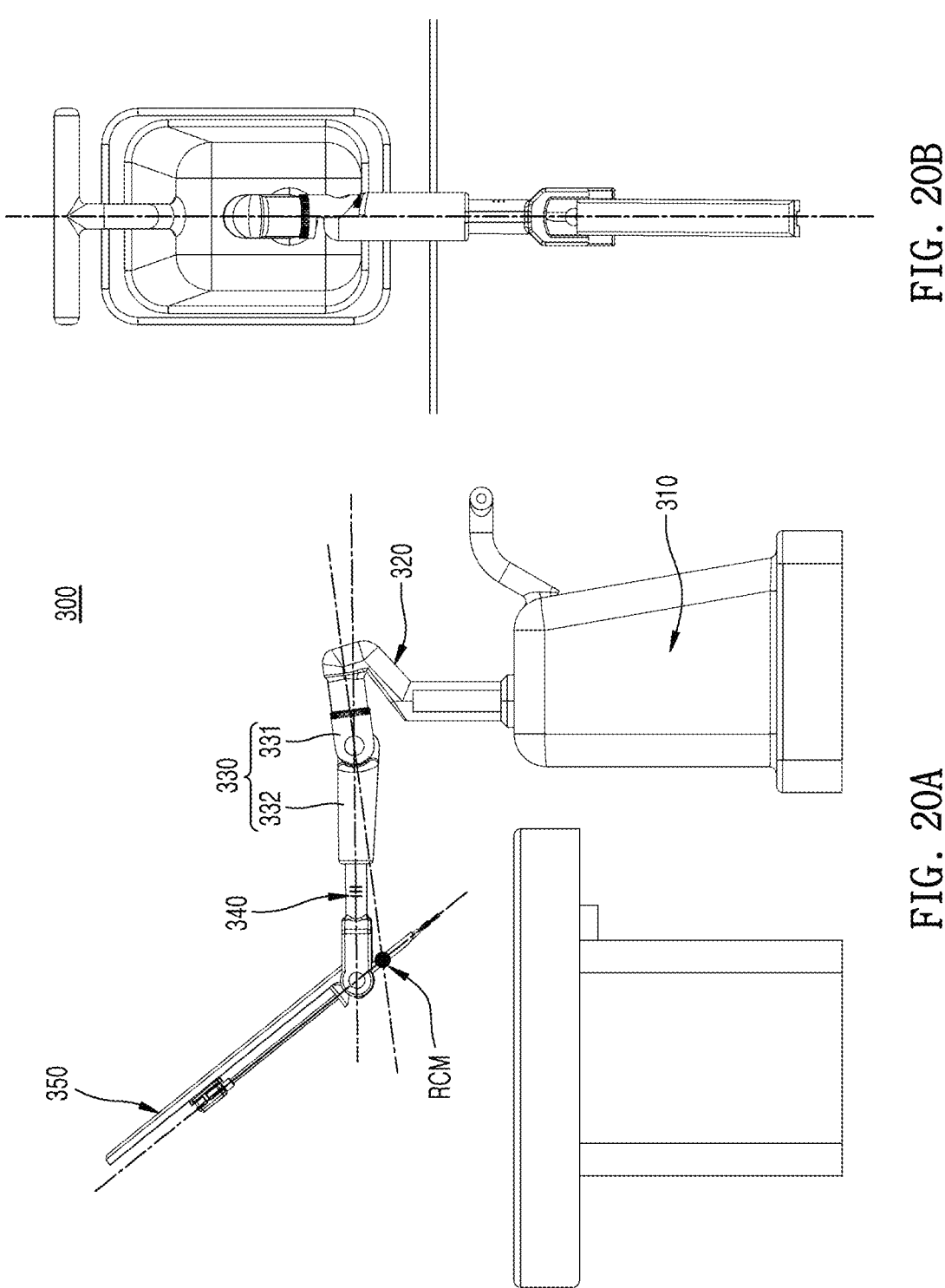
Figures 21A, 21B:
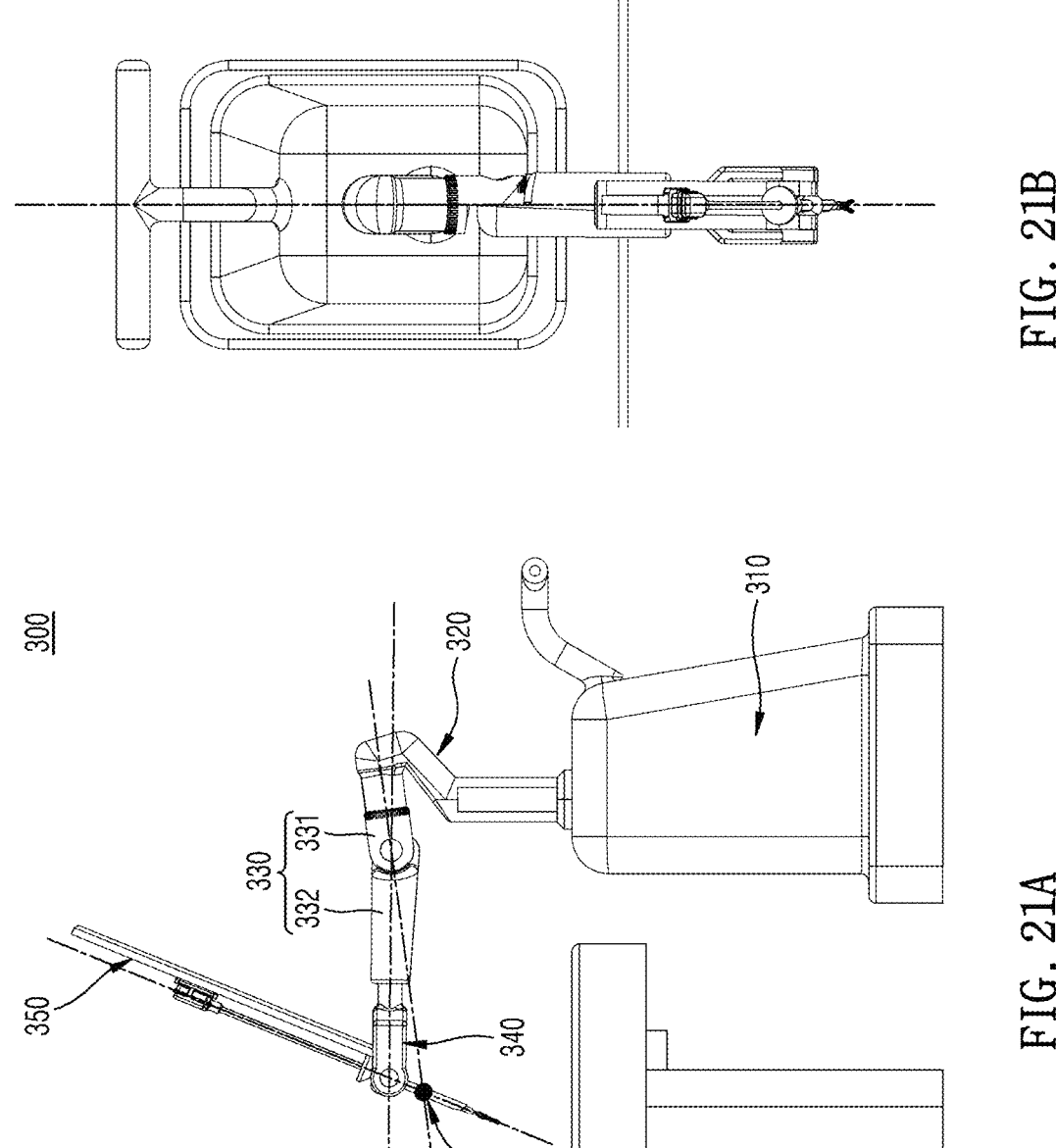
Figure 22:
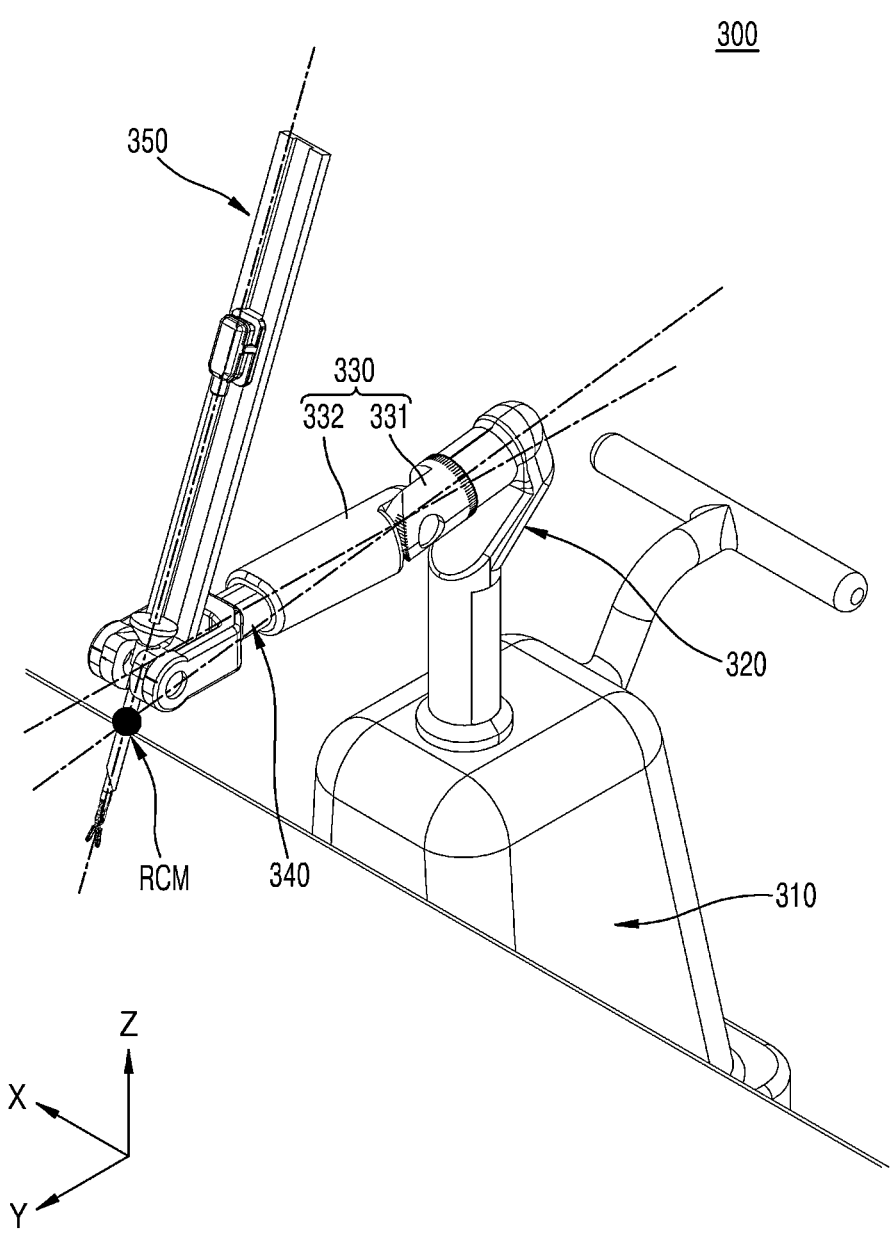
FIGS. 22 to 24 are perspective views illustrating a Y-axis RCM motion (a yaw motion) of the surgical robot arm of FIG. 17.
Figure 23:
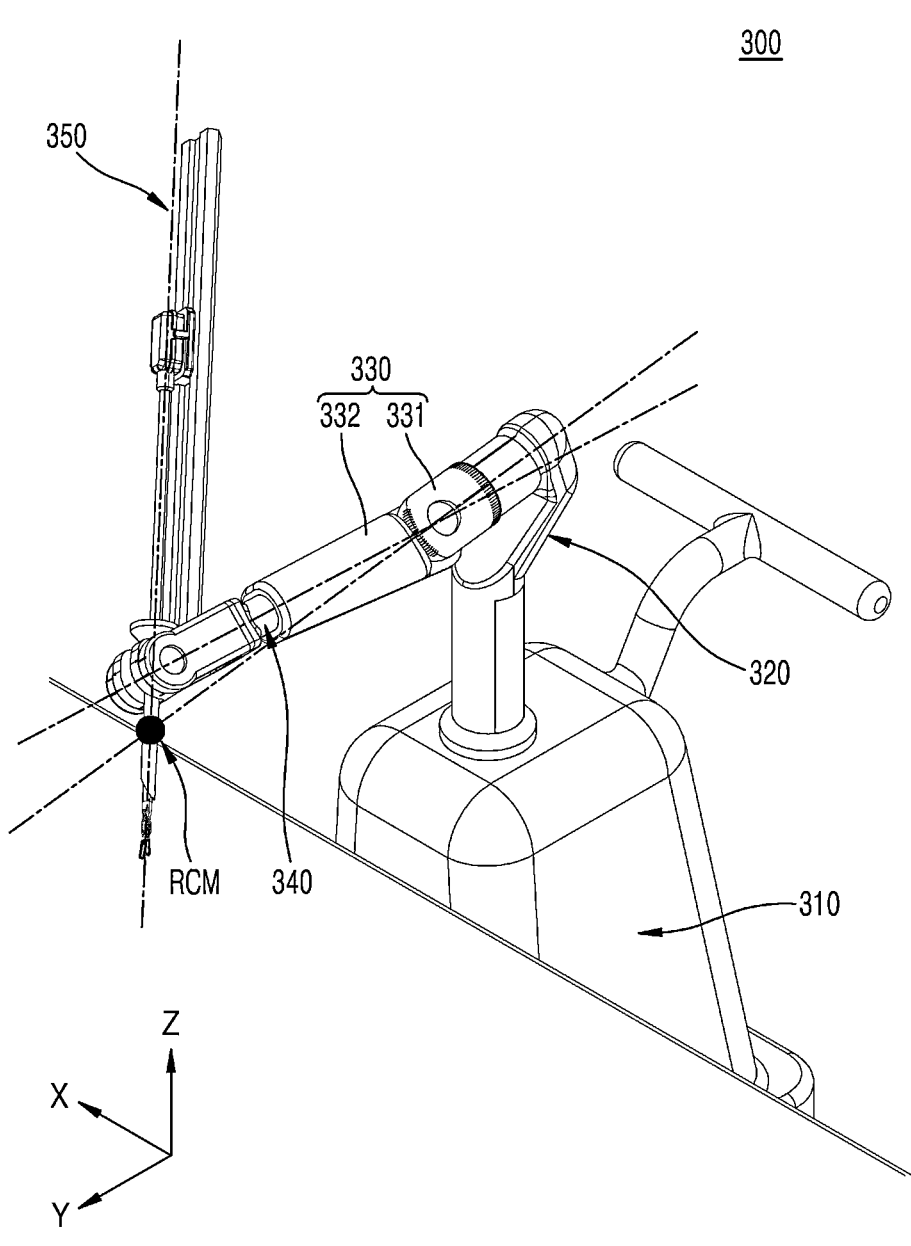
Figure 24:
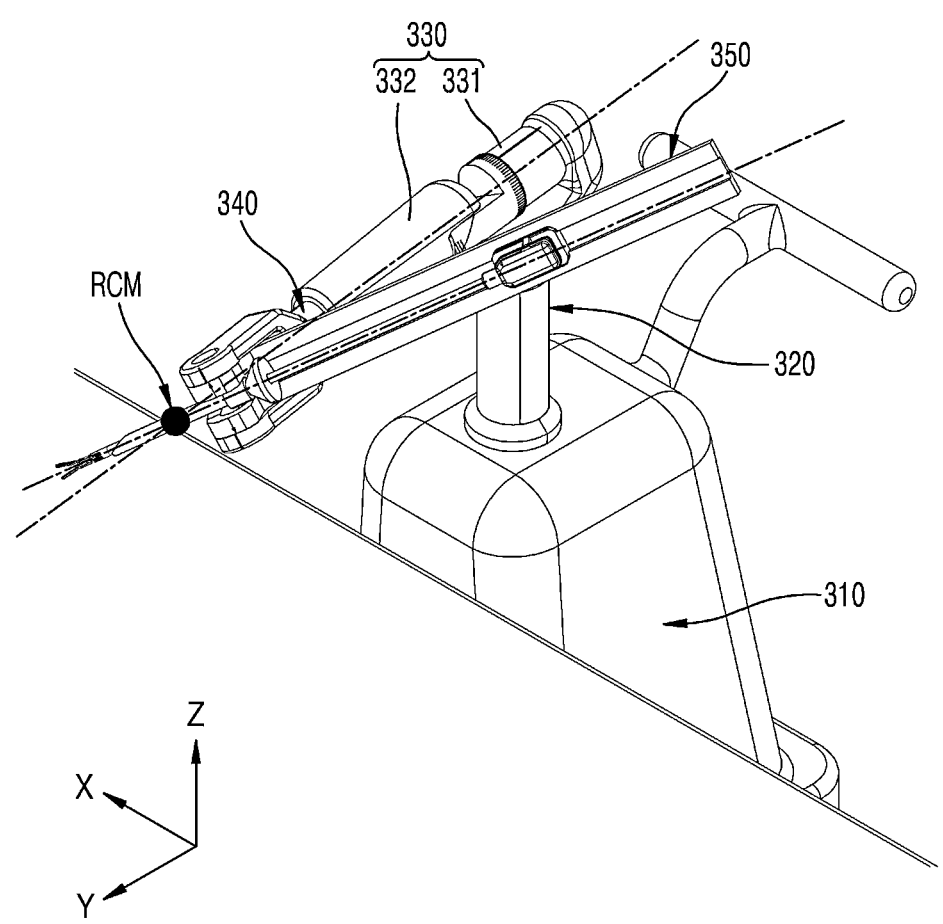
Figures 25A, 25B:
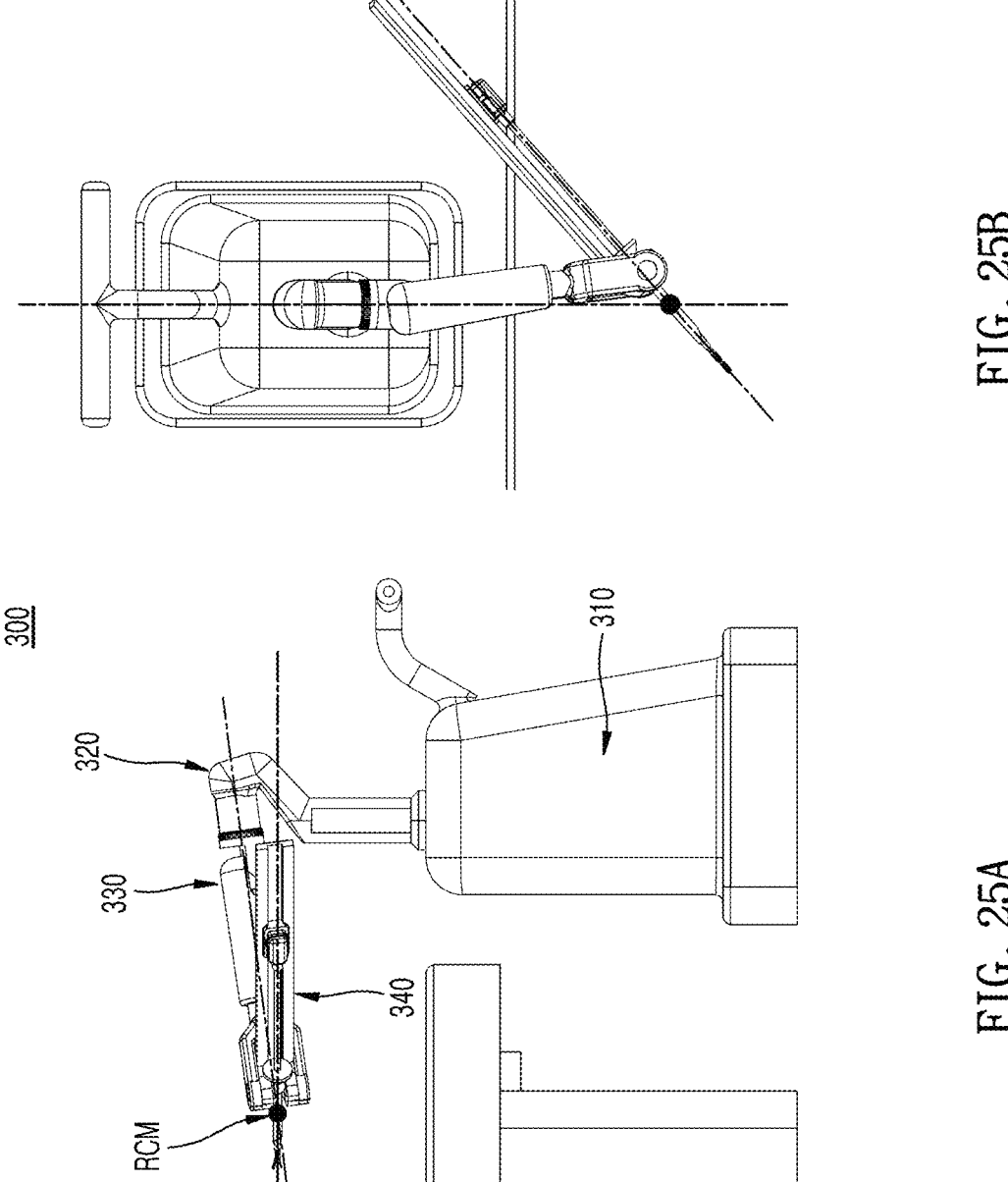
FIGS. 25A and 25B are a side view and a plan view, respectively, illustrating a state in which the surgical robot arm of FIG. 17 lies on its side.

FIG. 17 is a perspective view illustrating the overall structure of the surgical robot arm 300 according to the second embodiment of the present disclosure. FIG. 18 is a side view of the surgical robot arm of FIG. 4. FIGS. 19 to 21 are side views and plan views illustrating an X-axis RCM motion (a pitch motion) of the surgical robot arm of FIG. 17. FIGS. 22 to 24 are perspective views illustrating a Y-axis RCM motion (a yaw motion) of the surgical robot arm of FIG. 17. FIG. 25 is a side view and a plan view illustrating a state in which the surgical robot arm of FIG. 17 lies on its side.

Referring to FIGS. 17 to 25, the surgical robot arm 300 according to the second embodiment of the present disclosure includes a base 310, a base link 320, a first link 330, a second link 340, and an instrument mounting link 350. Here, in the surgical robot arm 300 according to the second embodiment of the present disclosure, the first link 330 includes two parts, that is, the first region 331 and the second region 332. The first region 331 and the second region 332 are formed to be rotatable around the pitch rotation shaft 335 with respect to each other.

The base 310 serves as a base part of the entire surgical robot arm 300. Here, a moving means (not shown) such as wheels may be formed on the lower surface of the base 310 so that the base 310 may serve as a kind of cart. In addition, a position fixing means (not shown) may be further formed on the base 310 so that the position of the base 310 may be fixed during surgery. However, the concept of the present disclosure is not limited thereto, and the base 310 may be formed in a shape that is detachably attachable to a bed, or may be formed in a shape that is detachably attachable a wall.

The base link 320 includes an extension portion 321 and a roll rotation base portion 322. The extension portion 321 may extend in one direction from the base 310. In the drawings, it is illustrated that the extension portion 321 of the base link 320 extends from the base 310 in the Z-axis direction. In other words, one end of the base link 320 is connected to the base 310. In the present embodiment, a case where the base link 320 is fixedly coupled to the base 310 is assumed.

On the other hand, the roll rotation base portion 322 is formed at the other end of the base link 320. The roll rotation base portion 322 may be formed to be inclined to a certain extent so as to have a certain angle with the extension portion 321.

Here, the roll rotation base portion 322 of the base link 320 may be formed in a cylindrical shape with respect to a first axis A1 formed in a first direction. The first link 330 connected to the roll rotation base portion 322 (together with the second link 340, the instrument mounting link 350, and the surgical instrument 20 sequentially connected to the first link 330) may be formed to roll around the first axis A1.

Here, the first axis A1 may be formed in an oblique direction that is not parallel to the X-axis/Y-axis/Z-axis. An RCM, which will be described later, may be formed on an extension line of the first axis A1.

The first link 330 may be coupled to the base link 320, and more specifically, to the roll rotation base portion 322 of the base link 320 and may be formed such that the entire first link 330 is rotatable around the first axis A1 of the roll rotation base portion 322. Alternatively, it may be expressed that the first link 330 rolls around the base link 320. In order to implement the rotational motion of the first link 330 with respect to the base link 320, a motor may be provided on either the base link 320 or the first link 330.

On the other hand, the first link 330 may include a first region 331 coupled to the base link 320 and a second region 332 coupled to the second link 340. Here, a central axis of the first region 331 and a central axis of the second region 332 may be defined to form a certain angle with each other. The first region 331 is axially coupled to the second region 332 by the pitch rotation shaft 335 formed in a direction of a fifth axis A5, and thus, the second region 332 is formed to be rotatable around the fifth axis A5 with respect to the first region 331. This is, the second region 332 may be rotatable around the X-axis when viewed from the drawing.

Here, the central axis of the first region 331 may coincide with the first axis A1, and therefore, the RCM may be located on an extension line of the central axis of the first region 331.

Here, when the first link 330 is rotated around the first axis A1, the second link 340, the instrument mounting link 350, and the surgical instrument 20 connected to the first link 330 are rotated together.

As described above, the central axis of the first region 331 and the central axis of the second region 332 may be defined to form a certain angle with each other. That is, a central axis of the first link 330 may coincide with the first axis A1, and therefore, the RCM may be located on an extension line of the central axis of the first region 331. In addition, the central axis of the second region 332 may coincide with the second axis A2 of the second link 340, which will be described later.

On the other hand, in order to implement the rotational motion of the second region 332 with respect to the first region 331, a motor may be provided on either the first region 331 or the second region 332.

The second link 340 may be coupled to the second region 332 of the first link 330 and may perform a linear reciprocating motion in one direction along the second axis A2 with respect to the second region 332 of the first link 330. Here, in the drawings, it is illustrated that the second link 340 performs a linear reciprocating motion in the X-axis direction with respect to the first link 330, but the concept of the present disclosure is not limited thereto, and a linear reciprocating axis of the second link 340 may be variously formed according to the shape and configuration of the links.

In order to implement such a linear motion, a linear actuator (not shown) may be provided on either the first link 330 or the second link 340.

Here, the first axis A1 and the second axis A2 may generally be different axes. Alternatively, even when the first link 330 or the second link 340 is bent to a certain extent and the first axis A1 and the second axis A2 are formed to be parallel to each other, the second axis A2 may be formed so as not to pass through the RCM.

The instrument mounting link 350 is axially coupled to the second link 340 by the link rotation shaft 360 coupled in a direction of a third axis A3, and thus, the instrument mounting link 350 is formed to be rotatable around the third axis A3 with respect to the second link 340. This is, the instrument mounting link 350 may be rotatable around the X-axis when viewed from the drawing. In order to implement such a rotational motion, a motor may be provided on either the second link 340 or the instrument mounting link 350.

On the other hand, an instrument mounting portion 351 and a guide rail 352 may be formed in the instrument mounting link 350. While the surgical instrument 20 is mounted on the instrument mounting portion 351, the instrument mounting portion 351 may perform a linear motion along the guide rail 352 formed in a direction of a fourth axis A4. In order to implement such a linear motion, a linear actuator (not shown) may be provided in the instrument mounting portion 351.

Here, the fourth axis A4 may be a direction in which the guide rail 352 is formed, and simultaneously, may be an extension direction of a shaft of the surgical instrument 20 coupled to the instrument mounting link 350.

The surgical instrument 20 is mounted on the instrument mounting portion 351 of the instrument mounting link 350 of the surgical robot arm 300.

Here, although not illustrated in the drawings, an interface part (not shown) coupled to the surgical instrument 20 and configured to control the motion of the surgical instrument 20 may be further formed in the instrument mounting portion 351. The interface part (not shown) may include a component configured to couple with a driving part 23 of the surgical instrument 20, a motor configured to transmit a driving force from the surgical robot arm 300 to the surgical instrument 20, and the like. The interface part (not shown) may allow an end tool 21 of the surgical instrument 20 to perform a pitch, yaw, or actuation motion. Furthermore, the interface part (not shown) may allow the shaft 22 and the end tool 21 of the surgical instrument 20 to perform a roll motion around the fourth axis A4.

On the other hand, a trocar 30 serving as an insertion passage for inserting the surgical instrument 20 into the patient's body may be further provided. While the trocar 30 is inserted into the body, the surgical instrument 20 may be inserted into the patient's body through the trocar 30. An RCM may be formed at a certain position on the trocar 30. As described above, the first axis A1, which is the roll rotation axis of the first link 330, may be formed to pass through the RCM.

In addition, the surgical instrument 20 may further include the driving part 23. A component configured to couple with the interface part (not shown) and a driving wheel operated in engagement with the motor may be formed in the driving part 23. As such, a coupling means and a driving transmission means may be respectively formed in the interface part (not shown) and the driving part 23 to correspond to each other. Accordingly, the surgical instrument 20 is operated by receiving a driving force from the surgical robot arm 300 in a state of being mounted on the instrument mounting link 350.

In the present disclosure, the RCM structure of the surgical robot arm 300 is a structure in which the surgical instrument 20 is mounted on one side of the surgical robot arm 300, and the surgical instrument 20 is operated and controlled to rotate around a certain point RCM on the trocar 30 into which the surgical instrument 20 is inserted. Here, the RCM structure according to the present embodiment is implemented through the electronic control for each link rather than the existing mechanical parallelogram link structure.

Hereinafter, for convenience, the control in the X-axis direction and the control in the Y-axis direction in the drawing are described separately, but it may be stated that the overall control is performed by combining the control in the X-axis direction with the control in the Y-axis direction. In addition, the coordinate system of each component may change relatively due to the rotation and linear motion of each link. However, for convenience, the following description is given based on the X-axis direction and the Y-axis direction of the bed by using the bed as the reference point. This will be described in more detail as follows.

First, the control in the X-axis direction may be implemented by a combination of:

1) the control of the linear motion of the second link 340 with respect to the first link 330, 2) the control of the rotational motion of the instrument mounting link 350 with respect to the second link 340, and 3) the control of the rotational motion of the second region 332 of the first link 330 with respect to the first region 331 of the first link 330.

In detail, in order to control the rotational motion of the surgical instrument 20 around the X-axis, the second link 340 first performs a linear motion along the second axis A2 with respect to the first link 330. At the same time, an RCM motion is performed by controlling the instrument mounting link 350 to perform a rotational motion around the third axis A3 with respect to the second link 340 and controlling the second region 332 of the first link 330 to perform a rotational motion with respect to the first region 331 of the first link 330. Accordingly, even when the links are moved, the RCM maintains a position thereof.

At this time, even when the surgical instrument 20 is rotated around the X-axis, the insertion depth (see LE of FIG. 6) of the instrument has not to change, and the distance (see Lt of FIG. 6) from the RCM to the end of the trocar 30 has not to change.

To this end, in the surgical robot arm 300 according to the second embodiment of the present disclosure, one degree of freedom is added, compared to the surgical robot arm (see 100 of FIG. 4) according to the first embodiment of the present disclosure. That is, the surgical robot arm 300 according to the second embodiment of the present disclosure is formed such that the first region 331 and the second region 332 of the first link 330 are rotatable around the pitch rotation shaft 335 with respect to each other.

Therefore, in controlling the rotational motion of the surgical instrument 20 around the X axis, the second region 332 of the first link 330 may be controlled to rotate with respect to the first region 331 of the first link 330, and thus, the insertion depths of the surgical instrument 20 and the trocar 30 may be maintained constant.

As such, even when the links are moved, the RCM in the X-axis direction maintains a position thereof by performing a combination of 1) the control of the linear motion of the second link 340 with respect to the first link 330, 2) the control of the rotational motion of the instrument mounting link 350 with respect to the second link 340, and 3) the control of the rotational motion of the second region 332 of the first link 330 with respect to the first region 331 of the first link 330.

Next, the RCM control in the Y-axis direction may be implemented by a combination of:

1) the control of the roll rotational motion of the first link 330 around the first link A1, 2) the control of the rotational motion of the instrument mounting link 350 with respect to the second link 340, and 3) the control of the linear motion of the second link 340 with respect to the first link 330, and 4) the control of the roll motion of the surgical instrument 20.

In detail, in order to control the rotational motion of the surgical instrument 20 around the Y axis, the first link 330 first performs a roll rotational motion around the first axis A1. The first link 330, and the second link 340, the instrument mounting link 350, and the surgical instrument 20, which are sequentially connected to the first link 330, may perform a roll motion around the first axis A1.

In this case, since the first axis A1, which is the rotation axis of the first link 330, and the Y-axis do not coincide with each other and are formed to be oblique, unintended motions are mixed when only the first link 330 is rotated. That is, as illustrated in the drawings, when the first link 330 is rotated, the second link 340, the instrument mounting link 350, and the surgical instrument 20 perform a kind of rolling.

In order to compensate for this, with the rotation of the first link 330, the instrument mounting link 350 is controlled to perform a rotational motion around the third axis A3 with respect to the second link 340, and simultaneously, the second link 340 is controlled to perform a linear motion with respect to the first link 330. In this manner, the RCM motion is performed. That is, even when the links are moved, the RCM maintains a position thereof.

In addition, the shaft 22 and the end tool 21 of the surgical instrument 20 are controlled to perform a roll motion around the fourth axis A4, so that the end tool 21 may also be compensated to maintain a posture thereof, regardless of the rotation of the first link 330.

As such, even when the links are moved, the RCM in the Y-axis direction maintains a position thereof by performing a combination of 1) the control of the roll rotational motion of the first link 330 around the first link A1, 2) the control of the rotational motion of the instrument mounting link 350 with respect to the second link 340, 3) the control of the linear motion of the second link 340 with respect to the first link 330, and 4) the control of the roll motion of the surgical instrument 20.

In conclusion, from the viewpoint of the degree of freedom of the surgical robot arm 300 itself (excluding the surgical instrument 20), the surgical robot arm 300 according to the second embodiment of the present disclosure may operate with four degrees of freedom of: 1) the roll rotational motion of the first link 330 around the first axis A1, 2) the linear motion of the second link 340 with respect to the first link 330, 3) the rotational motion of the instrument mounting link 350 with respect to the second link 340, and 4) the rotational motion of the second region 332 of the first link 330 with respect to the first region 331 of the first link 330. Here, a translation motion of the surgical instrument 20, that is, a linear motion of the surgical instrument 20 in the direction of the fourth axis A4, is also possible through the linear motion of the instrument mounting portion 351 with respect to the guide rail 352 of the instrument mounting link 350.

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm 100 and reducing the driving force required for operation may be obtained. Furthermore, the insertion depth of the trocar 30 is controlled to be constant through the control of the rotational motion of the second region 332 of the first link 330 with respect to the first region 331 of the first link 330, and thus, the risk of the trocar 30 coming out of the abdomen during surgery may be eliminated, thereby further improving safety.

<Second-1 Embodiment of Surgical Robot Arm>

Hereinafter, a surgical robot arm 700 according to a second-1 embodiment of the present disclosure will be described.

Here, the surgical robot arm 700 according to the second-1 embodiment of the present disclosure characteristically differs from the surgical robot arm (see 100 of FIG. 4) according to the first embodiment of the present disclosure in terms of a configuration of a first link 730 of the robot arm 700. In other words, in the robot arm 700 according to the second-1 embodiment of the present disclosure, a first link 730 includes two parts, that is, a first region 731 and a second region 732, and the first region 731 includes two parts, that is, a first-1 region 731-1 and a first-2 region 731-2, compared to the embodiment of FIG. 4. The second-1 embodiment of the present disclosure is an embodiment in which the first-1 region 731-1 and the first-2 region 731-2 of the first link 730 are formed to be rotatable around a yaw rotation shaft 736 with respect to each other, and the first region 731 and the second region 732 are formed to be rotatable around a pitch rotation shaft 735 with respect to each other.

In addition, the surgical robot arm 700 according to the second-1 embodiment of the present disclosure characteristically differs from the surgical robot arm (see 100 of FIG. 4) according to the first embodiment of the present disclosure in terms of an operation of a base link 720 of the robot arm 700. In other words, the surgical robot arm 700 according to the second-1 embodiment of the present disclosure is an embodiment in which the base link 720 is formed to enable a vertical linear motion along a sixth axis A6 with respect to a base 710, compared to the embodiment of FIG. 4.

Compared to the first embodiment, the change in configuration will be described in detail later.

Figure 26:
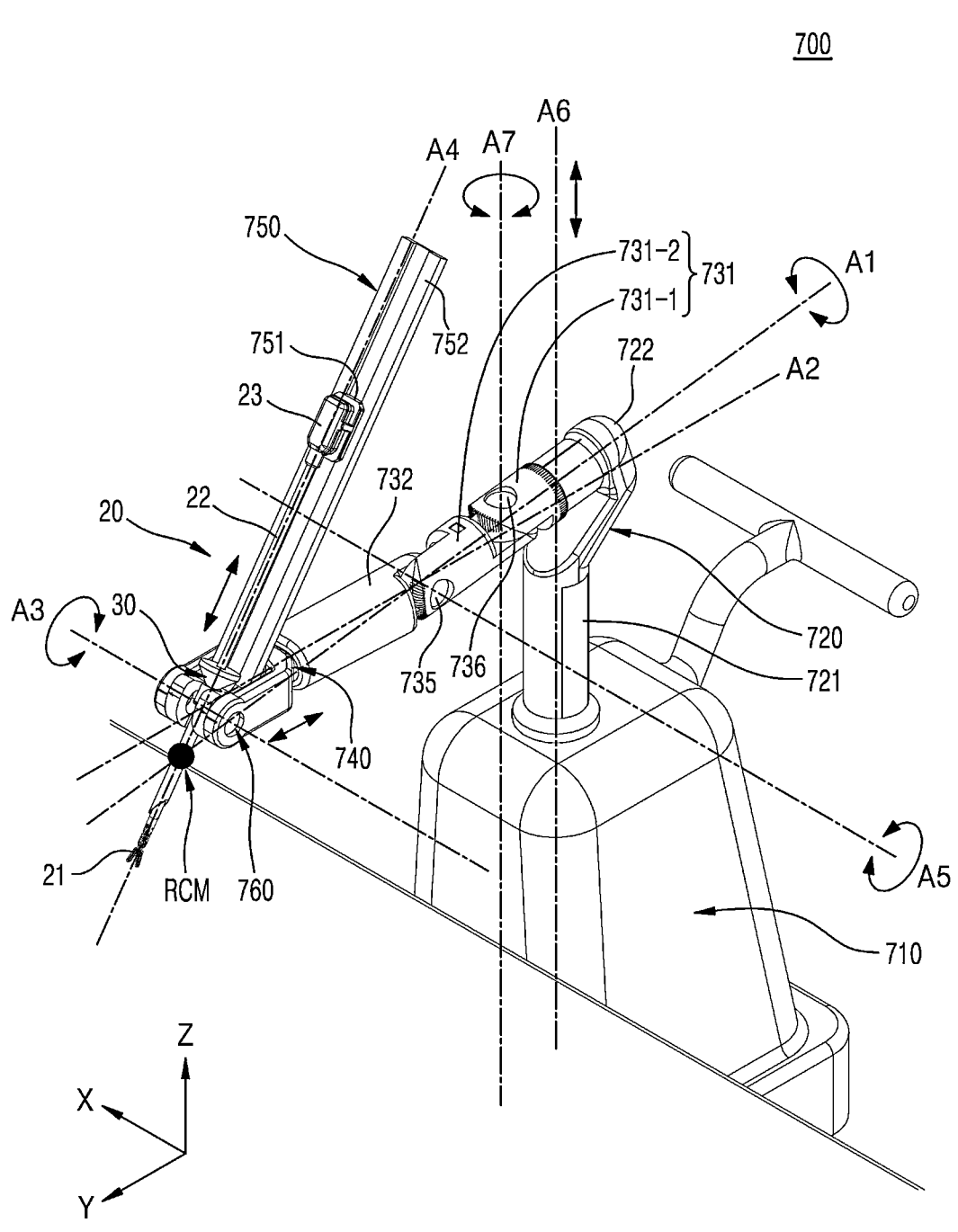
FIG. 26 is a perspective view illustrating an overall structure of a surgical robot arm (700) according to a second-1 embodiment of the present disclosure.
Figure 27:
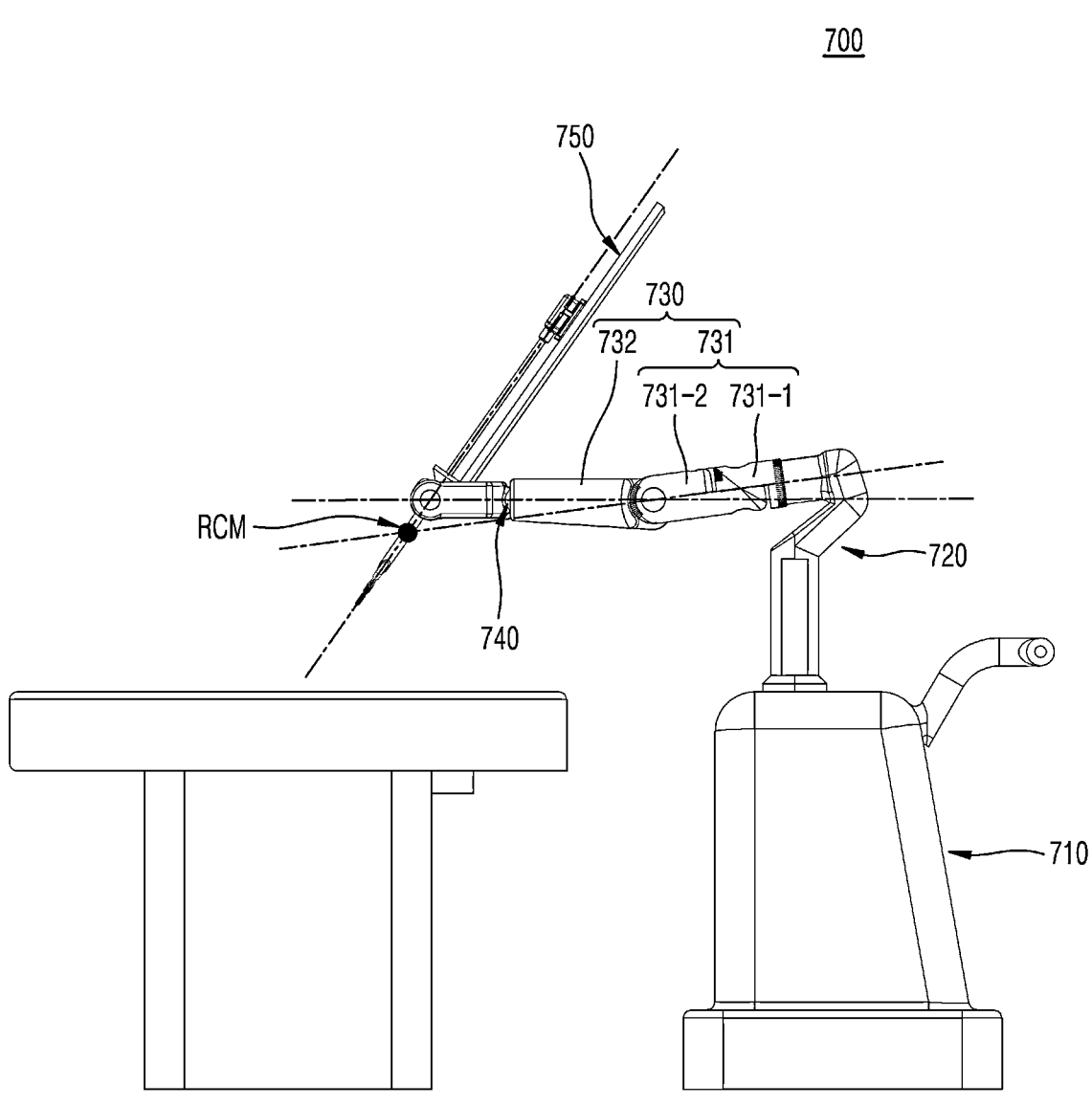
FIG. 27 is a side view of the surgical robot arm of FIG. 26.
Figure 28:
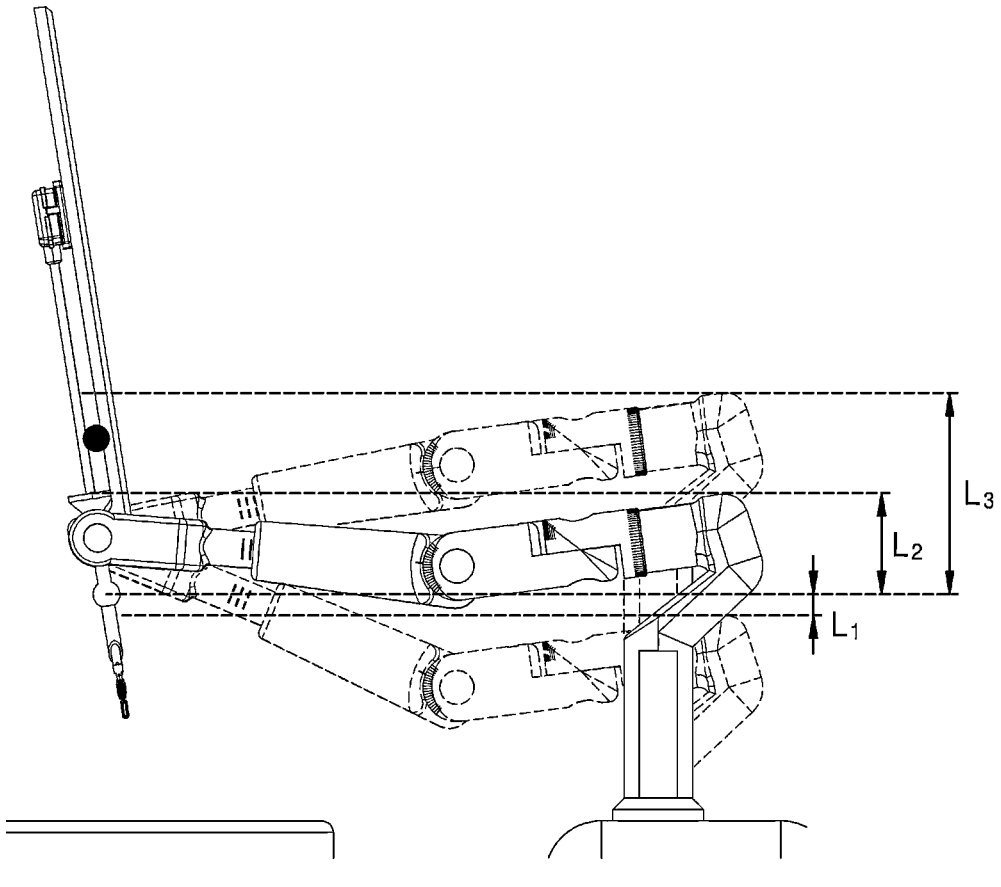
FIG. 28 is a side view illustrating the operating state of the surgical robot arm of FIG. 26.
Figures 29A, 29B:
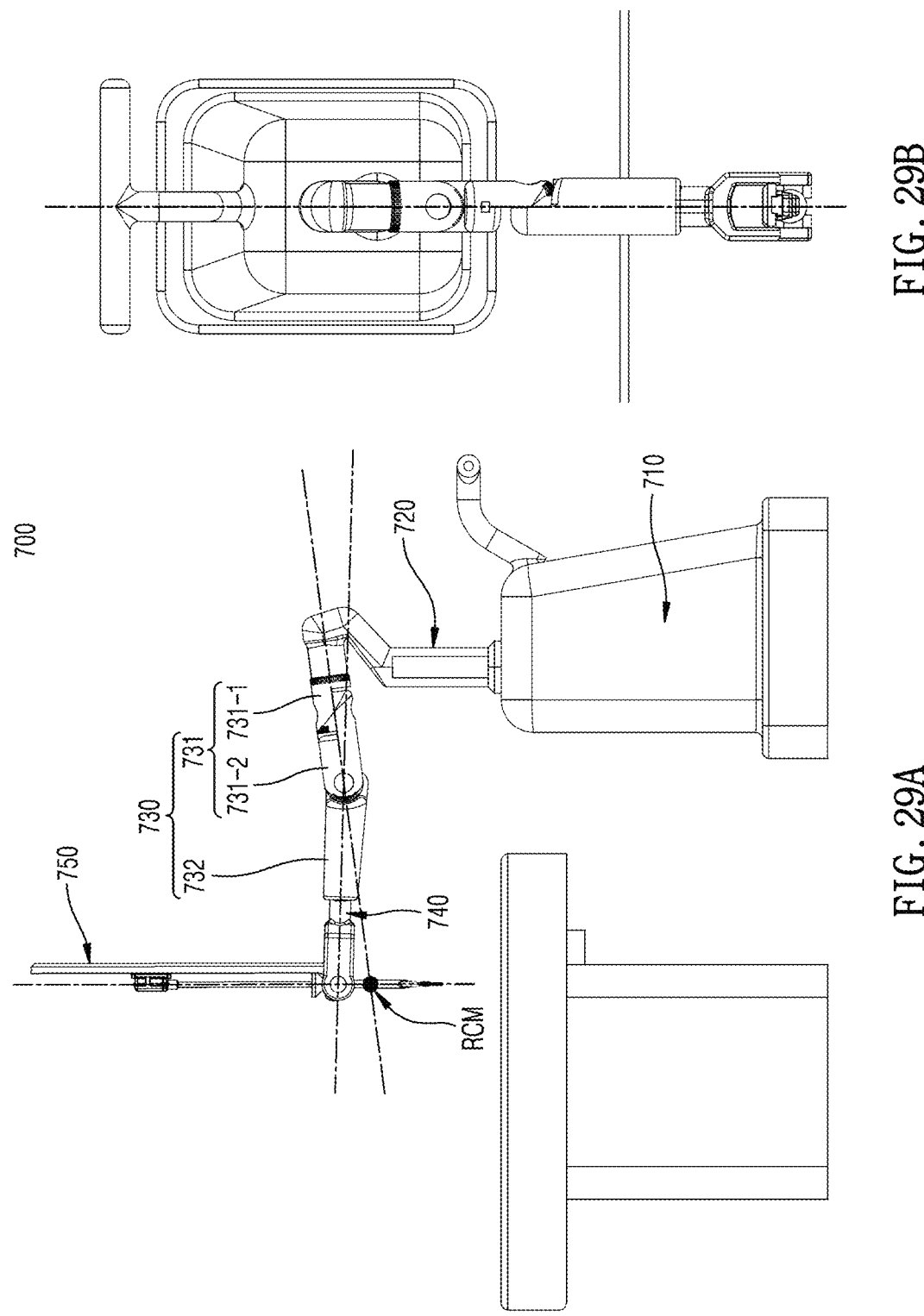
Figures 30A, 30B:
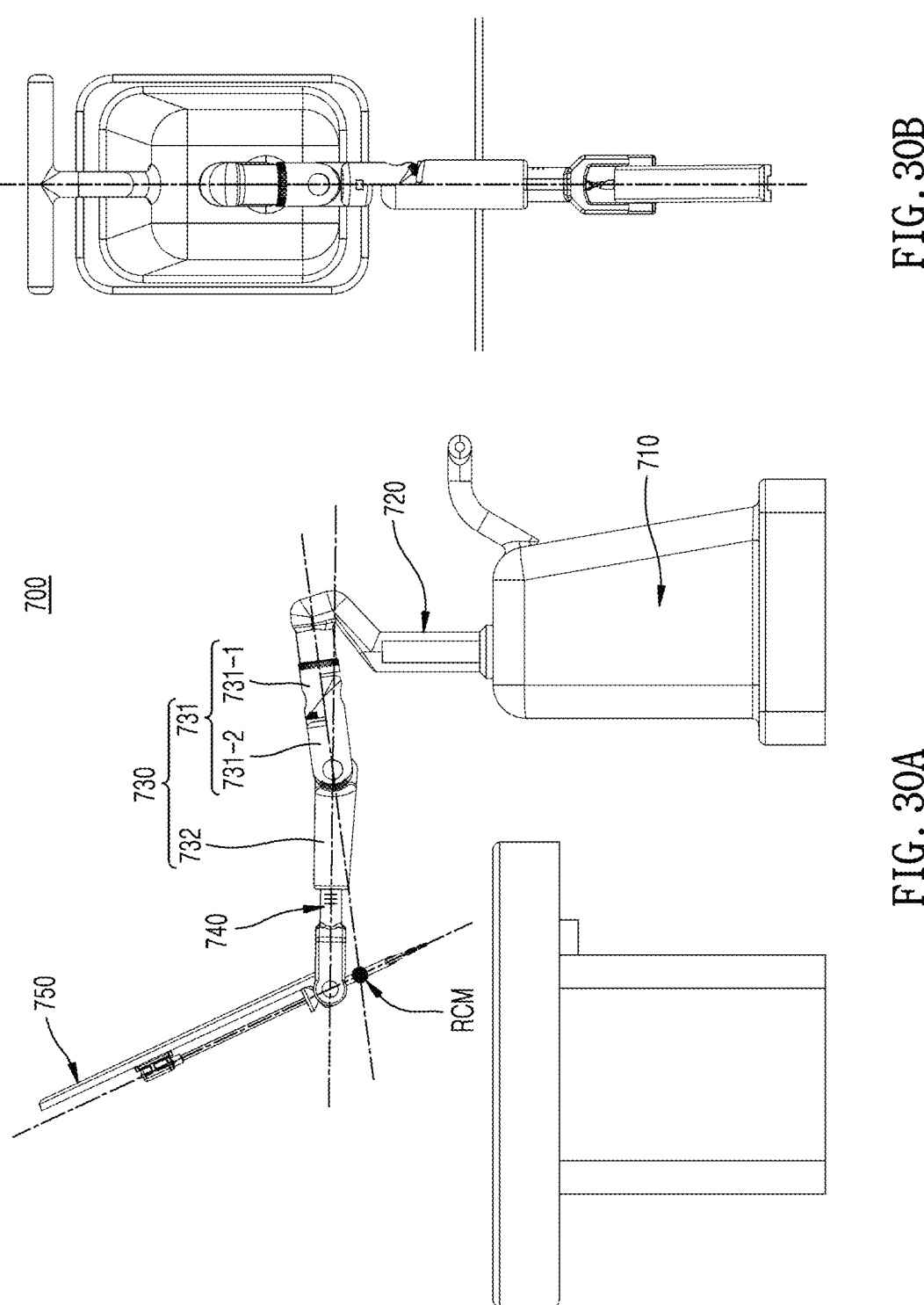
Figures 31A, 31B:
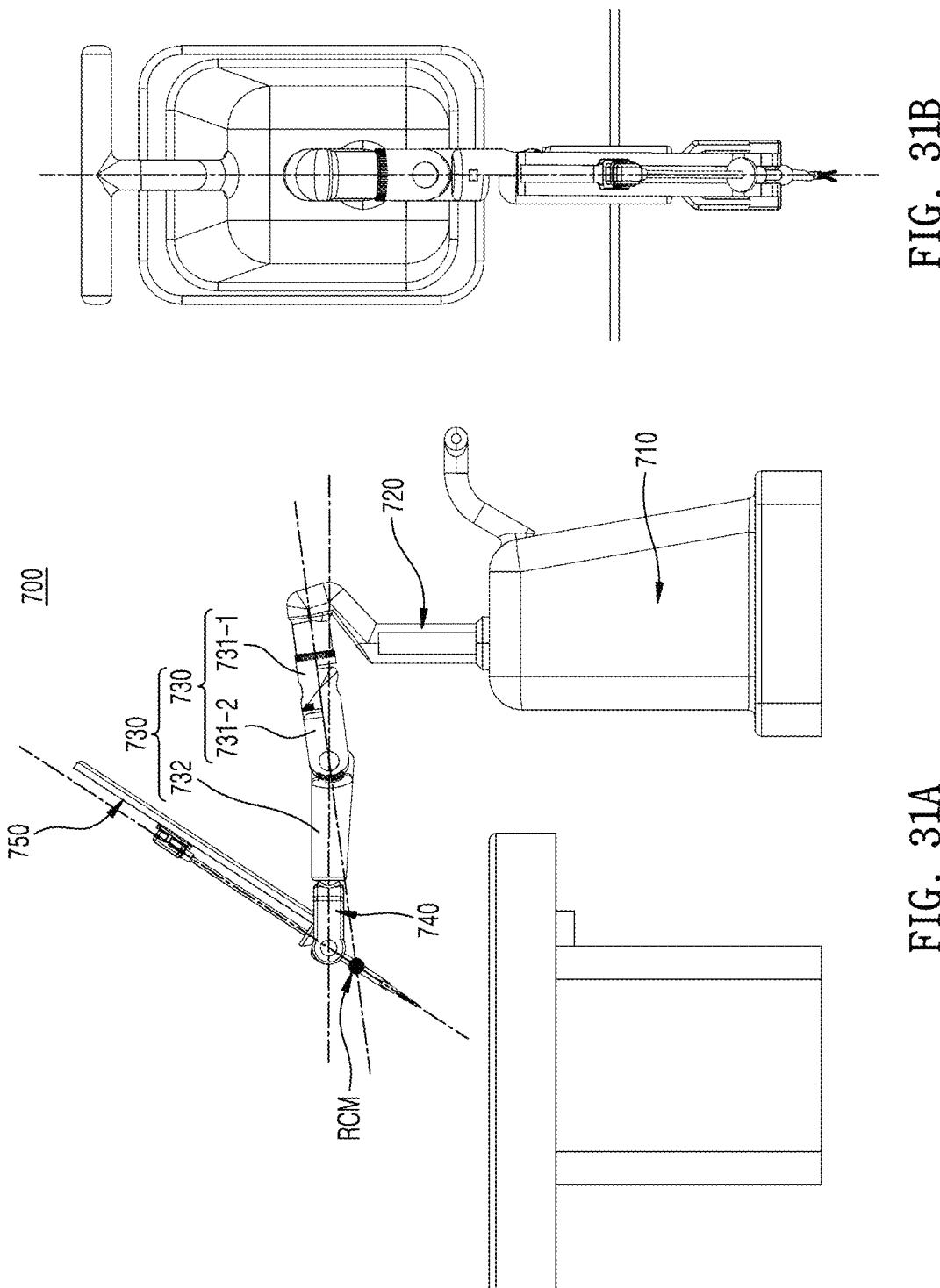
Figure 32:
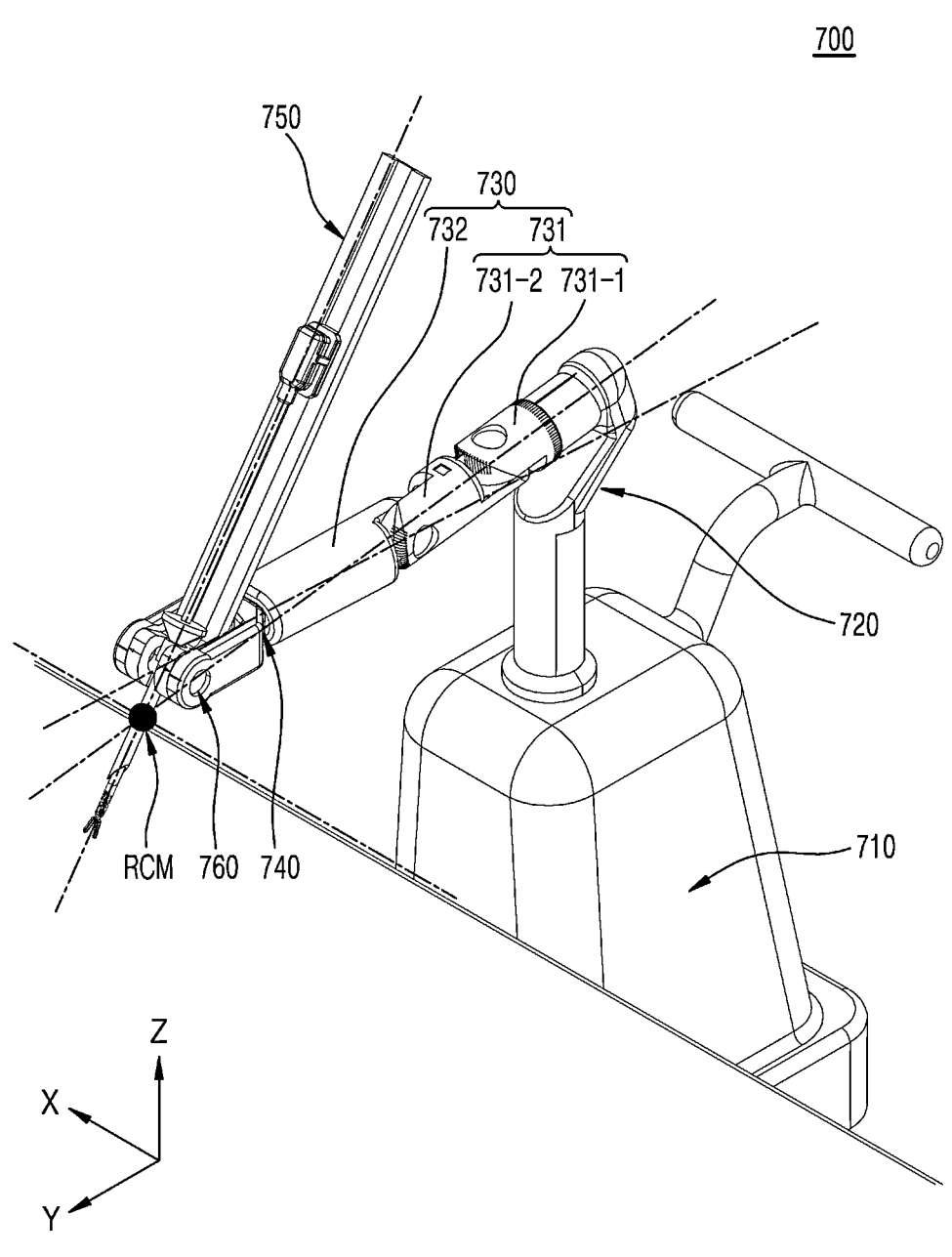
FIGS. 32 to 34 are perspective views illustrating a Y-axis RCM motion (a yaw motion) of the surgical robot arm of FIG. 26.
Figure 33:
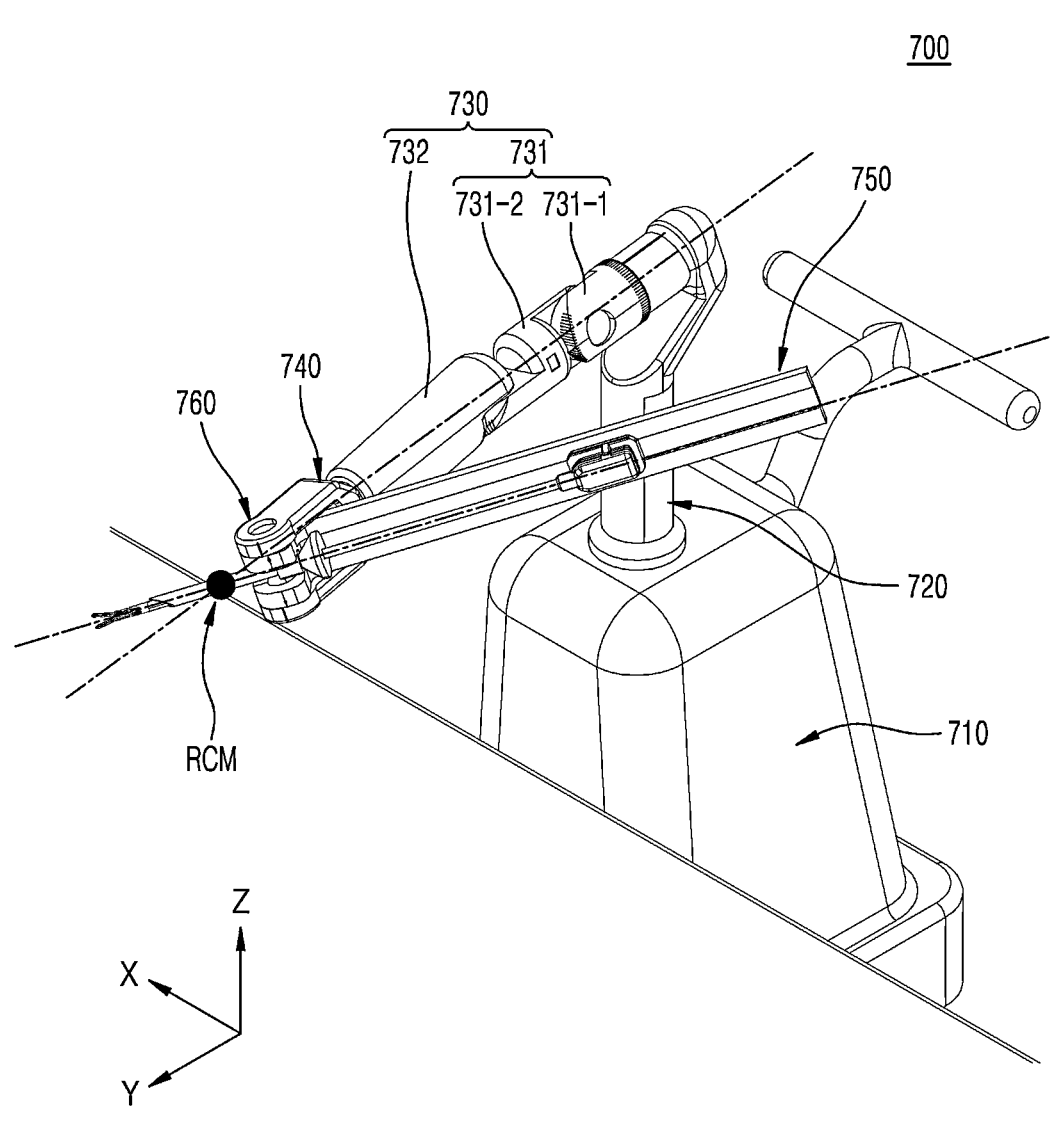
Figure 34:
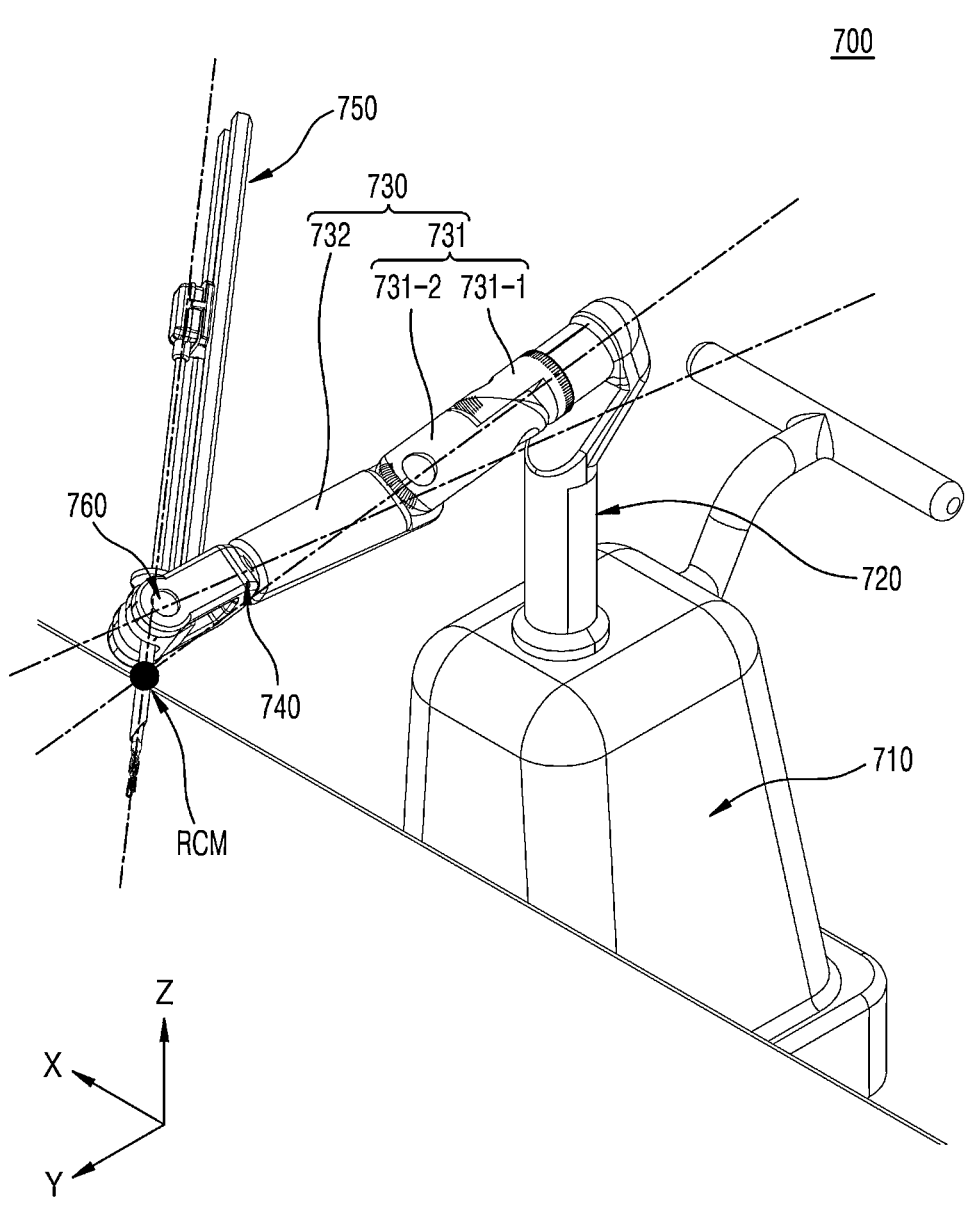
Figures 35A, 35B:
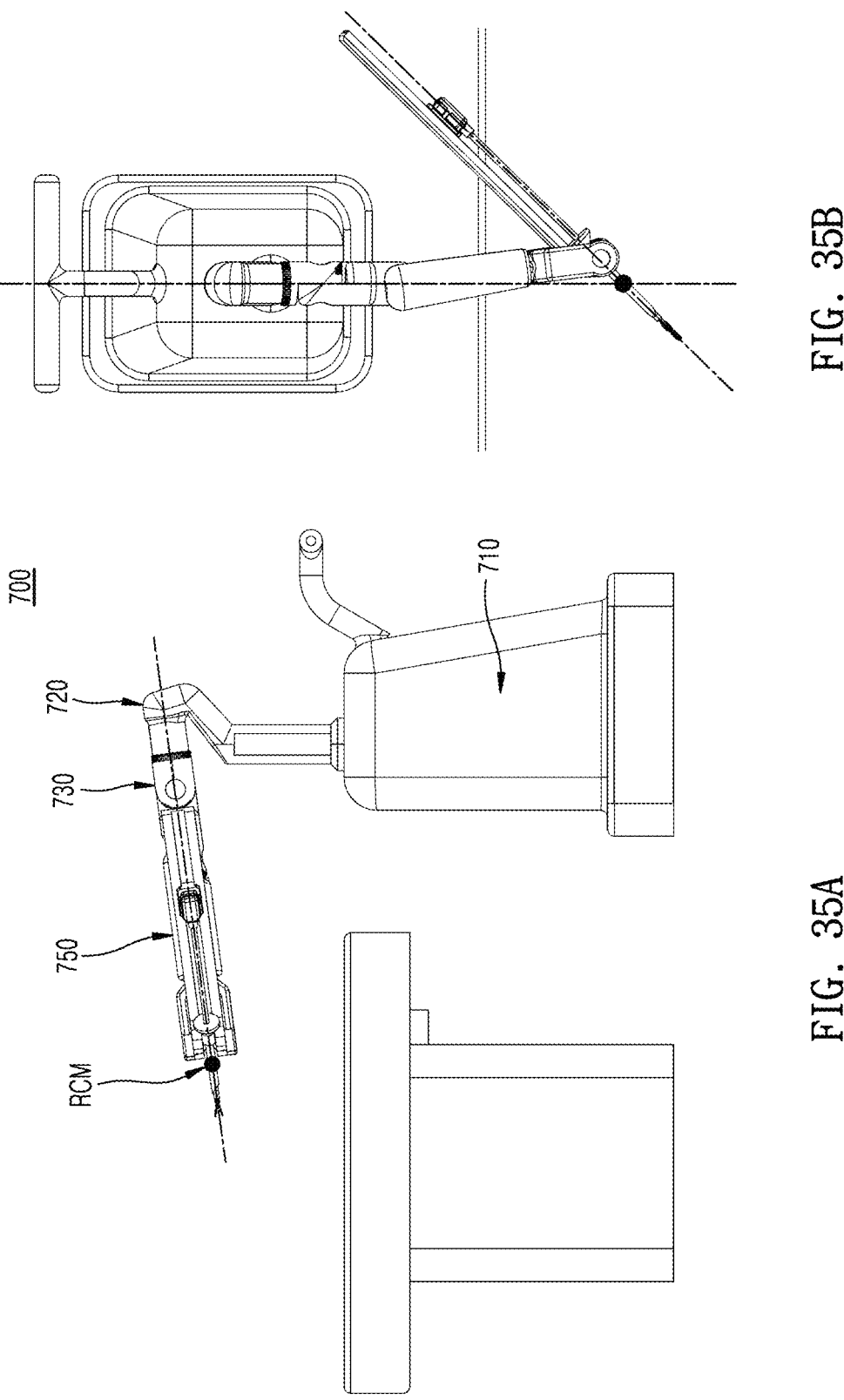
FIGS. 35A and 35B are a side view and a plan view, respectively, illustrating a state in which the surgical robot arm of FIG. 26 lies on its side.

FIG. 26 is a perspective view illustrating the overall structure of the surgical robot arm 700 according to the second-1 embodiment of the present disclosure. FIG. 27 is a side view of the surgical robot arm of FIG. 26. FIG. 28 is a side view illustrating the operating state of the surgical robot arm of FIG. 26. FIGS. 29 to 31 are side views and plan views illustrating an X-axis RCM motion (a pitch motion) of the surgical robot arm of FIG. 26. FIGS. 32 to 34 are perspective views illustrating a Y-axis RCM motion (a yaw motion) of the surgical robot arm of FIG. 26. FIG. 35 is a side view and a plan view illustrating a state in which the surgical robot arm of FIG. 26 lies on its side.

Referring to FIGS. 26 to 35, the surgical robot arm 700 according to the second-1 embodiment of the present disclosure includes a base 710, a base link 720, a first link 730, a second link 740, and an instrument mounting link 750.

The base 710 serves as a base part of the entire surgical robot arm 700. Here, a moving means (not shown) such as wheels may be formed on the lower surface of the base 710 so that the base 710 may serve as a kind of cart. In addition, a position fixing means (not shown) may be further formed on the base 710 so that the position of the base 710 may be fixed during surgery. However, the concept of the present disclosure is not limited thereto, and the base 710 may be formed in a shape that is detachably attachable to a bed, or may be formed in a shape that is detachably attachable a wall.

The base link 720 includes an extension portion 721 and a roll rotation base portion 722.

The extension portion 721 may extend in one direction from the base 710. In the drawings, it is illustrated that the extension portion 721 of the base link 720 extends from the base 710 in a Z-axis direction.

Here, the extension portion 721 is formed to enable a linear motion with respect to the base 710. That is, in the present embodiment, the base link 720 is formed to enable a linear motion in one direction (an up/down direction) along the sixth axis A6 with respect to the base 710. However, here, the linear motion of the base link 720 with respect to the base 710 is not performed in real time during the operation of the surgical robot arm 700, but may be performed in the set-up stage of the surgical robot arm 700 before starting surgery.

In detail, as illustrated in FIG. 28, the base link 720 may be formed to be inserted into or withdrawn from the base 710, so that the base link 720 may be located at various positions. That is, in the present embodiment, the RCM motion may be implemented even when the first axis A1, which is the roll rotation axis of the base link 720, does not coincide with the RCM in the Z-axis direction. That is, as illustrated in FIG. 28, the RCM motion may be implemented no matter where the base link 720 is located in the Z-axis direction. That is, the RCM motion may be implemented no matter where the base link 720 is located at any position, such as an L1 position, an L2 position, or an L3 position in FIG. 28.

To this end, the pitch rotation shaft 735 may be additionally provided in the first link 730, so that the first region 731 and the second region 732 of the first link 730 is formed to be rotatable with respect to each other. As such, since the RCM motion is possible even when the RCM and the first axis A1 of the base link 720 are spaced apart from each other without meeting each other in the Z-axis direction, the initial position of the surgical robot arm may be flexibly set. That is, various set-up positions of the surgical robot arm 700 are possible. This will be described later.

On the other hand, the roll rotation base portion 722 is formed at the other end of the base link 720. The roll rotation base portion 722 may be formed to be inclined to a certain extent so as to have a certain angle with the extension portion 721.

Here, the roll rotation base portion 722 of the base link 720 may be formed in a cylindrical shape with respect to the first axis A1 formed in a first direction. The first link 730 connected to the roll rotation base portion 722 (together with the second link 740, the instrument mounting link 750, and the surgical instrument 20 sequentially connected to the first link 730) may be formed to perform a roll motion around the first axis A1. Here, the first axis A1 may be formed in an oblique direction that is not parallel to the X-axis/Y-axis/Z-axis.

The first link 730 may be coupled to the base link 720, and more specifically, to the roll rotation base portion 722 of the base link 720 and may be formed such that the entire first link 730 is rotatable around the first axis A1 of the roll rotation base portion 722. Alternatively, it may be expressed that the first link 730 rolls around the base link 720. In order to implement the rotational motion of the first link 730 with respect to the base link 720, a motor may be provided on either the base link 720 or the first link 730.

On the other hand, the first link 730 may include the first region 731 coupled to the base link 720 and the second region 732 coupled to the second link 740. The first region 731 may include the first-1 region 731-1 coupled to the base link 720, and the first-2 region 731-2 disposed between the first-1 region 731-1 and the second region 732 and connected to the first-1 region 731-1 and the second region 732.

The first-1 region 731-1 and the first-2 region 731-2 are axially coupled by the yaw rotation shaft 736 formed in a direction of a seventh axis A7, and thus, the first-2 region 731-2 is formed to be rotatable around the seventh axis A7 with respect to the first-1 region 731-1. This is, the first-2 region 731-2 may be rotatable around the Z-axis when viewed from the drawing.

The first region 731 is axially coupled to the second region 732 by the pitch rotation shaft 735 formed in a direction of a fifth axis A5, and thus, the second region 732 is formed to be rotatable around the fifth axis A5 with respect to the first region 731. This is, the second region 732 may be rotatable around the X-axis when viewed from the drawing.

Here, when the first link 730 is rotated around the first axis A1, the second link 740, the instrument mounting link 750, and the surgical instrument 20 connected to the first link 730 are rotated together.

On the other hand, in order to implement the rotational motion of the first-2 region 731-2 with respect to the first-1 region 731-1, a motor may be provided on either the first-1 region 731-1 or the first-2 region 731-2. In addition, in order to implement the rotational motion of the second region 732 with respect to the first-2 region 731-2, a motor may be provided on either the first-2 region 731-2 or the second region 732.

Here, in the present embodiment, the first-2 region 731-2 of the first link 730 is formed to be rotatable around the seventh axis A7 with respect to the first-1 region 731-1 in a clockwise direction or a counterclockwise direction.

Here, the rotation of the first-2 region 731-2 with respect to the first-1 region 731-1 may be performed in the set-up stage of the surgical robot arm 700 before starting surgery. Due to the rotation of the first-2 region 731-2 with respect to the first-1 region 731-1 in the set-up stage, when the first axis A1, which is the roll rotation axis of the base link 720, is set up not to coincide with the RCM on an XY plane, the first-2 region 731-2 is rotated with respect to the first-1 region 731-1 in real time even while the surgical robot arm 700 is operating.

In detail, the first-2 region 731-2 may be formed to be rotatable around the seventh axis A7 with respect to the first-1 region 731-1, and the first-2 region 731-2, and the second link 740 and the instrument mounting link 750 connected thereto may be located at various positions on the XY plane. With this configuration, in the present embodiment, the RCM motion may be implemented even when the first axis A1, which is the roll rotation axis of the base link 720, does not coincide with the RCM. That is, as illustrated in (b) of FIG. 47 and (c) of FIG. 47 of the third embodiment, which will be described later, the RCM motion may be implemented no matter where the first-2 region 731-2, and the second link 740 and the instrument mounting link 750 connected thereto are located on the XY plane.

The second link 740 may be coupled to the second region 732 of the first link 730 and may perform a linear reciprocating motion in one direction along the second axis A2 with respect to the second region 732 of the first link 730. Here, in the drawings, it is illustrated that the second link 740 performs a linear reciprocating motion in the X-axis direction with respect to the first link 730, but the concept of the present disclosure is not limited thereto, and a linear reciprocating axis of the second link 740 may be variously formed according to the shape and configuration of the links.

In order to implement such a linear motion, a linear actuator (not shown) may be provided on either the first link 730 or the second link 740.

Here, the first axis A1 and the second axis A2 may generally be different axes. Alternatively, even when the first link 730 or the second link 740 is bent to a certain extent and the first axis A1 and the second axis A2 are formed to be parallel to each other, the second axis A2 may be formed so as not to pass through the RCM.

The instrument mounting link 750 is axially coupled to the second link 740 by the link rotation shaft 760 coupled in a direction of a third axis A3, and thus, the instrument mounting link 750 is formed to be rotatable around the third axis A3 with respect to the second link 740. This is, the instrument mounting link 750 may be rotatable around the X-axis when viewed from the drawing. In order to implement such a rotational motion, a motor may be provided on either the second link 740 or the instrument mounting link 750.

On the other hand, an instrument mounting portion 751 and a guide rail 752 may be formed in the instrument mounting link 750. While the surgical instrument 20 is mounted on the instrument mounting portion 751, the instrument mounting portion 751 may perform a linear motion along the guide rail 752 formed in a direction of a fourth axis A4. In order to implement such a linear motion, a linear actuator (not shown) may be provided in the instrument mounting portion 751.

Here, the fourth axis A4 may be a direction in which the guide rail 752 is formed, and simultaneously, may be an extension direction of a shaft of the surgical instrument 20 coupled to the instrument mounting link 750.

The surgical instrument 20 is mounted on the instrument mounting portion 751 of the instrument mounting link 750 of the surgical robot arm 700.

Here, although not illustrated in the drawings, an interface part (not shown) coupled to the surgical instrument 20 and configured to control the motion of the surgical instrument 20 may be further formed in the instrument mounting portion 751. The interface part (not shown) may include a component configured to couple with a driving part 23 of the surgical instrument 20, a motor configured to transmit a driving force from the surgical robot arm 700 to the surgical instrument 20, and the like. The interface part (not shown) may allow an end tool 21 of the surgical instrument 20 to perform a pitch, yaw, or actuation motion. Furthermore, the interface part (not shown) may allow the shaft 22 and the end tool 21 of the surgical instrument 20 to perform a roll motion around the fourth axis A4.

On the other hand, a trocar 30 serving as an insertion passage for inserting the surgical instrument 20 into the patient's body may be further provided. While the trocar 30 is inserted into the body, the surgical instrument 20 may be inserted into the patient's body through the trocar 30. An RCM may be formed at a certain position on the trocar 30. As described above, the first axis A1, which is the roll rotation axis of the first link 730, may be formed to pass through the RCM.

In addition, the surgical instrument 20 may further include the driving part 23. A component configured to couple with the interface part (not shown) and a driving wheel operated in engagement with the motor may be formed in the driving part 23. As such, a coupling means and a driving transmission means may be respectively formed in the interface part (not shown) and the driving part 23 to correspond to each other. Accordingly, the surgical instrument 20 is operated by receiving a driving force from the surgical robot arm 700 in a state of being mounted on the instrument mounting link 750.

In the present disclosure, the RCM structure of the surgical robot arm 700 is a structure in which the surgical instrument 20 is mounted on one side of the surgical robot arm 700, and the surgical instrument 20 is operated and controlled to rotate around a certain point RCM on the trocar 30 into which the surgical instrument 20 is inserted. Here, the RCM structure according to the present embodiment is implemented through the electronic control for each link rather than the existing mechanical parallelogram link structure.

In particular, the difference between the present embodiment and the previous embodiments is that the RCM motion is possible even when the RCM and the rotation axis A1 of the base link are spaced apart from each other without meeting each other, and thus, the initial setting of the surgical robot arm is simplified. That is, the RCM motion is possible even when the RCM and the base link are spaced apart from each other in both the yaw axis direction and the pitch axis direction.

That is, as illustrated in FIG. 28, etc., the RCM motion is possible even when the first axis A1, which is the roll rotation axis of the first link 730, is not arranged to pass through the RCM. This is enabled by the additional degrees of freedom given in the present embodiment, that is, the linear motion of the base link 720 with respect to the base 710, the rotational motion of the first-2 region 731-2 with respect to the first-1 region 731-1, and the rotational motion of the second region 732 with respect to the first-2 region 731-2. That is, the surgical robot arm 700 of the present embodiment has a total of seven degrees of freedom. Due to the motion of the seven degrees of freedom, the RCM motion is possible even when the first axis A1 does not pass through the RCM.

Hereinafter, for convenience, the control in the X-axis direction and the control in the Y-axis direction in the drawing are described separately, but it may be stated that the overall control is performed by combining the control in the X-axis direction with the control in the Y-axis direction. In addition, the coordinate system of each component may change relatively due to the rotation and linear motion of each link. However, for convenience, the following description is given based on the X-axis direction and the Y-axis direction of the bed by using the bed as the reference point. This will be described in more detail as follows.

First, the control in the X-axis direction may be implemented by a combination of:

1) the control of the linear motion of the second link 740 with respect to the first link 730, 2) the control of the rotational motion of the instrument mounting link 750 with respect to the second link 740, and 3) the control of the rotational motion of the second region 732 of the first link 730 with respect to the first region 731 of the first link 730.

In detail, in order to control the rotational motion of the surgical instrument 20 around the X-axis, the second link 740 first performs a linear motion along the second axis A2 with respect to the first link 730. At the same time, an RCM motion is performed by controlling the instrument mounting link 750 to perform a rotational motion around the third axis A3 with respect to the second link 740 and controlling the second region 732 of the first link 730 to perform a rotational motion with respect to the first region 731 of the first link 730. Accordingly, even when the links are moved, the RCM maintains a position thereof.

At this time, even when the surgical instrument 20 is rotated around the X-axis, the insertion depth (see LE of FIG. 6) of the instrument has not to change, and the distance (see Lt of FIG. 6) from the RCM to the end of the trocar 30 has not to change.

To this end, in the surgical robot arm 700 according to the second-1 embodiment of the present disclosure, one degree of freedom is added, compared to the surgical robot arm (see 100 of FIG. 4) according to the first embodiment of the present disclosure. That is, the surgical robot arm 700 according to the second embodiment of the present disclosure is formed such that the first region 731 and the second region 732 of the first link 730 are rotatable around the pitch rotation shaft 735 with respect to each other.

Therefore, in controlling the rotational motion of the surgical instrument 20 around the X axis, the second region 732 of the first link 730 may be controlled to rotate with respect to the first region 731 of the first link 730, and thus, the insertion depths of the surgical instrument 20 and the trocar 30 may be maintained constant.

As such, even when the links are moved, the RCM in the X-axis direction maintains a position thereof by performing a combination of 1) the control of the linear motion of the second link 740 with respect to the first link 730, 2) the control of the rotational motion of the instrument mounting link 750 with respect to the second link 740, and 3) the control of the rotational motion of the second region 732 of the first link 730 with respect to the first region 731 of the first link 730.

Next, the RCM control in the Y-axis direction may be implemented by a combination of:

1) the control of the roll rotational motion of the first link 730 around the first link A1, 2) the control of the rotational motion of the instrument mounting link 750 with respect to the second link 740, 3) the control of the linear motion of the second link 740 with respect to the first link 730, 4) the control of the roll motion of the surgical instrument 20, and 5) the control of the rotational motion of the first-2 region 731-2 of the first link 730 with respect to the first-1 region 731-1 of the first link 730.

In detail, in order to control the rotational motion of the surgical instrument 20 around the Y axis, the first link 730 first performs a roll rotational motion around the first axis A1. The first link 730, and the second link 740, the instrument mounting link 750, and the surgical instrument 20, which are sequentially connected to the first link 730, may perform a roll motion around the first axis A1.

In this case, since the first axis A1, which is the rotation axis of the first link 730, and the Y-axis do not coincide with each other and are formed to be oblique, unintended motions are mixed when only the first link 730 is rotated. That is, as illustrated in the drawings, when the first link 730 is rotated, the second link 740, the instrument mounting link 750, and the surgical instrument 20 perform a kind of rolling.

In order to compensate for this, with the rotation of the first link 730, the instrument mounting link 750 is controlled to perform a rotational motion around the third axis A3 with respect to the second link 740, the second link 740 is controlled to perform a linear motion with respect to the first link 730, and the first-2 region 731-2 of the first link 730 is controlled to perform a rotational motion with respect to the first-1 region 731-1 of the first link 730. In this manner, the RCM motion is performed. That is, even when the links are moved, the RCM maintains a position thereof.

In addition, the shaft 22 and the end tool 21 of the surgical instrument 20 are controlled to perform a roll motion around the fourth axis A4, so that the end tool 21 may also be compensated to maintain a posture thereof, regardless of the rotation of the first link 730.

As such, even when the links are moved, the RCM in the Y-axis direction maintains a position thereof by performing a combination of 1) the control of the roll rotational motion of the first link 730 around the first link A1, 2) the control of the rotational motion of the instrument mounting link 750 with respect to the second link 740, 3) the control of the linear motion of the second link 740 with respect to the first link 730, 4) the control of the roll motion of the surgical instrument 20, and 5) the control of the rotational motion of the first-2 region 731-2 of the first link 730 with respect to the first-1 region 731-1 of the first link 730.

In conclusion, from the viewpoint of the degree of freedom of the surgical robot arm 700 itself (excluding the surgical instrument 20), the surgical robot arm 700 according to the second-1 embodiment of the present disclosure may operate with six degrees of freedom of 1) the roll rotational motion of the first link 730 around the first axis A1, 2) the linear motion of the second link 740 with respect to the first link 730, 3) the rotational motion of the instrument mounting link 750 with respect to the second link 740, 4) the rotational motion of the second region 732 of the first link 730 with respect to the first region 731 of the first link 730, 5) the rotational motion of the first-2 region 731-2 of the first link 730 with respect to the first-1 region 731-1 of the first link 730, and 6) the linear motion of the base link 720 with respect to the base 710. Here, a translation motion of the surgical instrument 20, that is, a linear motion of the surgical instrument 20 in the direction of the fourth axis A4, is also possible through the linear motion of the instrument mounting portion 751 with respect to the guide rail 752 of the instrument mounting link 750.

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm 100 and reducing the driving force required for operation may be obtained. Furthermore, the insertion depth of the trocar 30 is controlled to be constant through the control of the rotational motion of the second region 732 of the first link 730 with respect to the first region 731 of the first link 730, and thus, the risk of the trocar 30 coming out of the abdomen during surgery may be eliminated, thereby further improving safety.

In addition, when the additional degree of freedom (i.e., the rotational motion of the first-2 region 731-2 of the first link 730 with respect to the first-1 region 731-1 of the first link 730) is given, the RCM motion may be implemented even when the first axis A1, which is the roll rotation axis of the base link 720, does not coincide with the RCM in the XY plane and the Z-axis directions. Accordingly, an effect of simplifying the initial setting of the surgical robot arm may be obtained.

<Second-2 Embodiment of Surgical Robot Arm>

Hereinafter, a surgical robot arm 800 according to a second-2 embodiment of the present disclosure will be described. Here, the surgical robot arm 800 according to the second-2 embodiment of the present disclosure characteristically differs from the surgical robot arm (see 300 of FIG. 17) according to the second embodiment of the present disclosure in terms of a coupling relationship between a second link 840 and an instrument mounting link 850 of the robot arm 800. In other words, compared to the second embodiment of FIG. 17, the robot arm 800 according to the second-2 embodiment of the present disclosure is an embodiment in which the second link 840 and the instrument mounting link 850 are not coupled at an intersection with a trocar 30, and are formed to be axially coupled at a separate second link coupling portion 853 that protrudes to a certain extent from the instrument mounting link 850 toward the second link 840. Compared to the second embodiment, the change in configuration will be described in detail later.

Figure 36:
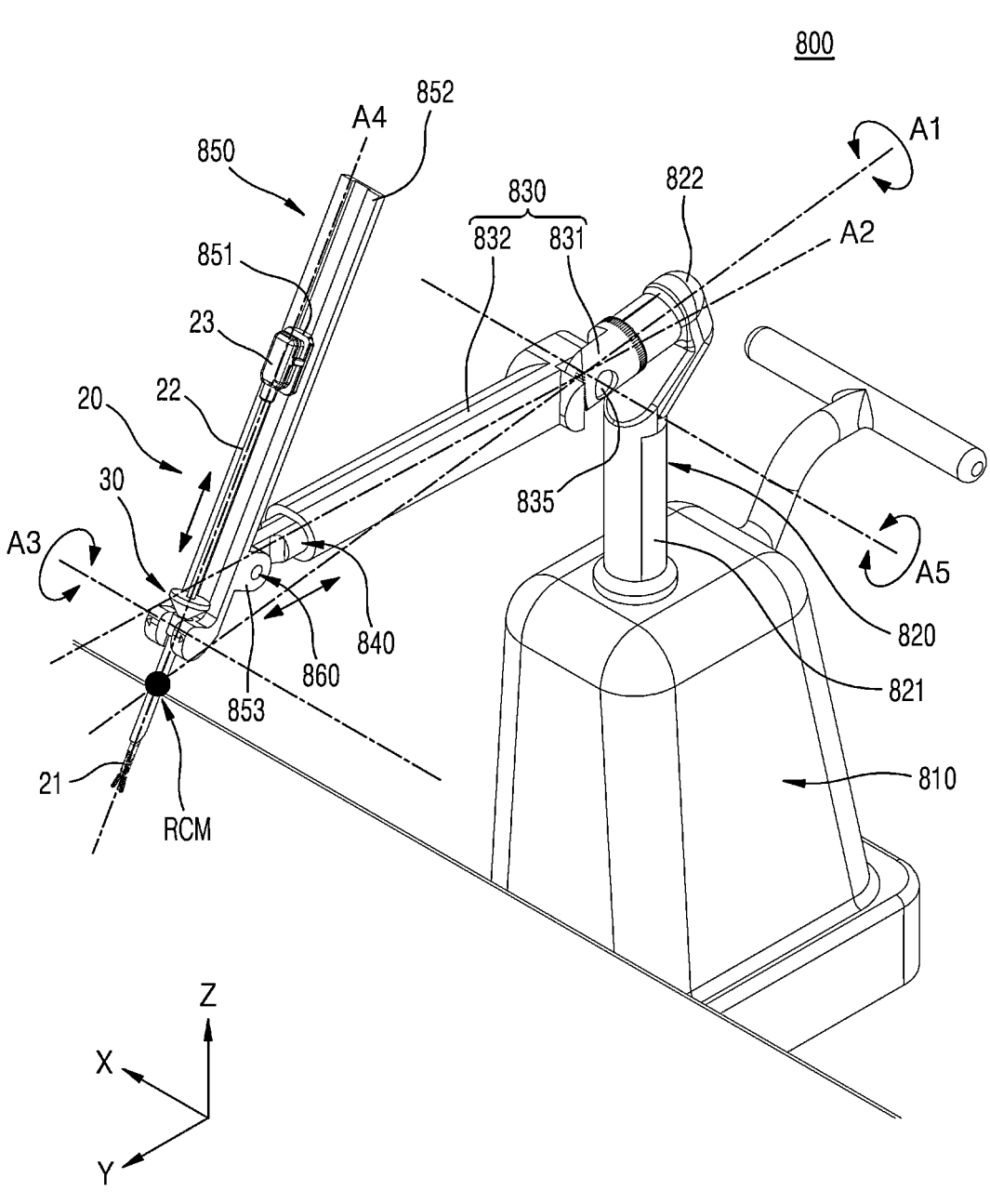
FIG. 36 is a perspective view illustrating an overall structure of a surgical robot arm (800) according to a second-2 embodiment of the present disclosure.
Figure 37:
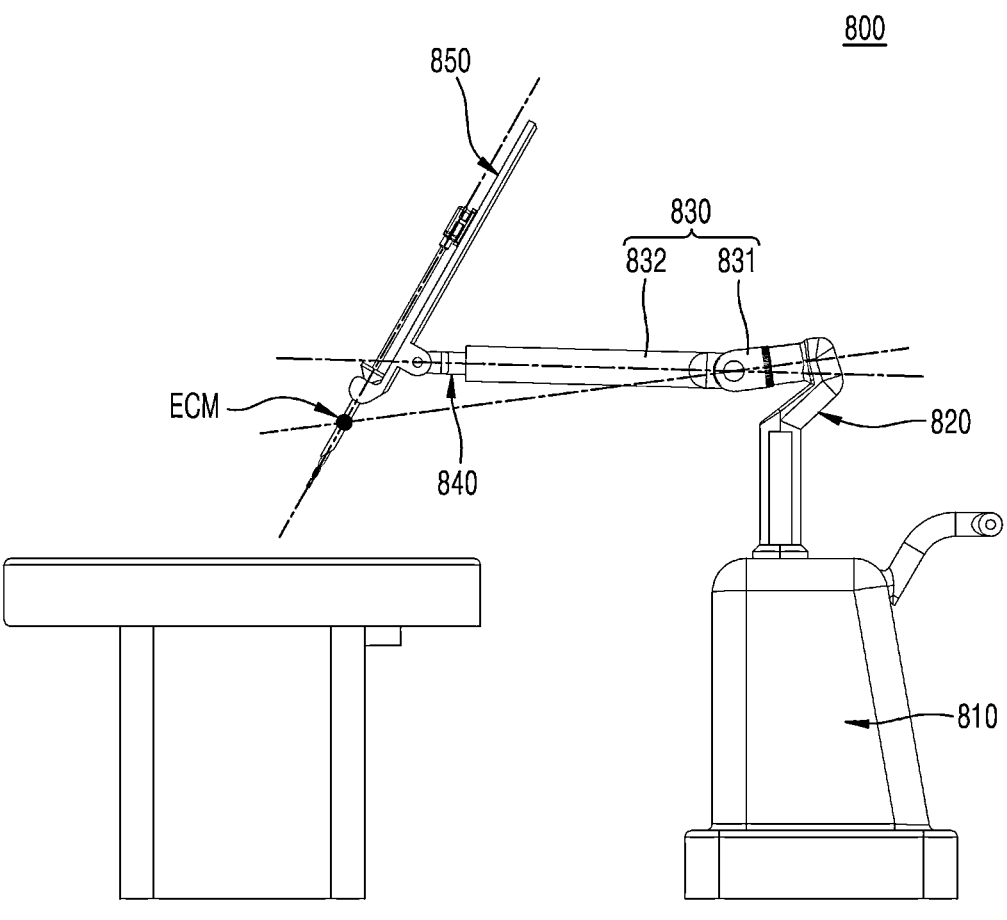
FIG. 37 is a side view of the surgical robot arm of FIG. 36.
Figure 38B:
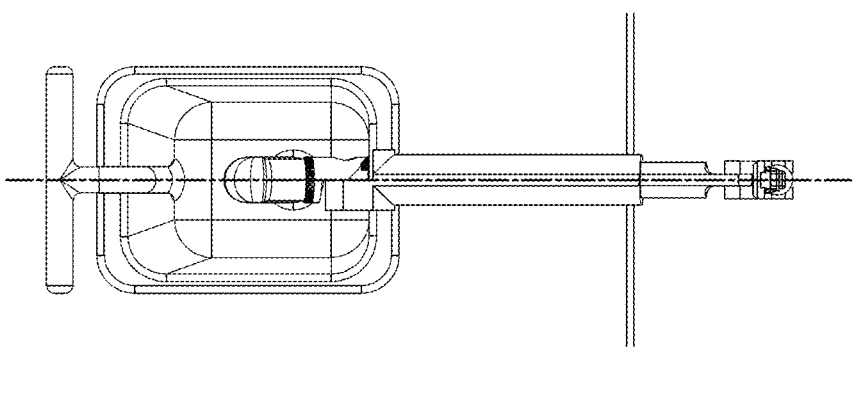
Figure 38A:
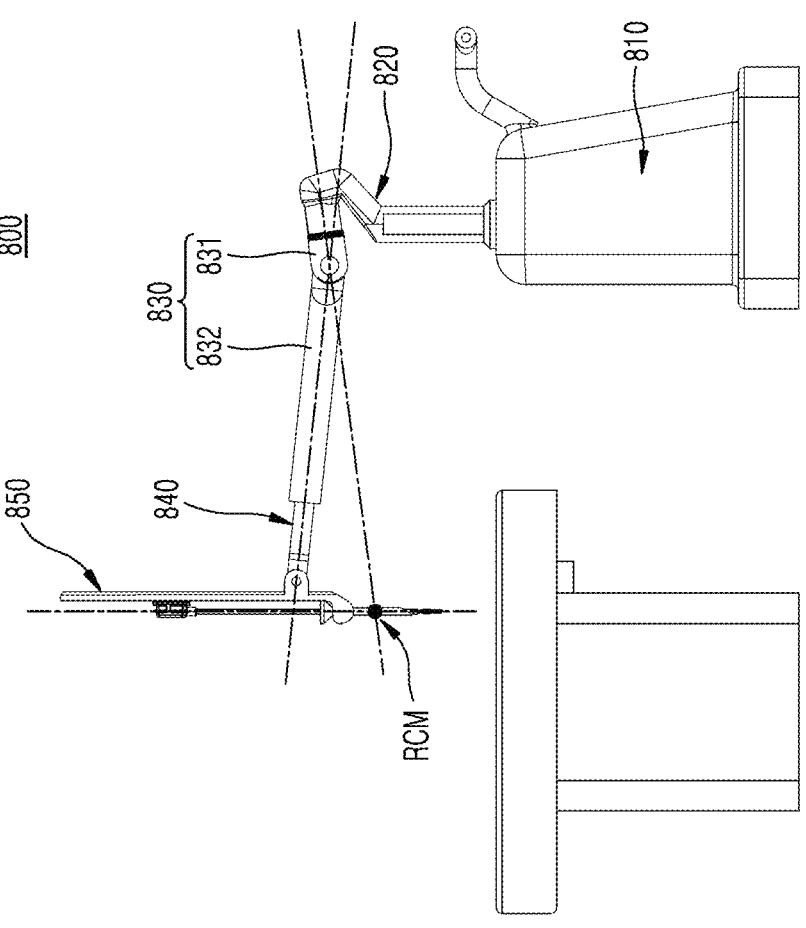
Figure 39B:
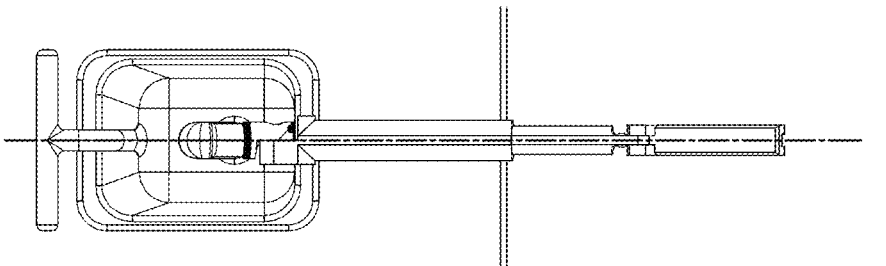
Figure 39A:
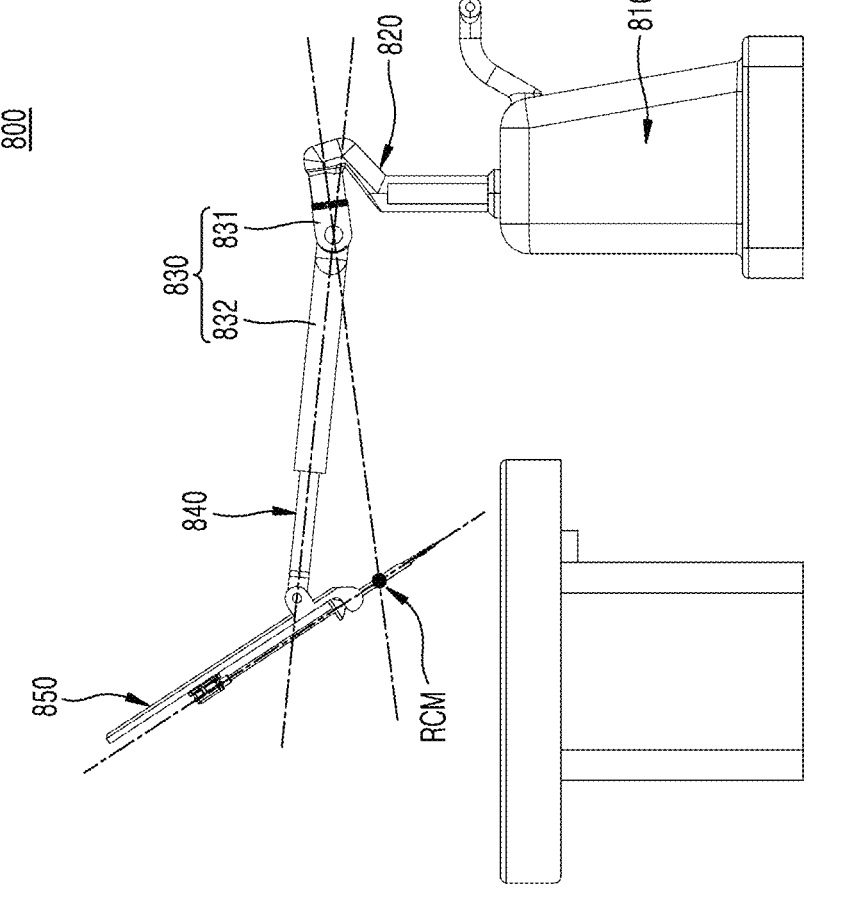
Figures 40A, 40B:
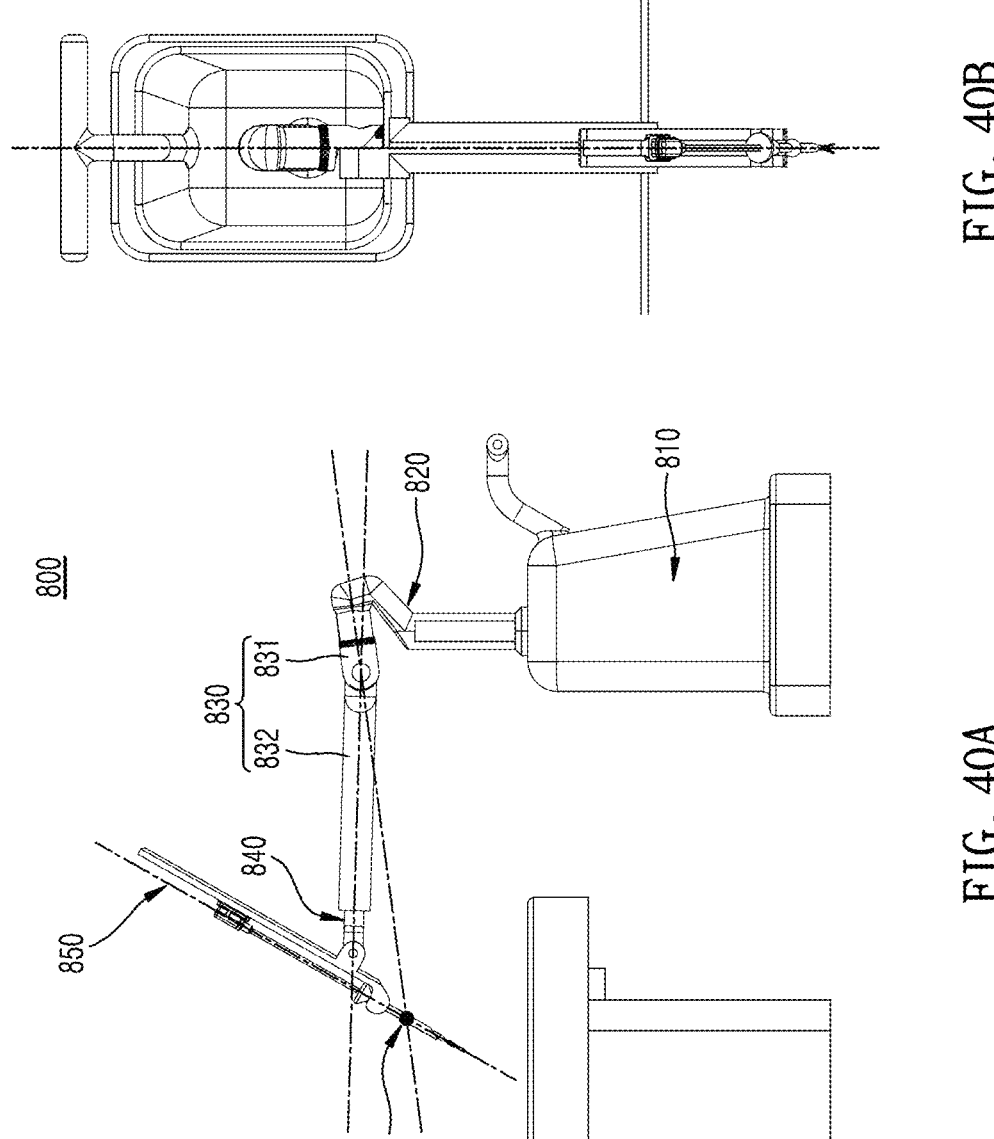
Figure 41:
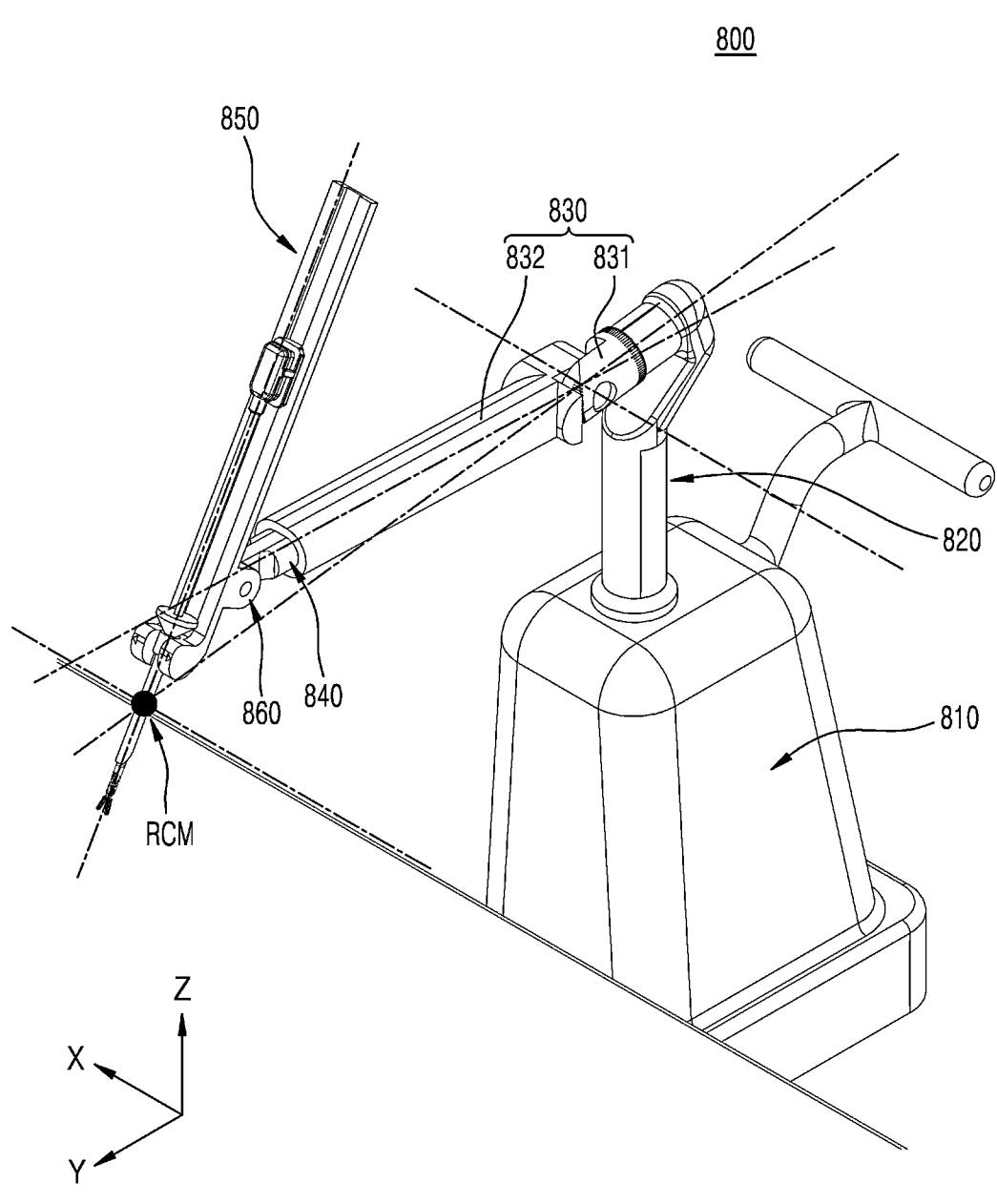
FIGS. 41 to 43 are perspective views illustrating a Y-axis RCM motion (a yaw motion) of the surgical robot arm of FIG. 36.
Figure 42:
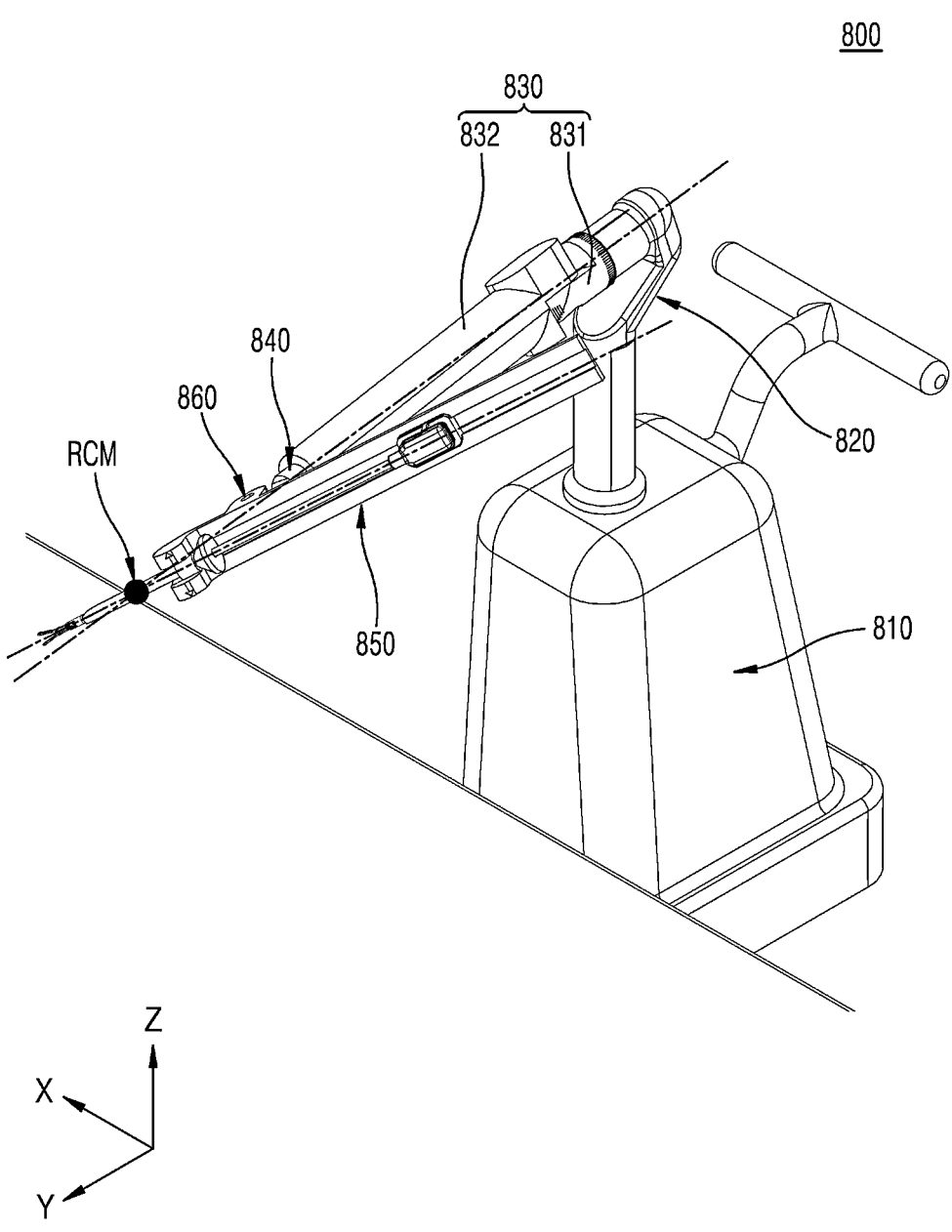
Figure 43:
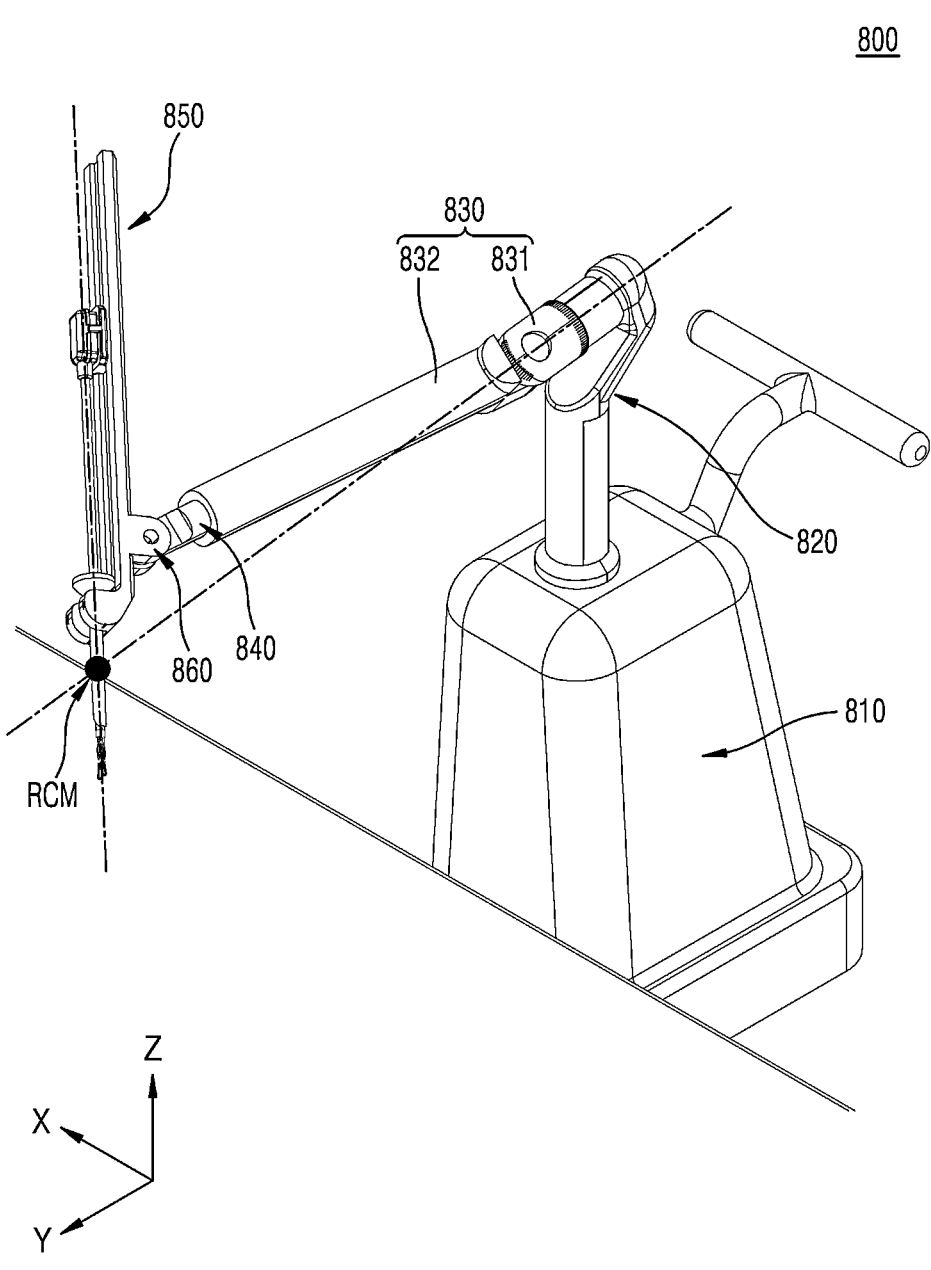
Figure 44B:
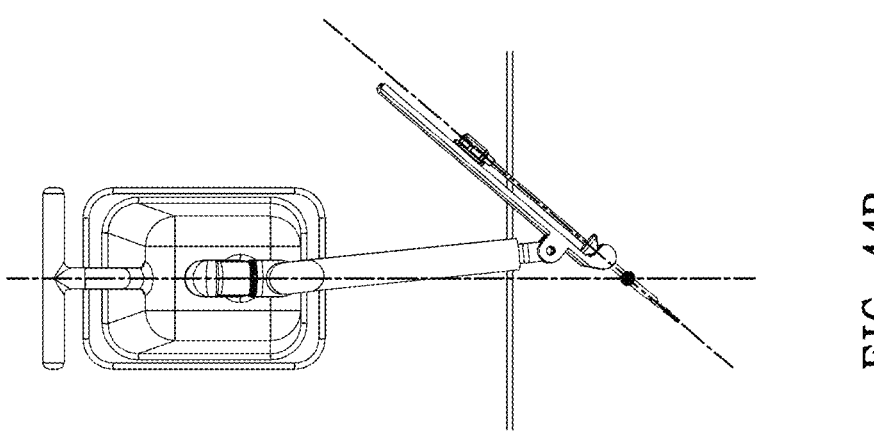
FIGS. 44A and 44B are a side view and a plan view, respectively, illustrating a state in which the surgical robot arm of FIG. 36 lies on its side.
Figure 44A:
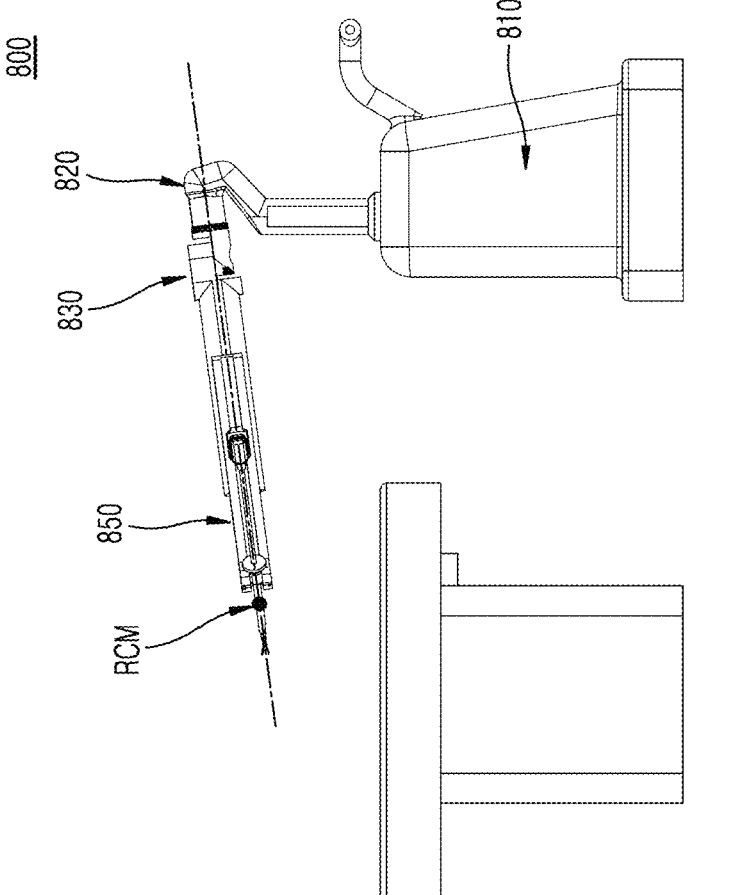

FIG. 36 is a perspective view illustrating the overall structure of the surgical robot arm 800 according to the second-2 embodiment of the present disclosure. FIG. 37 is a side view of the surgical robot arm of FIG. 36. FIGS. 38 to 40 are side views and plan views illustrating an X-axis RCM motion (a pitch motion) of the surgical robot arm of FIG. 36. FIGS. 41 to 43 are perspective views illustrating a Y-axis RCM motion (a yaw motion) of the surgical robot arm of FIG. 36. FIG. 44 is a side view and a plan view illustrating a state in which the surgical robot arm of FIG. 36 lies on its side.

Referring to FIGS. 36 to 44, the surgical robot arm 800 according to the second-2 embodiment of the present disclosure includes a base 810, a base link 820, a first link 830, a second link 840, and an instrument mounting link 850.

The base 810 serves as a base part of the entire surgical robot arm 800. Here, a moving means (not shown) such as wheels may be formed on the lower surface of the base 810 so that the base 810 may serve as a kind of cart. In addition, a position fixing means (not shown) may be further formed on the base 810 so that the position of the base 810 may be fixed during surgery. However, the concept of the present disclosure is not limited thereto, and the base 810 may be formed in a shape that is detachably attachable to a bed, or may be formed in a shape that is detachably attachable a wall.

The base link 820 includes an extension portion 821 and a roll rotation base portion 822. The extension portion 821 may extend in one direction from the base 810. In the drawings, it is illustrated that the extension portion 821 of the base link 820 extends from the base 810 in a Z-axis direction. In other words, one end of the base link 820 is connected to the base 810. In the present embodiment, a case where the base link 820 is fixedly coupled to the base 810 is assumed.

On the other hand, the roll rotation base portion 822 is formed at the other end of the base link 820. The roll rotation base portion 822 may be formed to be inclined to a certain extent so as to have a certain angle with the extension portion 821.

Here, the roll rotation base portion 822 of the base link 820 may be formed in a cylindrical shape with respect to the first axis A1 formed in a first direction. The first link 830 connected to the roll rotation base portion 822 (together with the second link 840, the instrument mounting link 850, and the surgical instrument 20 sequentially connected to the first link 830) may be formed to perform a roll motion around the first axis A1.

Here, the first axis A1 may be formed in an oblique direction that is not parallel to the X-axis/Y-axis/Z-axis. An RCM, which will be described later, may be formed on an extension line of the first axis A1.

The first link 830 may be coupled to the base link 820, and more specifically, to the roll rotation base portion 822 of the base link 820 and may be formed such that the entire first link 830 is rotatable around the first axis A1 of the roll rotation base portion 822. Alternatively, it may be expressed that the first link 830 rolls around the base link 820. In order to implement the rotational motion of the first link 830 with respect to the base link 820, a motor may be provided on either the base link 820 or the first link 830.

On the other hand, the first link 830 may include a first region 831 coupled to the base link 820 and a second region 832 coupled to the second link 840. Here, a central axis of the first region 831 and a central axis of the second region 832 may be defined to form a certain angle with each other. The first region 831 is axially coupled to the second region 832 by a pitch rotation shaft 835 formed in a direction of a fifth axis A5, and thus, the second region 832 is formed to be rotatable around the fifth axis A5 with respect to the first region 831. This is, the second region 832 may be rotatable around the X-axis when viewed from the drawing.

Here, the central axis of the first region 831 may coincide with the first axis A1, and therefore, the RCM may be located on an extension line of the central axis of the first region 831.

Here, when the first link 830 is rotated around the first axis A1, the second link 840, the instrument mounting link 850, and the surgical instrument 20 connected to the first link 830 are rotated together.

As described above, the central axis of the first region 831 and the central axis of the second region 832 may be defined to form a certain angle with each other. That is, a central axis of the first link 830 may coincide with the first axis A1, and therefore, the RCM may be located on an extension line of the central axis of the first region 831. In addition, the central axis of the second region 832 may coincide with the second axis A2 of the second link 840, which will be described later.

On the other hand, in order to implement the rotational motion of the second region 832 with respect to the first region 831, a motor may be provided on either the first region 831 or the second region 832.

The second link 840 may be coupled to the second region 832 of the first link 830 and may perform a linear reciprocating motion in one direction along the second axis A2 with respect to the second region 832 of the first link 830. Here, in the drawings, it is illustrated that the second link 840 performs a linear reciprocating motion in the X-axis direction with respect to the first link 830, but the concept of the present disclosure is not limited thereto, and a linear reciprocating axis of the second link 840 may be variously formed according to the shape and configuration of the links.

In order to implement such a linear motion, a linear actuator (not shown) may be provided on either the first link 830 or the second link 840.

Here, the first axis A1 and the second axis A2 may generally be different axes. Alternatively, even when the first link 830 or the second link 840 is bent to a certain extent and the first axis A1 and the second axis A2 are formed to be parallel to each other, the second axis A2 may be formed so as not to pass through the RCM.

The instrument mounting link 850 may include an instrument mounting portion 851, a guide rail 852, and a second link coupling portion 853.

In detail, while the surgical instrument 20 is mounted on the instrument mounting portion 851, the instrument mounting portion 851 may perform a linear motion along the guide rail 852 formed in the direction of the fourth axis A4. In order to implement such a linear motion, a linear actuator (not shown) may be provided in the instrument mounting portion 851.

Here, the fourth axis A4 may be a direction in which the guide rail 852 is formed, and simultaneously, may be an extension direction of a shaft of the surgical instrument 20 coupled to the instrument mounting link 850.

The surgical instrument 20 is mounted on the instrument mounting portion 851 of the instrument mounting link 850 of the surgical robot arm 800.

Here, although not illustrated in the drawings, an interface part (not shown) coupled to the surgical instrument 20 and configured to control the motion of the surgical instrument 20 may be further formed in the instrument mounting portion 851. The interface part (not shown) may include a component configured to couple with a driving part 23 of the surgical instrument 20, a motor configured to transmit a driving force from the surgical robot arm 800 to the surgical instrument 20, and the like. The interface part (not shown) may allow an end tool 21 of the surgical instrument 20 to perform a pitch, yaw, or actuation motion. Furthermore, the interface part (not shown) may allow the shaft 22 and the end tool 21 of the surgical instrument 20 to perform a roll motion around the fourth axis A4.

On the other hand, a trocar 30 serving as an insertion passage for inserting the surgical instrument 20 into the patient's body may be further provided. While the trocar 30 is inserted into the body, the surgical instrument 20 may be inserted into the patient's body through the trocar 30. An RCM may be formed at a certain position on the trocar 30. As described above, the first axis A1, which is the roll rotation axis of the first link 830, may be formed to pass through the RCM.

In addition, the surgical instrument 20 may further include the driving part 23. A component configured to couple with the interface part (not shown) and a driving wheel operated in engagement with the motor may be formed in the driving part 23. As such, a coupling means and a driving transmission means may be respectively formed in the interface part (not shown) and the driving part 23 to correspond to each other. Accordingly, the surgical instrument 20 is operated by receiving a driving force from the surgical robot arm 800 in a state of being mounted on the instrument mounting link 850.

On the other hand, the second link coupling portion 853 may be formed to protrude to a certain extent from the instrument mounting link 850 toward the second link 840. The second link coupling portion 853 is axially coupled to the second link 840 by a link rotation shaft 860 coupled in a direction of a third axis A3, and thus, the instrument mounting link 850 is formed to be rotatable around the third axis A3 with respect to the second link 840. This is, the instrument mounting link 850 may be rotatable around the X-axis when viewed from the drawing. In order to implement such a rotational motion, a motor may be provided on either the second link 840 or the instrument mounting link 850.

As such, the coupling portion at which the second link 840 and the instrument mounting link 850 are coupled to each other is not a neck portion of the trocar 30, and are spaced/separated from the trocar 30 to a certain extent and forming the instrument mounting link 850. Accordingly, the operating angle (rotation angle) of the second region 832 with respect to the first region 831 of the first link 830 may increase, thereby obtaining an effect of making it easier to control the RCM motion.

That is, when the operating angle is excessively small, the control has to be performed very finely, making it difficult to implement the control. Therefore, the second link coupling portion 853 is formed to protrude to a certain extent from the instrument mounting link 850 toward the second link 840, and thus, the operating angle (rotation angle) of the second region 832 with respect to the first region 831 of the first link 830 may increase, further facilitating the control for the RCM motion.

That is, in the case of the embodiment illustrated in FIG. 17, etc., the coupling portion at which the second link 340 and the instrument mounting link 350 are coupled to each other is located on the neck portion of the trocar 30 or the linear motion axis of the surgical instrument 20.

In contrast, in the case of the present embodiment illustrated in FIGS. 36 to 44, the coupling portion at which the second link 840 and the instrument mounting link 850 are coupled to each other is not the neck portion of the trocar 30, and is spaced/separated from the trocar 30 to a certain extent and formed in the instrument mounting link 850.

With this configuration, the operating angle (rotation angle) of the second region 832 with respect to the first region 831 of the first link 830 may increase, thereby obtaining an effect of further facilitating the control for the RCM motion.

In the present disclosure, the RCM structure of the surgical robot arm 800 is a structure in which the surgical instrument 20 is mounted on one side of the surgical robot arm 800, and the surgical instrument 20 is operated and controlled to rotate around a certain point RCM on the trocar 30 into which the surgical instrument 20 is inserted. Here, the RCM structure according to the present embodiment is implemented through the electronic control for each link rather than the existing mechanical parallelogram link structure.

Hereinafter, for convenience, the control in the X-axis direction and the control in the Y-axis direction in the drawing are described separately, but it may be stated that the overall control is performed by combining the control in the X-axis direction with the control in the Y-axis direction. In addition, the coordinate system of each component may change relatively due to the rotation and linear motion of each link. However, for convenience, the following description is given based on the X-axis direction and the Y-axis direction of the bed by using the bed as the reference point.

First, the control in the X-axis direction may be implemented by a combination of:

1) the control of the linear motion of the second link 840 with respect to the first link 830, 2) the control of the rotational motion of the instrument mounting link 850 with respect to the second link 840, and 3) the control of the rotational motion of the second region 832 of the first link 830 with respect to the first region 831 of the first link 830.

Since the specific control method thereof is the same as the second embodiment, a detailed description will be omitted.

Next, the RCM control in the Y-axis direction may be implemented by a combination of:

1) the control of the roll rotational motion of the first link 830 around the first link A1, 2) the control of the rotational motion of the instrument mounting link 850 with respect to the second link 840, 3) the control of the linear motion of the second link 840 with respect to the first link 830, and 4) the control of the roll motion of the surgical instrument 20.

Since the specific control method thereof is the same as the second embodiment, a detailed description will be omitted.

In conclusion, from the viewpoint of the degree of freedom of the surgical robot arm 800 itself (excluding the surgical instrument 20), the surgical robot arm 800 according to the second-2 embodiment of the present disclosure may operate with four degrees of freedom of 1) the roll rotational motion of the first link 830 around the first axis A1, 2) the linear motion of the second link 840 with respect to the first link 830, 3) the rotational motion of the instrument mounting link 850 with respect to the second link 840, and 4) the rotational motion of the second region 832 of the first link 830 with respect to the first region 831 of the first link 830. Here, a translation motion of the surgical instrument 20, that is, a linear motion of the surgical instrument 20 in the direction of the fourth axis A4, is also possible through the linear motion of the instrument mounting portion 851 with respect to the guide rail 852 of the instrument mounting link 850.

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm 100 and reducing the driving force required for operation may be obtained. Furthermore, the insertion depth of the trocar 30 is controlled to be constant through the control of the rotational motion of the second region 832 of the first link 830 with respect to the first region 831 of the first link 830, and thus, the risk of the trocar 30 coming out of the abdomen during surgery may be eliminated, thereby further improving safety.

<Third Embodiment of Surgical Robot Arm>

Hereinafter, a surgical robot arm 400 according to a third embodiment of the present disclosure will be described. Here, the surgical robot arm 400 according to the third embodiment of the present disclosure characteristically differs from the surgical robot arm (see 100 of FIG. 4) according to the first embodiment of the present disclosure in terms of an operation of a base link 420 of the robot arm 400. In other words, the surgical robot arm 400 according to the third embodiment of the present disclosure is an embodiment in which the base link 420 is formed to be rotatable with respect to a base 410, compared to the embodiment of FIG. 4. Compared to the first embodiment, the change in configuration will be described in detail later.

Figure 45:
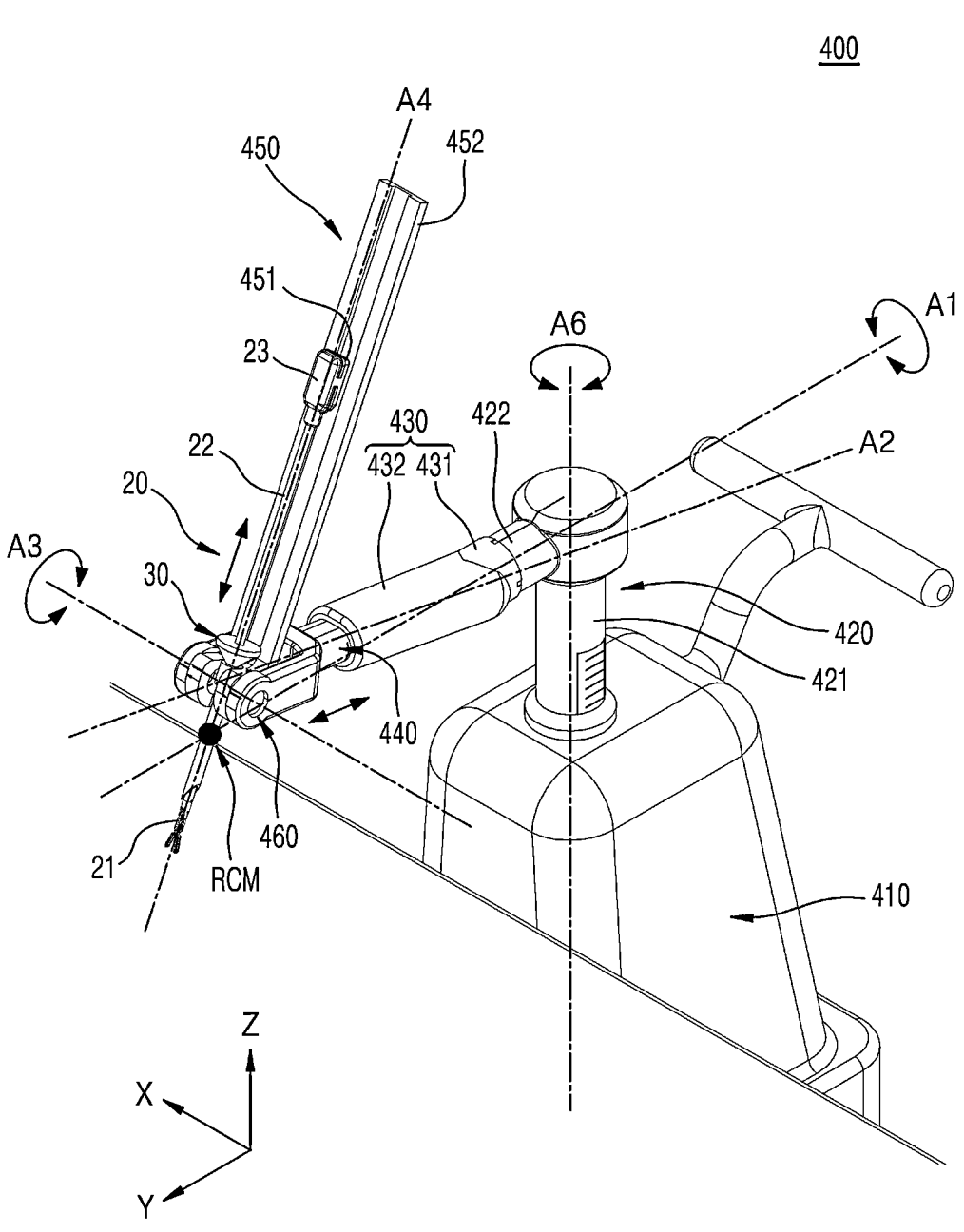
FIG. 45 is a perspective view illustrating an overall structure of a surgical robot arm (400) according to a third embodiment of the present disclosure.
Figure 46:
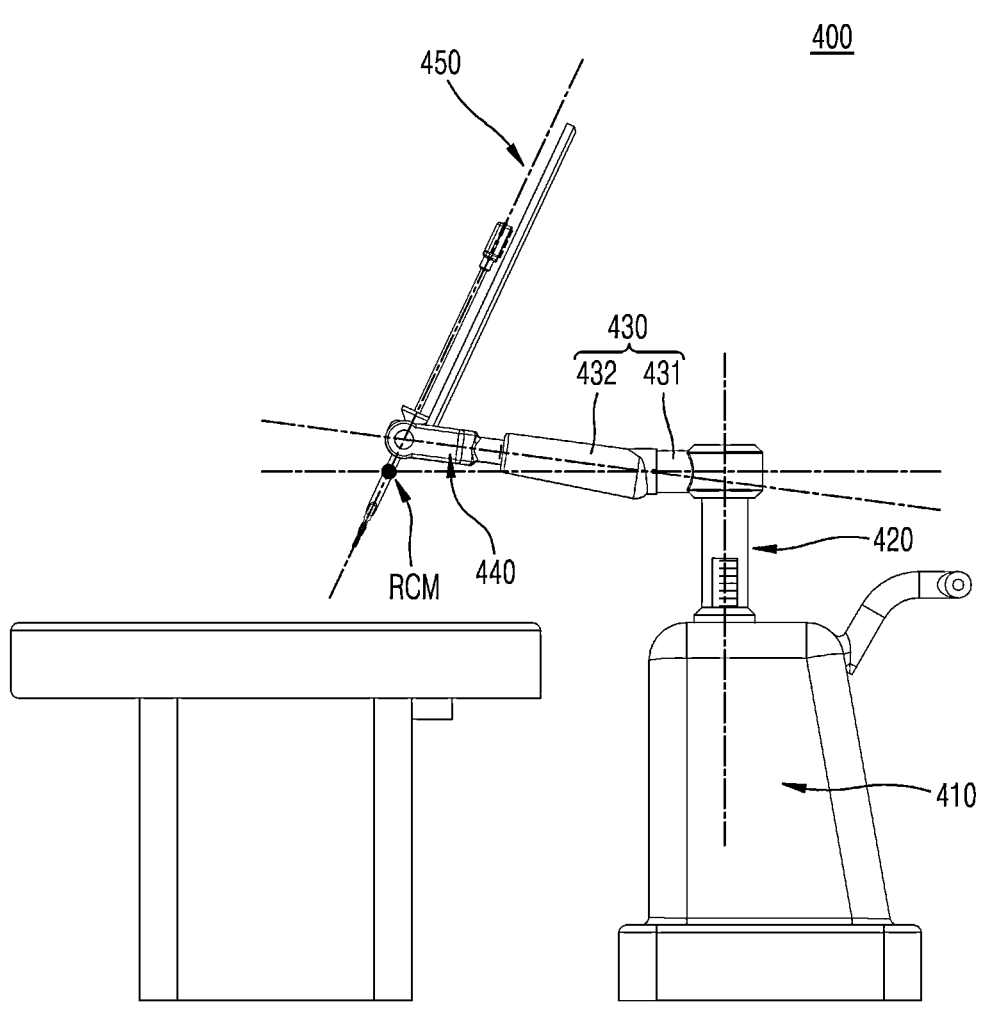
FIG. 46 is a side view of the surgical robot arm of FIG. 45.
Figures 47A, 47B, 47C:
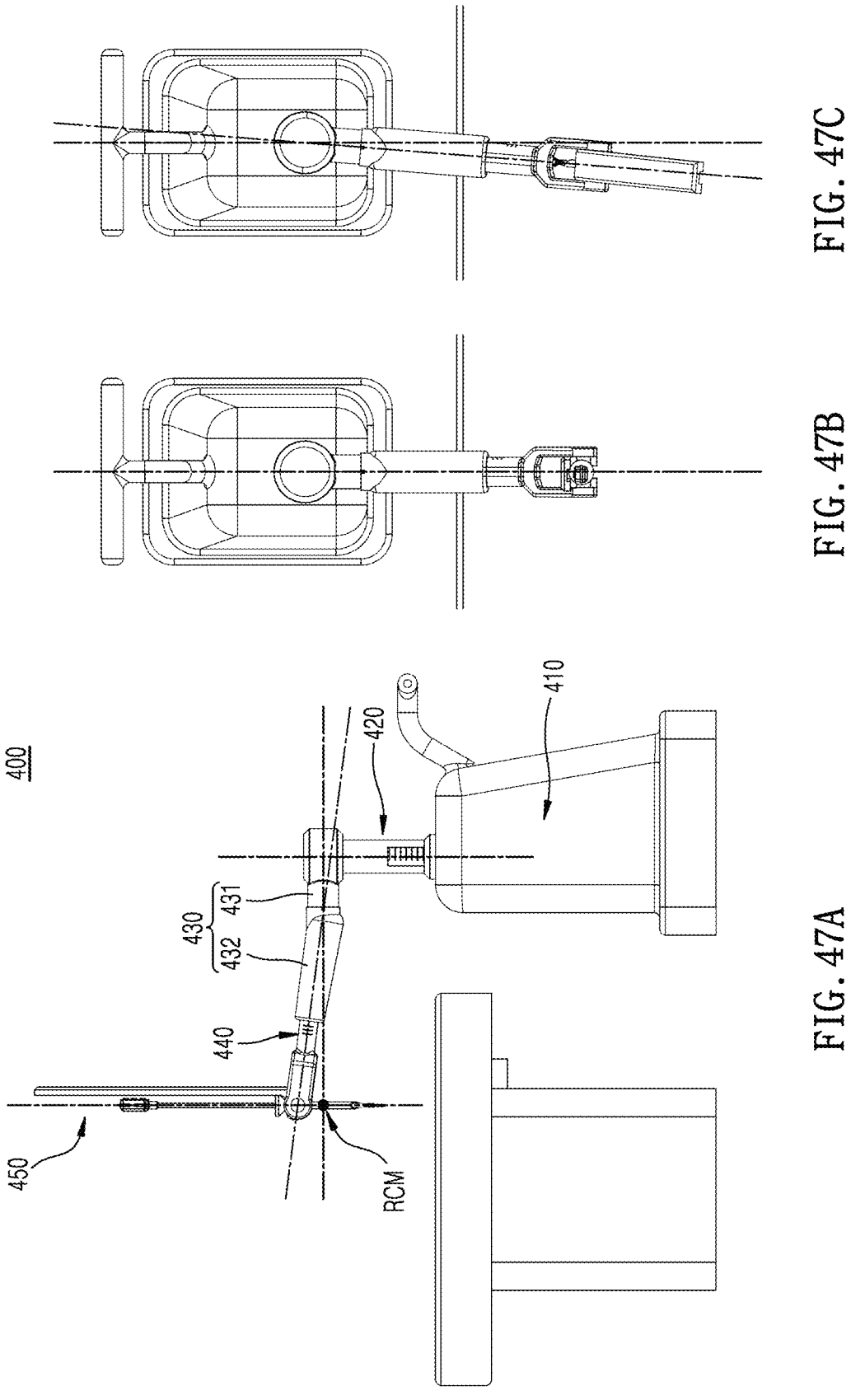
Figures 48A, 48B:
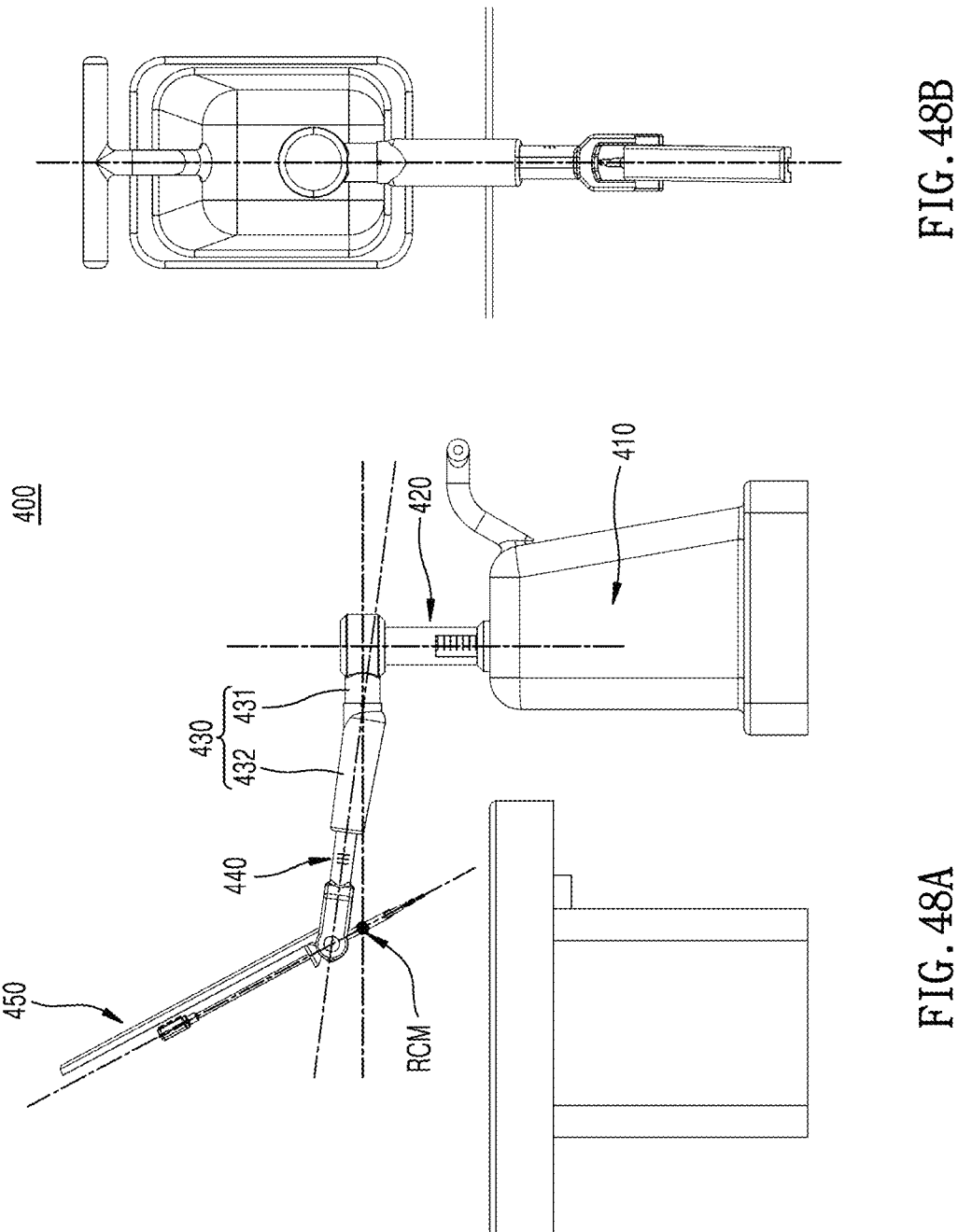
Figures 49A, 49B:
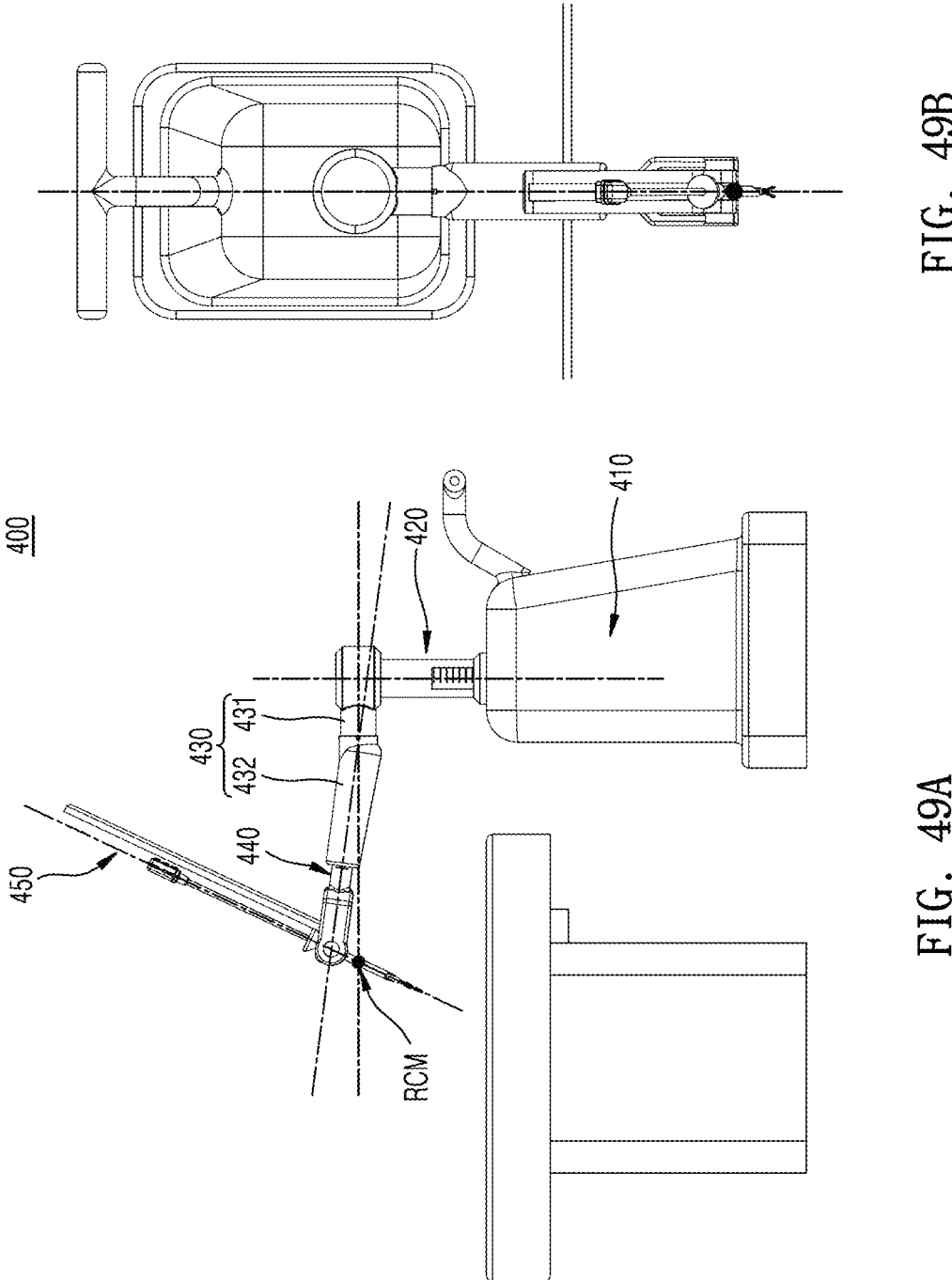
Figure 50:
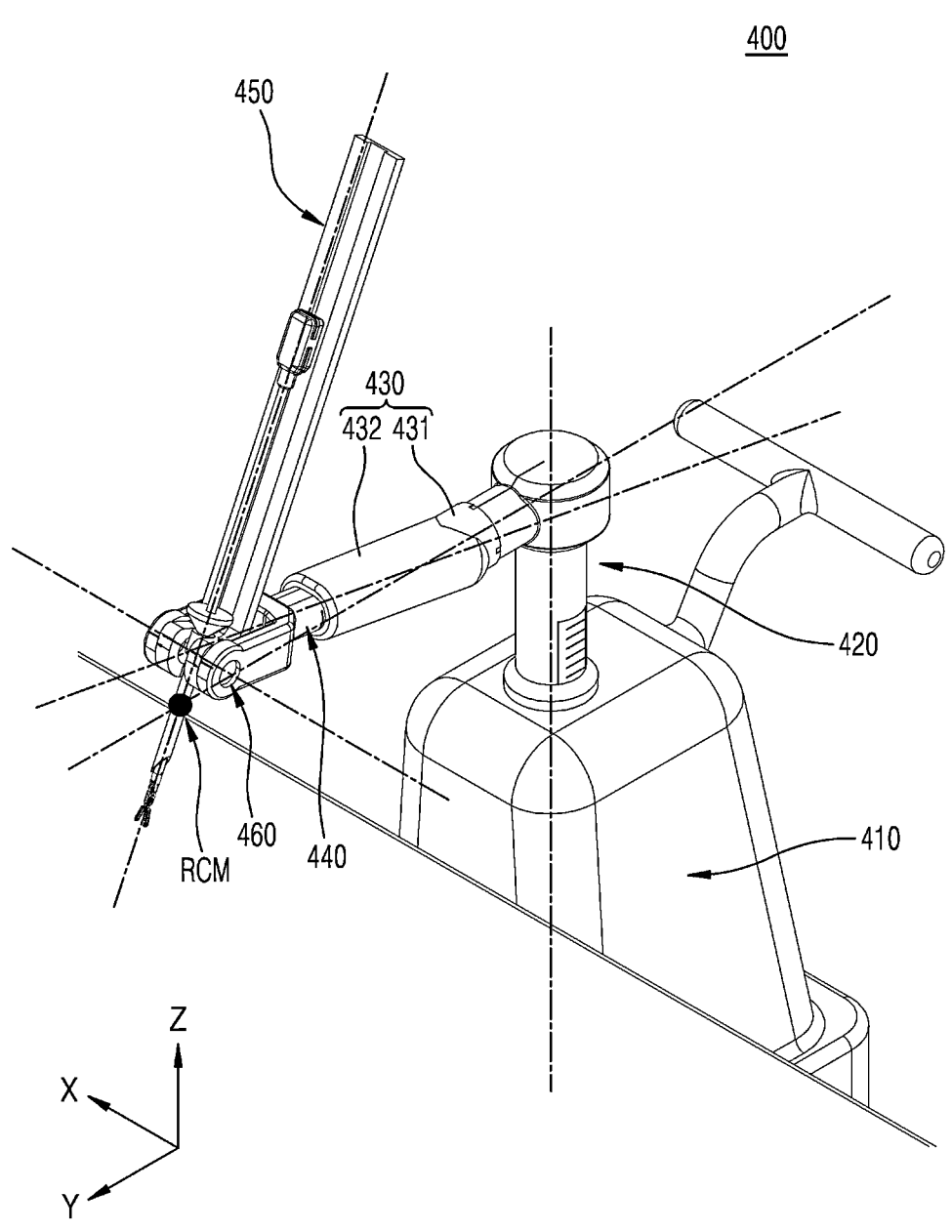
FIGS. 50 to 52 are perspective views illustrating a Y-axis RCM motion (a yaw motion) of the surgical robot arm of FIG. 45.
Figure 51:
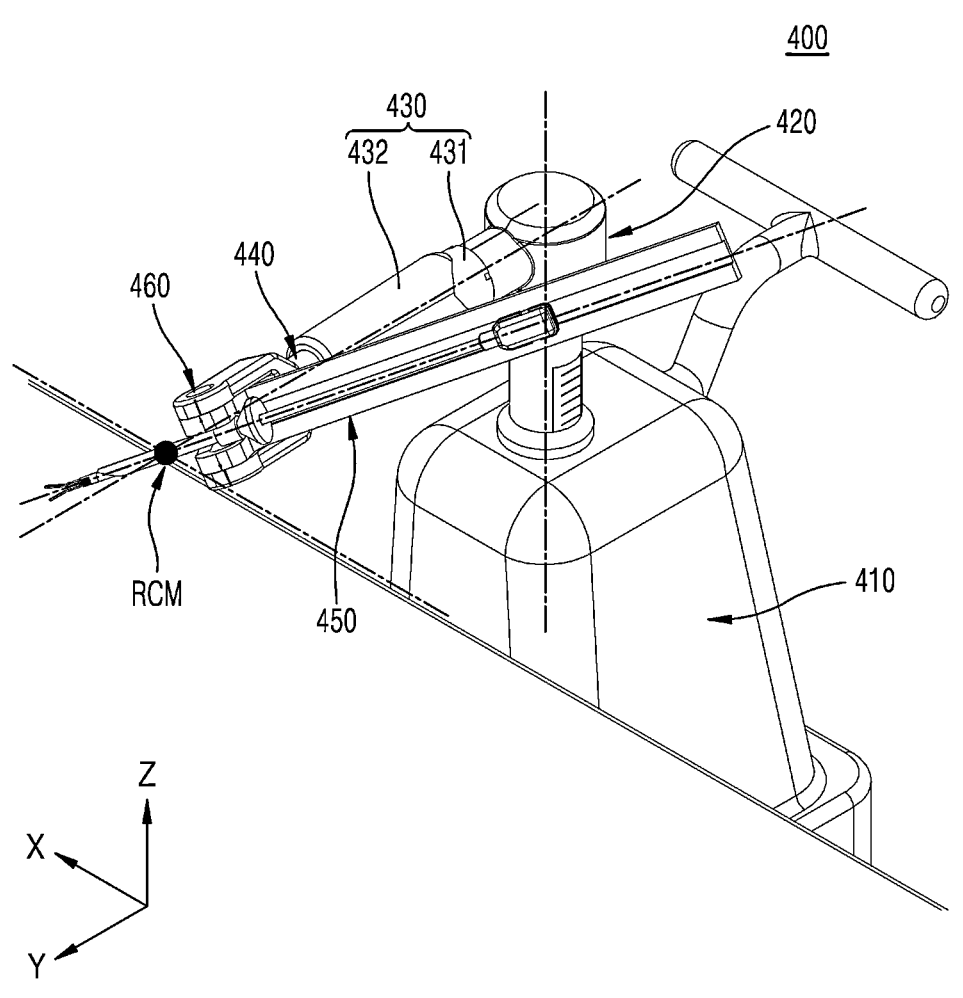
Figure 52:
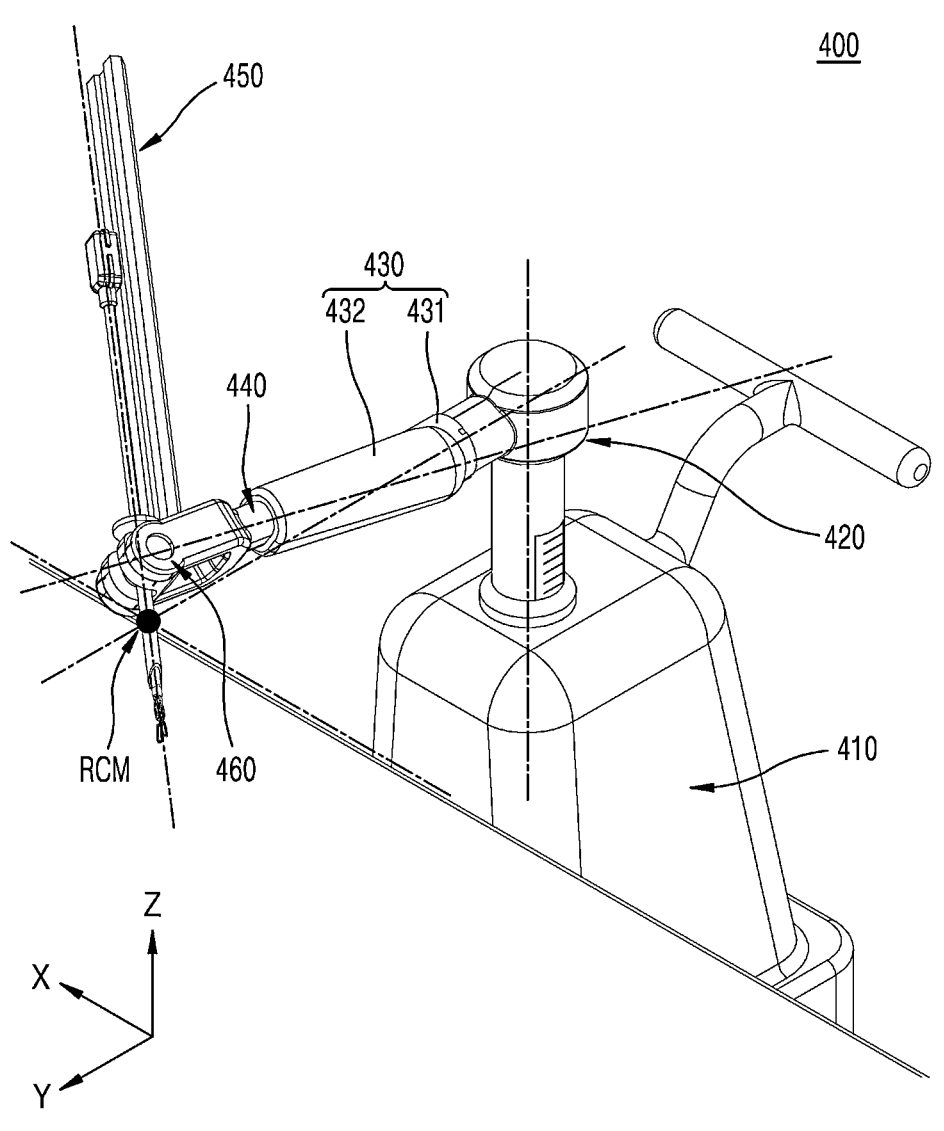
Figures 53A, 53B:
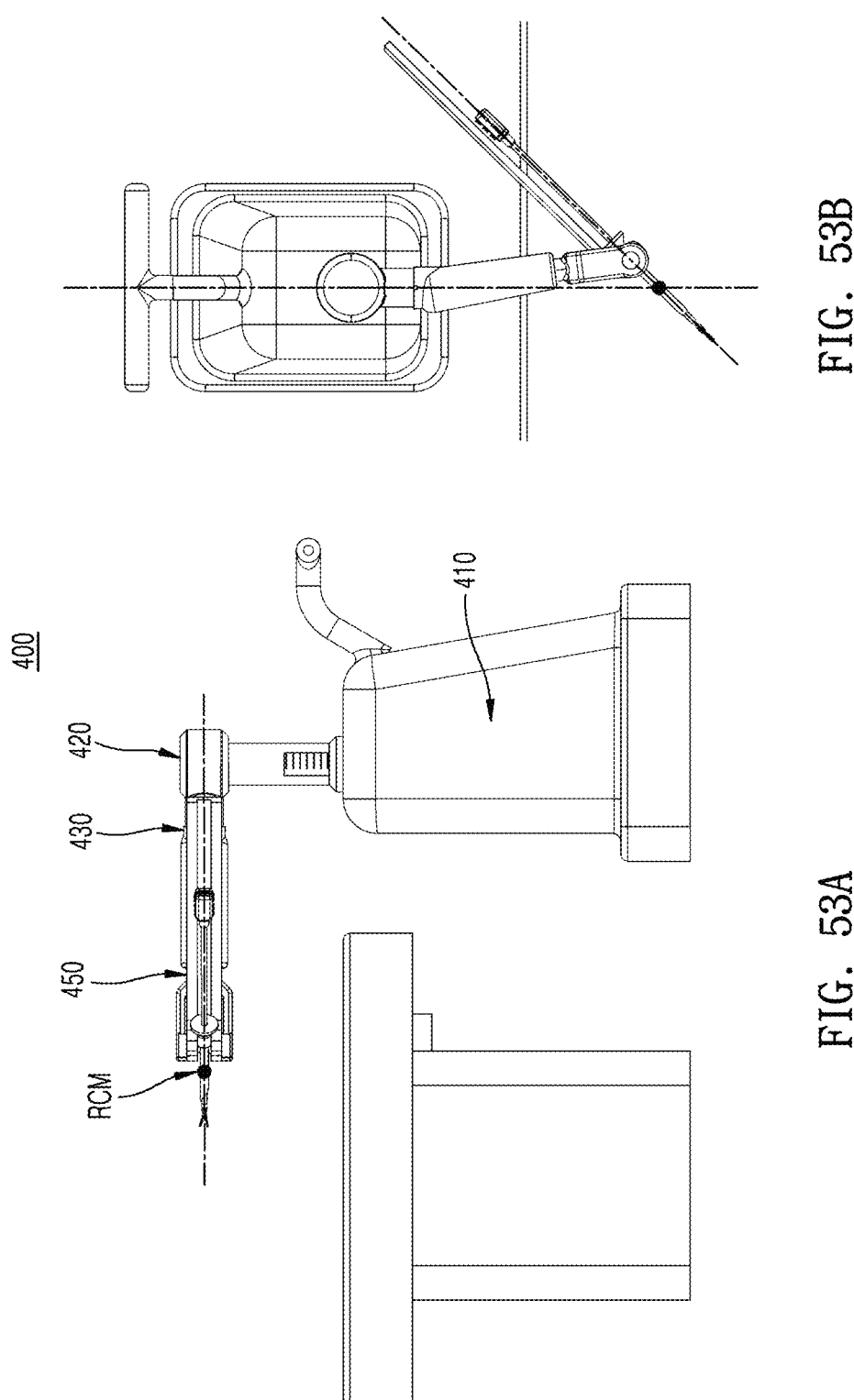
FIGS. 53A and 53B are a side view and a plan view, respectively, illustrating a state in which the surgical robot arm of FIG. 45 lies on its side.

FIG. 45 is a perspective view illustrating the overall structure of the surgical robot arm 400 according to the third embodiment of the present disclosure. FIG. 46 is a side view of the surgical robot arm of FIG. 45. FIGS. 47 to 49 are side views and plan views illustrating an X-axis RCM motion (a pitch motion) of the surgical robot arm of FIG. 45. FIGS. 50 to 52 are perspective views illustrating a Y-axis RCM motion (a yaw motion) of the surgical robot arm of FIG. 45. FIG. 53 is a side view and a plan view illustrating a state in which the surgical robot arm of FIG. 45 lies on its side.

Referring to FIGS. 45 to 53, the surgical robot arm 400 according to the third embodiment of the present disclosure includes a base 410, a base link 420, a first link 430, a second link 440, and an instrument mounting link 450. A trocar 30 and a surgical instrument 20 are coupled to the instrument mounting link 450 of the surgical robot arm 400. This will be described in more detail as follows.

The base 410 serves as a base part of the entire surgical robot arm 400. Here, a moving means (not shown) such as wheels may be formed on the lower surface of the base 410 so that the base 410 may serve as a kind of cart. In addition, a position fixing means (not shown) may be further formed on the base 410 so that the position of the base 410 may be fixed during surgery. However, the concept of the present disclosure is not limited thereto, and the base 410 may be formed in a shape that is detachably attachable to a bed, or may be formed in a shape that is detachably attachable a wall.

The base link 420 includes an extension portion 421 and a roll rotation base portion 422.

The extension portion 421 may extend in one direction from the base 410. In the drawings, it is illustrated that the extension portion 421 of the base link 420 extends from the base 410 in a Z-axis direction.

On the other hand, the roll rotation base portion 422 is formed at the other end of the base link 420. The roll rotation base portion 422 may be formed to be inclined to a certain extent so as to have a certain angle with the extension portion 421.

Here, the roll rotation base portion 422 of the base link 420 may be formed in a cylindrical shape with respect to the first axis A1 formed in a first direction. The first link 430 connected to the roll rotation base portion 422 (and the second link 440, the instrument mounting link 450, and the surgical instrument 20 sequentially connected to the first link 430) may be formed to roll around the first axis A1.

Here, the extension portion 421 of the base link 420 is formed to be rotatable around an axis A6 with respect to the base 410. That is, in the present embodiment, the base link 420 is rotated around the sixth axis A6 with respect to the base 410 in a clockwise direction or a counterclockwise direction.

Here, the rotation of the base link 420 with respect to the base 410 may be performed in a set-up stage of the surgical robot arm 400 before starting surgery. Due to the rotation of the base link 420 with respect to the base 410 in the set-up stage, when the first axis A1, which is the roll rotation axis of the base link 420, is set up not to coincide with the RCM on an XY plane, the base link 420 is rotated with respect to the base 410 in real time even while the surgical robot arm 400 is operating.

In detail, as illustrated in (b) of FIG. 47 and (c) of FIG. 47, the base link 420 may be formed to be rotatable around the sixth axis A6 with respect to the base 410, so that the base link 420 may be located at various positions on the XY plane. With this configuration, in the present embodiment, the RCM motion may be implemented even when the first axis A1, which is the roll rotation axis of the base link 420, does not coincide with the RCM. That is, as illustrated in (b) of FIG. 47 and (c) of FIG. 47, the RCM motion may be implemented no matter where the base link 420 is located on the XY plane.

The first link 430 may be coupled to the base link 420, and more specifically, to the roll rotation base portion 422 of the base link 420 and may be formed such that the entire first link 430 is rotatable around the first axis A1 of the roll rotation base portion 422. Alternatively, it may be expressed that the first link 430 rolls around the base link 420. In order to implement the rotational motion of the first link 430 with respect to the base link 420, a motor may be provided on either the base link 420 or the first link 430.

On the other hand, the first link 430 may include the first region 431 coupled to the base link 420 and the second region 432 coupled to the second link 440. Here, a central axis of the first region 431 and a central axis of the second region 432 may be defined to form a certain angle with each other.

In this case, the central axis of the first region 431 may coincide with the first axis A1, and therefore, the RCM may be located on an extension line of the central axis of the first region 431.

In the drawings, it is illustrated that the first link 430 includes two parts, that is, the first region 431 and the second region 432, and the first region 431 and the second region 432 each having a straight-line shape form a certain angle with each other. However, the concept of the present disclosure is not limited thereto. The first link 430 may be divided into two or more regions, each of which may be gently curved. In addition, in the present embodiment, it is illustrated that the first region 431 is integrally formed with the second region 432, but the first region 431 and the second region 432 may also be formed as separate members and coupled together.

Here, when the first link 430 is rotated around the first axis A1, the second link 440, the instrument mounting link 450, and the surgical instrument 20 connected to the first link 430 are rotated together. Due to this, the coordinate systems of the second link 440 and the instrument mounting link 450 are not fixed, but relatively continuously change according to the rotation of the first link 430. That is, FIG. 4, etc. illustrates that the second link 440 is parallel to the Y-axis and the instrument mounting link 450 is parallel to the Z-axis. However, when the first link 430 is rotated, the coordinate systems of the second link 440 and the instrument mounting link 450 are also rotated together. However, in the present specification, for convenience of explanation, the following description is given based on the state in which the second link 440 is located parallel to the Y-axis and the instrument mounting link 450 is located parallel to the Z-axis, as illustrated in FIG. 4, unless otherwise stated.

Similarly, when the second link 440 is moved linearly, the instrument mounting link 450 and the surgical instrument 20 is moved linearly together. Due to this, the coordinate systems of the instrument mounting link 450 and the surgical instrument 20 are not fixed and relatively continuously change according to the linear motion of the second link 440.

Similarly, when the instrument mounting link 450 is rotated, the surgical instrument 20 is rotated together. Due to this, the coordinate system of the surgical instrument 20 is not fixed and relatively continuously changes according to the rotation of the instrument mounting link 450.

The second link 440 may be coupled to the first link 430 and may perform a linear reciprocating motion in one direction along the second axis A2 with respect to the first link 430. Here, in the drawings, it is illustrated that the second link 440 performs a linear reciprocating motion in the X-axis direction with respect to the first link 430, but the concept of the present disclosure is not limited thereto, and a linear reciprocating axis of the second link 440 may be variously formed according to the shape and configuration of the links.

In order to implement such a linear motion, a linear actuator (not shown) may be provided on either the first link 430 or the second link 440.

Here, the first axis A1 and the second axis A2 may generally be different axes. Alternatively, even when the first link 430 or the second link 440 is bent to a certain extent and the first axis A1 and the second axis A2 are formed to be parallel to each other, the second axis A2 may be formed so as not to pass through the RCM.

The instrument mounting link 450 is axially coupled to the second link 440 by the link rotation shaft 460 coupled in a direction of a third axis A3, and thus, the instrument mounting link 450 is formed to be rotatable around the third axis A3 with respect to the second link 440. This is, the instrument mounting link 450 may be rotatable around the X-axis when viewed from the drawing.

In order to implement such a rotational motion, a motor may be provided on either the second link 440 or the instrument mounting link 450.

On the other hand, an instrument mounting portion 451 and a guide rail 452 may be formed in the instrument mounting link 450. While the surgical instrument 20 is mounted on the instrument mounting portion 451, the instrument mounting portion 451 may perform a linear motion along the guide rail 452 formed in a direction of a fourth axis A4. In order to implement such a linear motion, a linear actuator (not shown) may be provided in the instrument mounting portion 451.

Here, the fourth axis A4 may be a direction in which the guide rail 452 is formed, and simultaneously, may be an extension direction of a shaft 22 of the surgical instrument 20 coupled to the instrument mounting link 450.

The surgical instrument 20 is mounted on the instrument mounting portion 451 of the instrument mounting link 450 of the surgical robot arm 400.

Here, although not illustrated in the drawings, an interface part (not shown) coupled to the surgical instrument 20 and configured to control the motion of the surgical instrument 20 may be further formed in the instrument mounting portion 451. The interface part (not shown) may include a component configured to couple with a driving part 23 of the surgical instrument 20, a motor configured to transmit a driving force from the surgical robot arm 400 to the surgical instrument 20, and the like. The interface part (not shown) may allow an end tool 21 of the surgical instrument 20 to perform a pitch, yaw, or actuation motion. Furthermore, the interface part (not shown) may allow the shaft 22 and the end tool 21 of the surgical instrument 20 to perform a roll motion around the fourth axis A4.

On the other hand, the trocar 30, which serves as an insertion passage for inserting the surgical instrument 20 into the patient's body, may be coupled to the instrument mounting link 450. While the trocar 30 is inserted into the body, the surgical instrument 20 may be inserted into the patient's body through the trocar 30. An RCM may be formed at a certain position on the trocar 30. As described above, the first axis A1, which is the roll rotation axis of the first link 430, may be formed to pass through the RCM.

In addition, the surgical instrument 20 may further include the driving part 23. A component configured to couple with the interface part (not shown) and a driving wheel operated in engagement with the motor may be formed in the driving part 23. As such, a coupling means and a driving transmission means may be respectively formed in the interface part (not shown) and the driving part 23 to correspond to each other. Accordingly, the surgical instrument 20 is operated by receiving a driving force from the surgical robot arm 400 in a state of being mounted on the instrument mounting link 450.

In the present disclosure, the RCM structure of the surgical robot arm 400 is a structure in which the surgical instrument 20 is mounted on one side of the surgical robot arm 400, and the surgical instrument 20 is operated and controlled to rotate around a certain point RCM on the trocar 30 into which the surgical instrument 20 is inserted. Here, the RCM structure according to the present embodiment is implemented through the electronic control for each link rather than the existing mechanical parallelogram link structure.

In particular, the difference between the present embodiment and the previous embodiments is that the RCM motion is possible even when the RCM and the rotation axis A1 of the base link 420 are spaced apart from each other without meeting each other, and thus, the initial setting of the surgical robot arm is simplified. That is, the RCM motion is possible even when the RCM and the base link 420 are spaced apart from each other to a certain extent on the XY plane.

That is, as illustrated in (b) of FIG. 47 and (c) of FIG. 47, the RCM motion is possible even when the first axis A1, which is the roll rotation axis of the first link 430, is not arranged to pass through the RCM. This is enabled by the rotation of the base link 420 with respect to the base 410, which is an additional degree of freedom given in the present embodiment. That is, the surgical robot arm 400 of the present embodiment has a total of five degrees of freedom. Due to the motion of the five degrees of freedom, the RCM motion is possible even when the first axis A1 does not pass through the RCM on the XY plane.

Hereinafter, for convenience, the control in the X-axis direction and the control in the Y-axis direction in the drawing are described separately, but it may be stated that the overall control is performed by combining the control in the X-axis direction with the control in the Y-axis direction. In addition, the coordinate system of each component may change relatively due to the rotation and linear motion of each link. However, for convenience, the following description is given based on the X-axis direction and the Y-axis direction of the bed by using the bed as the reference point.

This will be described in more detail as follows.

First, the control in the X-axis direction may be implemented by a combination of:
  1) the control of the linear motion of the second link 440 with respect to the first link 430,
  2) the control of the rotational motion of the instrument mounting link 450 with respect to the second link 440, and
  3) the control of the linear motion of the instrument mounting portion 451 with respect to the guide rail 452 of the instrument mounting link 450.

In detail, in order to control the rotational motion of the surgical instrument 20 around the X-axis, the second link 440 first performs a linear motion along the second axis A2 with respect to the first link 430. At the same time, an RCM motion is performed by controlling the instrument mounting link 450 to perform a rotational motion around a third axis A3 with respect to the second link 440. Accordingly, even when the links are moved, the RCM maintains a position thereof.

In addition, even when the surgical instrument 20 performs a rotational motion around the X-axis, the insertion depth (see LE of FIG. 6) of the instrument should not change. Accordingly, the insertion depth (see LE of FIG. 6) of the instrument may be maintained constant by linearly moving the instrument mounting portion 451 (and the surgical instrument 20 coupled thereto) along the guide rail 452 formed along the fourth axis A4.

To explain this from another viewpoint, the length (see L2 of FIG. 9) from the inlet portion (see 31 of FIG. 9) of the trocar 30 to the RCM when the second link 440 performs a linear motion with respect to the first link 430 and is withdrawn from the first link 430 (see FIG. 48) or is inserted into the first link 430 (see FIG. 49) becomes longer than the length (see L1 of FIG. 9) from the inlet portion (see 31 of FIG. 9) of the trocar 30 to the RCM when the surgical instrument 20 is perpendicular to the Z-axis. In contrast, at this time, the distance from the outlet portion (see 32 of FIG. 9) of the trocar 30 to the RCM becomes shorter. Therefore, when the surgical instrument 20 is moved together with the trocar 30, the trocar 30 and the surgical instrument 20 therein are moved relatively in an exiting direction from the inside of the human body to the outside.

In this case, in order to ensure that at least the insertion depth (see of LE of FIG. 6) of the surgical instrument 20 into the patient's body is maintained constant, the distance from the end of the end tool 21 to the RCM is maintained constant by linearly moving the instrument mounting portion 451 (and the surgical instrument 20 coupled thereto) along the guide rail 452 in the direction of insertion into the human body.

As such, even when the links are moved, the RCM in the X-axis direction maintains a position thereof by performing a combination of 1) the control of the linear motion of the second link 440 with respect to the first link 430, 2) the control of the rotational motion of the instrument mounting link 450 with respect to the second link 440, and 3) the control of the linear motion of the instrument mounting portion 451 with respect to the guide rail 452 of the instrument mounting link 150.

Of course, strictly speaking, the RCM of the surgical robot arm 400 itself may be implemented only by 1) the control of the linear motion of the second link 440 with respect to the first link 430 and 2) the control of the rotational motion of the instrument mounting link 450 with respect to the second link 440. However, during actual surgery, the RCM of the surgical robot arm 400 itself has to be maintained and the insertion depth of the surgical instrument 20 into the human body has also to be maintained constant. Therefore, the control of the linear motion of the instrument mounting portion 451 with respect to the guide rail 452 of the instrument mounting link 450 is also performed together.

Next, the RCM control in the Y-axis direction may be implemented by a combination of:

1) the control of the roll rotational motion of the first link 430 around the first link A1, 2) the control of the rotational motion of the instrument mounting link 450 with respect to the second link 440, 3) the control of the linear motion of the second link 440 with respect to the first link 430, 4) the control of the roll motion of the surgical instrument 20, and 5) the control of the rotational motion of the base link 420 with respect to the base 410.

In detail, in order to control the rotational motion of the surgical instrument 20 around the Y axis, the first link 430 first performs a roll rotational motion around the first axis A1. The first link 430, and the second link 440, the instrument mounting link 450, and the surgical instrument 20, which are sequentially connected to the first link 430, may perform a roll motion around the first axis A1.

In this case, since the first axis A1, which is the rotation axis of the first link 430, and the Y-axis do not coincide with each other and are formed to be oblique, unintended motions are mixed when only the first link 430 is rotated. That is, as illustrated in the drawings, when the first link 430 is rotated, the second link 440, the instrument mounting link 450, and the surgical instrument 20 perform a kind of rolling.

In order to compensate for this, with the rotation of the first link 430, the instrument mounting link 450 is controlled to perform a rotational motion around the link rotation shaft 460 with respect to the second link 440, and simultaneously, the second link 440 is controlled to perform a linear motion with respect to the first link 430. In addition, at the same time, the RCM motion is performed by controlling the base link 420 to perform a rotational motion around the axis A6 with respect to the base 410. That is, even when the links are moved, the RCM maintains a position thereof.

In addition, the shaft 22 and the end tool 21 of the surgical instrument 20 are controlled to perform a roll motion around the fourth axis A4, so that the end tool 21 may also be compensated to maintain a posture thereof, regardless of the rotation of the first link 430.

As such, even when the links are moved, the RCM in the Y-axis direction maintains a position thereof by performing a combination of 1) the control of the roll rotational motion of the first link 430 around the first link A1, 2) the control of the rotational motion of the instrument mounting link 450 with respect to the second link 440, 3) the control of the linear motion of the second link 440 with respect to the first link 430, 4) the control of the roll motion of the surgical instrument 20, and 5) the control of the rotational motion of the base link 420 with respect to the base 410.

In conclusion, from the viewpoint of the degree of freedom of the surgical robot arm 400 itself (excluding the surgical instrument 20), the surgical robot arm 400 according to the third embodiment of the present disclosure may operate with five degrees of freedom of: 1) the roll rotational motion of the first link 430 around the first axis A1, 2) the linear motion of the second link 440 with respect to the first link 430, 3) the rotational motion of the instrument mounting link 450 with respect to the second link 440, 4) the linear motion of the instrument mounting portion 451 with respect to the guide rail 452 of the instrument mounting link 450; and 5) the rotational motion of the base link 420 with respect to the base 410.

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm 400 and reducing the driving force required for operation may be obtained.

<Fourth Embodiment of Surgical Robot Arm>

Hereinafter, a surgical robot arm 600 according to a fourth embodiment of the present disclosure will be described. Here, the surgical robot arm 600 according to the fourth embodiment of the present disclosure characteristically differs from the surgical robot arm (see 100 of FIG. 4) according to the first embodiment of the present disclosure in terms of a configuration of a first link 630 of the robot arm 600 and an operation of a base link 620 of the robot arm 600. In other words, compared to the embodiment of FIG. 4, the robot arm 600 according to the fourth embodiment of the present disclosure is an embodiment in which a first region 631 and a second region 632 of the first link 630 are formed to be rotatable around a pitch rotation shaft 635 with respect to each other. Furthermore, the surgical robot arm 600 according to the fourth embodiment of the present disclosure is an embodiment in which the base link 620 is formed to be rotatable with respect to a base 610, compared to the embodiment of FIG. 4. Compared to the first embodiment, the change in configuration will be described in detail later.

Figure 54:
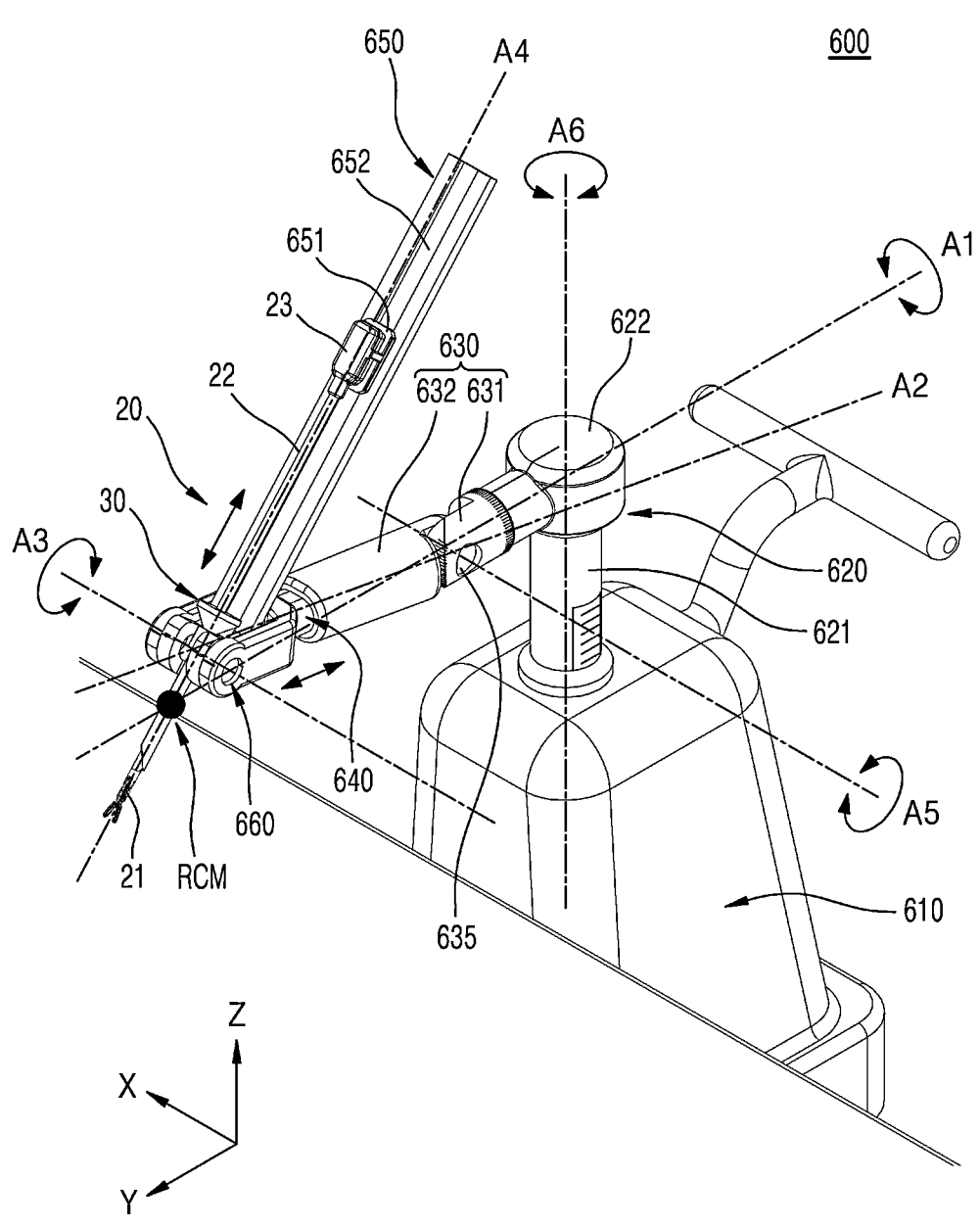
FIG. 54 is a perspective view illustrating an overall structure of a surgical robot arm (600) according to a fourth embodiment of the present disclosure.
Figure 55:
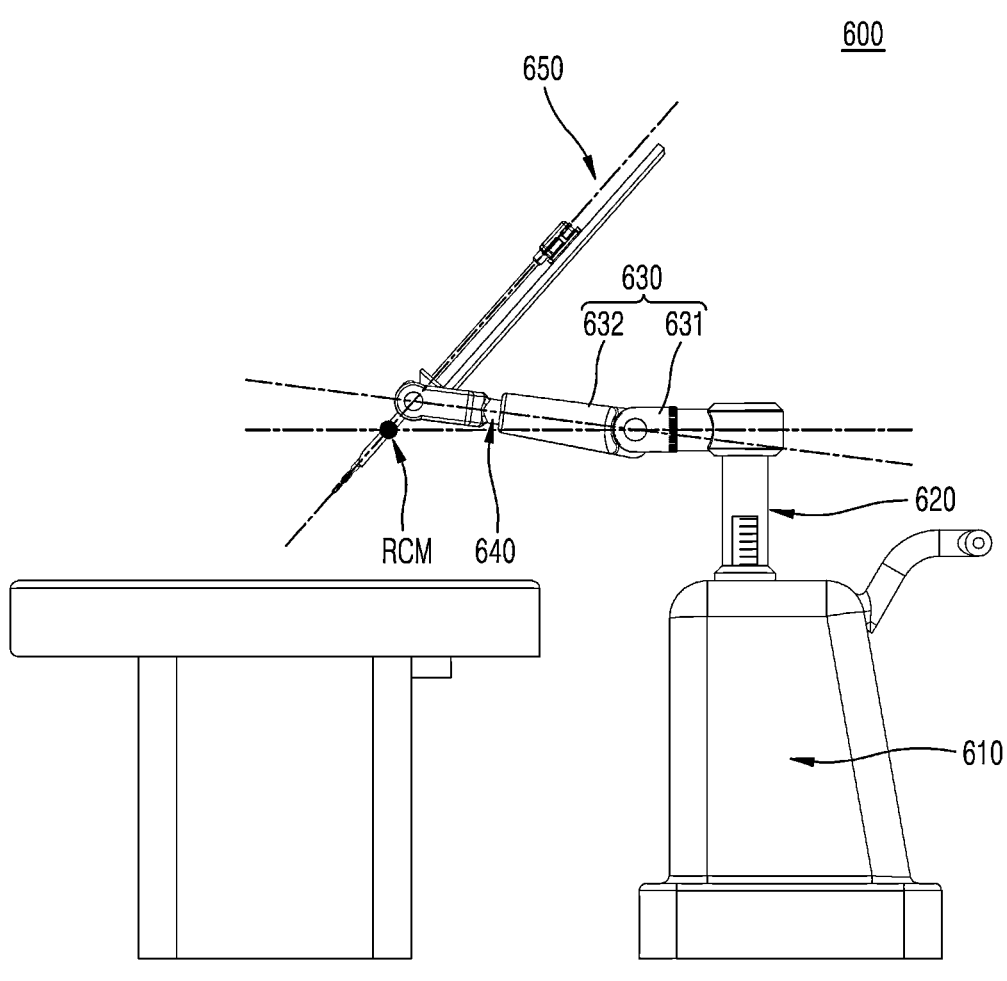
FIG. 55 is a side view of the surgical robot arm of FIG. 54.
Figures 56A, 56B:
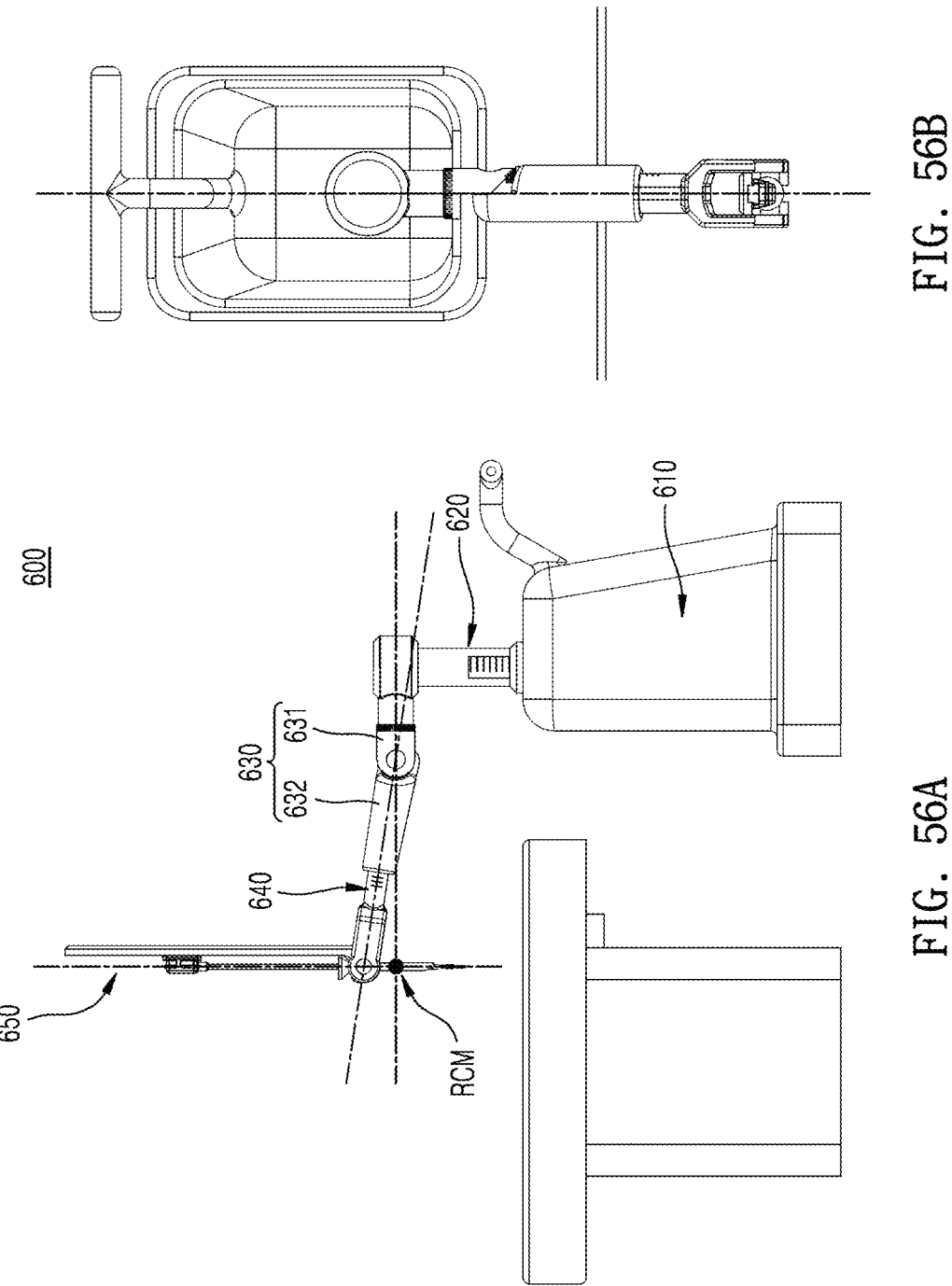
Figures 57A, 57B:
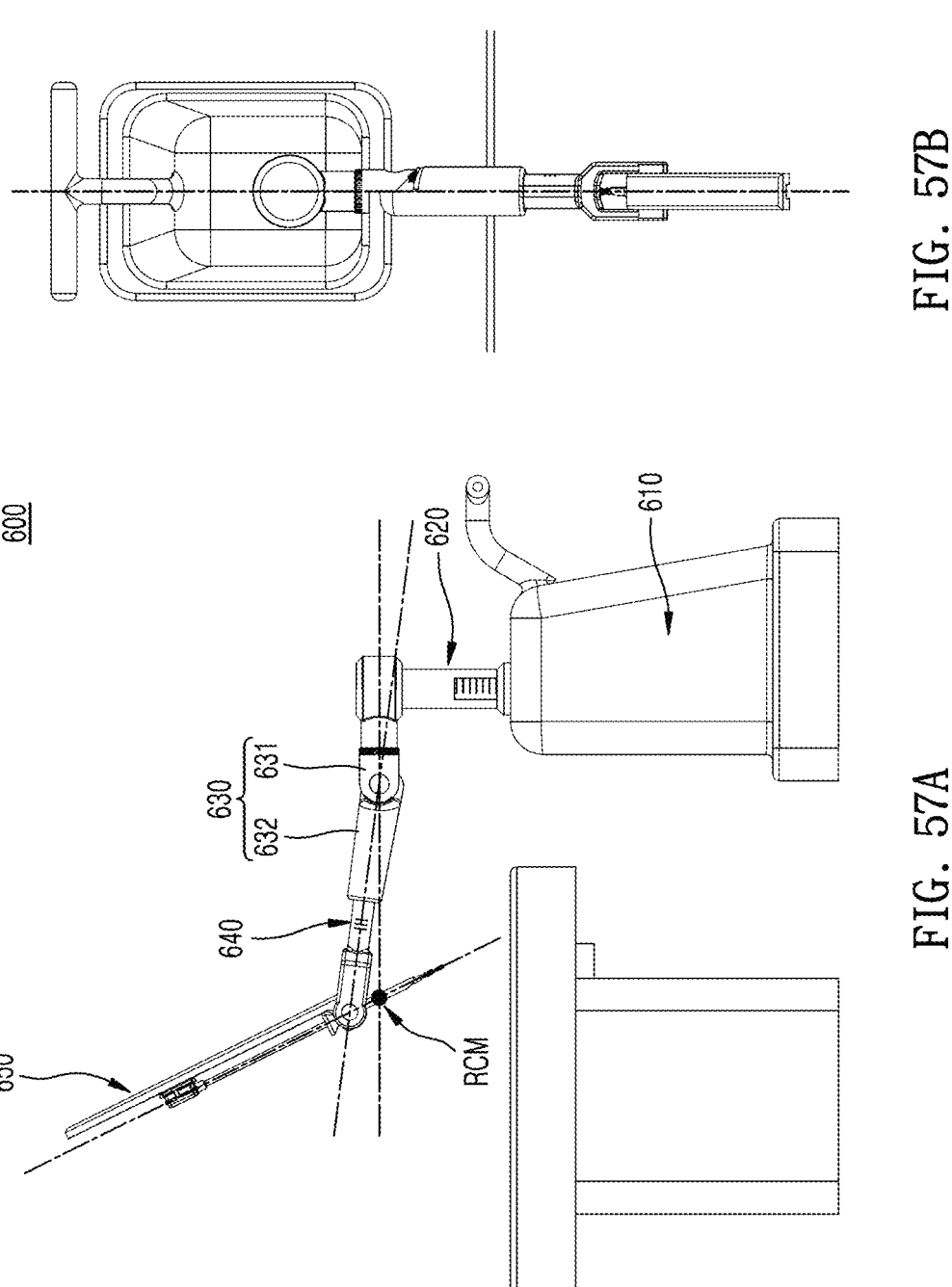
Figures 58A, 58B:
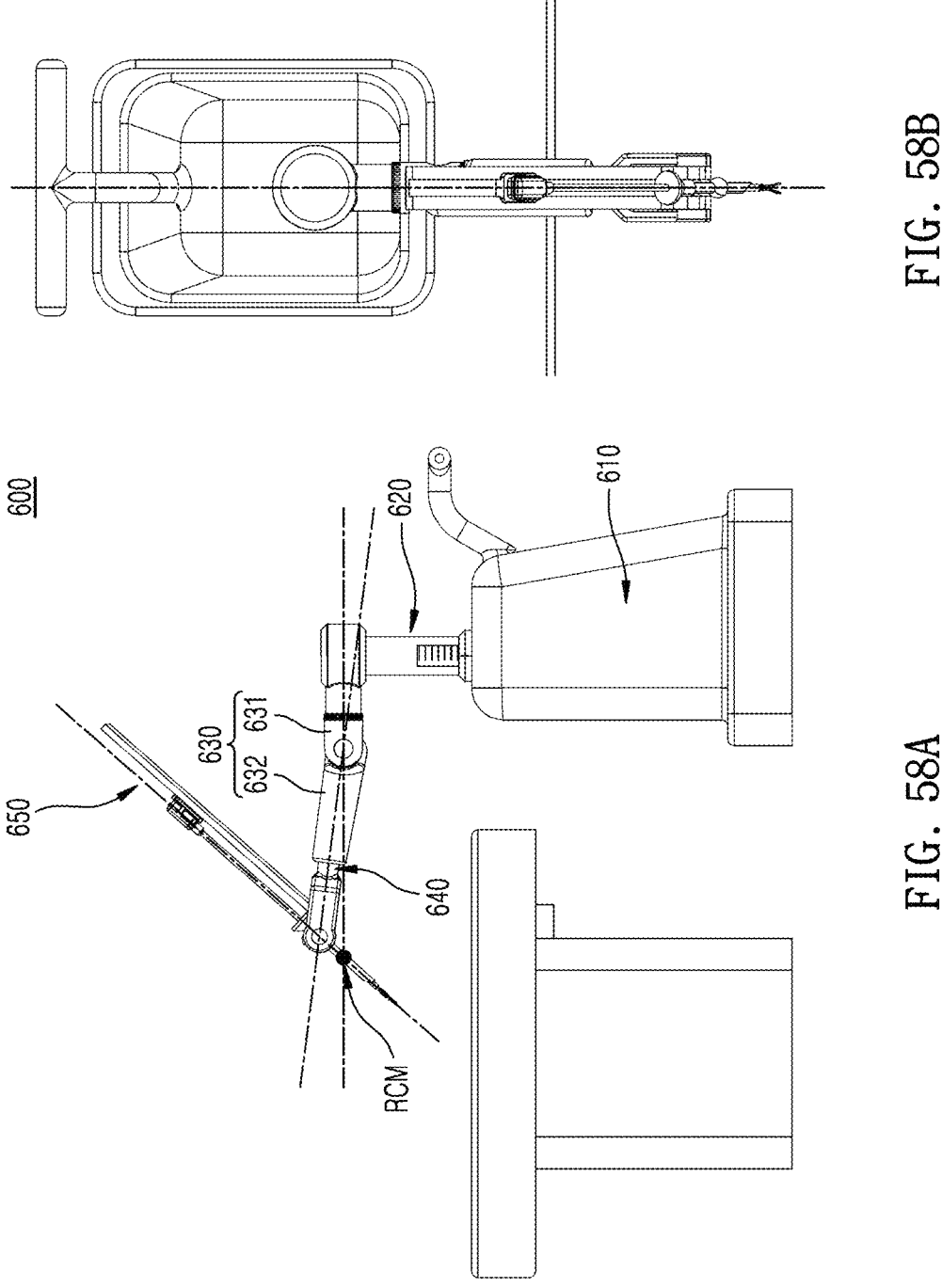
Figure 59:
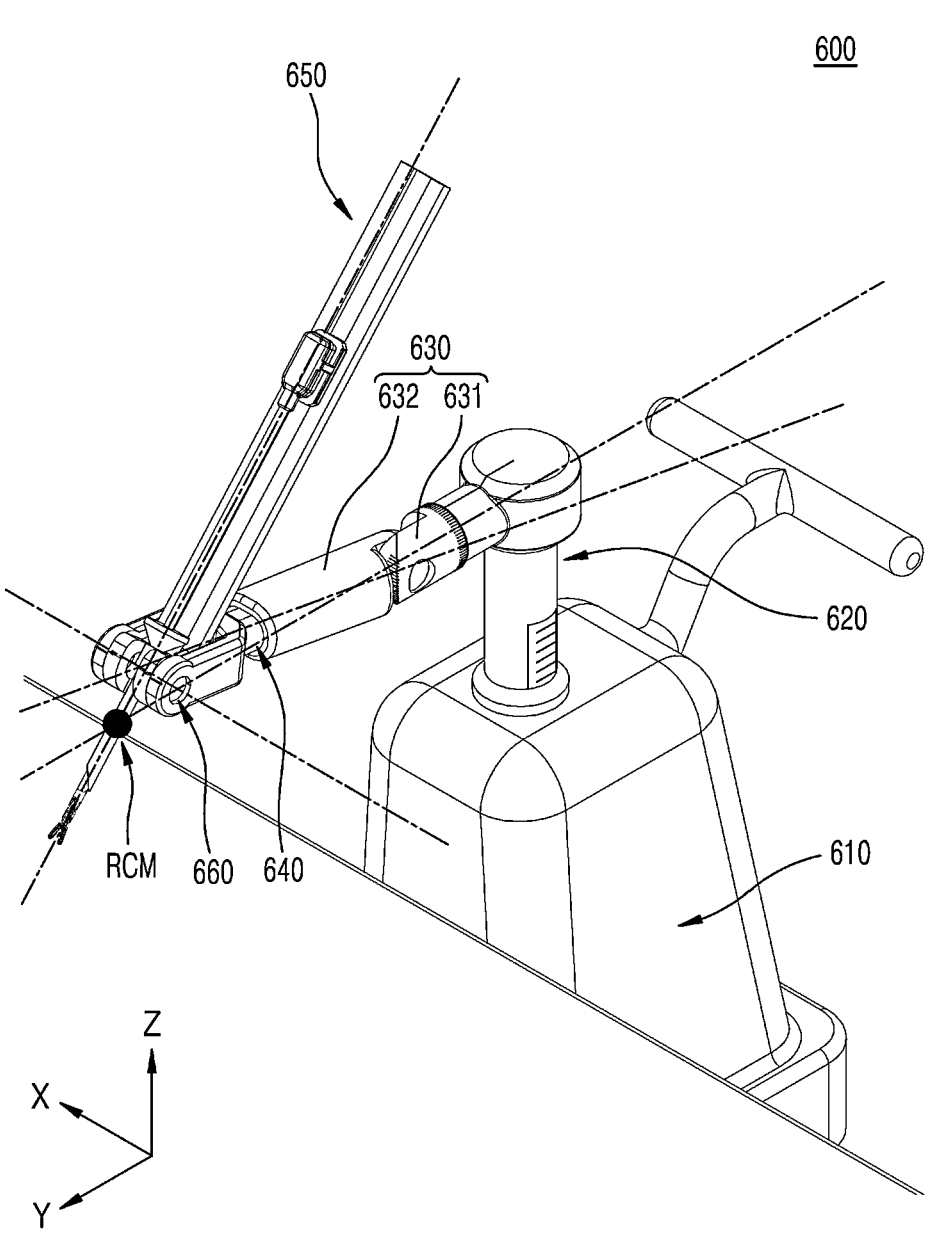
FIGS. 59 to 61 are perspective views illustrating a Y-axis RCM motion (a yaw motion) of the surgical robot arm of FIG. 54.
Figure 60:
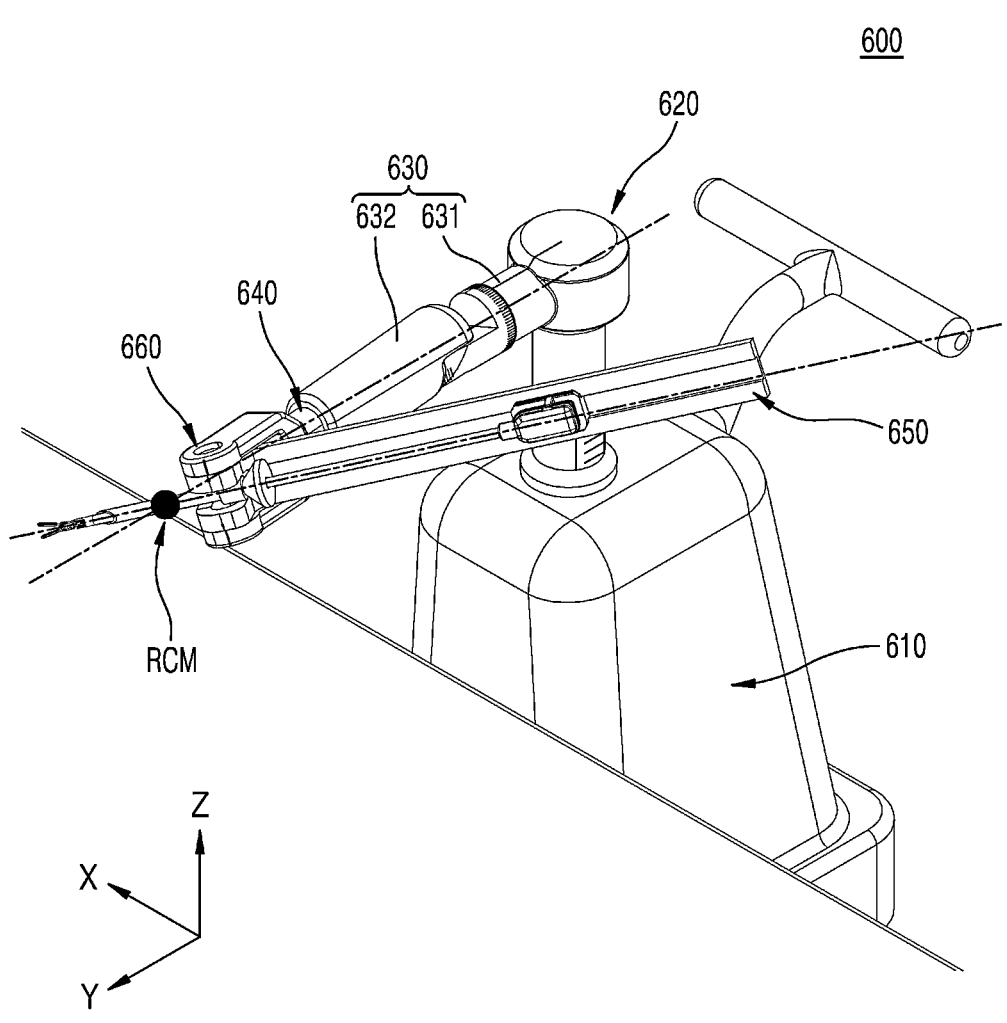
Figure 61:
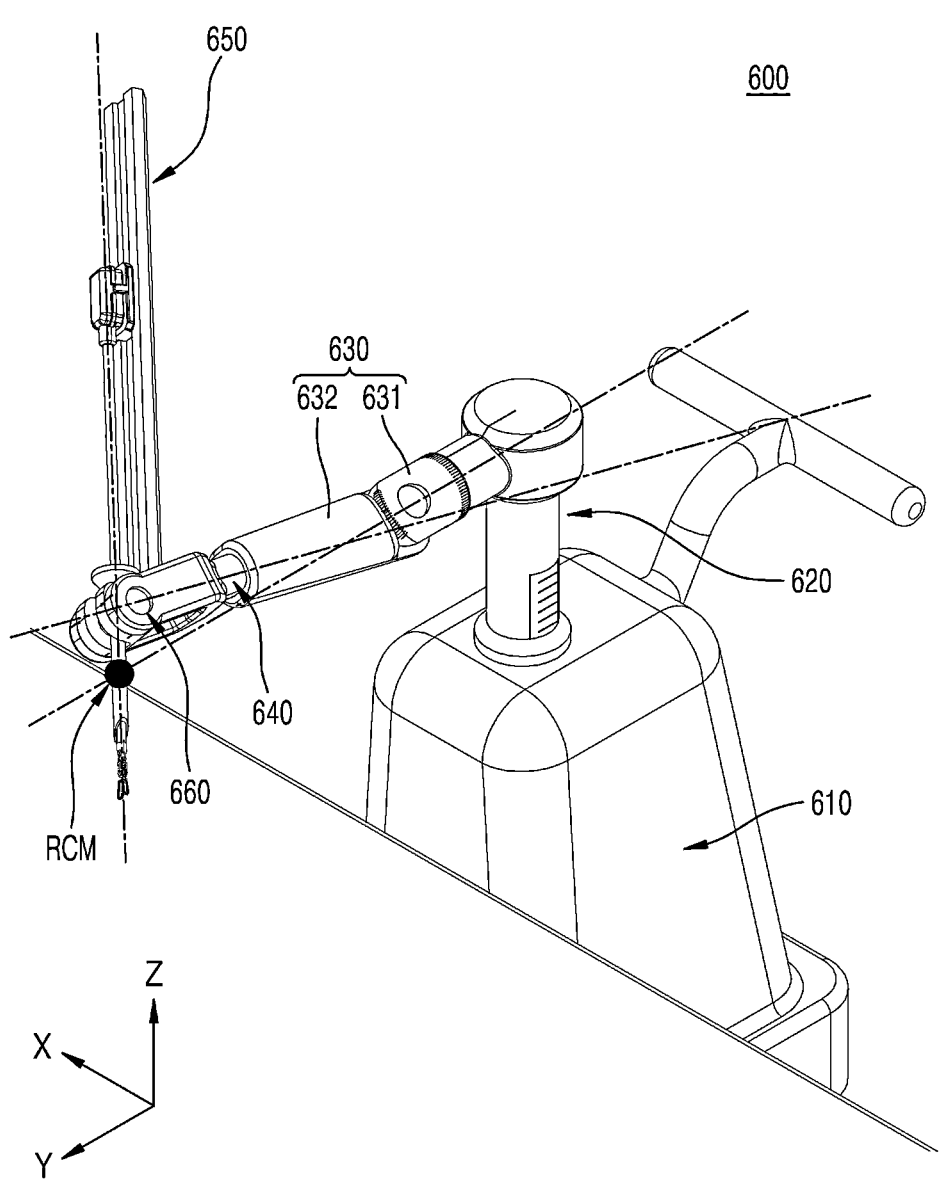
Figures 62A, 62B:
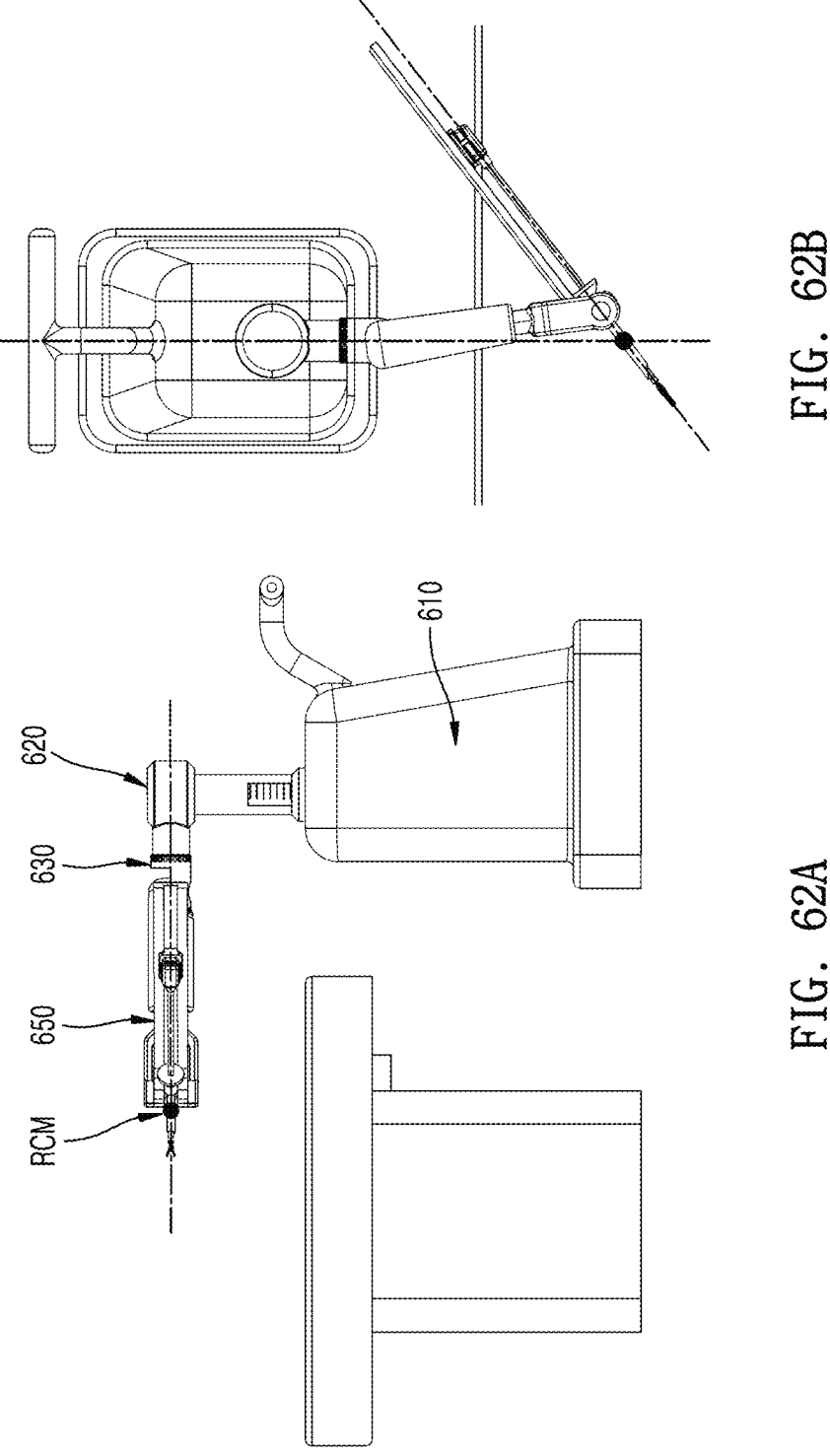
FIGS. 62A and 62B are a side view and a plan view, respectively, illustrating a state in which the surgical robot arm of FIG. 54 lies on its side.

FIG. 54 is a perspective view illustrating the overall structure of the surgical robot arm 600 according to the fourth embodiment of the present disclosure. FIG. 55 is a side view of the surgical robot arm of FIG. 54. FIGS. 56 to 58 are side views and plan views illustrating an X-axis RCM motion (a pitch motion) of the surgical robot arm of FIG. 54. FIGS. 59 to 61 are perspective views illustrating a Y-axis RCM motion (a yaw motion) of the surgical robot arm of FIG. 54. FIG. 62 is a side view and a plan view illustrating a state in which the surgical robot arm of FIG. 54 lies on its side.

Referring to FIGS. 54 to 62, the surgical robot arm 600 according to the fourth embodiment of the present disclosure includes a base 610, a base link 620, a first link 630, a second link 640, and an instrument mounting link 650. Here, in the surgical robot arm 600 according to the fourth embodiment of the present disclosure, the first link 630 includes two parts, that is, the first region 631 and the second region 632. The first region 631 and the second region 632 are formed to be rotatable around the pitch rotation shaft 635 with respect to each other.

The base 610 serves as a base part of the entire surgical robot arm 600. Here, a moving means (not shown) such as wheels may be formed on the lower surface of the base 610 so that the base 610 may serve as a kind of cart. In addition, a position fixing means (not shown) may be further formed on the base 610 so that the position of the base 610 may be fixed during surgery. However, the concept of the present disclosure is not limited thereto, and the base 610 may be formed in a shape that is detachably attachable to a bed, or may be formed in a shape that is detachably attachable a wall.

The base link 620 includes an extension portion 621 and a roll rotation base portion 622. The extension portion 621 may extend in one direction from the base 610. In the drawings, it is illustrated that the extension portion 621 of the base link 620 extends from the base 610 in a Z-axis direction. In other words, one end of the base link 620 is connected to the base 610.

Here, in the present embodiment, the base link 620 is formed to be rotatable along a sixth axis A6 with respect to the base 610. Here, in the drawings, it is illustrated that the base link 620 is rotated around the sixth axis A6 with respect to the base 610, but the concept of the present disclosure is not limited thereto, and a rotation center axis of the base link 620 may be variously formed according to the shape and configuration of the links.

On the other hand, the roll rotation base portion 622 is formed at the other end of the base link 620. The roll rotation base portion 622 may be formed to be inclined to a certain extent so as to have a certain angle with the extension portion 621. In the drawings, it is illustrated that the roll rotation base portion 622 protrudes from the extension portion 621 so as to form an almost right angle with the extension portion 621.

Here, the roll rotation base portion 622 of the base link 620 may be formed in a cylindrical shape with respect to the first axis A1 formed in a first direction. The first link 630 connected to the roll rotation base portion 622 (together with the second link 640, the instrument mounting link 650, and the surgical instrument 20 sequentially connected to the first link 630) may be formed to perform a roll motion around the first axis A1.

Here, the extension portion 621 of the base link 620 is formed to be rotatable around the axis A6 with respect to the base 610. That is, in the present embodiment, the base link 620 is rotated around the sixth axis A6 with respect to the base 610 in a clockwise direction or a counterclockwise direction.

Here, the rotation of the base link 620 with respect to the base 610 may be performed in a set-up stage of the surgical robot arm 600 before starting surgery. Due to the rotation of the base link 620 with respect to the base 610 in the set-up stage, when the first axis A1, which is the roll rotation axis of the base link 620, is set up not to coincide with the RCM on an XY plane, the base link 620 is rotated with respect to the base 610 in real time even while the surgical robot arm 600 is operating.

In detail, as described with reference to FIG. 45, etc. illustrating the third embodiment of the present disclosure, the base link 620 may be formed to be rotatable around the sixth axis A6 with respect to the base 610, so that the base link 620 may be located at various positions on the XY plane. With this configuration, in the present embodiment, the RCM motion may be implemented even when the first axis A1, which is the roll rotation axis of the base link 620, does not coincide with the RCM. That is, the RCM motion may be implemented no matter where the base link 720 is located on the XY plane.

The first link 630 may be coupled to the base link 620, and more specifically, to the roll rotation base portion 622 of the base link 620 and may be formed such that the entire first link 630 is rotatable around the first axis A1 of the roll rotation base portion 622. Alternatively, it may be expressed that the first link 630 rolls around the base link 620. In order to implement the rotational motion of the first link 630 with respect to the base link 620, a motor may be provided on either the base link 620 or the first link 630.

On the other hand, the first link 630 may include the first region 631 coupled to the base link 620 and the second region 632 coupled to the second link 640. Here, a central axis of the first region 631 and a central axis of the second region 632 may be defined to form a certain angle with each other. The first region 631 is axially coupled to the second region 632 by the pitch rotation shaft 635 formed in a direction of a fifth axis A5, and thus, the second region 632 is formed to be rotatable around the fifth axis A5 with respect to the first region 631. This is, the second region 632 may be rotatable around the X-axis when viewed from the drawing.

Here, the central axis of the first region 631 may coincide with the first axis A1.

Here, when the first link 630 is rotated around the first axis A1, the second link 640, the instrument mounting link 650, and the surgical instrument 20 connected to the first link 630 are rotated together.

As described above, the central axis of the first region 631 and the central axis of the second region 632 may be defined to form a certain angle with each other. That is, the central axis of the first link 630 may coincide with the first axis A1, and the central axis of the second region 632 may coincide with the second axis A2 of the second link, which will be described later.

On the other hand, in order to implement the rotational motion of the second region 632 with respect to the first region 631, a motor may be provided on either the first region 631 or the second region 632.

The second link 640 may be coupled to the second region 632 of the first link 630 and may perform a linear reciprocating motion in one direction along the second axis A2 with respect to the second region 632 of the first link 630. Here, in the drawings, it is illustrated that the second link 640 performs a linear reciprocating motion in the X-axis direction with respect to the first link 630, but the concept of the present disclosure is not limited thereto, and a linear reciprocating axis of the second link 640 may be variously formed according to the shape and configuration of the links.

In order to implement such a linear motion, a linear actuator (not shown) may be provided on either the first link 630 or the second link 640.

Here, the first axis A1 and the second axis A2 may generally be different axes. Alternatively, even when the first link 630 or the second link 640 is bent to a certain extent and the first axis A1 and the second axis A2 are formed to be parallel to each other, the second axis A2 may be formed so as not to pass through the RCM.

The instrument mounting link 650 is axially coupled to the second link 640 by the link rotation shaft 660 coupled in a direction of a third axis A3, and thus, the instrument mounting link 650 is formed to be rotatable around the third axis A3 with respect to the second link 640. This is, the instrument mounting link 650 may be rotatable around the X-axis when viewed from the drawing. In order to implement such a rotational motion, a motor may be provided on either the second link 640 or the instrument mounting link 650.

On the other hand, an instrument mounting portion 651 and a guide rail 652 may be formed in the instrument mounting link 650. While the surgical instrument 20 is mounted on the instrument mounting portion 651, the instrument mounting portion 651 may perform a linear motion along the guide rail 652 formed in a direction of a fourth axis A4. In order to implement such a linear motion, a linear actuator (not shown) may be provided in the instrument mounting portion 651.

Here, the fourth axis A4 may be a direction in which the guide rail 652 is formed, and simultaneously, may be an extension direction of a shaft of the surgical instrument 20 coupled to the instrument mounting link 650.

The surgical instrument 20 is mounted on the instrument mounting portion 651 of the instrument mounting link 650 of the surgical robot arm 600.

Here, although not illustrated in the drawings, an interface part (not shown) coupled to the surgical instrument 20 and configured to control the motion of the surgical instrument 20 may be further formed in the instrument mounting portion 651. The interface part (not shown) may include a component configured to couple with a driving part 23 of the surgical instrument 20, a motor configured to transmit a driving force from the surgical robot arm 600 to the surgical instrument 20, and the like. The interface part (not shown) may allow an end tool 21 of the surgical instrument 20 to perform a pitch, yaw, or actuation motion. Furthermore, the interface part (not shown) may allow the shaft 22 and the end tool 21 of the surgical instrument 20 to perform a roll motion around the fourth axis A4.

On the other hand, a trocar 30 serving as an insertion passage for inserting the surgical instrument 20 into the patient's body may be further provided. While the trocar 30 is inserted into the body, the surgical instrument 20 may be inserted into the patient's body through the trocar 30. An RCM may be formed at a certain position on the trocar 30. As described above, the first axis A1, which is the roll rotation axis of the first link 630, may be formed to pass through the RCM.

In addition, the surgical instrument 20 may further include the driving part 23. A component configured to couple with the interface part (not shown) and a driving wheel operated in engagement with the motor may be formed in the driving part 23. As such, a coupling means and a driving transmission means may be respectively formed in the interface part (not shown) and the driving part 23 to correspond to each other. Accordingly, the surgical instrument 20 is operated by receiving a driving force from the surgical robot arm 600 in a state of being mounted on the instrument mounting link 650.

In the present disclosure, the RCM structure of the surgical robot arm 600 is a structure in which the surgical instrument 20 is mounted on one side of the surgical robot arm 600, and the surgical instrument 20 is operated and controlled to rotate around a certain point RCM on the trocar 30 into which the surgical instrument 20 is inserted. Here, the RCM structure according to the present embodiment is implemented through the electronic control for each link rather than the existing mechanical parallelogram link structure.

In particular, the difference between the present embodiment and the previous embodiments is that the RCM motion is possible even when the RCM and the rotation axis A1 of the base link 620 are spaced apart from each other without meeting each other, and thus, the initial setting of the surgical robot arm is simplified. That is, the RCM motion is possible even when the RCM and the base link 620 are spaced apart from each other to a certain extent on the XY plane.

That is, as illustrated in FIG. 47 of the third embodiment, etc., the RCM motion is possible even when the first axis A1, which is the roll rotation axis of the first link 630, is not arranged to pass through the RCM on the XY plane. This is enabled by the additional degrees of freedom given in the present embodiment, that is, the rotational motion of the base link 620 with respect to the base 610 and the rotational motion of the second region 632 with respect to the first region 631 of the first link 630. That is, the surgical robot arm 600 of the present embodiment has a total of six degrees of freedom. Due to the motion of the six degrees of freedom, the RCM motion is possible even when the first axis A1 does not pass through the RCM on the XY plane.

Hereinafter, for convenience, the control in the X-axis direction and the control in the Y-axis direction in the drawing are described separately, but it may be stated that the overall control is performed by combining the control in the X-axis direction with the control in the Y-axis direction. In addition, the coordinate system of each component may change relatively due to the rotation and linear motion of each link. However, for convenience, the following description is given based on the X-axis direction and the Y-axis direction of the bed by using the bed as the reference point.

This will be described in more detail as follows.

First, the control in the X-axis direction may be implemented by a combination of:

1) the control of the linear motion of the second link 640 with respect to the first link 630, 2) the control of the rotational motion of the instrument mounting link 650 with respect to the second link 640, and 3) the control of the rotational motion of the second region 632 of the first link 630 with respect to the first region 631 of the first link 630.

In detail, in order to control the rotational motion of the surgical instrument 20 around the X-axis, the second link 640 first performs a linear motion along the second axis A2 with respect to the first link 630. At the same time, an RCM motion is performed by controlling the instrument mounting link 650 to perform a rotational motion around the third axis A3 with respect to the second link 640 and controlling the second region 632 of the first link 630 to perform a rotational motion with respect to the first region 631 of the first link 630. Accordingly, even when the links are moved, the RCM maintains a position thereof.

At this time, even when the surgical instrument 20 is rotated around the X-axis, the insertion depth (see LE of FIG. 6) of the instrument has not to change, and the distance (see Lt of FIG. 6) from the RCM to the end of the trocar 30 has not to change.

To this end, in the surgical robot arm 600 according to the fourth embodiment of the present disclosure, one degree of freedom is added, compared to the surgical robot arm (see 100 of FIG. 4) according to the first embodiment of the present disclosure. That is, the surgical robot arm 600 according to the fourth embodiment of the present disclosure is formed such that the first region 631 and the second region 632 of the first link 630 are rotatable around the pitch rotation shaft 635 with respect to each other.

Therefore, in controlling the rotational motion of the surgical instrument 20 around the X axis, the second region 632 of the first link 630 may be controlled to rotate with respect to the first region 631 of the first link 630, and thus, the insertion depths of the surgical instrument 20 and the trocar 30 may be maintained constant.

As such, even when the links are moved, the RCM in the X-axis direction maintains a position thereof by performing a combination of 1) the control of the linear motion of the second link 640 with respect to the first link 630, 2) the control of the rotational motion of the instrument mounting link 650 with respect to the second link 640, and 3) the control of the rotational motion of the second region 632 of the first link 630 with respect to the first region 631 of the first link 630.

Next, the RCM control in the Y-axis direction may be implemented by a combination of:

1) the control of the roll rotational motion of the first link 630 around the first link A1, 2) the control of the rotational motion of the instrument mounting link 650 with respect to the second link 640, 3) the control of the linear motion of the second link 640 with respect to the first link 630, 4) the control of the roll motion of the surgical instrument 20, and 5) the control of the rotational motion of the base link 620 with respect to the base 610.

In detail, in order to control the rotational motion of the surgical instrument 20 around the Y axis, the first link 630 first performs a roll rotational motion around the first axis A1. The first link 630, and the second link 640, the instrument mounting link 650, and the surgical instrument 20, which are sequentially connected to the first link 630, may perform a roll motion around the first axis A1.

In this case, since the first axis A1, which is the rotation axis of the first link 630, and the Y-axis do not coincide with each other and are formed to be oblique, unintended motions are mixed when only the first link 630 is rotated. That is, as illustrated in the drawings, when the first link 630 is rotated, the second link 640, the instrument mounting link 650, and the surgical instrument 20 perform a kind of rolling.

In order to compensate for this, with the rotation of the first link 630, the instrument mounting link 650 is controlled to perform a rotational motion around the third axis A3 with respect to the second link 640, the second link 640 is controlled to perform a linear motion with respect to the first link 630, and simultaneously, the base link 620 is controlled to perform a rotational motion around the sixth axis A6 with respect to the base 610. In this manner, the RCM motion is performed. That is, even when the links are moved, the RCM maintains a position thereof.

In addition, the shaft 22 and the end tool 21 of the surgical instrument 20 are controlled to perform a roll motion around the fourth axis A4, so that the end tool 21 may also be compensated to maintain a posture thereof, regardless of the rotation of the first link 630.

As such, even when the links are moved, the RCM in the Y-axis direction maintains a position thereof by performing a combination of 1) the control of the roll rotational motion of the first link 630 around the first link A1, 2) the control of the rotational motion of the instrument mounting link 650 with respect to the second link 640, 3) the control of the linear motion of the second link 640 with respect to the first link 630, 4) the control of the roll motion of the surgical instrument 20, and 5) the control of the rotational motion of the base link 620 with respect to the base 610.

In conclusion, from the viewpoint of the degree of freedom of the surgical robot arm 600 itself (excluding the surgical instrument 20), the surgical robot arm 600 according to the fourth embodiment of the present disclosure may operate with five degrees of freedom of: 1) the roll rotational motion of the first link 630 around the first axis A1, 2) the linear motion of the second link 640 with respect to the first link 630, 3) the rotational motion of the instrument mounting link 650 with respect to the second link 640, 4) the rotational motion of the second region 632 of the first link 630 with respect to the first region 631 of the first link 630, and 5) the rotational motion of the base link 620 with respect to the base 610. Here, a translation motion of the surgical instrument 20, that is, a linear motion of the surgical instrument 20 in the direction of the fourth axis A4, is also possible through the linear motion of the instrument mounting portion 651 with respect to the guide rail 652 of the instrument mounting link 650.

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm 100 and reducing the driving force required for operation may be obtained. Furthermore, the insertion depth of the trocar 30 is controlled to be constant through the control of the rotational motion of the second region 632 of the first link 630 with respect to the first region 631 of the first link 630, and thus, the risk of the trocar 30 coming out of the abdomen during surgery may be eliminated, thereby further improving safety.

<Fourth-1 Embodiment of Surgical Robot Arm>

Hereinafter, a surgical robot arm 900 according to a fourth-1 embodiment of the present disclosure will be described. Here, the surgical robot arm 900 according to the fourth-1 embodiment of the present disclosure characteristically differs from the surgical robot arm (see 600 of FIG. 54) according to the fourth embodiment of the present disclosure in terms of a configuration of a first link 930 and a second link 940 of the robot arm 900.

In detail, while the first link 630 in the robot arm 600 according to the fourth embodiment of the present disclosure includes the first region 631, the second region 632, and the pitch rotation shaft 635, the robot arm 900 according to the fourth-1 embodiment of the present disclosure is an embodiment in which the second link 940 includes a first region 941, a second region 942, and a pitch rotation shaft 945. Compared to the fourth embodiment, the change in configuration will be described in detail later.

Figure 63:
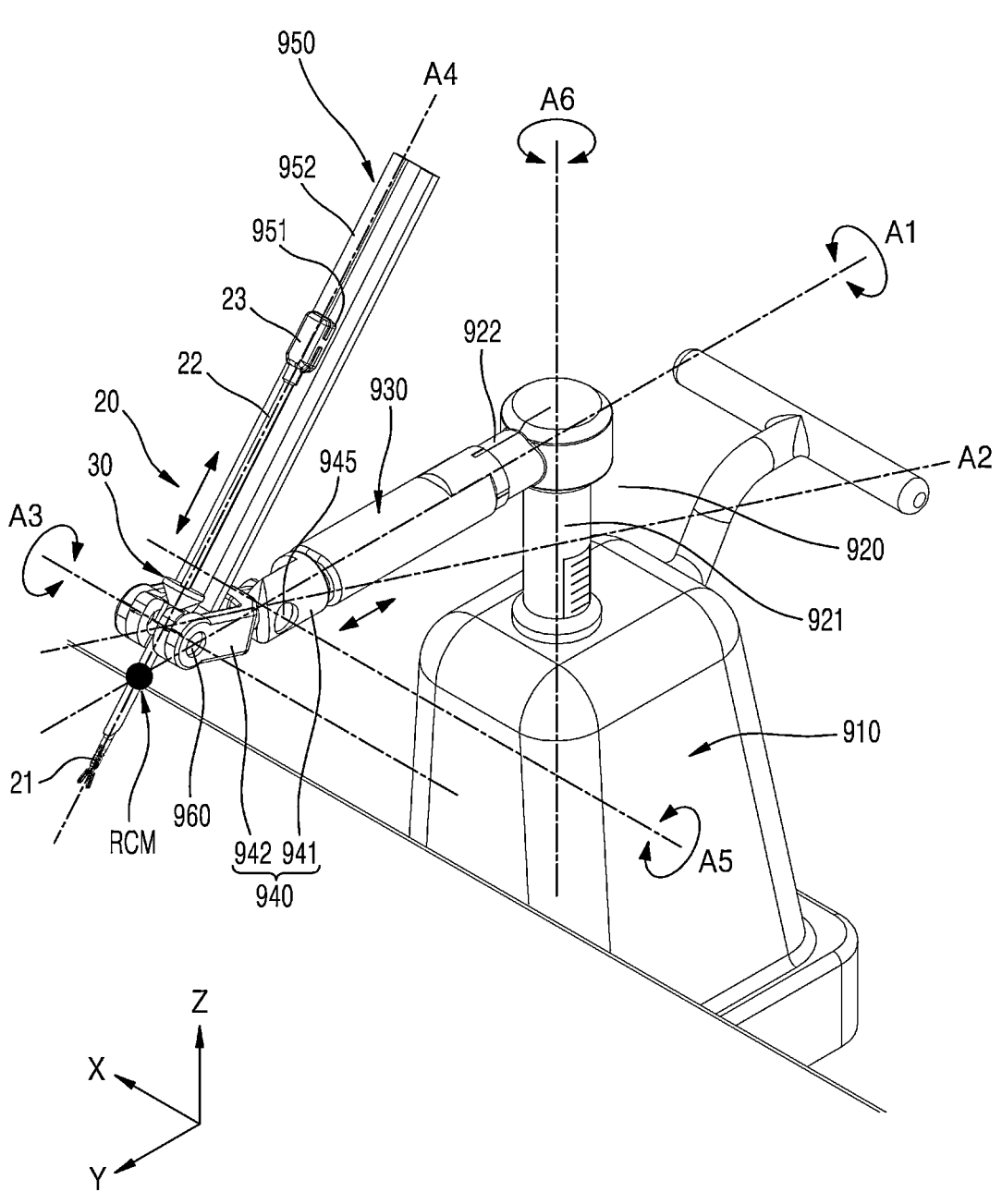
FIG. 63 is a perspective view illustrating an overall structure of a surgical robot arm (900) according to a fourth-1 embodiment of the present disclosure.
Figure 64:
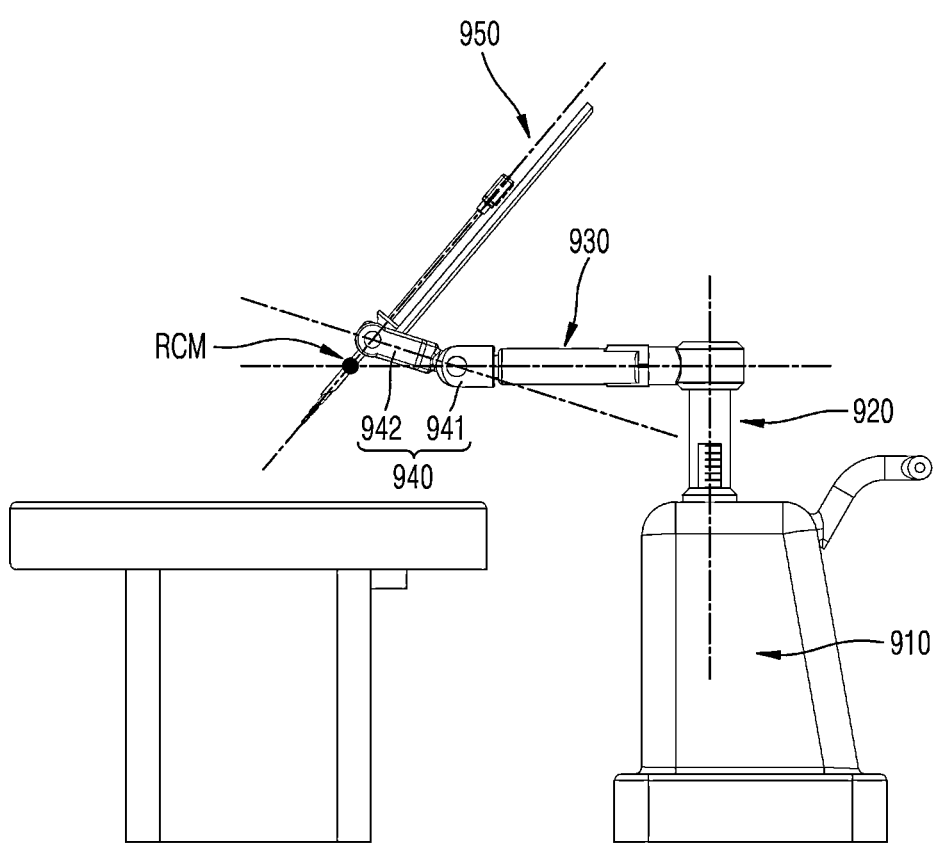
FIG. 64 is a side view of the surgical robot arm of FIG. 63.
Figures 65A, 65B:
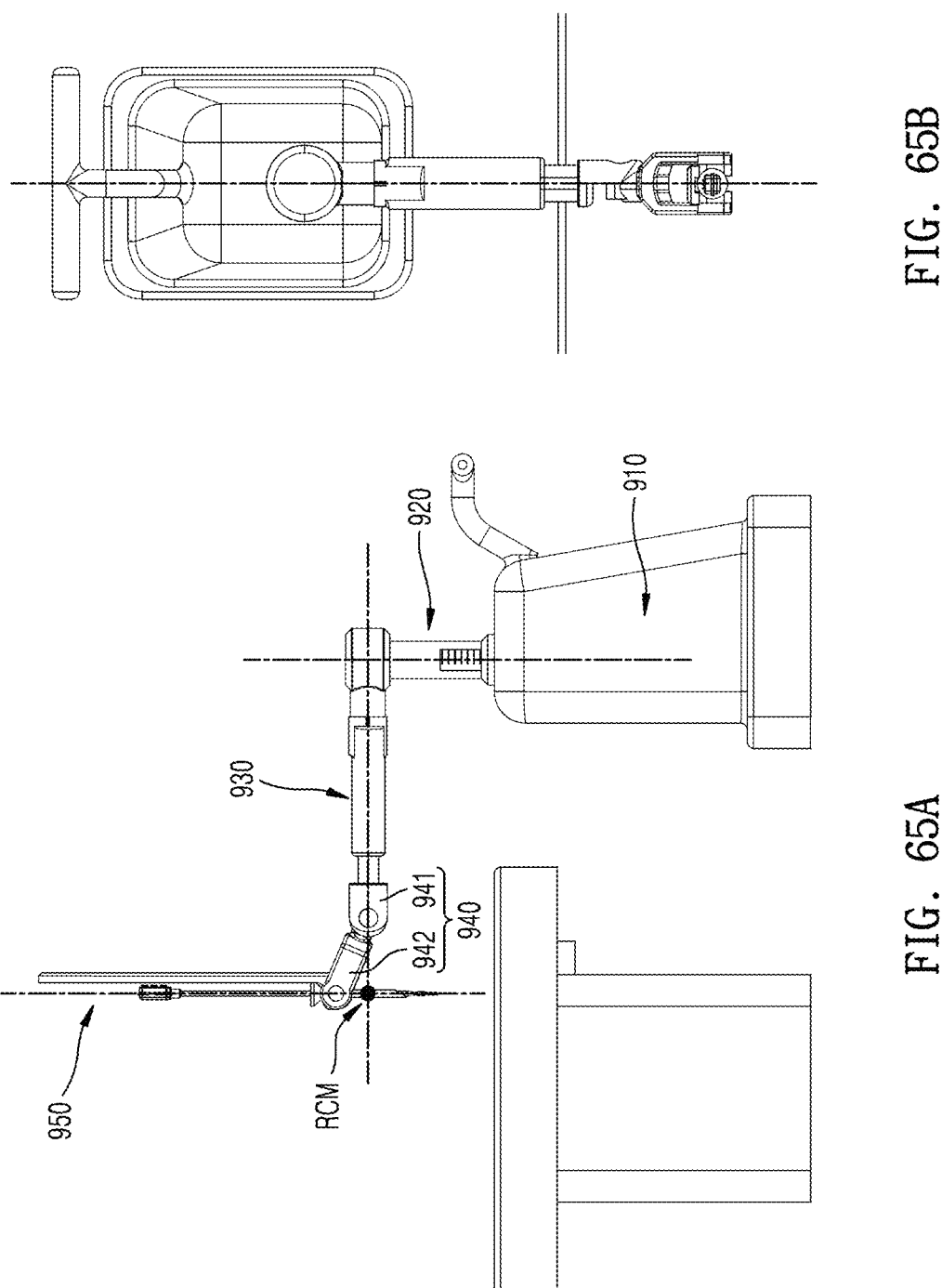
Figures 66A, 66B:
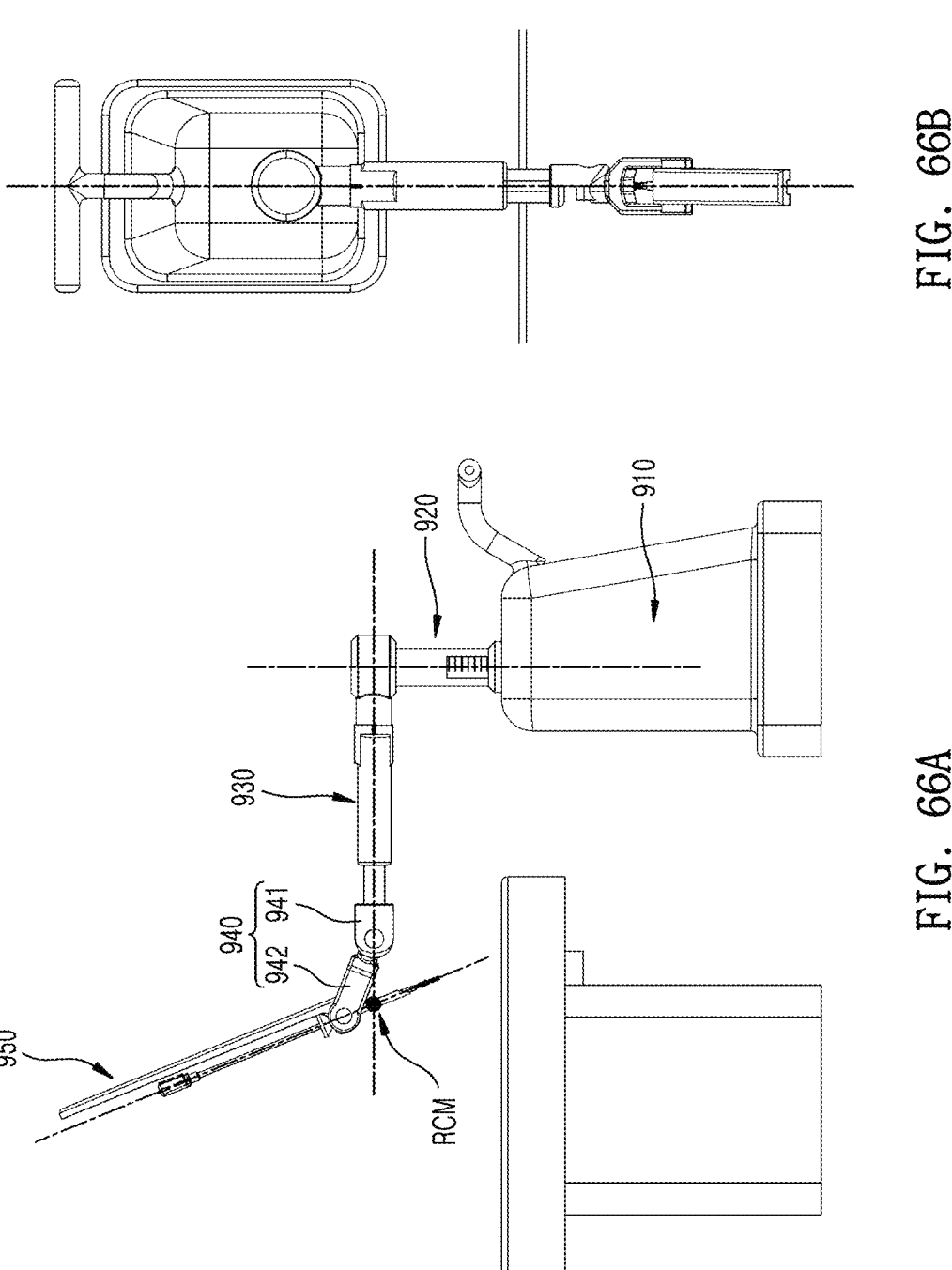
Figures 67A, 67B:
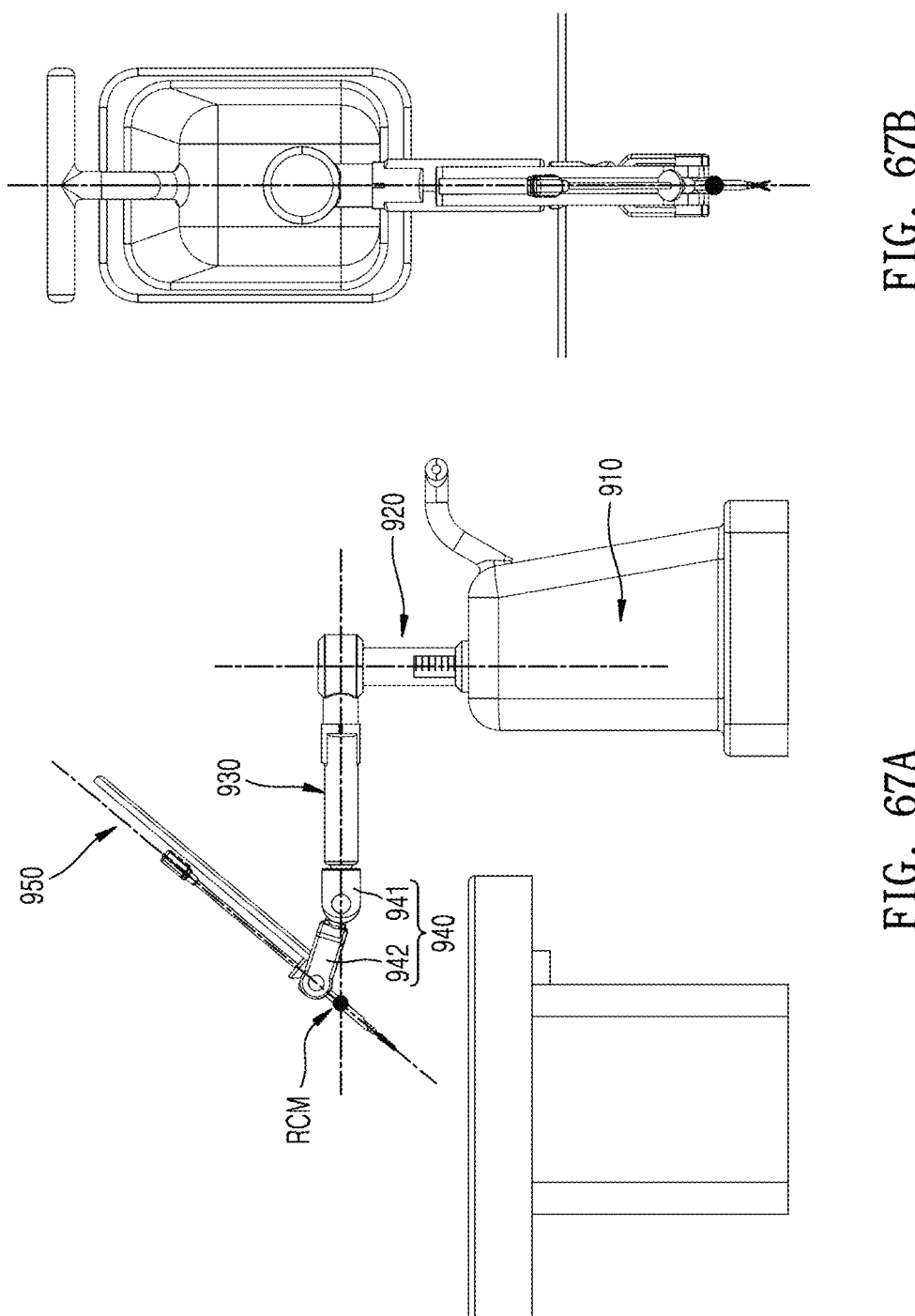
Figure 68:
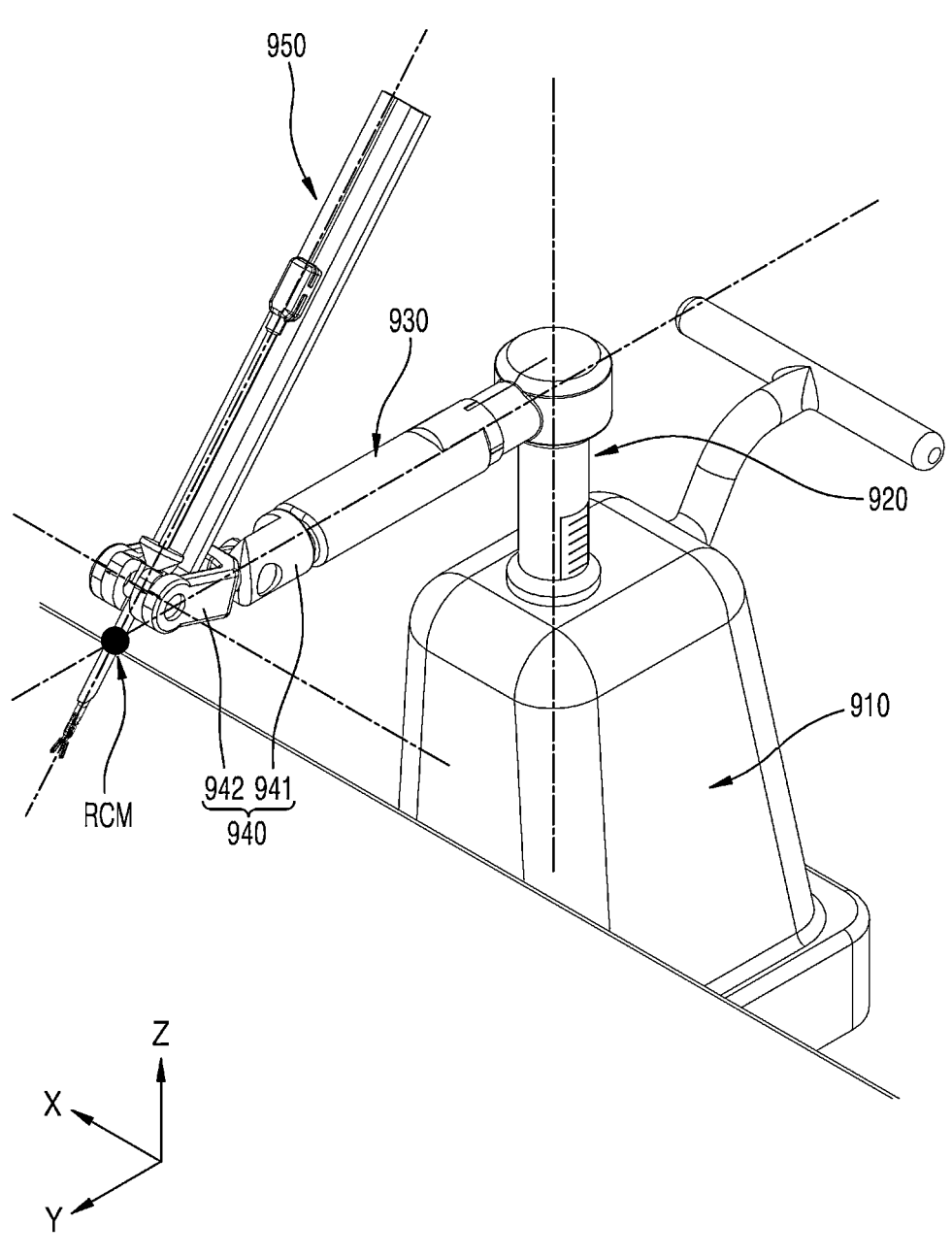
FIGS. 68 to 70 are perspective views illustrating a Y-axis RCM motion (a yaw motion) of the surgical robot arm of FIG. 63.
Figure 69:
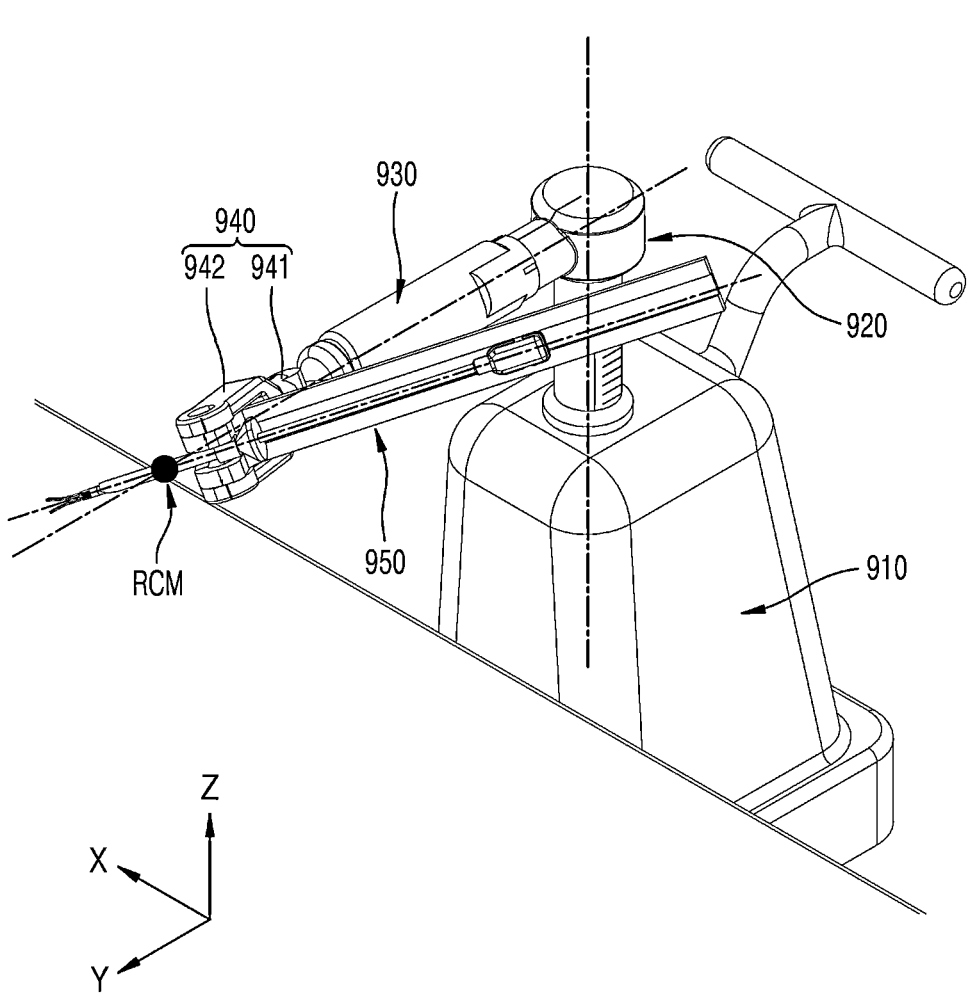
Figure 70:
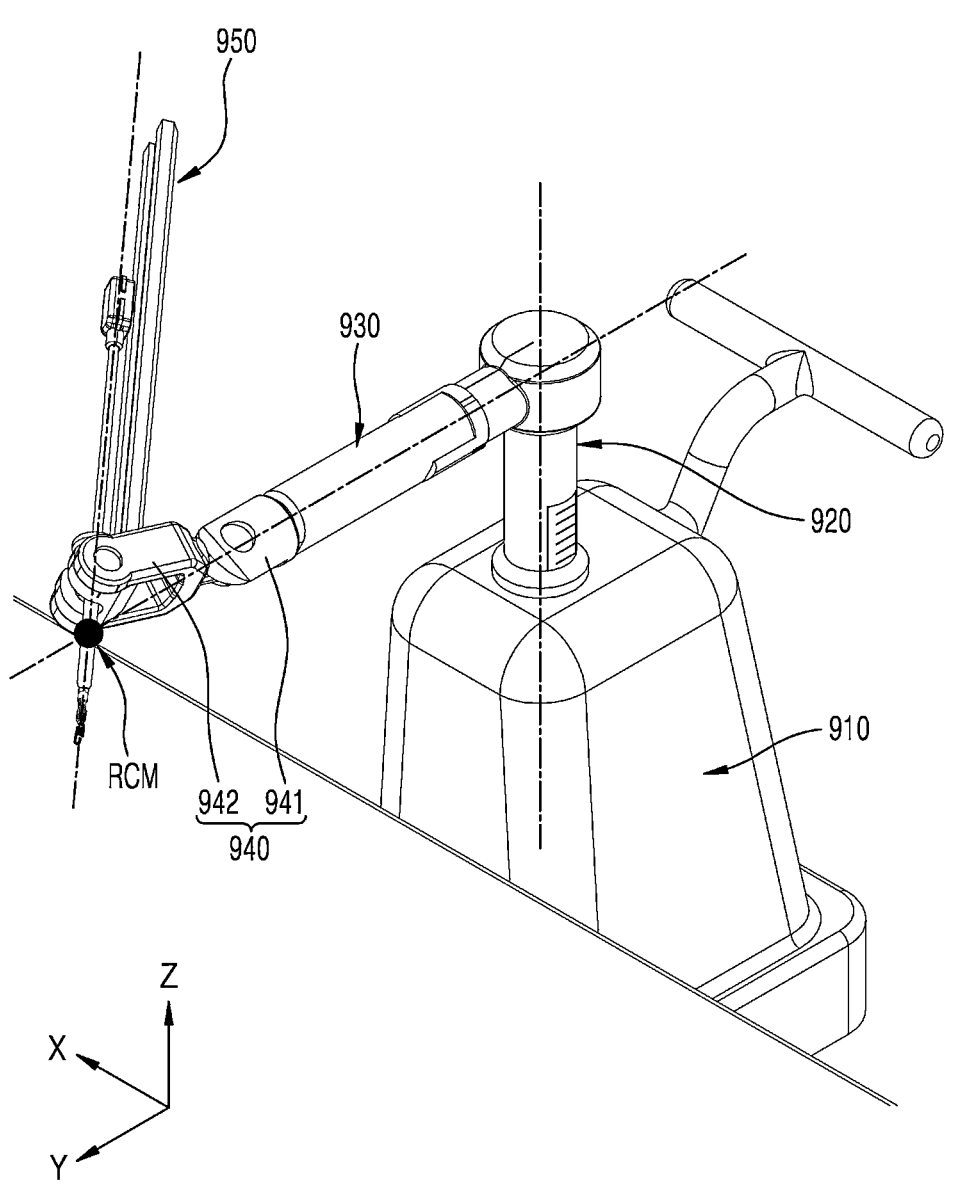
Figures 71A, 71B:
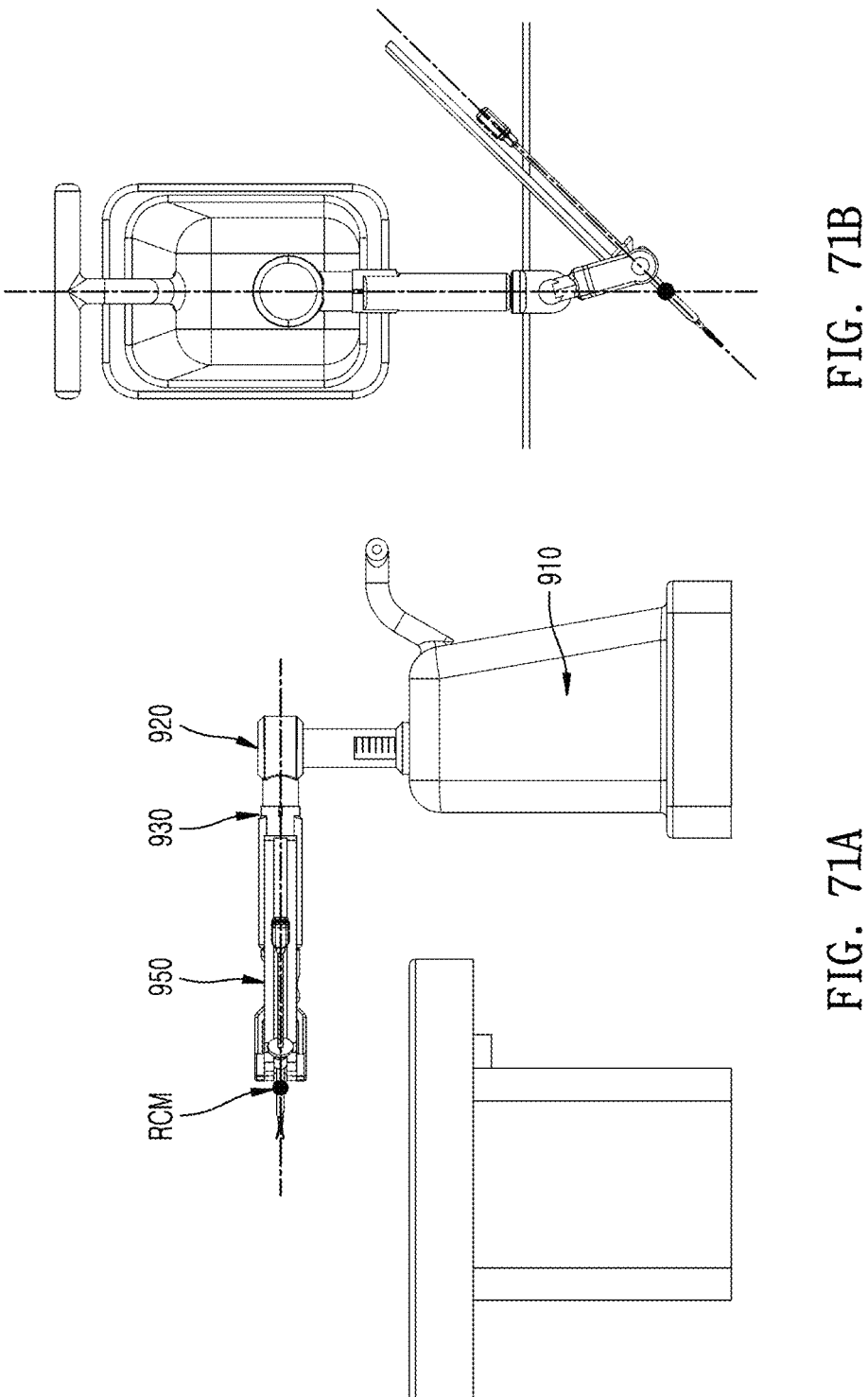
FIGS. 71A and 71B are a side view and a plan view, respectively, illustrating a state in which the surgical robot arm of FIG. 63 lies on its side.

FIG. 63 is a perspective view illustrating the overall structure of the surgical robot arm 900 according to the fourth-1 embodiment of the present disclosure. FIG. 64 is a side view of the surgical robot arm of FIG. 63. FIGS. 65 to 67 are side views and plan views illustrating an X-axis RCM motion (a pitch motion) of the surgical robot arm of FIG. 63. FIGS. 68 to 70 are perspective views illustrating a Y-axis RCM motion (a yaw motion) of the surgical robot arm of FIG. 63. FIG. 71 is a side view and a plan view illustrating a state in which the surgical robot arm of FIG. 63 lies on its side.

Referring to FIGS. 63 to 71, the surgical robot arm 900 according to the fourth-1 embodiment of the present disclosure includes a base 910, a base link 920, a first link 930, a second link 940, and an instrument mounting link 950. Here, in the surgical robot arm 900 according to the fourth-1 embodiment of the present disclosure, the second link 940 includes two parts, that is, the first region 941 and the second region 942. The first region 941 and the second region 942 are formed to be rotatable around the pitch rotation shaft 945 with respect to each other.

The base 910 serves as a base part of the entire surgical robot arm 900.

The base link 920 includes an extension portion 921 and a roll rotation base portion 922. The extension portion 921 may extend in one direction from the base 910. In the drawings, it is illustrated that the extension portion 921 of the base link 920 extends from the base 910 in a Z-axis direction. In other words, one end of the base link 920 is connected to the base 910. Here, in the present embodiment, the base link 920 is formed to be rotatable along a sixth axis A6 with respect to the base 910.

Here, the roll rotation base portion 922 of the base link 920 may be formed in a cylindrical shape with respect to the first axis A1 formed in a first direction. The first link 930 connected to the roll rotation base portion 922 (together with the second link 940, the instrument mounting link 950, and the surgical instrument 20 sequentially connected to the first link 930) may be formed to perform a roll motion around the first axis A1.

Here, the extension portion 921 of the base link 920 is formed to be rotatable around the axis A6 with respect to the base 910. That is, in the present embodiment, the base link 920 is rotated around the sixth axis A6 with respect to the base 910 in a clockwise direction or a counterclockwise direction.

Here, the rotation of the base link 920 with respect to the base 910 may be performed in a set-up stage of the surgical robot arm 900 before starting surgery. Due to the rotation of the base link 920 with respect to the base 910 in the set-up stage, when the first axis A1, which is the roll rotation axis of the base link 920, is set up not to coincide with the RCM on an XY plane, the base link 920 is rotated with respect to the base 910 in real time even while the surgical robot arm 900 is operating.

In detail, as described with reference to FIG. 47, etc. illustrating the third embodiment of the present disclosure, the base link 920 may be formed to be rotatable around the sixth axis A6 with respect to the base 910, so that the base link 920 may be located at various positions on the XY plane. With this configuration, in the present embodiment, the RCM motion may be implemented even when the first axis A1, which is the roll rotation axis of the base link 920, does not coincide with the RCM. That is, the RCM motion may be implemented no matter where the base link 720 is located on the XY plane.

The first link 930 may be coupled to the base link 920, and more specifically, to the roll rotation base portion 922 of the base link 920 and may be formed such that the entire first link 930 is rotatable around the first axis A1 of the roll rotation base portion 922. Alternatively, it may be expressed that the first link 930 rolls around the base link 920. In order to implement the rotational motion of the first link 930 with respect to the base link 920, a motor may be provided on either the base link 920 or the first link 930.

Here, when the first link 930 is rotated around the first axis A1, the second link 940, the instrument mounting link 950, and the surgical instrument 20 connected to the first link 930 are rotated together.

The second link 940 may be coupled to the first link 930 and may perform a linear reciprocating motion in one direction along the second axis A2 with respect to the first link 930. Here, in the drawings, it is illustrated that the second link 940 performs a linear reciprocating motion in the X-axis direction with respect to the first link 930, but the concept of the present disclosure is not limited thereto, and a linear reciprocating axis of the second link 940 may be variously formed according to the shape and configuration of the links. In order to implement such a linear motion, a linear actuator (not shown) may be provided on either the first link 930 or the second link 940.

On the other hand, the second link 940 may include the first region 941 coupled to the first link 930 and the second region 942 coupled to the instrument mounting link 950. Here, a central axis of the first region 941 and a central axis of the second region 942 may be defined to form a certain angle with each other. The first region 941 is axially coupled to the second region 942 by the pitch rotation shaft 945 formed in a direction of a fifth axis A5, and thus, the second region 942 is formed to be rotatable around the fifth axis A5 with respect to the first region 941. This is, the second region 942 may be rotatable around the X-axis when viewed from the drawing. Here, in order to implement the rotational motion of the second region 942 with respect to the first region 941, a motor may be provided on either the first region 941 or the second region 942.

The instrument mounting link 950 is axially coupled to the second link 940 by the link rotation shaft 960 coupled in a direction of a third axis A3, and thus, the instrument mounting link 950 is formed to be rotatable around the third axis A3 with respect to the second link 940. This is, the instrument mounting link 950 may be rotatable around the X-axis when viewed from the drawing. In order to implement such a rotational motion, a motor may be provided on either the second link 940 or the instrument mounting link 950.

On the other hand, an instrument mounting portion 951 and a guide rail 952 may be formed in the instrument mounting link 950. While the surgical instrument 20 is mounted on the instrument mounting portion 951, the instrument mounting portion 951 may perform a linear motion along the guide rail 952 formed in a direction of a fourth axis A4. In order to implement such a linear motion, a linear actuator (not shown) may be provided in the instrument mounting portion 951.

Here, the fourth axis A4 may be a direction in which the guide rail 952 is formed, and simultaneously, may be an extension direction of a shaft of the surgical instrument 20 coupled to the instrument mounting link 950.

The surgical instrument 20 is mounted on the instrument mounting portion 951 of the instrument mounting link 950 of the surgical robot arm 900.

Here, although not illustrated in the drawings, an interface part (not shown) coupled to the surgical instrument 20 and configured to control the motion of the surgical instrument 20 may be further formed in the instrument mounting portion 951. The interface part (not shown) may include a component configured to couple with a driving part 23 of the surgical instrument 20, a motor configured to transmit a driving force from the surgical robot arm 900 to the surgical instrument 20, and the like. The interface part (not shown) may allow an end tool 21 of the surgical instrument 20 to perform a pitch, yaw, or actuation motion. Furthermore, the interface part (not shown) may allow the shaft 22 and the end tool 21 of the surgical instrument 20 to perform a roll motion around the fourth axis A4.

On the other hand, a trocar 30 serving as an insertion passage for inserting the surgical instrument 20 into the patient's body may be further provided. While the trocar 30 is inserted into the body, the surgical instrument 20 may be inserted into the patient's body through the trocar 30. An RCM may be formed at a certain position on the trocar 30. As described above, the first axis A1, which is the roll rotation axis of the first link 930, may be formed to pass through the RCM.

In addition, the surgical instrument 20 may further include the driving part 23. A component configured to couple with the interface part (not shown) and a driving wheel operated in engagement with the motor may be formed in the driving part 23. As such, a coupling means and a driving transmission means may be respectively formed in the interface part (not shown) and the driving part 23 to correspond to each other. Accordingly, the surgical instrument 20 is operated by receiving a driving force from the surgical robot arm 900 in a state of being mounted on the instrument mounting link 950.

In the present disclosure, the RCM structure of the surgical robot arm 900 is a structure in which the surgical instrument 20 is mounted on one side of the surgical robot arm 900, and the surgical instrument 20 is operated and controlled to rotate around a certain point RCM on the trocar 30 into which the surgical instrument 20 is inserted. Here, the RCM structure according to the present embodiment is implemented through the electronic control for each link rather than the existing mechanical parallelogram link structure.

In particular, the difference between the present embodiment and the previous embodiments is that the RCM motion is possible even when the RCM and the rotation axis A1 of the base link 920 are spaced apart from each other without meeting each other, and thus, the initial setting of the surgical robot arm is simplified. That is, the RCM motion is possible even when the RCM and the base link 920 are spaced apart from each other to a certain extent on the XY plane.

That is, as illustrated in FIG. 47, etc. illustrating the third embodiment, the RCM motion is possible even when the first axis A1, which is the roll rotation axis of the first link 930, is not arranged to pass through the RCM on the XY plane. This is enabled by the additional degrees of freedom given in the present embodiment, that is, the rotational motion of the base link 920 with respect to the base 910 and the rotational motion of the second region 942 with respect to the first region 941 of the second link 940. That is, the surgical robot arm 900 of the present embodiment has a total of six degrees of freedom. Due to the motion of the six degrees of freedom, the RCM motion is possible even when the first axis A1 does not pass through the RCM on the XY plane.

Hereinafter, for convenience, the control in the X-axis direction and the control in the Y-axis direction in the drawing are described separately, but it may be stated that the overall control is performed by combining the control in the X-axis direction with the control in the Y-axis direction. In addition, the coordinate system of each component may change relatively due to the rotation and linear motion of each link. However, for convenience, the following description is given based on the X-axis direction and the Y-axis direction of the bed by using the bed as the reference point.

This will be described in more detail as follows.

First, the control in the X-axis direction may be implemented by a combination of:

1) the control of the linear motion of the second link 940 with respect to the first link 930, 2) the control of the rotational motion of the instrument mounting link 950 with respect to the second link 940, and 3) the control of the rotational motion of the second region 942 of the second link 940 with respect to the first region 941 of the second link 940.

In detail, in order to control the rotational motion of the surgical instrument 20 around the X-axis, the second link 940 first performs a linear motion along the second axis A2 with respect to the first link 930. At the same time, an RCM motion is performed by controlling the instrument mounting link 950 to perform a rotational motion around the third axis A3 with respect to the second link 940 and controlling the second region 942 of the second link 940 to perform a rotational motion with respect to the first region 941 of the second link 940. Accordingly, even when the links are moved, the RCM maintains a position thereof.

At this time, even when the surgical instrument 20 is rotated around the X-axis, the insertion depth (see LE of FIG. 6) of the instrument has not to change, and the distance (see Lt of FIG. 6) from the RCM to the end of the trocar 30 has not to change.

To this end, in the surgical robot arm 900 according to the fourth-1 embodiment of the present disclosure, one degree of freedom is added, compared to the surgical robot arm (see 100 of FIG. 4) according to the first embodiment of the present disclosure. That is, the surgical robot arm 900 according to the fourth-1 embodiment of the present disclosure is formed such that the first region 941 and the second region 942 of the second link 940 are rotatable around the pitch rotation shaft 945 with respect to each other.

Therefore, in controlling the rotational motion of the surgical instrument 20 around the X axis, the second region 942 of the second link 940 may be controlled to rotate with respect to the first region 941 of the second link 940, and thus, the insertion depths of the surgical instrument 20 and the trocar 30 may be maintained constant.

As such, even when the links are moved, the RCM in the X-axis direction maintains a position thereof by performing a combination of 1) the control of the linear motion of the second link 940 with respect to the first link 930, 2) the control of the rotational motion of the instrument mounting link 950 with respect to the second link 940, and 3) the control of the rotational motion of the second region 942 of the second link 940 with respect to the first region 941 of the second link 940.

Next, the RCM control in the Y-axis direction may be implemented by a combination of:

1) the control of the roll rotational motion of the first link 930 around the first link A1, 2) the control of the rotational motion of the instrument mounting link 950 with respect to the second link 940, 3) the control of the linear motion of the second link 940 with respect to the first link 930, 4) the control of the roll motion of the surgical instrument 20, and 5) the control of the rotational motion of the base link 920 with respect to the base 910.

In detail, in order to control the rotational motion of the surgical instrument 20 around the Y axis, the first link 930 first performs a roll rotational motion around the first axis A1. The first link 930, and the second link 940, the instrument mounting link 950, and the surgical instrument 20, which are sequentially connected to the first link 930, may perform a roll motion around the first axis A1.

In this case, since the first axis A1, which is the rotation axis of the first link 930, and the Y-axis do not coincide with each other and are formed to be oblique, unintended motions are mixed when only the first link 930 is rotated. That is, as illustrated in the drawings, when the first link 930 is rotated, the second link 940, the instrument mounting link 950, and the surgical instrument 20 perform a kind of rolling.

In order to compensate for this, with the rotation of the first link 930, the instrument mounting link 950 is controlled to perform a rotational motion around the third axis A3 with respect to the second link 940, the second link 940 is controlled to perform a linear motion with respect to the first link 930, and simultaneously, the base link 920 is controlled to perform a rotational motion around the sixth axis A6 with respect to the base 910. In this manner, the RCM motion is performed. That is, even when the links are moved, the RCM maintains a position thereof.

In addition, the shaft 22 and the end tool 21 of the surgical instrument 20 are controlled to perform a roll motion around the fourth axis A4, so that the end tool 21 may also be compensated to maintain a posture thereof, regardless of the rotation of the first link 930.

As such, even when the links are moved, the RCM in the Y-axis direction maintains a position thereof by performing a combination of 1) the control of the roll rotational motion of the first link 930 around the first link A1, 2) the control of the rotational motion of the instrument mounting link 950 with respect to the second link 940, 3) the control of the linear motion of the second link 940 with respect to the first link 930, 4) the control of the roll motion of the surgical instrument 20, and 5) the control of the rotational motion of the base link 920 with respect to the base 910.

In conclusion, from the viewpoint of the degree of freedom of the surgical robot arm 900 itself (excluding the surgical instrument 20), the surgical robot arm 900 according to the fourth-1 embodiment of the present disclosure may operate with five degrees of freedom of 1) the roll rotational motion of the first link 930 around the first axis A1, 2) the linear motion of the second link 940 with respect to the first link 830, 3) the rotational motion of the instrument mounting link 950 with respect to the second link 940, 4) the rotational motion of the second region 942 of the second link 940 with respect to the first region 941 of the second link 940, and 5) the rotational motion of the base link 920 with respect to the base 910. Here, a translation motion of the surgical instrument 20, that is, a linear motion of the surgical instrument 20 in the direction of the fourth axis A4, is also possible through the linear motion of the instrument mounting portion 951 with respect to the guide rail 952 of the instrument mounting link 950.

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm 100 and reducing the driving force required for operation may be obtained. Furthermore, the insertion depth of the trocar 30 is controlled to be constant through the control of the rotational motion of the second region 942 of the second link 940 with respect to the first region 941 of the second link 940, and thus, the risk of the trocar 30 coming out of the abdomen during surgery may be eliminated, thereby further improving safety.

<Fifth Embodiment of Surgical Robot Arm>

Hereinafter, a surgical robot arm 500 according to a fifth embodiment of the present disclosure will be described.

Here, the surgical robot arm 500 according to the fifth embodiment of the present disclosure characteristically differs from the surgical robot arm (see 100 of FIG. 4) according to the first embodiment of the present disclosure in terms of a configuration of a first link 530 of the robot arm 500. In other words, compared to the embodiment of FIG. 4, the robot arm 500 according to the fourth embodiment of the present disclosure is an embodiment in which a first link 530 includes three parts, that is, a first region 531, a second region 532, and a third region 533. The second region 532 of the first link 530 is formed to be movable in the vertical direction (i.e., the Z-axis direction) with respect to the first region 531, and the third region 533 of the first link 530 is formed to be rotatable around an axis A2 with respect to the second region 532.

In addition, the surgical robot arm 500 according to the fifth embodiment of the present disclosure characteristically differs from the surgical robot arm (see 100 of FIG. 4) according to the first embodiment of the present disclosure in terms of an operation of a base link 520 of the robot arm 500. In other words, the surgical robot arm 500 according to the fifth embodiment of the present disclosure is an embodiment in which the base link 520 is formed to be linearly movable in the vertical direction with respect to the base 510, compared to the embodiment of FIG. 4.

Compared to the first embodiment, the change in configuration will be described in detail later.

Figure 72:
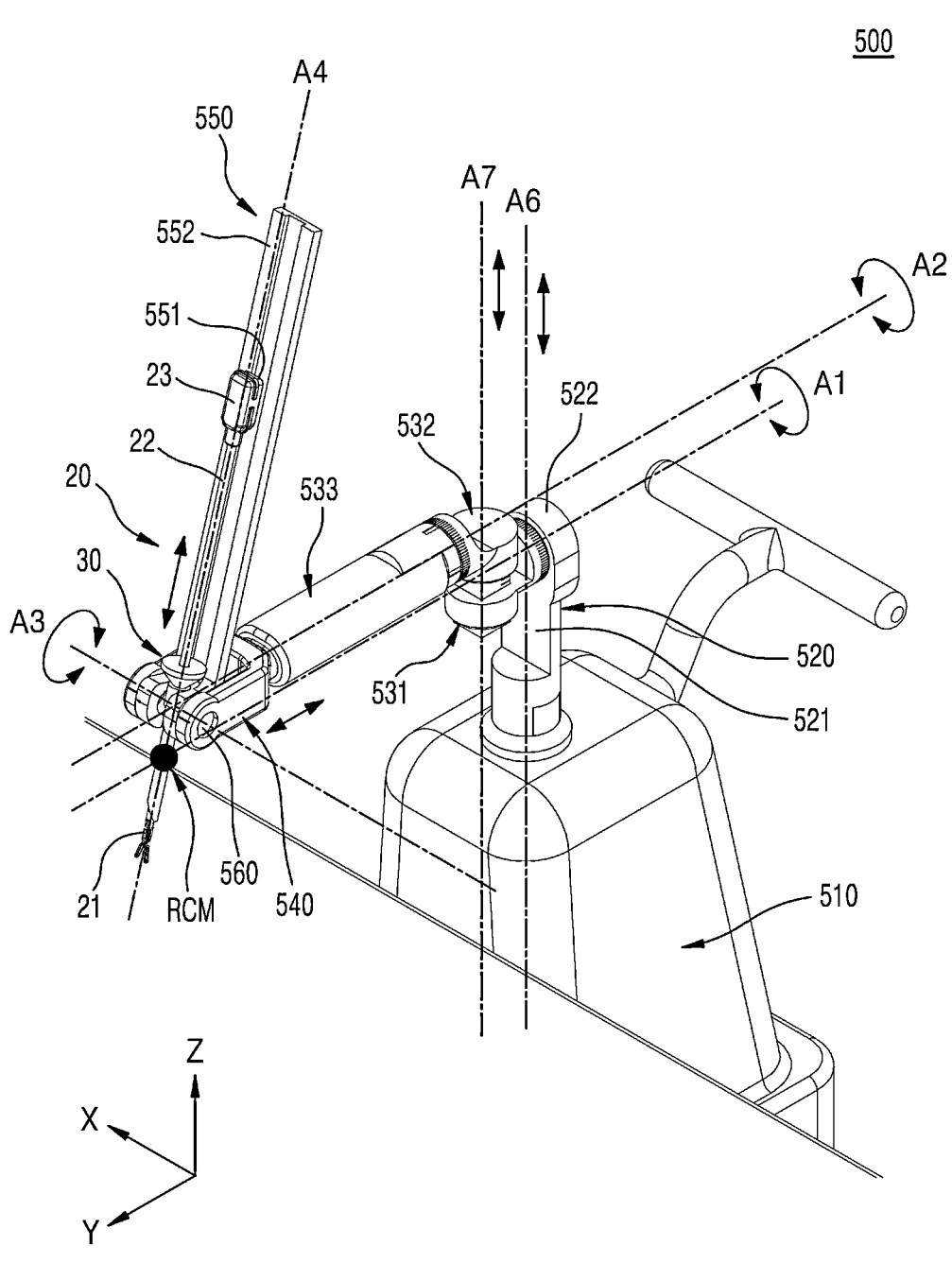
FIG. 72 is a perspective view illustrating an overall structure of a surgical robot arm (500) according to a fifth embodiment of the present disclosure.
Figure 73:
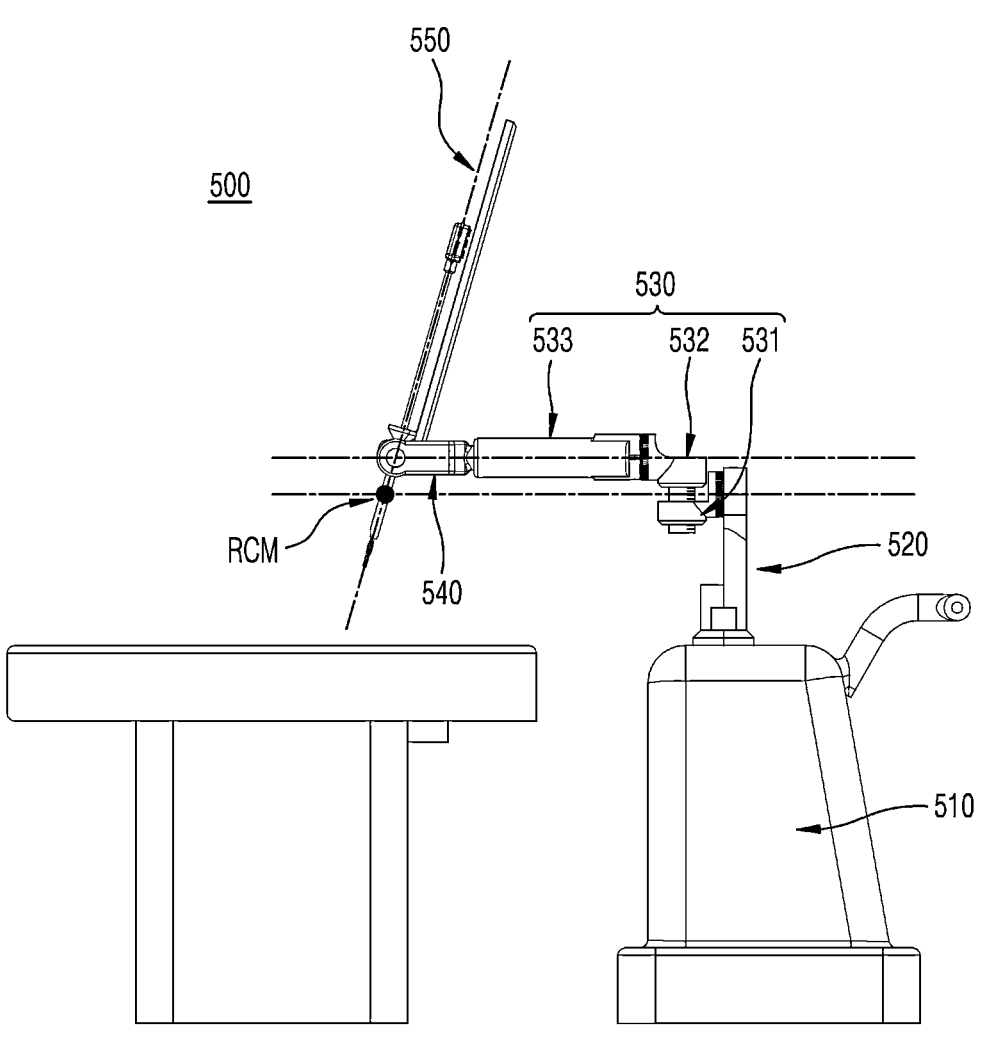
FIG. 73 is a side view of the surgical robot arm of FIG. 72.
Figures 74A, 74B:
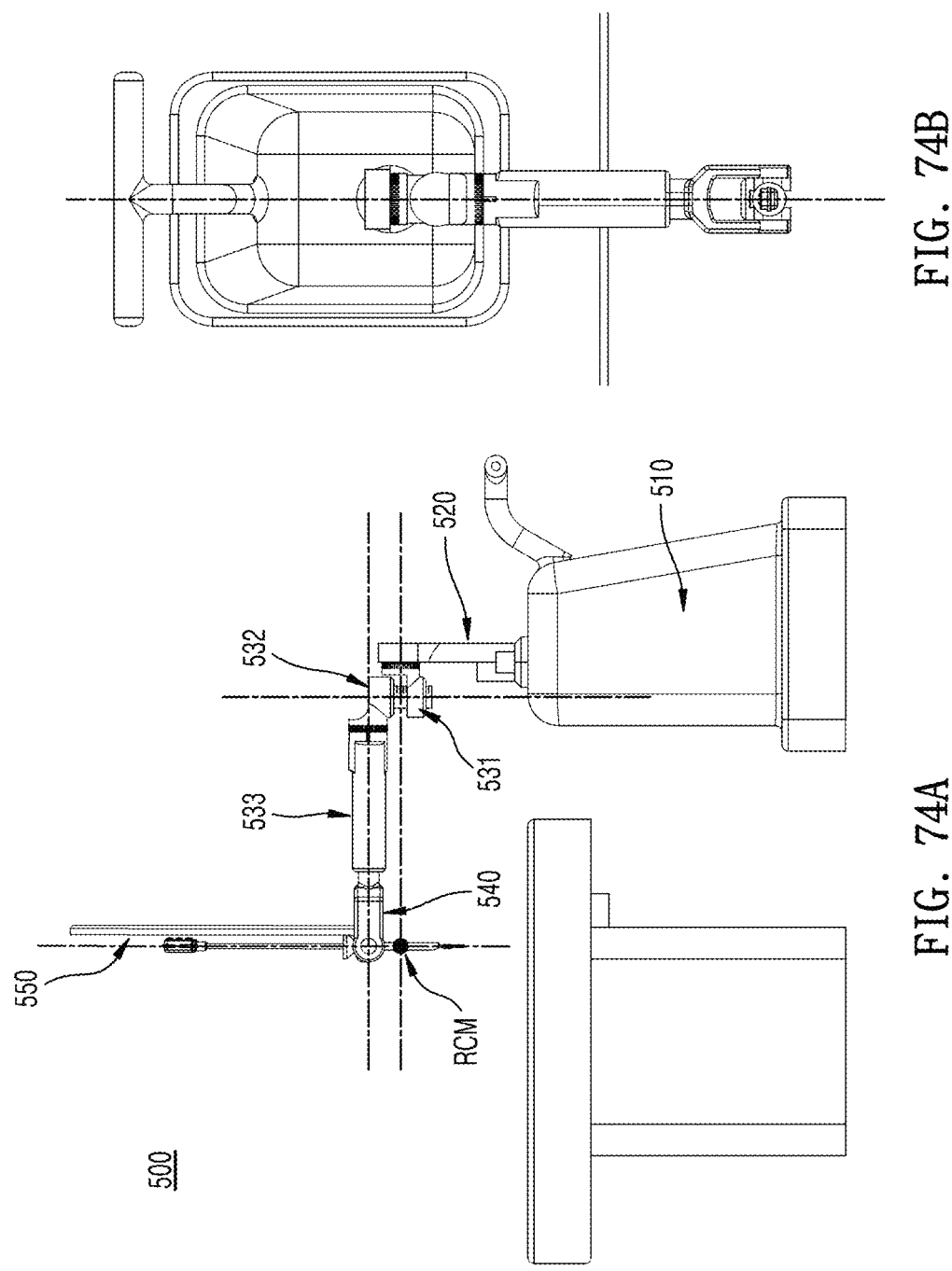
Figures 75A, 75B:
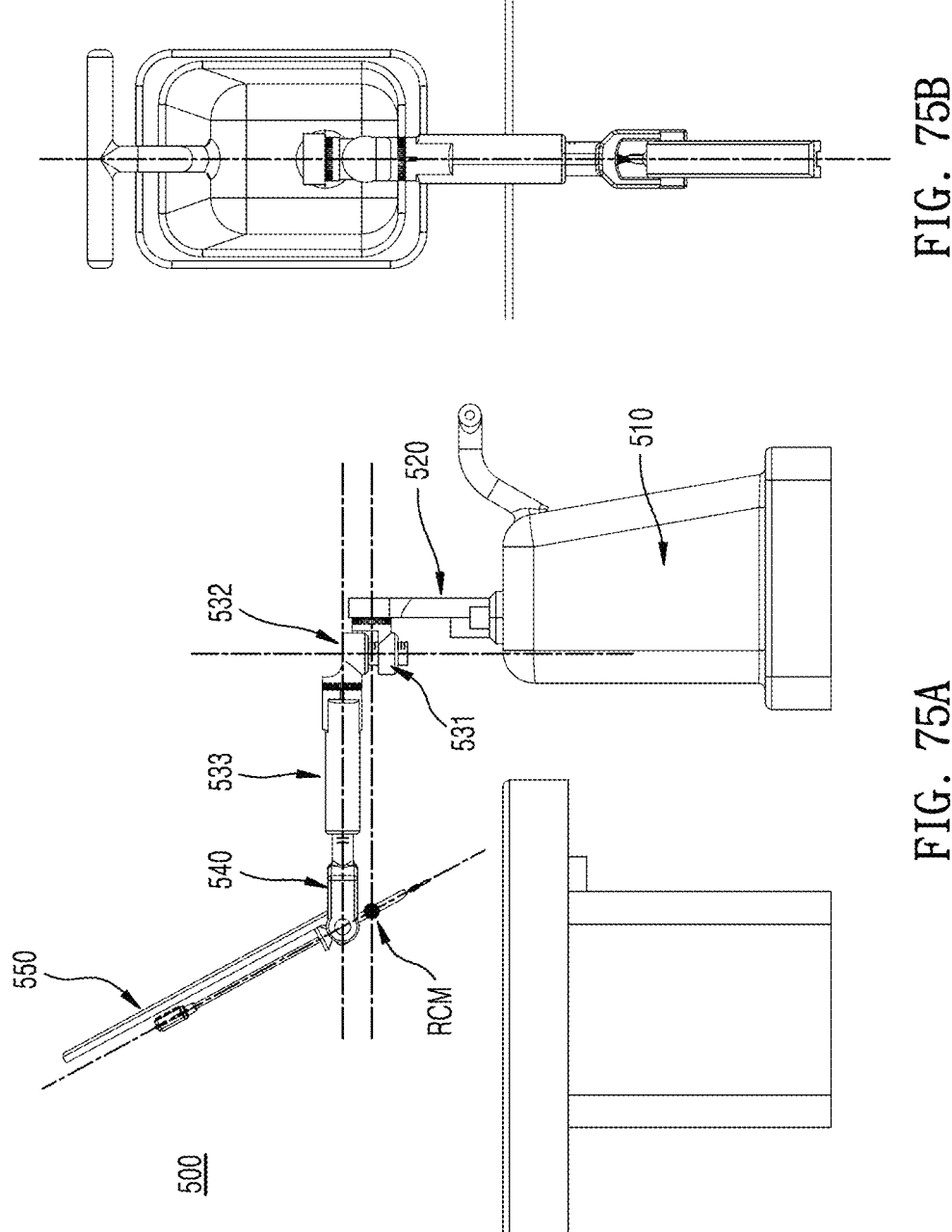
Figures 76A, 76B:
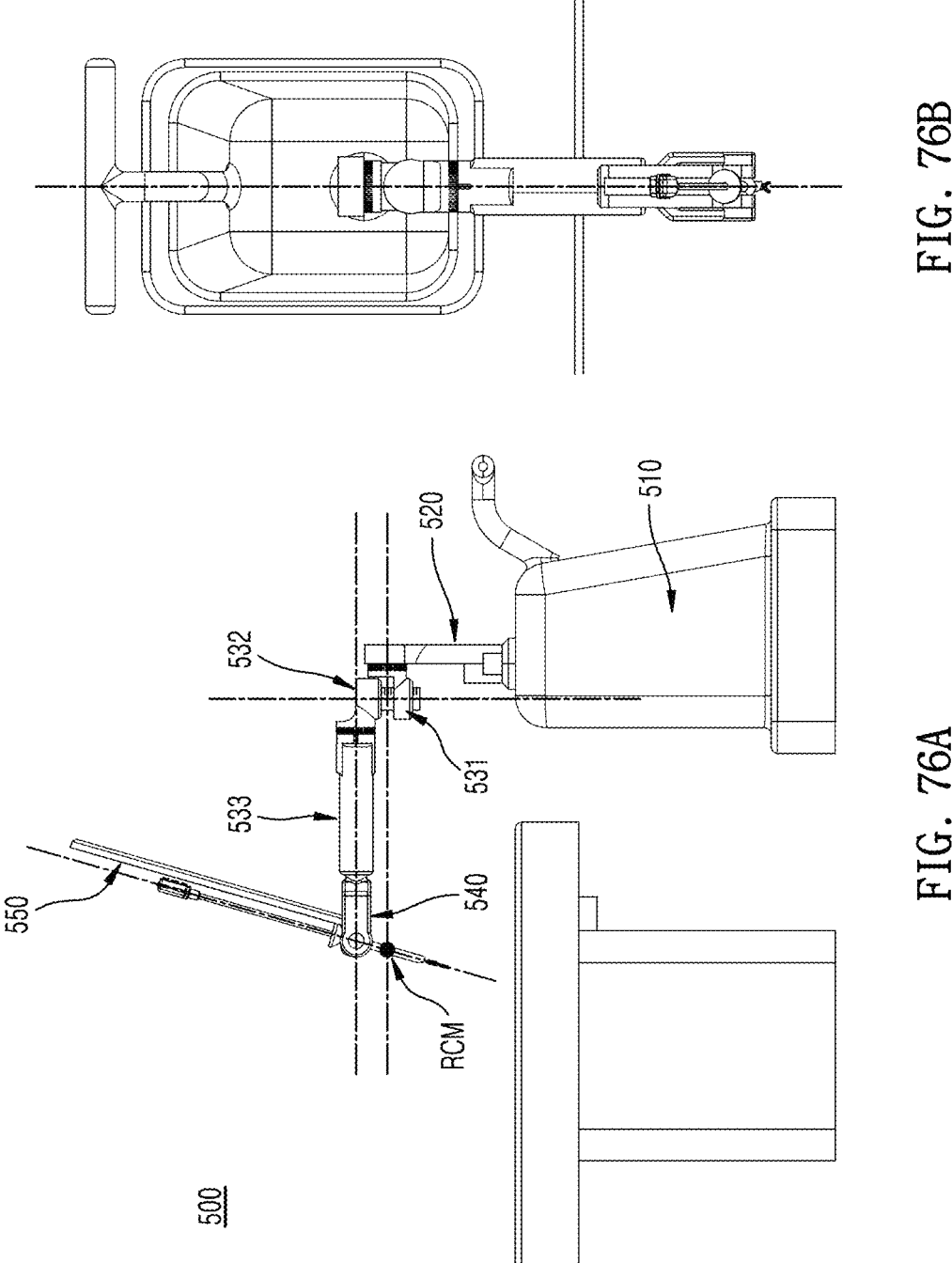
Figure 77:
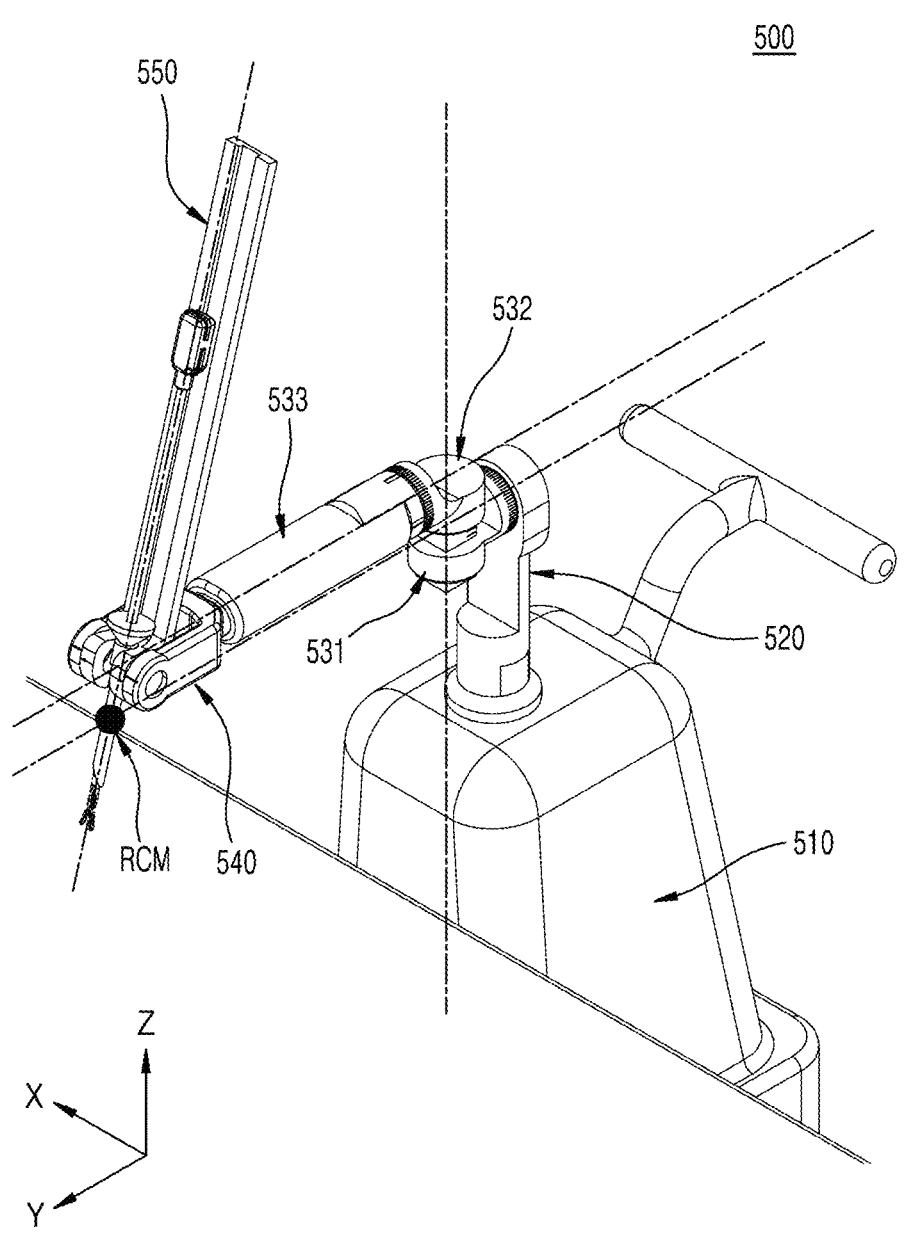
FIGS. 77 to 79 are perspective views illustrating a Y-axis RCM motion (a yaw motion) of the surgical robot arm of FIG. 72.
Figure 78:
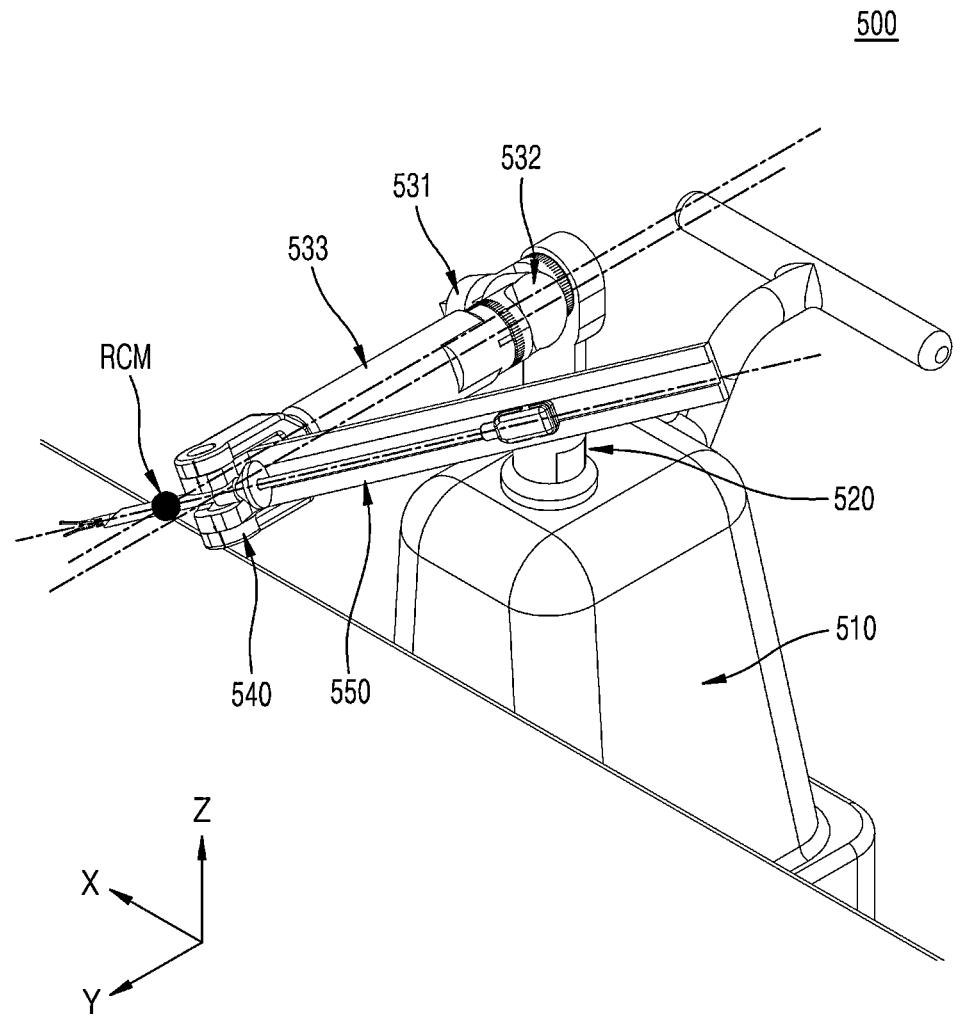
Figure 79:
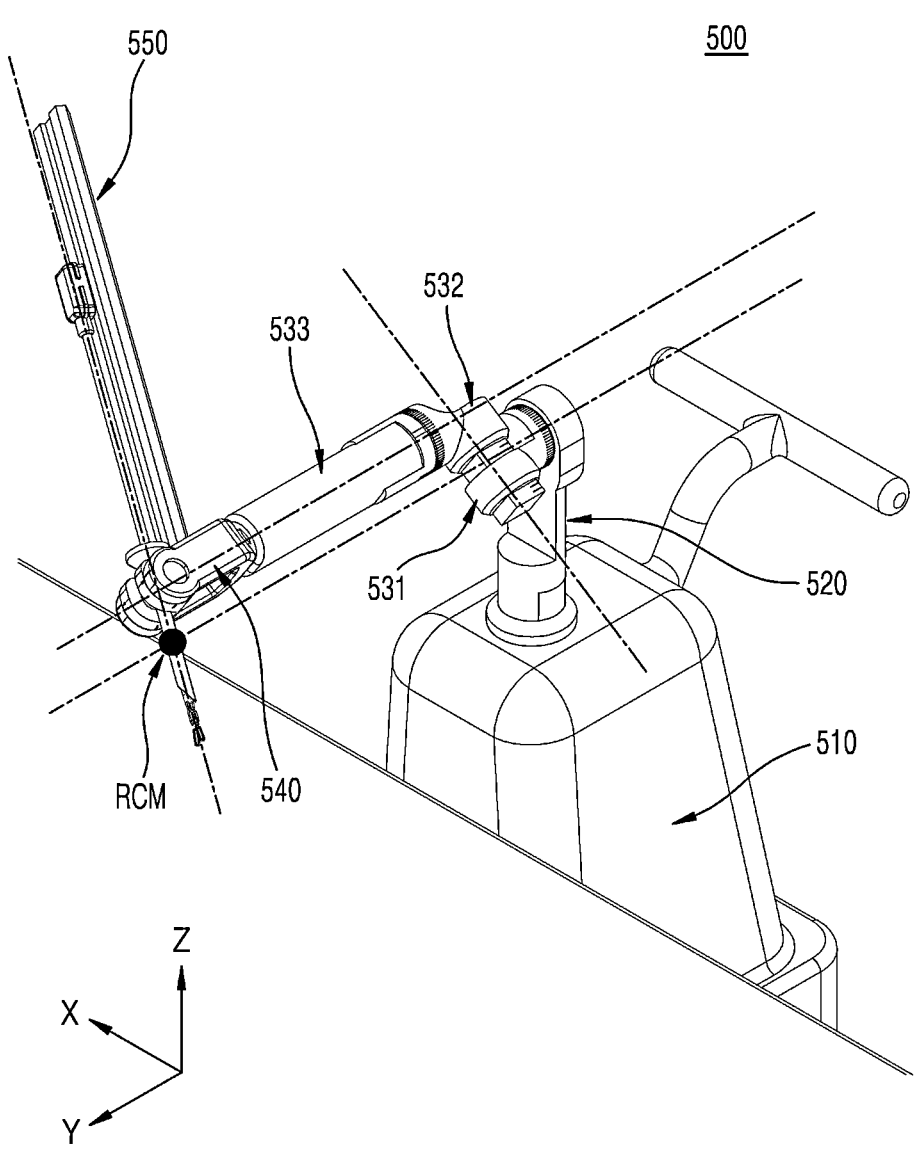
Figures 80A, 80B:
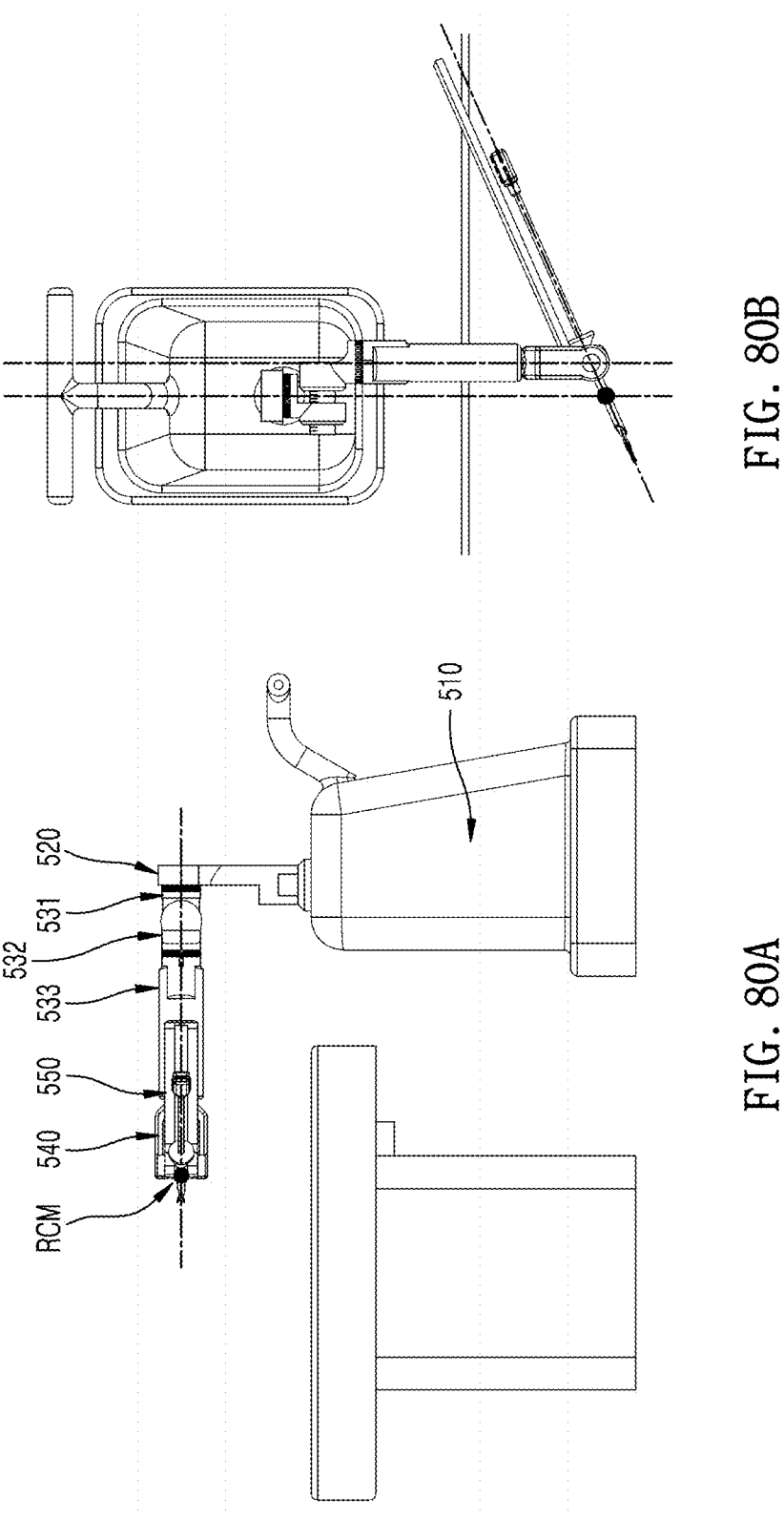
FIGS. 80A and 80B are a side view and a plan view, respectively, illustrating a state in which the surgical robot arm of FIG. 72 lies on its side.

FIG. 72 is a perspective view illustrating the overall structure of the surgical robot arm 500 according to the fifth embodiment of the present disclosure. FIG. 73 is a side view of the surgical robot arm of FIG. 72. FIGS. 74 to 76 are side views and plan views illustrating an X-axis RCM motion (a pitch motion) of the surgical robot arm of FIG. 72. FIGS. 77 to 79 are perspective views illustrating a Y-axis RCM motion (a yaw motion) of the surgical robot arm of FIG. 72. FIG. 80 is a side view and a plan view illustrating a state in which the surgical robot arm of FIG. 72 lies on its side.

Referring to FIGS. 72 to 80, the surgical robot arm 500 according to the fifth embodiment present disclosure includes a base 510, a base link 520, a first link 530, a second link 540, and an instrument mounting link 550.

The base 510 serves as a base part of the entire surgical robot arm 500. Here, a moving means (not shown) such as wheels may be formed on the lower surface of the base 510 so that the base 510 may serve as a kind of cart. In addition, a position fixing means (not shown) may be further formed on the base 510 so that the position of the base 510 may be fixed during surgery. However, the concept of the present disclosure is not limited thereto, and the base 510 may be formed in a shape that is detachably attachable to a bed, or may be formed in a shape that is detachably attachable a wall.

The base link 520 includes an extension portion 521 and a roll rotation base portion 522.

The extension portion 521 may extend in one direction from the base 510. In the drawings, it is illustrated that the extension portion 521 of the base link 520 extends from the base 510 in a Z-axis direction.

Here, the extension portion 521 is formed to enable a linear motion with respect to the base 510. That is, in the present embodiment, the base link 520 is formed to enable a linear motion in one direction (an up/down direction) along a sixth axis A6 with respect to the base 510. However, here, the linear motion of the base link 520 with respect to the base 510 is not performed in real time during the operation of the surgical robot arm 500, and may be performed in the set-up stage of the surgical robot arm 500 before starting surgery. That is, as illustrated in FIG. 28 illustrating the second-1 embodiment, the RCM motion may be implemented no matter where the base link 720 is located in the Z-axis direction.

In detail, as illustrated in FIG. 72, the base link 520 may be formed to be inserted into or withdrawn from the base 510, so that the base link 520 may be located at various positions. That is, in the present embodiment, the RCM motion may be implemented even when the first axis A1, which is the roll rotation axis of the base link 520, does not coincide with the RCM in the Z-axis direction.

To this end, the second region 532 of the first link 530 may be formed to be linearly movable with respect to the first region 531. As such, since the RCM motion is possible even when the RCM and the first axis A1 of the base link 520 are spaced apart from each other, the initial position of the surgical robot arm may be flexibly set. That is, various set-up positions of the surgical robot arm 500 are possible. This will be described later.

On the other hand, the roll rotation base portion 522 is formed at the other end of the base link 520. Here, the roll rotation base portion 522 of the base link 520 may be formed in a cylindrical shape with respect to the first axis A1 formed in a first direction. The first link 530 connected to the roll rotation base portion 522 (together with the second link 540, the instrument mounting link 550, and the surgical instrument 20 sequentially connected to the first link 530) may be formed to perform a roll motion around the first axis A1. Here, the first axis A1 may be formed in a direction parallel to the X-axis.

The first link 530 may be coupled to the base link 520, and more specifically, to the roll rotation base portion 522 of the base link 520 and may be formed such that the entire first link 530 is rotatable around the first axis A1 of the roll rotation base portion 522. Alternatively, it may be expressed that the first link 530 rolls around the base link 520. In order to implement the rotational motion of the first link 530 with respect to the base link 520, a motor may be provided on either the base link 520 or the first link 530.

On the other hand, the first link 530 may include a first region 531 coupled to the base link 520, a third region 533 coupled to the second link 540, and a second region 532 connecting the first region 531 to the third region 533.

Here, the second region 532 may be formed to be movable in the vertical direction along a seventh axis A7 with respect to the first region 531.

The second region 532 and the third region 533 are coupled to each other by a roll rotation shaft (not shown) formed in a direction of a second axis A2, and the third region 533 is formed to be roll-rotatable around the second axis A2 with respect to the second region 532. This is, the third region 533 may be rotatable around the Y-axis when viewed from the drawing.

Here, when the first link 530 is rotated around the first axis A1, the second link 540, the instrument mounting link 550, and the surgical instrument 20 connected to the first link 530 are rotated together.

On the other hand, in order to implement the rotational motion of the second region 532 with respect to the first region 531, a motor may be provided on either the first region 531 or the second region 532. In addition, in order to implement the rotational motion of the third region 533 with respect to the second region 532, a motor may be provided on either the second region 532 or the third region 533.

The second link 540 may be coupled to the third region 533 of the first link 530 and may perform a linear reciprocating motion in one direction along the second axis A2 with respect to the third region 533 of the first link 530. Here, in the drawings, it is illustrated that the second link 540 performs a linear reciprocating motion in the X-axis direction with respect to the first link 530, but the concept of the present disclosure is not limited thereto, and a linear reciprocating axis of the second link 540 may be variously formed according to the shape and configuration of the links.

In order to implement such a linear motion, a linear actuator (not shown) may be provided on either the first link 530 or the second link 540.

Here, the first axis A1 and the second axis A2 may be parallel to each other. In this case, the second axis A2 may be formed not to pass through the RCM.

The instrument mounting link 550 is axially coupled to the second link 540 by the link rotation shaft 560 coupled in a direction of a third axis A3, and thus, the instrument mounting link 550 is formed to be rotatable around the third axis A3 with respect to the second link 540. This is, the instrument mounting link 550 may be rotatable around the X-axis when viewed from the drawing. In order to implement such a rotational motion, a motor may be provided on either the second link 540 or the instrument mounting link 550.

On the other hand, an instrument mounting portion 551 and a guide rail 552 may be formed in the instrument mounting link 550. While the surgical instrument 20 is mounted on the instrument mounting portion 551, the instrument mounting portion 551 may perform a linear motion along the guide rail 552 formed in a direction of a fourth axis A4. In order to implement such a linear motion, a linear actuator (not shown) may be provided in the instrument mounting portion 551.

Here, the fourth axis A4 may be a direction in which the guide rail 552 is formed, and simultaneously, may be an extension direction of a shaft of the surgical instrument 20 coupled to the instrument mounting link 550.

The surgical instrument 20 is mounted on the instrument mounting portion 551 of the instrument mounting link 550 of the surgical robot arm 500.

Here, although not illustrated in the drawings, an interface part (not shown) coupled to the surgical instrument 20 and configured to control the motion of the surgical instrument 20 may be further formed in the instrument mounting portion 551. The interface part (not shown) may include a component configured to couple with a driving part 23 of the surgical instrument 20, a motor configured to transmit a driving force from the surgical robot arm 500 to the surgical instrument 20, and the like. The interface part (not shown) may allow an end tool 21 of the surgical instrument 20 to perform a pitch, yaw, or actuation motion. Furthermore, the interface part (not shown) may allow the shaft 22 and the end tool 21 of the surgical instrument 20 to perform a roll motion around the fourth axis A4.

On the other hand, a trocar 30 serving as an insertion passage for inserting the surgical instrument 20 into the patient's body may be further provided. While the trocar 30 is inserted into the body, the surgical instrument 20 may be inserted into the patient's body through the trocar 30. An RCM may be formed at a certain position on the trocar 30. As described above, the first axis A1, which is the roll rotation axis of the first link 530, may be formed to pass through the RCM.

In addition, the surgical instrument 20 may further include the driving part 23. A component configured to couple with the interface part (not shown) and a driving wheel operated in engagement with the motor may be formed in the driving part 23. As such, a coupling means and a driving transmission means may be respectively formed in the interface part (not shown) and the driving part 23 to correspond to each other. Accordingly, the surgical instrument 20 is operated by receiving a driving force from the surgical robot arm 500 in a state of being mounted on the instrument mounting link 550.

In the present disclosure, the RCM structure of the surgical robot arm 500 is a structure in which the surgical instrument 20 is mounted on one side of the surgical robot arm 500, and the surgical instrument 20 is operated and controlled to rotate around a certain point RCM on the trocar 30 into which the surgical instrument 20 is inserted. Here, the RCM structure according to the present embodiment is implemented through the electronic control for each link rather than the existing mechanical parallelogram link structure.

In particular, the difference between the present embodiment and the previous embodiments is that the RCM motion is possible even when the RCM and the rotation axis A1 of the base link are spaced apart from each other without meeting each other, and thus, the initial setting of the surgical robot arm is simplified. That is, the RCM motion is possible even when the RCM and the base link are spaced apart from each other in both the yaw axis direction and the pitch axis direction.

That is, the RCM motion is possible even when the first axis A1, which is the roll rotation axis of the first link 530, is not arranged to pass through the RCM. This is enabled by the additional degrees of freedom given in the present embodiment, that is, the linear motion of the base link 520 with respect to the base 510, the linear motion of the second region 532 with respect to the first region 531, and the rotational motion of the third region 533 with respect to the second region 532. That is, the surgical robot arm 500 of the present embodiment has a total of seven degrees of freedom. Due to the motion of the seven degrees of freedom, the RCM motion is possible even when the first axis A1 does not pass through the RCM.

Hereinafter, for convenience, the control in the X-axis direction and the control in the Y-axis direction in the drawing are described separately, but it may be stated that the overall control is performed by combining the control in the X-axis direction with the control in the Y-axis direction. In addition, the coordinate system of each component may change relatively due to the rotation and linear motion of each link. However, for convenience, the following description is given based on the X-axis direction and the Y-axis direction of the bed by using the bed as the reference point.

This is described in more detail as follows.

First, the control in the X-axis direction may be implemented by a combination of:

1) the control of the linear motion of the second link 540 with respect to the first link 530, 2) the control of the rotational motion of the instrument mounting link 550 with respect to the second link 540, and 3) the control of the linear motion of the second region 532 of the first link 530 with respect to the first region 531 of the first link 530.

In detail, in order to control the rotational motion of the surgical instrument 20 around the X-axis, the second link 540 first performs a linear motion along the second axis A2 with respect to the first link 530. At the same time, an RCM motion is performed by controlling the instrument mounting link 550 to perform a rotational motion around the third axis A3 with respect to the second link 540 and controlling the second region 532 of the first link 530 to perform a rotational motion with respect to the first region 531 of the first link 530. Accordingly, even when the links are moved, the RCM maintains a position thereof.

At this time, even when the surgical instrument 20 is rotated around the X-axis, the insertion depth (see LE of FIG. 6) of the instrument has not to change, and the distance (see Lt of FIG. 6) from the RCM to the end of the trocar 30 has not to change.

To this end, in the surgical robot arm 500 according to the fifth embodiment of the present disclosure, one degree of freedom is added, compared to the surgical robot arm (see 100 of FIG. 4) according to the first embodiment of the present disclosure. That is, the surgical robot arm 500 according to the second embodiment of the present disclosure is formed such that the second region 532 of the first link 530 is vertically rotatable along a seventh axis A7 with respect to the first region 531.

Therefore, in controlling the rotational motion of the surgical instrument 20 around the X axis, the second region 532 of the first link 530 may be controlled to perform a linear motion with respect to the first region 531 of the first link 530, and thus, the insertion depths of the surgical instrument 20 and the trocar 30 may be maintained constant.

As such, even when the links are moved, the RCM in the X-axis direction maintains a position thereof by performing a combination of 1) the control of the linear motion of the second link 540 with respect to the first link 530, 2) the control of the rotational motion of the instrument mounting link 550 with respect to the second link 540, and 3) the control of the linear motion of the second region 532 of the first link 530 with respect to the first region 531 of the first link 530.

Next, the RCM control in the Y-axis direction may be implemented by a combination of:

1) the control of the roll rotational motion of the first link 530 around the first link A1,
2) the control of the rotational motion of the instrument mounting link 550 with respect to the second link 540,
3) the control of the linear motion of the second link 540 with respect to the first link 530,
4) the control of the roll motion of the surgical instrument 20, and
5) the control of the rotational motion of the third region 533 of the first link 530 with respect to the second region 532 of the first link 530.

In detail, in order to control the rotational motion of the surgical instrument 20 around the Y axis, the first link 530 first performs a roll rotational motion around the first axis A1. The first link 530, and the second link 540, the instrument mounting link 550, and the surgical instrument 20, which are sequentially connected to the first link 530, may perform a roll motion around the first axis A1.

At this time, unintended motions are mixed when only the first link 530 is rotated. That is, as illustrated in the drawings, when the first link 530 is rotated, the second link 540, the instrument mounting link 550, and the surgical instrument 20 perform a kind of rolling.

In order to compensate for this, with the rotation of the first link 530, the instrument mounting link 550 is controlled to perform a rotational motion around the third axis A3 with respect to the second link 540, the second link 540 is controlled to perform a linear motion with respect to the first link 530, and the third region 533 of the first link 530 is controlled to perform a rotational motion with respect to the second region 532 of the first link 530. In this manner, the RCM motion is performed. That is, even when the links are moved, the RCM maintains a position thereof.

In addition, the shaft 22 and the end tool 21 of the surgical instrument 20 are controlled to perform a roll motion around the fourth axis A4, so that the end tool 21 may also be compensated to maintain a posture thereof, regardless of the rotation of the first link 530.

As such, even when the links are moved, the RCM in the Y-axis direction maintains a position thereof by performing a combination of 1) the control of the roll rotational motion of the first link 530 around the first link A1, 2) the control of the rotational motion of the instrument mounting link 550 with respect to the second link 540, 3) the control of the linear motion of the second link 540 with respect to the first link 530, 4) the control of the roll motion of the surgical instrument 20, and 5) the control of the rotational motion of the third region 533 of the first link 530 with respect to the second region 532 of the first link 530.

In conclusion, from the viewpoint of the degree of freedom of the surgical robot arm 500 itself (excluding the surgical instrument 20), the surgical robot arm 500 according to the fifth embodiment of the present disclosure may operate with six degrees of freedom of 1) the roll rotational motion of the first link 530 around the first axis A1, 2) the linear motion of the second link 540 with respect to the first link 530, 3) the rotational motion of the instrument mounting link 550 with respect to the second link 540, 4) the linear motion of the second region 532 of the first link 530 with respect to the first region 531 of the first link 530, 5) the rotational motion of the third region 533 of the first link 530 with respect to the second region 532 of the first link 530, and 6) the linear motion of the base link 520 with respect to the base 510. Here, a translation motion of the surgical instrument 20, that is, a linear motion of the surgical instrument 20 in the direction of the fourth axis A4, is also possible through the linear motion of the instrument mounting portion 551 with respect to the guide rail 552 of the instrument mounting link 550.

By implementing the RCM control through the electronic control, the present disclosure may obtain an effect of reducing the overall size of the device and simplifying the configuration, thereby increasing space efficiency and preventing collisions between robot arms. In particular, in order to operate the surgical instrument 20, the surgical instrument 20 is driven by holding the coupling portion with the trocar 30 relatively close to the end tool 21 rather than holding the rear side of the surgical instrument 20 (i.e., the opposite side of the end tool 21) as in the past. Therefore, an effect of reducing the operating range of the surgical robot arm 100 and reducing the driving force required for operation may be obtained. Furthermore, the insertion depth of the trocar 30 is controlled to be constant through the control of the rotational motion of the second region 532 of the first link 530 with respect to the first region 531 of the first link 530, and thus, the risk of the trocar 30 coming out of the abdomen during surgery may be eliminated, thereby further improving safety.

In addition, when the additional degree of freedom (i.e., the rotational motion of the third region 533 of the first link 530 with respect to the second region 532 of the first link 530) is given, the RCM motion may be implemented even when the first axis A1, which is the roll rotation axis of the base link 520, does not coincide with the RCM. Accordingly, an effect of simplifying the initial setting of the surgical robot arm may be obtained.

The specific implementations described in the present disclosure are only embodiments and do not limit the scope of the present disclosure in any way. For the sake of conciseness of the specification, descriptions of conventional electronic components, control systems, software, and other functional aspects of the systems may be omitted. In addition, connecting lines or connecting members illustrated in the drawings are intended to represent exemplary functional connections and/or physical or circuit connections. In an actual device, it may appear as a variety of alternative or additional functional, physical, or circuit connections. In addition, when there is no specific mention such as "essential," "important," etc., it may not be a necessary component for the application of the present disclosure.

The use of the term "the" and similar demonstratives in the context of describing the present specification (especially in the context of the claims) is to be construed to cover both the singular and the plural. In addition, when a range is described in the present disclosure, it includes the invention to which individual values within the range are applied (unless otherwise indicated herein). This is the same as stating each individual value constituting the above range in the detailed description of the present disclosure. Finally, operations constituting methods according to the present disclosure may be performed in any suitable order unless otherwise indicated herein or otherwise clearly contradicted by context. The present disclosure is not necessarily limited by the order of operations. The use of any and all examples or exemplary terms (e.g., "such as") provided herein is simply intended to describe the present disclosure in detail, and the scope of the present disclosure is not limited by the examples or exemplary terms unless otherwise claimed. In addition, it will be understood by those of ordinary skill in the art that various modifications, combinations and changes may be made according to design conditions and factors within the scope of the appended claims or equivalents thereof.

While the present disclosure has been described by particular matters such as specific components and limited embodiments and drawings, this is provided only for helping the comprehensive understanding of the present disclosure. The present disclosure is not limited to the embodiments described above, and it will be understood by those of ordinary skill in the art that various modifications and variations may be made thereto without departing from the scope of the present disclosure.

Therefore, it will be understood that the spirit of the present disclosure should not be limited to the embodiments described above, and the claims and all equivalent modifications fall within the scope of the present disclosure.

INDUSTRIAL APPLICABILITY

By implementing a remote center of motion (RCM) control through an electronic control, the present disclosure may be applied to a surgical robot arm in which the overall size of the device is reduced and the configuration is simplified, thereby increasing space efficiency and preventing collisions between robot arms.

The invention claimed is:

1. A surgical robot arm, on which a surgical instrument is mounted, the surgical robot arm comprising:
   a base link including an extension portion extending in one direction and a roll rotation base portion disposed at one end of the extension portion and formed to have a predetermined angle with the extension portion;
   a first link coupled to the roll rotation base portion of the base link and configured to be roll-rotatable around a first axis;
   a second link coupled to the first link and configured to be linearly movable along a second axis which is formed to have a predetermined angle with respect to the first link; and
   an instrument mounting link axially coupled to the second link only by a link rotation shaft formed in a third axis direction, including a guide rail extending in a fourth axis direction, and configured to be rotatable around the link rotation shaft,
   wherein the first link includes:
      a first region coupled to the base link in a direction parallel to the first axis,
      a second region connecting the first region and a third region, and configured to linearly move along a seventh axis with respect to the first region, and
      the third region coupled to the second link at one end and coupled to the second region at another end by a roll rotation shaft, and configured to be rotatable around the second axis with respect to the second region,
   wherein a remote center of motion (RCM) is formed on a trocar into which the surgical instrument is inserted, and the RCM is disposed on an extension line of the first axis, wherein the surgical instrument includes an end tool at one end and other end of the surgical instrument is coupled to the instrument mounting link,
wherein the trocar is disposed closer to the one end of the surgical instrument than the other end of the surgical instrument,
wherein the second axis, the third axis, and the fourth axis intersect at a point on the trocar,
wherein the trocar and the surgical instrument inserted thereinto are controlled to rotate around the RCM,
wherein during an RCM motion around the RCM in a first direction which is a rotational direction about an axis substantially parallel to the second axis, at least one of a roll rotational motion of the first link with respect to the base link, a rotational motion of the instrument mounting link with respect to the second link, and a linear motion of the second link with respect to the first link is controlled to maintain a position of the RCM, and
wherein during an RCM motion around the RCM in a second direction which is a rotational direction about an axis substantially parallel to the third axis, at least one of the linear motion of the second link with respect to the first link and the rotational motion of the instrument mounting link with respect to the second link is controlled to maintain the position of the RCM.

2. The surgical robot arm of claim 1, further comprising a base configured to form a base portion of the surgical robot arm and having one surface to which the base link is coupled.

3. The surgical robot arm of claim 1, wherein the instrument mounting link includes:
   an instrument mounting portion to which the surgical instrument is coupled and which is configured to be linearly movable along the guide rail.

4. The surgical robot arm of claim 3, wherein a distance from an end of an end tool of the surgical instrument to the RCM is controllable to be maintained constant by a linear motion of the instrument mounting portion with respect to the guide rail.

5. The surgical robot arm of claim 1, wherein a control of an RCM motion around the RCM in the first direction is performed by a control of:
   the roll rotational motion of the first link around the first axis with respect to the base link;
   the rotational motion of the instrument mounting link around the third axis with respect to the second link; and
   the linear motion of the second link with respect to the first link moving along the second axis.

6. The surgical robot arm of claim 5, wherein, for the RCM control in the first direction, a roll motion of the surgical instrument is controlled together.

7. The surgical robot arm of claim 6, wherein a direction of an end tool of the surgical instrument is controlled to be maintained constant by the roll motion of the surgical instrument.

8. The surgical robot arm of claim 1, wherein an RCM control in the second direction is implemented by a control of:
   the linear motion of the second link with respect to the first link moving along the second axis; and
   the rotational motion of the instrument mounting link around the third axis with respect to the second link.

9. The surgical robot arm of claim 1, wherein the link rotation shaft is actively controlled by a motor.

\* \* \* \* \*